US009090902B2

(12) United States Patent
Bauer et al.

(10) Patent No.: US 9,090,902 B2
(45) Date of Patent: Jul. 28, 2015

(54) NUCLEIC ACIDS ENCODING DESATURASES AND MODIFIED PLANT OIL

(75) Inventors: Jörg Bauer, Limburgerhof (DE); Toralf Senger, Weinheim (DE); Thorsten Zank, Mannheim (DE); Xiao Qiu, Saskatoon (CA); Guohai Wu, Saskatoon (CA)

(73) Assignees: BASF Plant Science GmbH, Ludwigshafen (DE); Bioriginal Food & Science Corp., Saskatoon (CA)

( * ) Notice: Subject to any disclaimer, the term of this patent is extended or adjusted under 35 U.S.C. 154(b) by 444 days.

(21) Appl. No.: 13/060,458

(22) PCT Filed: Aug. 25, 2009

(86) PCT No.: PCT/EP2009/060923

§ 371 (c)(1), (2), (4) Date: Feb. 24, 2011

(87) PCT Pub. No.: WO2010/023202

PCT Pub. Date: Mar. 4, 2010

(65) Prior Publication Data

US 2011/0162105 A1 Jun. 30, 2011

(30) Foreign Application Priority Data

Aug. 26, 2008 (EP) .................................... 08162988

(51) Int. Cl.

*C12N 15/82* (2006.01)
*C12N 5/14* (2006.01)
*C12N 9/02* (2006.01)
*C12N 9/00* (2006.01)

(52) U.S. Cl.

CPC .............. *C12N 15/8247* (2013.01); *C12N 5/14* (2013.01); *C12N 9/00* (2013.01); *C12N 9/0004* (2013.01)

(58) Field of Classification Search

None

See application file for complete search history.

(56) References Cited

U.S. PATENT DOCUMENTS

| | | | | |
|---|---|---|---|---|
| 6,872,872 | B1 * | 3/2005 | Lightner et al. | 800/298 |
| 6,929,933 | B1 | 8/2005 | Revuelta Doval et al. | |
| 7,537,920 | B2 | 5/2009 | Renz et al. | |
| 2005/0132441 | A1 * | 6/2005 | Damude et al. | 800/281 |
| 2006/0094092 | A1 | 5/2006 | Damude et al. | |
| 2009/0209774 | A1 | 8/2009 | Renz et al. | |
| 2009/0222951 | A1 | 9/2009 | Cirpus et al. | |
| 2010/0199365 | A1 | 8/2010 | Senger et al. | |

FOREIGN PATENT DOCUMENTS

| | | | |
|---|---|---|---|
| WO | WO-94/11515 | A1 | 5/1994 |
| WO | WO-2004/076617 | A2 | 9/2004 |
| WO | WO-2005/083093 | A2 | 9/2005 |
| WO | WO-2009/016202 | A2 | 2/2009 |

OTHER PUBLICATIONS

Birren et al May 2008 NCBI accession XM_001933922.*
Biology online defintion of microbe: http://www.biology-online.org/dictionary/Microbe. There is no author or date availbable from the reference. The date is not important, because the reference is not being used as prior art.*
Hane et al 2007 The Plant Cell 19: p. 3347-3368.*
Barmore et al 1984 Phytopathology 74:6 p. 735-737.*
Ellerstrom et al 1996 Plant Molecular Biology 32: p. 1019-1027.*
Scheuerbrandt and Bloch Jul. 1962 vol. 237:7 p. 2064-2068.*
Damude and Kinney 2007 Lipids 42: p. 179-185.*
Lamb et al 2008 PNAS 105:15 p. 5792-5796.*
Birren et al 2008 Genbank accession XP_001933957).*
pSPORT1 map found online. http://xenbase.org/reagents/vectorAction.do?method=displayVectorSummary&vectorId=1221265 No date was available and the date is not necessary for the rejection.*
Birren et al 2008 (Genbank accession No. XM_001933922.1).*
"Pyrenophora Tritici-Repentis Pt-1C-BFP Delta(12) Fatty Acid Desaturase, mRNA", NCBI Database, Genbank Accession No. XM_001933922, May 30, 2008.
"SubName: Full = Putative Uncharacterized Protein", UniProt Database, Genbank Accession No. Q0V3E3, Sep. 5, 2006.

* cited by examiner

*Primary Examiner* — Eileen B O Hara
*Assistant Examiner* — Matthew Keogh
(74) *Attorney, Agent, or Firm* — Drinker Biddle & Reath LLP

(57) ABSTRACT

The present invention relates to nucleic acids derived from *Drechslera tritici-repentis, Cylindorcarpon herteronema, Diploida natalensis, Stagonospora nodorum, Microdochium nivalae* and *Periplaneta americana*. The invention also relates to the individual coding sequences and to proteins encoded by these sequences in combination with other sequences as well as to a process for converting oleic acid to linoleic acid to linoleic acid and the production of arachidonic acid, eicosapentaenoic acid and/or docosahexaenoic acid in a plant.

27 Claims, 10 Drawing Sheets

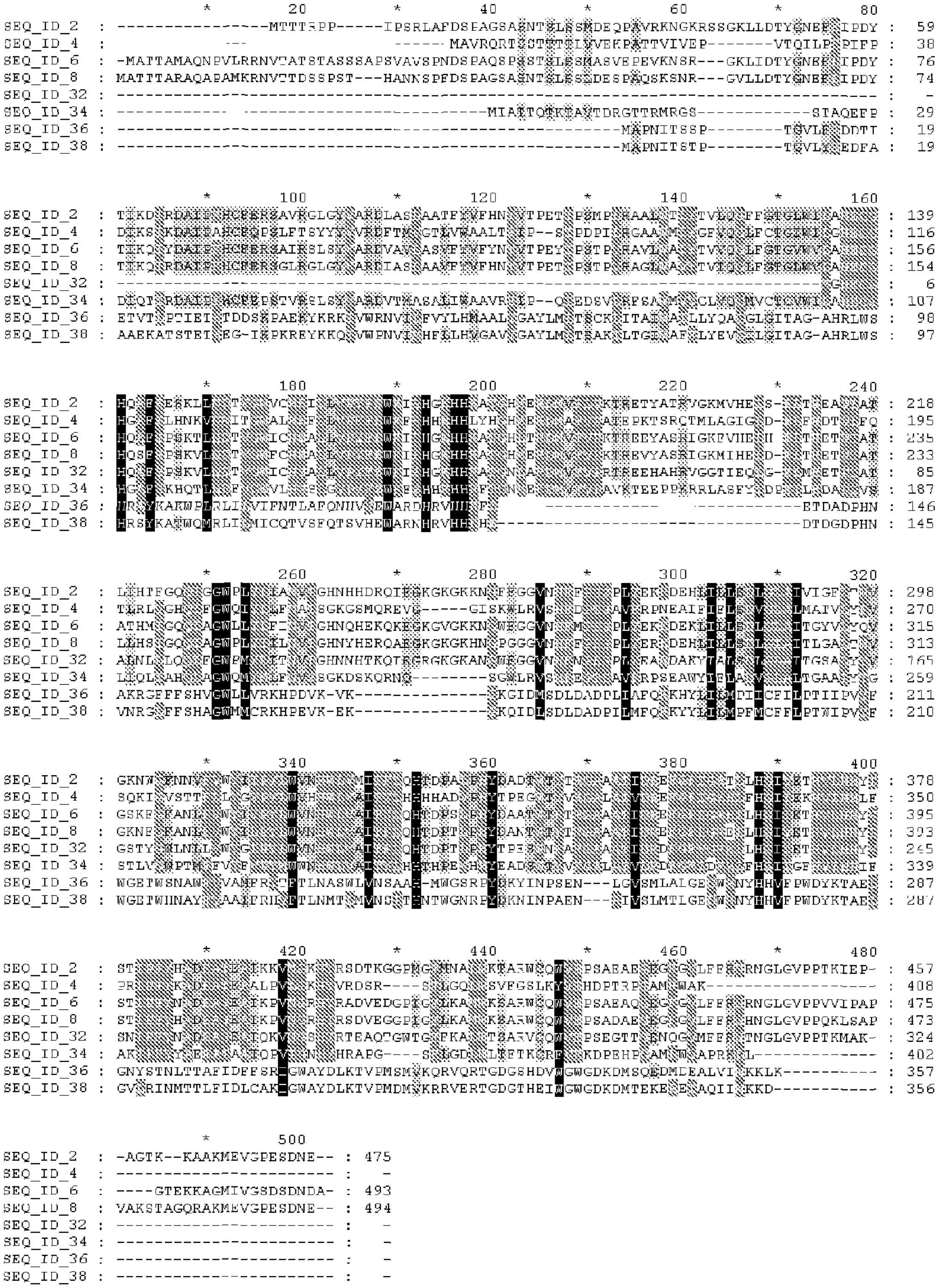

Fig. 2

```
                       *         20         *         40         *         60         *         80
SEQ_ID_2  : ----------------MTTTRPP-----IPSRLAFDSEAGSANTELSSMDEQPAVRKNGKRSSGKLLDTYGNEETPDY :  59
SEQ_ID_4  : ---------------------------MAVRQRTSTSTELVVEKPATTVIVEP-------VTQILPEPIFP :  38
SEQ_ID_6  : -MATTAMAQNPVLRRNVTATSTASSSAPSVAVSPNDSPAQSPSSTSLESMASVEPEVKNSR---GKLIDTYGNEETPDY :  76
SEQ_ID_8  : MATTTARAQAPAMKRNVTDSSPST---HANKSPFDSEAGSANTELESDESPQSKSNR---GVLLDTYGNEETPDY :  74
SEQ_ID_32 : -------------------------------------------------------------------------- :   -
SEQ_ID_34 : ----------------------------MIASTQEKEAYTDRGTTRMRGS-----------SIAQEFP :  29
SEQ_ID_36 : ------------------------------------------------MAPNITSSP--------TGVLEDDTT :  19
SEQ_ID_38 : ------------------------------------------------MAPNITSTP--------TGVLEEDFA :  19

                       *        100         *        120         *        140         *        160
SEQ_ID_2  : TIKDSRDAIEHCFERSAVRGLGYSARDLASSAATFYVFHNSYTPETSPSMPSKAALSTSTVLGSFFSTGLMISA    : 139
SEQ_ID_4  : DIKSSKDAIEAHCEQDSLFTSYYSVREFTMSGTIVRAALTSIP--SSPDPISRCAANMSGFVQSLFCTGLMISG    : 116
SEQ_ID_6  : TIKDSYDAIEHCEERSAIKSLSYSAREVAVSASWFYVFYNSYTPEYSPSTPSRAVLSASTVVQSLFSTGVMVFA    : 156
SEQ_ID_8  : TIKDSRDAIEHCFERSGLRGLGYSARDIASSAAKFYVFHNSYTPETSPSTPSRAGLSASTVELSLFSTGLMVFA    : 154
SEQ_ID_32 : -----------------------------------------------------------------------G    :   6
SEQ_ID_34 : DIQTSRDAIEHCFERDSTVRELSYSARDVTRASALIRAAVRSIP--QSEDSVSRFSAMSGLMYSMVCTGVMISA    : 107
SEQ_ID_36 : ETVTSPTIEISTDDSSPAEKYKRKSVWRNVISFVYLHMAALSGAYLMSTSCKSITASLASLLYDAGLSITAG-AHRLWS :  98
SEQ_ID_38 : AAEKATSTEISEG-ISPKREYKKQSVWPNVISHFELHMGAVSGAYLMSTSAKSLTGESAFSLYEVELSITAG-AHRLWS :  97

                       *        180         *        200         *        220         *        240
SEQ_ID_2  : HQSESESKLSSVCSISLSSISTSHGHHAHSESKRETYATRVGKMVHESS--ISTSEASSAS : 218
SEQ_ID_4  : HGSESSLHNKSITSALSISLSSISTGHHSHLYHSHSASATEPKTSRCTMLAGIGSD--ISFSDTSSFQ : 195
SEQ_ID_6  : HQSESPSKTLSTSICSARSLSSISTSHGHHRASHSTSAVSKTREEYASRIGKPVIIESII-STSDTSSAR : 235
SEQ_ID_8  : HQSESPSKVSSTSFCSASLSSISTSHGHHRASASVSKREVYASRIGKMIHESD--ISTSETSSAR : 233
SEQ_ID_32 : HQSESPSKVSSTSICSASSLSSISTSHGHHRASASVSRTEEHAHRVGGTIEQSG--SWSETSSAR :  85
SEQ_ID_34 : HGSESKHQTLSRFSVLSESSVSSMSHSHHSPSNSESAVKTEEPPKRRLASFYSDSESLLDASVS : 187
SEQ_ID_36 : NRSYKAKWPDRLISVTFNTLAFQNIIVSDDARDHRVHSF-------------ETDADPHN : 146
SEQ_ID_38 : HRSYKASWQMRLISMICQTVSFQTSVHEDARKSHRVHSH--------------DTDGDPHN : 145

                       *        260         *        280         *        300         *        320
SEQ_ID_2  : LIHTFGQSSGSMPLSTASSGHNHHDRQIESKGKGKKNSFSGGSMNSFSSPLSEKSDEHISLSLSTVIGFSSV : 298
SEQ_ID_4  : TLRLNGHSSFGSMQSSITSAGKGSMQREVE-----GISKSLRVSSSSSASSVSRPNEAIFSESVSSDMAIVSSV : 270
SEQ_ID_6  : ATHMSGQSSAGSMLLSSPISSAGHNQHEKQESKGKVGKKMSMEGGSMNSMSSPLSEKSDEKISLSLSTGYVSSQV : 315
SEQ_ID_8  : LLHSSGQSSAGMPLSILSAGHNYHEROAESGKGKGKHNSPGGSMNSFSSPLSERSDEHISLSLSTLGASCSV : 313
SEQ_ID_32 : ALNLSLQSSFGMPVSITSAGHNNHTKQTEASDMAQSFSRASDAKYSASSSSSKSDAKSFSTNGFSSSV : 165
SEQ_ID_34 : LIQLSAHSSAGMQMSLFFSGKDSKQRNQ--------SGMLRVSSESASRPSEARYSELSASSSVTGAASSG : 259
SEQ_ID_36 : AKRGFFFSHVSGMLSLVRKHPDVK-VK--------------KGIDSLSDLDADDLSLAFQSKHYLSSVDISCFILDTIIDVSSF : 211
SEQ_ID_38 : VNRGSSFFSHAGMMSCRKHPEVK-EK--------------KQIDSLSDLDADPISLMFQSKYYLSMPFMCFFLPTWIPVSSF : 210

                       *        340         *        360         *        380         *        400
SEQ_ID_2  : GKNWSFNNYSWSISVKSMSSQETDAASEDAATSSYSTSASESTSLRNSETSSY : 378
SEQ_ID_4  : SQKISVSTTSLSGSSWSIHSASSHHHADSESTPEGSTVSSLSESFSELSEKSSLF : 350
SEQ_ID_6  : GSKFSFANESWSISVSMSASSSQHEDSSRYSDANTSYTSASASSSLSRTSESY : 395
SEQ_ID_8  : GKNESFANESWSISLSMSAISSQTDETSFSYDANTSYTSSASEESSLLSRTSESY : 393
SEQ_ID_32 : GSTYSMLNLLSWSSISLSAISSHSQHEDETSFSYTPRSASASASRLSELSETSSY : 245
SEQ_ID_34 : STLVSSPTMSFVSESSISLSWSLSALSHSHETHREESHDAMSSYASFSRTNGFSIF : 339
SEQ_ID_36 : WGEFWSNAWSVSAMFPRSTPTLNASWLSWNSAAESMWGSREPSBKYINPSEN---LGVSMLALGESWSNYHVFPWDYKTAES : 287
SEQ_ID_38 : WGEFWIHNAYSSAALFPRIESTLNMTSMVNSSTENTWGNREPSDKNINPAEN---SIVSLMTLGESWSNYHSVFPWDYKTAES : 287

                       *        420         *        440         *        460         *        480
SEQ_ID_2  : STSSSHSDSSTKKVSSKSRSDTKGGEMGSMNASKEARWSQMSPSAEABSEGSGSLFFSRNGLGVPPTKIEP- : 457
SEQ_ID_4  : PRSSKSDSSEALPVSSKESVRDSR----SSSLGQSGSVFGSLKYSHDPTRPSAMSWAK-------------- : 408
SEQ_ID_6  : STSSVSDSESTKPVSRSRADVEDGPISGSLKASKEARWSQMSPSABAQSEGSGSLFFSRNGLGVPPVVIPAP : 475
SEQ_ID_8  : STSSSHSDSSTKPVSSKSRSDVEGGPIGSLKASKEARWSQMSPSADAESEGSGSLFFSHNGLGVPPQKLSAP : 473
SEQ_ID_32 : SNSSSNSDSESTOKVSSSISRTEAQTGWTGSPKASSTSARVQMSPSEGTTSENQGSMFESTNGLGVPPTKMAK- : 324
SEQ_ID_34 : AKSSSYSESSASTQPVSSNSSHRAPG----SSIGDSLFETKQRDSSKDPBHFSAMSWSAPRKSL------- : 402
SEQ_ID_36 : GNYSTNLTTAFIDFFSRSGWAYDLKTVPMSMSKQRVQRTGDGSHDVSGWDKDMSQEDMEALVISKKKLK--- : 357
SEQ_ID_38 : GVSSRINMTTLFIDLCAKSGWAYDLKTVPMDMSKRRVERTGDGTHEISGWGDKDMTEKESESAQIISKKD--- : 356

                       *        500
SEQ_ID_2  : -AGTK--KAAKMEVSPESDNE-- : 475
SEQ_ID_4  : ----------------------- :   -
SEQ_ID_6  : ----GTEKKAGMIVSDSDNDA-- : 493
SEQ_ID_8  : VAKSTAGQRAKMEVGPESDNE-- : 494
SEQ_ID_32 : ----------------------- :   -
SEQ_ID_34 : ----------------------- :   -
SEQ_ID_36 : ----------------------- :   -
SEQ_ID_38 : ----------------------- :   -
```

A:

B:

| No Feeding: | 16:0 | 16:1 | 18:0 | 18:1c9 | 18:1c11 | 18:2 |
|---|---|---|---|---|---|---|
| | 18.63 | 40.95 | 7.39 | 19.36 | 1.65 | 7.35 |

| Feeding 18:2: | 16:0 | 16:1 | 18:0 | 18:1c9 | 18:1c11 | 18:2 | 18:3 |
|---|---|---|---|---|---|---|---|
| | 17.78 | 20.66 | 8.32 | 16.87 | 0.76 | 28.44 | 1.91 |

C:

| No Feeding: | 16:0 | 16:1 | 16:2 | 18:0 | 18:1c9 | 18:1c11 | 18:2 |
|---|---|---|---|---|---|---|---|
| | 16.72 | 16.16 | 15.74 | 10.03 | 7.81 | 0.70 | 25.10 |

| No Feeding: | 16:0 | 16:1 | 16:2 | 18:0 | 18:1c9 | 18:1c11 | 18:2 |
|---|---|---|---|---|---|---|---|
| | 16.41 | 22.42 | 10.15 | 9.62 | 15.80 | 0.90 | 17.49 |

A:

| Feeding 18:2: | 16:0 | 16:1 | 18:0 | 18:1c9 | 18:1c11 | 18:2 | 18:3 |
|---|---|---|---|---|---|---|---|
| | 17.55 | 21.42 | 7.70 | 21.48 | 0.87 | 22.42 | 3.92 |

B:

NUCLEIC ACIDS ENCODING DESATURASES AND MODIFIED PLANT OIL

RELATED APPLICATIONS

This application is a national stage application (under 35 U.S.C. §371) of PCT/EP2009/060923, filed Aug. 25, 2009, which claims benefit of European application 08162988.3, filed Aug. 26, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing__17418__00064. The size of the text file is 234 KB, and the text file was created on Feb. 23, 2011.

The present invention relates to nucleic acids derived from *Drechslera tritici-repentis, Cylindorcarpon herteronema, Diploida natalensis, Microdochium nivalae, Periplaneta americana* and *Stagonospora nodorum*. The invention also relates to the individual coding sequences and to proteins encoded by these sequences in combination with other sequences as well as to a process for converting oleic acid to linoleic acid to linoleic acid and the production of arachidonic acid, eicosapentaenoic acid and/or docosahexaenoic acid.

Fatty acids and triacylglycerides have a multiplicity of applications in the food industry, in animal nutrition, in cosmetics and in the pharmacological sector. Depending on whether they are free saturated or unsaturated fatty acids or else triacylglycerides with an elevated content of saturated or unsaturated fatty acids, they are suitable for very different applications. Polyunsaturated fatty acids such as linoleic acid and linolenic acid are essential for mammals, since they cannot be produced by the latter. Polyunsaturated ω3-fatty acids and ω6-fatty acids are therefore an important constituent in animal and human nutrition.

Hereinbelow, polyunsaturated fatty acids are referred to as PUFA, PUFAs, LCPUFA or LCPUFAs (poly unsaturated fatty acids, PUFA, long chain poly unsaturated fatty acids, LCPUFA).

The various fatty acids and triglycerides are mainly obtained from microorganisms such as *Mortierella* and *Schizochytrium* or from oil-producing plants such as soybean, oilseed rape, algae such as *Crypthecodinium* or *Phaeodactylum* and others, where they are obtained, as a rule, in the form of their triacylglycerides (=triglycerides=triglycerols). However, they can also be obtained from animals, such as, for example, fish. The free fatty acids are advantageously prepared by hydrolysis. Very long-chain polyunsaturated fatty acids such as docosahexaenoic acid (=DHA, $C22:6^{\Delta4,7,10,13,16,19}$), eicosapentaenoic acid (=EPA, $C20:5^{\Delta5,8,11,14,17}$), arachidonic acid (=ARA, $C20:4^{\Delta5,8,11,14}$), dihomo-γ-linolenic acid ($C20:3^{\Delta8,11,14}$) or docosapentaenoic acid (DPA, $C22:5^{\Delta7,10,13,16,19}$) are not synthesized in oil crops such as oilseed rape, soybean, sunflower or safflower. Conventional natural sources of these fatty acids are fish such as herring, salmon, sardine, redfish, eel, carp, trout, halibut, mackerel, zander or tuna, or algae. Depending on the intended use, oils with saturated or unsaturated fatty acids are preferred. In human nutrition, for example, lipids with unsaturated fatty acids, specifically polyunsaturated fatty acids, are preferred. The polyunsaturated ω3-fatty acids are said to have a positive effect on the cholesterol level in the blood and thus on the possibility of preventing heart disease. The risk of heart disease, stroke or hypertension can be reduced markedly by adding these ω3-fatty acids to the food. Also, ω3-fatty acids have a positive effect on inflammatory, specifically on chronically inflammatory, processes in association with immunological diseases such as rheumatoid arthritis. They are therefore added to foodstuffs, specifically to dietetic foodstuffs, or are employed in medicaments. ω6-Fatty acids such as arachidonic acid tend to have a negative effect on these disorders in connection with these rheumatic diseases on account of our usual dietary intake.

ω3- and ω6-fatty acids are precursors of tissue hormones, known as eicosanoids, such as the prostaglandins, which are derived from dihomo-γ-linolenic acid, arachidonic acid and eicosapentaenoic acid, and of the thromboxanes and leukotrienes, which are derived from arachidonic acid and eicosapentaenoic acid. Eicosanoids (known as the $PG_2$ series) which are formed from ω6-fatty acids generally promote inflammatory reactions, while eicosanoids (known as the $PG_3$ series) from ω3-fatty acids have little or no proinflammatory effect.

Owing to the positive characteristics of the polyunsaturated fatty acids, there has been no lack of attempts in the past to make available genes which are involved in the synthesis of these fatty acids or triglycerides for the production of oils in various organisms with a modified content of unsaturated fatty acids. Thus, WO 91/13972 and its US equivalent describes a Δ9-desaturase. WO 93/11245 claims a Δ15-desaturase and WO 94/11516 a Δ12-desaturase. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ6-Desaturases are described in WO 93/06712, U.S. Pat. No. 5,614,393, U.S. Pat. No. 5,614,393, WO 96/21022, WO 00/21557 and WO 99/27111 and the application for the production of fatty acids in transgenic organisms is described in WO 98/46763, WO 98/46764 and WO 98/46765. In this context, the expression of various desaturases and the formation of polyunsaturated fatty acids is also described and claimed in WO 99/64616 or WO 98/46776. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Moreover, a mixture of ω3- and ω6-fatty acids was obtained, as a rule.

Especially suitable microorganisms for the production of PUFAs are microalgae such as *Phaeodactylum tricornutum, Porphiridium* species, *Thraustochytrium* species, *Schizochytrium* species or *Crypthecodinium* species, ciliates such as *Stylonychia* or *Colpidium*, fungae such as *Mortierella, Entomophthora* or *Mucor* and/or mosses such as *Physcomitrella, Ceratodon* and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult process. This is why recombinant methods as described above are preferred whenever possible.

A variety of synthetic pathways is being discussed for the synthesis of arachidonic acid, eicosapentaenoic acid (EPA) and docosahexaenoic acid (DHA) (FIG. 1). Thus, EPA or DHA are produced in marine bacteria such as *Vibrio* sp. or *Shewanella* sp. via the polyketide pathway (Yu, R. et al. Lipids 35:1061-1064, 2000; Takeyama, H. et al. Microbiology 143:2725-2731, 1997).

An alternative strategy is the alternating activity of desaturases and elongases (Zank, T. K. et al. Plant Journal 31:255-268, 2002; Sakuradani, E. et al. Gene 238:445-453, 1999). A modification of the above-described pathway by Δ6-desaturase, Δ6-elongase, Δ5-desaturase, Δ5-elongase and Δ4-desaturase is the Sprecher pathway (Sprecher 2000, Biochim. Biophys. Acta 1486:219-231) in mammals. Instead of the Δ4-desaturation, a further elongation step is effected here to give $C_{24}$, followed by a further Δ6-desaturation and finally β-oxidation to give the $C_{22}$ chain length. Thus what is known as Sprecher pathway (see FIG. 1) is, however, not suitable for the production in plants and microorganisms since the regulatory mechanisms are not known.

Depending on their desaturation pattern, the polyunsaturated fatty acids can be divided into two large classes, viz. ω6- or ω3-fatty acids, which differ with regard to their metabolic and functional activities (FIG. 1).

The starting material for the ω6-metabolic pathway is the fatty acid linoleic acid ($18:2^{\Delta 9,12}$) while the ω3-pathway proceeds via linolenic acid ($18:3^{\Delta 9,12,15}$). Linolenic acid is formed by the activity of an ω3-desaturase (Tocher et al. 1998, Prog. Lipid Res. 37, 73-117; Domergue et al. 2002, Eur. J. Biochem. 269, 4105-4113).

Mammals, and thus also humans, have no corresponding desaturase activity (Δ12- and ω3-desaturase) and must take up these fatty acids (essential fatty acids) via the food. Starting with these precursors, the physiologically important polyunsaturated fatty acids arachidonic acid (=ARA, $20:4^{\Delta 5,8,11,14}$), an ω6-fatty acid and the two ω3-fatty acids eicosapentaenoic acid (=EPA, $20:5^{\Delta 5,8,11,14}$) and docosahexaenoic acid (DHA, $22:6^{\Delta 4,7,10,13,17,19}$) are synthesized via the sequence of desaturase and elongase reactions. The application of ω3-fatty acids shows the therapeutic activity described above in the treatment of cardiovascular diseases (Shimikawa 2001, World Rev. Nutr. Diet. 88, 100-108), Entzündungen (Calder 2002, Proc. Nutr. Soc. 61, 345-358) and Arthritis (Cleland and James 2000, J. Rheumatol. 27, 2305-2307).

The elongation of fatty acids, by elongases, by 2 or 4 C atoms is of crucial importance for the production of $C_{20}$- and $C_{22}$-PUFAs, respectively. This process proceeds via 4 steps. The first step is the condensation of malonyl-CoA with the fatty-acid-acyl-CoA by ketoacyl-CoA synthase (KCS, hereinbelow referred to as elongase). This is followed by a reduction step (ketoacyl-CoA reductase, KCR), a dehydratation step (dehydratase) and a final reduction step (enoyl-CoA reductase). It has been postulated that the elongase activity affects the specificity and rate of the entire process (Millar and Kunst, 1997 Plant Journal 12:121-131).

There have been a large number of attempts in the past to obtain elongase genes. Millar and Kunst, 1997 (Plant Journal 12:121-131) and Millar et al. 1999, (Plant Cell 11:825-838) describe the characterization of plant elongases for the synthesis of monounsaturated long-chain fatty acids (C22:1) and for the synthesis of very long-chain fatty acids for the formation of waxes in plants ($C_{28}$-$C_{32}$). Descriptions regarding the synthesis of arachidonic acid and EPA are found, for example, in WO0159128, WO0012720, WO02077213 and WO0208401. The synthesis of polyunsaturated $C_{24}$-fatty acids is described, for example, in Tvrdik et al. 2000, JCB 149:707-717 or WO0244320.

Higher plants comprise polyunsaturated fatty acids such as linoleic acid ($18:2^{\Delta 9,12}$) and linolenic acid ($18:3^{\Delta 9,12,15}$). ARA, EPA and DHA are found not at all in the seed oil of higher plants or only in miniscule amounts (E. Ucciani: Nouveau Dictionnaire des Huiles Végétales [New Dictionary of Vegetable Oils]. Technique & Documentation—Lavoisier, 1995. ISBN: 2-7430-0009-0). However, the production of LCPUFAs in higher plants, preferably in oil crops such as oilseed rape, linseed, sunflower and soybeans, would be advantageous since large amounts of high-quality LCPUFAs for the food industry, animal nutrition and pharmaceutical purposes might be obtained economically. To this end, it is advantageous to introduce, into oil crops, genes which encode enzymes of the LCPUFA biosynthesis via recombinant methods and to express them therein. These genes can advantageously be isolated from microorganisms and lower plants which produce LCPUFAs and incorporate them in the membranes or triacylglycerides. Thus, it has already been possible to isolate Δ6-desaturase genes from the moss *Physcomitrella patens* and Δ6-elongase genes from *P. patens* and from the nematode *C. elegans.*

The first transgenic plants which comprise and express genes encoding LCPUFA biosynthesis enzymes and which, as a consequence, produce LCPUFAs were described for the first time, for example, in WO2003/064638, WO2003/093482 (process for the production of polyunsaturated fatty acids in plants). However, these plants produce LCPUFAs in amounts which require further optimization for processing the oils which are present in the plants. Increases of PUFA levels were demonstrated in WO2004/071467 for soybean and in WO2005/083093 for *Brassica juncea.*

Although biotechnology offers an attractive route for the production of PUFA, current techniques fail to provide an efficient means for the large scale production. Accordingly, there exists a need for an improved and efficient method of production PUFA, such as ARA, EPA and DHA.

The technical problem underlying the present invention could be seen as the provision of means and methods for complying with the aforementioned needs. The technical problem is solved by the embodiments characterized in the claims and herein below.

Thus, the present invention, in principle, contemplates nucleic acid molecules encoding novel desaturases from the fungi *Drechslera tritici-repentis, Cylindrocarpon heteronema, Diplodia natalensis, Microdochium nivalae, Periplaneta americana* and *Stagonospora nodorum*. In particular the *Drechslera tritici-repentis* delta 12-desaturase, *Diplodia natalensis* delta 12-desaturase, *Microdochium nivalae delta* 12-desaturase, *Periplaneta americana* delta 12-desaturase and *Stagonospora nodorum* delta 12-desaturase, further the *Cylindrocarpon heteronema* delta 15-desaturase and *Microdochium nivalae* d12-desaturase have been identified. Yet further the use of these nucleic acids in the process of manufacturing high levels of ARA, EPA and DHA is provided.

Specifically, the present invention pertains to polynucleotides comprising a nucleic acid selected from the group consisting of:

a) a nucleic acid having a nucleic acid sequence as shown in any one of SEQ ID Nos: 1, 3, 5, 7, 31, 33, 35 or 37;

b) a nucleic acid encoding a polypeptide having an amino acid sequence as shown in any one of SEQ ID Nos: 2, 4, 6, 8, 32, 34, 36, or 38;

c) a nucleic acid which has a nucleic acid sequence being at least 60% identical to the nucleic acid sequence as shown in any one of SEQ ID Nos: 1, 3, 5, 7, 31, 33, or 37, wherein said nucleic acid encodes a polypeptide having desaturase activity;

d) a nucleic acid encoding a polypeptide having an amino acid sequence being at least 74.1% identical to the amino acid sequence shown in any one of SEQ ID Nos: 2, 4, 6, 8, 32, 34, 36, or 38, wherein said nucleic acid encodes a polypeptide having desaturase activity;

e) a nucleic acid which hybridizes under stringent hybridization conditions to the nucleic acid of any one of a) to d), wherein said nucleic acid encodes a polypeptide having desaturase activity;

f) a nucleic acid encoding a fragment of a polypeptide encoded by the nucleic acid sequence of any one of a) to e) having desaturase activity; and g) a nucleic acid comprising at least 15 contigous nucleotides of the nucleic acid of any one of a) to f).

The term "polynucleotide" as used herein relates to nucleic acid molecules being either DNA or RNA as well as chemically modified derivatives thereof, e.g., biotinylated or methylated nucleic acid molecules. DNA as used herein includes cDNA and genomic DNA. The polynucleotides may be in linear or circular form and may be single or double stranded.

In accordance with the present invention it has been found that the polynucleotides of the present invention referred to above encode polypeptides having desaturase activity, i.e. being desaturases.

The term "desaturase" refers to an enzymatic activity which allows for introduction of double bonds in carbohydrates, in general. Particularly preferred in accordance with the present invention are desaturases which introduce a double bond at position 12 or 15 into a fatty acid. More preferably, the desaturase activity referred to in accordance with the present invention is, therefore, a delta 12 or delta 15 desaturase activity. Most preferably, the delta 12 or delta 15 desaturase allows for conversion of substrates into products as shown in the accompanying Figures, below. Specifically, polynucleotides comprising nucleic acids having a nucleic acid sequence as shown in any one of SEQ ID NOs: 2, 6, 8, 32, or 34, or variants thereof as specified above encode, preferably, desaturases which exhibit delta 12 desaturase activity while polynucleotides comprising nucleic acids having a nucleic acid sequence as shown in any one of SEQ ID NOs: 4 or variants thereof as specified above, preferably, encode desaturases which exhibit delta 15 desaturase activity. Polynucleotides encoding the polypeptide according to SEQ ID NOs: 36 or 38 or the aforementioned variants thereof encode desaturase enzymes. A polypeptide encoded by a polynucleotide can be tested for desaturase activity, preferably, as described in the accompanying Examples below.

The polynucleotides of the present invention encompass also variant polynucleotides of those referred to above by specific nucleic acid or amino acid sequences. Said variant polynucleotides include homolgs, preferably, alleic variants, paralogs or orthologs. Such polynucleotide variants, preferably, comprise a nucleic acid sequence characterized in that the sequence can be derived from the aforementioned specific nucleic acid sequences shown in SEQ ID NO: 1, 3, 5, 7, 31, 33, 35 or 37 by at least one nucleotide substitution, addition and/or deletion whereby the variant nucleic acid sequence shall still encode a polypeptide having desaturase activity as specified above. Variants also encompass nucleic acid molecules comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6× sodium chloride/sodium citrate (=SSC) at approximately 65° C., preferably, followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, nucleic acid molecule variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequence of the nucleic acid molecule or the amino acid sequence of the polypeptide of the present invention with other desaturase sequences, see also FIG. 2, below. Oligonucleotides suitable as PCR primers as well as suitable PCR conditions are described in the accompanying Examples. As a template, DNA or cDNA from bacteria, fungi, plants or animals may be used. Further, variants include nucleic acid molecule comprising nucleic acid sequences which are at least 74.1%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical to the nucleic acid sequences shown in SEQ ID NO: 1, 3, 5, 7, 31, 33, 35 or 37 retaining desaturase activity. Moreover, also encompassed are nucleic acid molecule which comprise nucleic acid sequences encoding amino acid sequences which are at least 74.1%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical to the amino acid sequences shown in SEQ ID NO: 2, 4, 6, 8 or 32, 34, 36 or 38, wherein the polypeptide comprising the amino acid sequence retains desaturase activity. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution, 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981))), which are part of the GCG software packet [Genetics Computer Group, 575 Science Drive, Madison, Wis., USA 53711 (1991)], are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide encoding a biologically active fragment of the polypeptide encoding by the aforementioned polynucleotides of the invention, i.e. a fragment exhibiting desaturase activity as specified above, is also encompassed by the present invention. Accordingly, the polypeptide may comprise or consist of the domains of the polypeptide of the present invention conferring the said biological activity. A fragment as meant herein, preferably, comprises at least 15, at least 20, at least 50, at least 100, at least 250 or at least 500 consecutive nucleotides of any one of the aforementioned nucleic acid sequences or encodes an amino acid sequence comprising at least 5, at least 10, at least 20, at least 30, at least 50, at least 80, at least 100 or at least 150 consecutive amino acids of any one of the aforementioned amino acid sequences.

The variant polynucleotides referred to above, preferably, encode polypeptides retaining at least 10%, at least 20%, at least 30%, at least 40%, at least 50%, at least 60%, at least 70%, at least 80% or at least 90% of the desaturase activity exhibited by the polypeptide shown in SEQ ID NO: 2, 4, 6, 8 or 32, 34, 36 or 38. The activity may be tested as described in the accompanying Examples.

The nucleic acid molecules of the present invention either essentially consist of the aforementioned nucleic acid sequences or comprise the aforementioned nucleic acid sequences. Thus, they may contain further nucleic acid sequences as well. Preferably, the nucleic acid molecule of the present invention may comprise further untranslated sequence at the 3' and at the 5' terminus of the coding gene region: at least 500, preferably 200, more preferably 100 nucleotides of the sequence upstream of the 5' terminus of the coding region and at least 100, preferably 50, more preferably 20 nucleotides of the sequence downstream of the 3' terminus of the coding gene region. Furthermore, the nucleic acid molecule of the present invention may encode fusion proteins wherein one partner of the fusion protein is a polypeptide being encoded by a nucleic acid sequence recited above and the other partner of the fusion protein is a heterologous polypeptide. Such fusion proteins may comprise as additional part other enzymes of the fatty acid or lipid biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

Variant polynucleotides as referred to in accordance with the present invention may be obtained by various natural as well as artificial sources. For example, nucleic acid molecules may be obtained by in vitro and in vivo mutagenesis approaches using the above mentioned mentioned specific nucleic acid molecules as a basis. Moreover, nucleic acid molecules being homologs or orthologs may be obtained from various animal, plant or fungus species. Preferably, they are obtained from plants such as algae, for example *Isochrysis, Mantoniella, Ostreococcus or Crypthecodinium*, algae/diatoms such as *Phaeodactylum* or *Thraustochytrium*, mosses such as *Physcomitrella* or *Ceratodon*, or higher plants such as the Primulaceae such as *Aleuritia, Calendula stellata, Osteospermum spinescens* or *Osteospermum hyoseroides*, microorganisms such as fungi, such as *Aspergillus, Thraustochytrium, Phytophthora, Entomophthora, Mucor, Drechslera, Diplodia, Microdochium, Periplaneta, Stagonospora, Cylindrocarpon, Microdochium* or *Mortierella*, bacteria such as *Shewanella*, yeasts or animals. Preferred animals are nematodes such as *Caenorhabditis*, insects or vertebrates. Among the vertebrates, the nucleic acid molecules may, preferably, be derived from *Euteleostomi, Actinopterygii; Neopterygii; Teleostei; Euteleostei, Protacanthopterygii, Salmoniformes; Salmonidae* or *Oncorhynchus*, more preferably, from the order of the Salmoniformes, most preferably, the family of the Salmonidae, such as the genus *Salmo*, for example from the genera and species *Oncorhynchus mykiss, Trutta trutta* or *Salmo trutta* fario. Moreover, the nucleic acid molecules may be obtained from the diatoms such as the genera *Thallasiosira* or *Crypthecodinium.*

The polynucleotides of the present invention shall be provided, preferably, either as an isolated nucleic acid molecule (i.e. isolated from its natural context such as a gene locus) or in genetically modified form. An isolated nucleic acid molecule can, for example, comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. The nucleic acid molecule, preferably, is double or single stranded DNA including cDNA or RNA. The term encompasses single as well as double stranded nucleic acid molecules. Moreover, comprised are also chemically modified nucleic acid molecules including naturally occurring modified nucleic acid molecules such as glycosylated or methylated nucleic acid molecules or artificial modified ones such as biotinylated nucleic acid molecules.

Specifically, polynucleotides encoding polypeptides with Δ12-desaturase are variants of the polynucleotide encoding such a desaturase shown in SEQ ID NO: 1 wherein the variants encode polypeptides with at least 75.1% identity at the amino acid level with SEQ ID NO: 2.

Moreover, polynucleotides encoding polypeptides with Δ15-desaturase are variants of the polynucleotide encoding such a desaturase shown in SEQ ID NO: 3 wherein the variants encode polypeptides with at least 74.1% identity at the amino acid level with SEQ ID NO: 4.

Moreover, polynucleotides encoding polypeptides with Δ12-desaturase are variants of the polynucleotide encoding such a desaturase shown in SEQ ID NO: 5 wherein the variants encode polypeptides with at least 74.1% identity at the amino acid level with SEQ ID NO: 6.

Moreover, polynucleotides encoding polypeptides with Δ12-desaturase are variants of the polynucleotide encoding such a desaturase shown in SEQ ID NO: 7 wherein the variants encode polypeptides with at least 95% identity at the amino acid level with SEQ ID NO: 8.

Moreover, polynucleotides encoding polypeptides with Δ12-desaturase are variants of the polynucleotide encoding such a desaturase shown in SEQ ID NO: 31 wherein the variants encode polypeptides with at least 75% identity at the amino acid level with SEQ ID NO: 32.

Moreover, polynucleotides encoding polypeptides with Δ15-desaturase are variants of the polynucleotide encoding such a desaturase shown in SEQ ID NO: 33 wherein the variants encode polypeptides with at least 75% identity at the amino acid level with SEQ ID NO: 34.

Moreover, polynucleotides encoding polypeptides with desaturase are variants of the polynucleotide encoding such a desaturase shown in SEQ ID NO: 35 or 37 wherein the variants encode polypeptides with at least 75% identity at the amino acid level with SEQ ID NO: 36 or 38, respectively.

In the studies underlying the present invention, advantageously, polynucleotides were identified encoding novel desaturases from various fungi which can be applied for the manufacture of PUFAs and LCPUFAs as specified herein. An overview of the desaturases is given in the following table:

| Name | Organism | Activity | SEQ ID NO |
|---|---|---|---|
| D12Des(Dt) | *Drechslera tritici-repentis* | D12-Desaturase | 1 |
| D15Des(Cyh) | *Cylindrocarpon heteronema* | D15-Desaturase | 3 |
| D12Des(Dn) | *Diplodia natalensis* | D12-Desaturase | 5 |
| D12Des(Sn) | *Stagonospora nodorum* | D12-Desaturase | 7 |
| D12Des(Mn) | *Microdochium nivalae* | D12-Desaturase | 31 |
| D15Des(Mn) | *Microdochium nivalae* | D15-Desaturase | 33 |
| dXDes(Pa) | *Periplaneta americana* | Desaturase | 35 |
| dXDes(Pa)_2 | *Periplaneta americana* | Desaturase | 37 |

The present invention also pertains to polynucleotide variants which are derived from the polynucleotides of the present invention and are capable of interfering with the transcription or translation of the polynucleotides of the present invention. Such variant polynucleotides include anti-sense nucleic acids, ribozymes, siRNA molecules, morpholino nucleic acids (phosphorodiamidate morpholino oligos), triple-helix forming oligonucleotides, inhibitory oligonucleotides, or micro RNA molecules all of which shall specifically recognize the polynucleotide of the invention. These techniques are well known to the skilled artisan. Suitable variant polynucleotides of the aforementioned kind can be readily designed based on the structure of the polynucleotides of this invention.

The present invention also contemplates polynucleotides encoding acyltransferases. For further increase of special fatty acids like ARA, EPA and/or DHA or for the increase of overall production of novel fatty acids, such acyltransferases are beneficial. These enzymes are involved in shuffling of different fatty acids from their respective pools of production (phospholipids, Acyl-CoA) or by esterifying the novel fatty acids to different molecules (diacylglycerol, lysophosphatic acid, lysophosphatidylcholine, lysophosphatidylethanolamine, lysophosphatidylglycerol, lysophosphatidylinositol, lysophosphatidylserine, 1-acyl-phosphatidylcholine etc.). How to apply said enzymes is described in the accompanying Examples and in, e.g., WO2004/076617 or WO2004/087902.

Thus, the invention contemplates acyltransferase-encoding polynucleotides comprising a nucleic acid selected from the group consisting of:

a) a nucleic acid having a nucleic acid sequence as shown in any one of SEQ ID Nos: 102, 104, 106, 108, 110, 112, 135, 137 or 139;
b) a nucleic acid encoding a polypeptide having the amino acid sequence of a polypeptide encoded by a nucleic acid sequence as shown in any one of SEQ ID Nos: 102, 104, 106, 108, 110, 112, 135, 137 or 139;
c) a nucleic acid which has a nucleic acid sequence being at least 60% identical to the nucleic acid sequence specified in a), wherein said nucleic acid encodes a polypeptide having acyltransferase activity;
d) a nucleic acid encoding a polypeptide having an amino acid sequence being at least 60% identical to the amino acid sequence encoded by a nucleic acid sequence as shown in any one of SEQ ID Nos: 102, 104, 106, 108, 110, 112, 135, 137 or 139, wherein said nucleic acid encodes a polypeptide is having acyltransferase activity;
e) a nucleic acid which hybridizes under stringent hybridization conditions to the nucleic acid of any one of a) to d), wherein said nucleic acid encodes a polypeptide having desaturase activity;
f) a nucleic acid encoding a fragment of a polypeptide encoded by the nucleic acid sequence of any one of a) to e) having acyltransferase activity; and
g) a nucleic acid comprising at least 15 contigous nucleotides of the nucleic acid of any one of a) to f).

The definitions made above for the desaturase-encoding polynucleotides of the invention apply mutatis mutandis to the acyltransferase-encoding polynucleotides.

The term "acyltransferase activity" or "acyltransferase" as used herein encompasses all enymatic activities and enzymes which are capable of transferring or are involved in the transfer of PUFA and, in particular; LCPUFA from the acly-CoA pool or the membrane phospholipis to the triglycerides, from the acyl-CoA pool to membrane lipids and from membrane lipids to the acyl-CoA pool by a transesterification process. It will be understood that this acyltransferase activity will result in an increase of the LCPUFA esterified to triglycerides in, e.g., seed oils. In particular, it is envisaged that these acyltransferases are capable of producing triglycerides having esterified ARA, EPA or even DHA, or that these acyltransferases are capable of enhancing synthesis of desired PUFA by increasing the flux for specific intermediates of the desired PUFA between the acyl-CoA pool (the site of elongation) and membrane lipids (the predominant site of desaturation). Specifically, acyltransferase activity as used herein pertains to lysophospholipid acyltransferase (LPLAT) activity, preferably, to Lysophosphophatidylethanolamine acyltransferase (LPEAT) activity. Specifically, the aclytransferase encoding nucleic acid sequences as shown in SEQ ID NOs: 102, 104, and 106 as well as 135, 137 and 139 encode LPLAT activity. The aclytransferase encoding nucleic acid sequences as shown in SEQ ID NOs: 108, 110, and 112 encode LPEAT activity.

The acyltransferase polynucleotides of the present invention encompass also variant polynucleotides of those referred to above by specific nucleic acid or amino acid sequences. Said variant polynucleotides include homolgs, preferably, alleic variants, paralogs or orthologs. Such polynucleotide variants, preferably, comprise a nucleic acid sequence characterized in that the sequence can be derived from the aforementioned specific nucleic acid sequences shown in SEQ ID NO: 102, 104, 106, 108, 110, 112, 135, 137 or 139 by at least one nucleotide substitution, addition and/or deletion whereby the variant nucleic acid sequence shall still encode a polypeptide having desaturase activity as specified above. Variants also encompass nucleic acid molecules comprising a nucleic acid sequence which is capable of hybridizing to the aforementioned specific nucleic acid sequences, preferably, under stringent hybridization conditions. Alternatively, nucleic acid molecule variants are obtainable by PCR-based techniques as specified elsewhere herein. Further, variants include nucleic acid molecule comprising nucleic acid sequences which are at least 60%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical to the nucleic acid sequences shown in SEQ ID NO: 102, 104, 106, 108, 110, 112, 135, 137 or 139 retaining acyltransferase activity. Moreover, also encompassed are nucleic acid molecule which comprise nucleic acid sequences encoding amino acid sequences which are at least 60%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical to the amino acid sequences encoded by the nucleic acid sequences shown in SEQ ID NO: 102, 104, 106, 108, 110, 112, 135, 137 or 139, wherein the polypeptide comprising the amino acid sequence retains acyltransferase activity.

A polynucleotide encoding a biologically active fragment of the polypeptide encoding by the aforementioned polynucleotides of the invention, i.e. a fragment exhibiting acyltransferase activity as specified above, is also encompassed by the present invention.

The variant polynucleotides referred to above, preferably, encode polypeptides retaining at least 10%, at least 20%, at least 30%, at least 40%, at least 50%, at least 60%, at least 70%, at least 80% or at least 90% of the acyltransferase activity exhibited by the polypeptide encoded by a nucleic acid sequence as shown in SEQ ID NO: 102, 104, 106, 108, 110, 112, 135, 137 or 139. The activity may be tested as described in the accompanying Examples.

The present invention contemplates a vector comprising the polynucleotide of the present invention (i.e. the desaturase or acyltransferase encoding polynucleotides).

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homolgous or heterologous recombination as described in detail below. The vector encompassing the polynucleotide of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride coprecipitation, DEAE-dextran-mediated transfection, lipofection, natural competence, carbon-based clusters, chemically mediated transfer, electroporation or particle bombardment. Suitable methods for the transformation or transfection of host cells, including plant cells, can be found in Sambrook et al. (Molecular Cloning: A Laboratory Manual, $2^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cisregulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pB1101, pBinAR, pGPTV and pCAMBIA. An overview of binary vectors and their use can be found in Hellens et al, Trends in Plant Science (2000) 5, 446-451. Furthermore, by using appropriate cloning vectors, the polynucleotides can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus, Annu. Rev. Plant Physiol. Plant Molec. Biol. 42 (1991), 205-225.

More preferably, the vector of the present invention is an expression vector. In such an expression vector, the nucleic acid molecule is operatively linked to expression control sequences (also called "expression cassette") allowing expression in prokaryotic or eukaryotic cells or isolated fractions thereof. Expression of said polynucleotide comprises transcription of the nucleic acid molecule, preferably, into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. Preferably, the expression vector is also a gene transfer or targeting vector. Expression vectors derived from viruses such as retroviruses, vaccinia virus, adeno-associated virus, herpes viruses, or bovine papilloma virus, may be used for delivery of the nucleic acid molecule or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Suitable expression vectors are known in the art such as Okayama-Berg cDNA expression vector pcDV1 (Pharmacia), pCDM8, pRc/CMV, pcDNΔ1, pcDNΔ3 (Invitrogene) or pSPORT1 (GIBCO BRL). Further examples of typical fusion expression vectors are pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the recombinant target protein. Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the lacUV 5 promoter. The skilled worker is familiar with other vectors which are suitable in prokaryotic organisms; these vectors are, for example, in *E. coli*, pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667. Examples of vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEMBLYe23. As an alternative, the polynucleotides of the present invention can be also expressed in insect cells using baculovirus expression vectors. Baculovirus vectors which are available for the expression of proteins in cultured insect cells (for example Sf9 cells) comprise the pAc series (Smith et al. (1983) Mol. Cell. Biol. 3:2156-2165) and the pVL series (Lucklow and Summers (1989) Virology 170:31-39).

The following promoters and expression control sequences may be, preferably, used in an expression vector according to the present invention. The cos, tac, trp, tet, trp-tet, lpp, lac, lpp-lac, lacIq, T7, T5, T3, gal, trc, ara, SP6, λ-PR or λ-PL promoters are, preferably, used in Gram-negative bacteria. For Gram-positive bacteria, promoters amy and SPO2 may be used. From yeast or fungal promoters ADC1, MFα, AC, P-60, CYC1, GAPDH, TEF, rp28, ADH are, preferably, used or from plant the promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or the ubiquitin or phaseolin promoter. Also preferred in this context are inducible promoters, such as the promoters described in EPA 0 388 186 (benzylsulfonamide-inducible), Plant J. 2, 1992: 397-404 (Gatz et al., tetracyclin-inducible), EP A 0 335 528 (abscisic-acid-inducible) or WO 93/21334 (ethanol- or cyclohexenol-inducible). Further suitable plant promoters are the promoter of cytosolic FBPase or the ST-LSI promoter from potato (Stockhaus et al., EMBO J. 8, 1989, 2445), the phosphoribosyl-pyrophosphate amidotransferase promoter from *Glycine max* (Genbank accession No. U87999) or the node-specific promoter described in EP-A-0 249 676. Particularly preferred are promoters which enable the expression in tissues which are involved in the biosynthesis of fatty acids. Also particularly preferred are seed-specific promoters such as the USP promoter in accordance with the practice, but also other promoters such as the LeB4, DC3, phaseolin or napin promoters. Further especially advantageous promoters are seed-specific promoters which can be used for monocotyledonous or dicotyledonous plants and which are described in U.S. Pat. No. 5,608,152 (napin promoter from oilseed rape), WO 98/45461 (oleosin promoter from Arobidopsis, U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for example for monocots: lpt-2 or lpt-1 promoter from barley (WO 95/15389 and WO 95/23230), hordein promoter from barley and other promoters which are suitable and which are described in WO 99/16890. In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890.

The polynucleotide of the present invention can be expressed in single-cell plant cells (such as algae), see Falciatore et al., 1999, Marine Biotechnology 1 (3):239-251 and the references cited therein, and plant cells from higher plants (for example Spermatophytes, such as arable crops) by using plant expression vectors. Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as the gene 3 of the Ti plasmid pTiACH5, which is known as octopine synthase (Gielen et al., EMBO J. 3 (1984) 835 et seq.) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie et al., 1987, Nucl. Acids Research 15:8693-8711). As described above, plant gene expression must be functionally linked to a suitable promoter which performs the expression of the gene in a timely, cell-specific or tissue-specific manner. Promoters which can be used are constitutive promoters (Benfey et al., EMBO J. 8 (1989) 2195-2202) such as those which are derived from plant viruses such as 35S CAMV (Franck et al., Cell 21 (1980) 285-294), 19S CaMV (see also U.S. Pat. No. 5,352,605 and WO 84/02913) or plant promoters such as the promoter of the Rubisco small subunit, which is described in U.S. Pat. No. 4,962,028. Other preferred sequences for the use in functional linkage in plant gene expression cassettes are targeting sequences which are required for targeting the gene product into its relevant cell compartment (for a review, see Kermode, Crit. Rev. Plant Sci. 15, 4 (1996) 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells. As described above, plant gene expression can also be facilitated via a chemically inducible promoter (for a review, see Gatz 1997, Annu. Rev. Plant Physiol. Plant Mol. Biol., 48:89-108). Chemically inducible promoters are particularly suitable if it is desired that genes are expressed in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter. Promoters which respond to biotic or abiotic stress conditions are also suitable promoters, for example the pathogen-induced PRP1-gene promoter (Ward et al., Plant Mol. Biol. 22 (1993) 361-366), the heat-inducible hsp80 promoter from tomato (U.S. Pat. No. 5,187,267), the cold-inducible alpha-amylase promoter from potato (WO 96/12814) or the wound-inducible pinII promoter (EP A 0 375 091). The promoters which are especially preferred are those which bring about the expression of genes in tissues and organs in which fatty acid, lipid and oil biosynthesis takes place, in seed cells such as the cells of endosperm and of the developing embryo. Suitable promoters are the napin gene promoter from oilseed rape (U.S. Pat. No. 5,608,152), the USP promoter from *Vicia faba* (Baeumlein et al., Mol. Gen. Genet., 1991, 225 (3):459-67), the oleosin promoter from *Arabidopsis* (WO 98/45461), the phaseolin promoter from *Phaseolus vulgaris* (U.S. Pat. No. 5,504,200), the Bce4 promoter from *Brassica* (WO 91/13980) or the legumin B4 promoter (LeB4; Baeumlein et al., 1992, Plant Journal, 2 (2): 233-9), and promoters which bring about the seed-specific expression in monocotyledonous plants such as maize, barley, wheat, rye, rice and the like. Suitable promoters to be taken into consideration are the lpt2 or lpt1 gene promoter from barley (WO 95/15389 and WO 95/23230) or those which are described in WO 99/16890 (promoters from the barley hordein gene, the rice glutelin gene, the rice oryzin gene, the rice prolamin gene, the wheat gliadin gene, wheat glutelin gene, the maize zein gene, the oat glutelin gene, the *sorghum* kasirin gene, the rye secalin gene). Likewise, especially suitable are promoters which bring about the plastid-specific expression since plastids are the compartment in which the precursors and some end products of lipid biosynthesis are synthesized. Suitable promoters such as the viral RNA-polymerase promoter, are described in WO 95/16783 and WO 97/06250, and the clpP promoter from *Arabidopsis*, described in WO 99/46394.

The abovementioned vectors are only a small overview of vectors to be used in accordance with the present invention. Further vectors are known to the skilled worker and are described, for example, in: Cloning Vectors (Ed., Pouwels, P. H., et al., Elsevier, Amsterdam-New York-Oxford, 1985, ISBN 0 444 904018). For further suitable expression systems for prokaryotic and eukaryotic cells see the chapters 16 and 17 of Sambrook, J., Fritsch, E. F., and Maniatis, T., Molecular Cloning: A Laboratory Manual, $2^{nd}$ edition, Cold Spring Harbor Laboratory, Cold Spring Harbor Laboratory Press, Cold Spring Harbor, N.Y., 1989.

It follows from the above that, preferably, said vector is an expression vector. More preferably, the said polynucleotide of the present invention is under the control of a seed-specific promoter in the vector of the present invention. A preferred seed-specific promoter as meant herein is selected from the group consisting of Conlinin 1, Conlinin 2, napin, LuFad3, USP, LeB4, Arc, Fae, ACP, LuPXR, and SBP.

The present invention, furthermore, relates to a host cell comprising the polynucleotide of the invention or which is transformed with the vector of the invention.

Preferably, said host cell is a plant cell and, more preferably, a plant cell obtained from an oilseed crop. More preferably, said oilseed crop is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, crambe, oil palm, coconuts, groundnuts, sesame seed, castor bean, lesquerella, tallow tree, sheanuts, tungnuts, kapok fruit, poppy seed, jojoba seeds and perilla.

Also preferably, said host cell is a microbial cell. More preferably, said microbial cell is selected from the group consisting of *Candida, Cryptococcus, Lipomyces, Rhodosporidium, Yarrowia, Thraustochytrium, Pythium, Schizochytrium* and *Crythecodinium.*

The present invention relates to a plant or plant seed comprising the nucleic acid molecule of the invention, the vector of the invention or the host cell of the invention.

Preferred plants to be used for introducing the polynucleotide or the vector of the invention are plants which are capable of synthesizing fatty acids, such as all dicotyledonous or monocotyledonous plants, algae or mosses. It is to be understood that host cells derived from a plant may also be used for producing a plant according to the present invention. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*. Examples which may be mentioned are the following plants selected from the group consisting of: Adelotheciaceae such as the genera *Physcomitrella*, such as the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula oficinalis* [common marigold], *Carthamus tinctorius* [safflower], *Centaurea cyanus* [cornflower], *Cichorium intybus* [chicory], *Cynara scholymus* [artichoke]. *Helianthus annus* [sunflower], *Lactuca sativa, Lactuca crispa, Lactuca esculenta, Lactuca scariola* L. ssp. *sativa, Lactuca scariola* L. var. *integrate, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], *Cannabacae*, such as the genus *Cannabis*, such as the genus and species *Cannabis* sativa [hemp], Convolvulaceae, such as the genera Ipomea, *Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], *Cymbellaceae* such as the genera *Amphora, Cymbella, Okedenia, Phaeodactylum, Reimeria*, for example the genus and species *Phaeodactylum tricornutum*, Ditrichaceae such as the genera *Ditrichaceae, Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpureus, Ceratodon purpureus, Ceratodon purpureus* ssp. *convolutus, Ceratodon, purpureus* spp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulaturn, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta [manihot*] or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus, Soja*, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcata, Medicago varia* [alfalfa], *Glycine max Dolichos soja, Glycine gracilis, Glycine hispida, Phaseolus max, Soja hispida* or *Soja max* [soybean], Funariaceae such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense,*

*Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientate, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa. Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum, Proteaceae*, such as the genus *Macadamia*, for example the genus and species *Macadamia intergrifolia [macadamia*], Prasinophyceae such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae such as the genus *Cofea*, for example the genera and species *Cofea* spp., *Coffea arabica, Coffea canephora* or *Coffea liberica* [coffee], Scrophulariaceae such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum or Verbascum thapsus* [mullein], Solanaceae such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], *Sterculiaceae*, such as the genus *Theobroma*, for example the genus and species *Theobroma cacao* [cacao] or *Theaceae*, such as the genus *Camellia*, for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica*, evening primrose, mullein, thistle, wild roses, hazelnut, almond, *macadamia*, avocado, bay, pumpkin/squash, linseed, soybean, pistachios, borage, trees (oil palm, coconut, walnut) or crops such as maize, wheat, rye, oats, triticale, rice, barley, cotton, cassaya, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

Preferred mosses are *Physcomitrella* or *Ceratodon*. Preferred algae are *lsochrysis, Mantoniella, Ostreococcus* or *Crypthecodinium*, and algae/diatoms such as *Phaeodactylum* or *Thraustochytrium*. More preferably, said algae or mosses are selected from the group consisting of: *Shewanella, Physcomitrella, Thraustochytrium, Fusarium, Phytophthora, Ceratodon, lsochrysis, Aleurita, Muscarioides, Mortierella, Phaeodactylum, Cryphthecodinium*, specifically from the genera and species *Thallasiosira pseudonona, Euglena gracilis, Physcomitrella patens, Phytophtora infestans, Fusarium graminaeum, Cryptocodinium cohnii, Ceratodon purpureus, lsochrysis galbana, Aleurita farinosa, Thraustochytrium* sp., *Muscarioides viallii, Mortierella alpina, Phaeodactylum tricornutum* or *Caenorhabditis elegans* or especially advantageously *Phytophtora infestans, Thallasiosira pseudonona* and *Cryptocodinium cohnii.*

Transgenic plants may be obtained by transformation techniques as published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Preferably, transgenic plants can be obtained by T-DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

The host cell of the present invention, more preferably, is capable of producing the unsaturated fatty acids specified in detail below. To this end, further enzymes including other desaturases or elongases may be required dependent on the enzymatic setup which is endogenously present in the host cell. It is to be understood that further enzymes which might be required for the production of the unsaturated fatty acid may be exogenously supplied, e.g., by transforming the host cell with expressible polynucleotides encoding said enzymes. Alternatively, the activity of undesired endogenously present enzymes may be inhibited, e.g., by applying anti-sense nucleic acids, ribozymes, siRNA molecules, morpholino nucleic acids (phosphorodiamidate morpholino oligos), triple-helix forming oligonucleotides, inhibitory oligonucleotides, or micro RNA molecules. In particular, the host cell envisaged by the present invention, more preferably, comprises at least one enzymatic activity selected from the group consisting of: Δ-4-desaturase, Δ-5-desaturase, Δ-5-elongase, Δ-6-desaturase, Δ12-desaturase, Δ15-desaturase, ω3-desaturase and Δ-6-elongase activity. Moreover, it will be understood that the desaturases and acyltransferases of the present invention may be coexpressed in order to increase the PUFA production and, in particular for ARA, EPA and/or DHA manufacture.

The present invention also provides for a method of producing a polypeptide comprising culturing the host cell of the invention in an appropriate culture medium to, thereby, produce the polypeptide encoded by a polynucleotide of the invention.

The polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide. A polypeptide obtained by the said method includes variant polypeptides which are post-translationally modified, e.g., phosphorylated or myristylated, or which are processed on either RNA or protein level.

In principle, the present invention, however, relates to a polypeptide encoded by the polynucleotide of the present invention.

The term "polypeptide" as used herein encompasses essentially purified polypeptides or polypeptide preparations comprising other proteins in addition. Moreover, the term also, preferably, includes polypeptides which are present in a host cell, plant or plant seed wherein the said host cell, plant or plant seed is not the biological source in which the polypeptide occurs naturally. Further, the term also relates to the fusion proteins or polypeptide fragments being at least partially encoded by the polynucleotide of the present invention referred to above. Moreover, it includes chemically modified polypeptides. Such modifications may be artificial modifications or naturally occurring modifications such as phosphorylation, glycosylation, myristylation and the like. The terms "polypeptide", "peptide" or "protein" are used interchangeable throughout this specification. As referred to above, the polypeptide of the present invention shall exhibit dehydratase activity and, thus, can be used for the manufacture of unsaturated fatty acids, either in a host cell or in a transgenic animal or plant as described elsewhere in this specification.

The present invention also relates to an antibody which specifically recognizes the polypeptide of the present invention.

Antibodies against the polypeptides of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the antibody of the present invention is a monoclonal antibody, a polyclonal antibody, a single chain antibody, a human or humanized antibody or primatized, chimerized or fragment thereof. Also comprised as antibodies by the present invention are a bispecific antibody, a synthetic antibody, an antibody fragment, such as Fab, Fv or scFv fragments etc., or a chemically modified derivative of any of these. The antibody of the present invention shall specifically bind (i.e. does not cross react with other polypeptides or peptides) to the polypeptide of the invention. Specific binding can be tested by various well known techniques.

Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature 256 (1975), 495, and Galfré, Meth. Enzymol. 73 (1981), 3, which comprise the fusion of mouse myeloma cells to spleen cells derived from immunized mammals.

The antibodies can be used, for example, for the immunoprecipitation, immunolocalization or purification (e.g., by affinity chromatography) of the polypeptides of the invention as well as for the monitoring of the presence of said variant polypeptides, for example, in recombinant organisms, and for the identification of compounds interacting with the proteins according to the invention.

Encompassed by the present invention is a method for manufacturing an unsaturated fatty acid, comprising culturing the host cell of the invention or the plant or plant seed of the invention such that the unsaturated fatty acid is produced. It is to be understood that, preferably, the method may comprise further steps which are required for isolating the unsaturated fatty acid from the host cell.

Also contemplated is a method of modulating the production of an unsaturated fatty acid comprising culturing the host cell of the invention or the plant or plant seed of the invention, such that modulation of the production of an unsaturated fatty acid occurs.

In a preferred embodiment of the methods of the present invention, said methods further comprises the step of recovering the unsaturated fatty acid from said culture.

The present invention, further, relates to a method of manufacturing an unsaturated fatty acid comprising contacting a composition comprising at least one desaturase target molecule with at least one polypeptide of the invention under conditions such that the unsaturated fatty acid is produced.

The term “unsaturated fatty acid” or “elongated fatty acid” as used herein, preferably, encompasses compounds having a structure as shown in the general formula I (I)

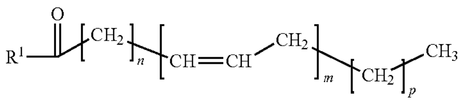

wherein the variables and substituents in formula I are $R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II (II)

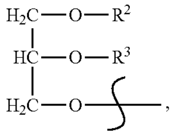

$R^2$=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl, $R^3$=hydrogen, saturated or unsaturated $C_2$-$C_{24}$-alkylcarbonyl, or $R^2$ and $R^3$ independently of each other are a radical of the formula Ia:

(Ia)

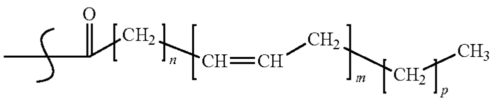

n=2, 3, 4, 5, 6, 7 or 9, m=2, 3, 4, 5 or 6 and p=0 or 3;

Preferably, $R^1$ in the general formula I is hydroxyl, coenzyme A (thioester), ysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II (II)

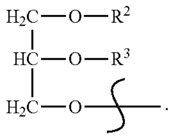

The abovementioned radicals of $R^1$ are always bonded to the compounds of the general formula I in the form of their thioesters.

Preferably, $R^2$ in the general formula II is hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl. Moreover, alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl- or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds, are preferred. Preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Particularly preferred are saturated or unsaturated $C_{20}$-$C_{22}$-alkylcarbonyl radicals such as $C_{20}$-alkylcarbonyl or $C_{22}$-alkylcarbonyl radicals which comprise one or more double bonds. These preferred radicals can comprise two, three, four, five or six double bonds. The particularly preferred radicals with 20 or 22 carbon atoms in the fatty acid chain comprise up to six double bonds, advantageously two, three, four or five double bonds, especially preferably two, three or four double bonds. All the abovementioned radicals are derived from the corresponding fatty acids.

Preferably, $R^3$ in the formula II is hydrogen, saturated or unsaturated $C_2$-$C_{24}$-alkylcarbonyl. Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl-, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl- or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds, are preferred. Preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Particularly preferred are saturated or unsaturated $C_{20}$-$C_{22}$-alkylcarbonyl radicals such as $C_{20}$-alkylcarbonyl or $C_{22}$-alkylcarbonyl radicals which comprise one or more double bonds. These preferred radicals can comprise two, three, four, five or six double bonds. The particularly preferred radicals with 20 or 22 carbon atoms in the fatty acid chain comprise up to six double bonds, advantageously two, three, four or five double bonds, especially preferably two, three or four double bonds. All the abovementioned radicals are derived from the corresponding fatty acids.

The abovementioned radicals of $R^1$, $R^2$ and $R^3$ can be substituted by hydroxyl and/or epoxy groups and/or can comprise triple bonds.

The unsaturated fatty acids according to the present invention are, preferably, polyunsaturated fatty acids (PUFAs). The polyunsaturated fatty acids according to the invention advantageously comprise at least two, advantageously three, four, five or six, double bonds. The fatty acids especially advantageously comprise two, three, four or five double bonds. Unsaturated fatty acids, preferably, comprise 20 or 22 carbon atoms in the fatty acid chain. Saturated fatty acids are advantageously reacted to a minor degree, or not at all, by the nucleic acids used in the process. To a minor degree is to be understood as meaning that the saturated fatty acids are reacted with less than 5% of the activity, advantageously less than 3%, especially advantageously with less than 2% of the activity in comparison with polyunsaturated fatty acids. These fatty acids which have been produced can be produced in the process as a single product or be present in a fatty acid mixture.

Advantageously, the substituents $R^2$ or $R^3$ in the general formulae I and II independently of one another are saturated or unsaturated $C_{20}$-$C_{22}$-alkylcarbonyl; especially advantageously, are independently of one another unsaturated $C_{20}$- or $C_{22}$-alkylcarbonyl with at least two double bonds.

The polyunsaturated fatty acids according to the present invention are, preferably, bound in membrane lipids and/or triacylglycerides, but may also occur in the organisms as free fatty acids or else bound in the form of other fatty acid esters. In this context, they may be present as "pure products" or else advantageously in the form of mixtures of various fatty acids or mixtures of different glycerides. The various fatty acids which are bound in the triacylglycerides can be derived from short-chain fatty acids with 4 to 6 C atoms, medium-chain fatty acids with 8 to 12 C atoms or long-chain fatty acids with 14 to 24 C atoms. In accordance with the method of the present invention, preferred are the long-chain fatty acids, especially the long chain PUFAs (LCPUFAs) of $C_{20}$- and/or $C_{22}$-fatty acids.

Preferred unsaturated fatty acids in the sense of the present invention are selected from the group consisting of ARA 20:4 (5,8,11,14), EPA 20:5 (5,8,11,14,17), and DHA 22:6 (4,7,10, 13,16,19). The ARA, EPA and/or DHA produced in the process may be, as described above, in the form of fatty acid derivatives, for example sphingolipids, phosphoglycerides, lipids, glycolipids, phospholipids, monoacylglycerol, diacylglycerol, triacylglycerol or other fatty acid esters. The ARA, EPA and/or DHA and other polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

The term "desaturase target molecule", preferably, encompasses substrates of the polypeptides of the invention. A particular preferred target molecule is oleic acid, linoleic acid, γ-linolenic acid, α-linolenic acid, dihomo-γ-linolenic acid, stearidonic acid, eicosatetraenoic acid (n-3), arachidonic acid, eicosapentaenoic acid and docosapentaenoic acid.

The present invention provides for a method for the manufacture of oil comprising the steps of the aforementioned methods and the further step of formulating or isolating oil comprising the said unsaturated fatty acid.

The present invention also relates to a method of producing a host cell, plant or plant seed capable of generating an unsaturated fatty acid comprising introducing into said host cell, plant or plant seed the nucleic acid molecule of the present invention or the vector of the present invention.

The present invention includes oil produced by the plant or plant seed of the invention, obtainable by the method of the invention or obtainable by a host cell, plant or plant seed produced by the aforementioned method.

The term "oil" refers to a fatty acid mixture comprising unsaturated or saturated, preferably esterified, fatty acid(s). The oil is preferably high in polyunsaturated free or, advantageously, esterified fatty acid(s), in particular the preferred LCPUFAs referred to herein above. The amount of unsaturated esterified fatty acids preferably amounts to approximately 30%, a content of 50% is more preferred, a content of 60%, 70%, 80% or more is even more preferred. For the analysis, the fatty acid content can, for example, be determined by GC after converting the fatty acids into the methyl esters by transesterification. The oil can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism. The oil, however, shall have a non-naturally occurring composition with respect to the unsaturated fatty acid composition and content. Moreover, the oil of the invention may comprise other molecular species as well. Specifically, it may comprise minor impurities of the nucleic acid molecules of the invention. Such impurities, however, can be detected only by highly sensitive techniques such as PCR.

The present invention also includes a method for the manufacture of a medicament comprising the steps of the methods of the invention and the further step of formulating medicament comprising the said unsaturated fatty acid.

The term "medicament" is used herein interchangeably with the term "pharmaceutical composition" explained in detail below. The term "medicament" or "pharmaceutical composition" as used herein comprises the compounds of the present invention and optionally one or more pharmaceutically acceptable carrier. The compounds of the present invention can be formulated as pharmaceutically acceptable salts. Acceptable salts comprise acetate, methylester, HCl, sulfate, chloride and the like. The pharmaceutical compositions are, preferably, administered topically or systemically. Suitable routes of administration conventionally used for drug administration are oral, intravenous, or parenteral administration as well as inhalation. However, depending on the nature and mode of action of a compound, the pharmaceutical compositions may be administered by other routes as well. For example, polynucleotide compounds may be administered in a gene therapy approach by using viral vectors or viruses or liposomes.

Moreover, the compounds can be administered in combination with other drugs either in a common pharmaceutical composition or as separated pharmaceutical compositions wherein said separated pharmaceutical compositions may be provided in form of a kit of parts.

The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, *acacia*, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 μg; however, doses below or above this exemplary range are envisioned, especially considering the aforementioned factors. Generally, the regimen as a regular administration of the pharmaceutical composition should be in the range of 1 μg to 10 mg units per day. If the regimen is a continuous infusion, it should also be in the range of 1 μg to 10 mg units per kilogram of body weight per minute, respectively. Progress can be monitored by periodic assessment. However, depending on the subject and the mode of administration, the quantity of substance administration may vary over a wide range.

The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adapted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

For cosmetic applications, the compounds referred to herein as pharmaceutically active ingredients of the medicament can be formulated as a hair tonic, a hair restorer composition, a shampoo, a powder, a jelly, a hair rinse, an ointment, a hair lotion, a paste, a hair cream, a hair spray and/or a hair aerosol.

The present invention relatest to a medicament comprising the polynucleotide, the vector, the host cell, the polypeptide, the plant or plant seed or the oil of the present invention.

Moreover, the present invention relates to the use of the polynucleotide, the vector, the host cell, the polypeptide, the plant or plant seed or the oil of the invention for the manufacture of animal feed, a dietary supplement, or food.

Finally, the present invention relates to a cell comprising a nucleic acid molecule selected from the group consisting of:

a) a nucleic acid molecule comprising the nucleotide sequence of SEQ ID NO: 1, 3, 5, 7, 31, 33, 35, 37, 102, 104, 106, 108, 110, 112, 135, 137 or 139, wherein the nucleic acid molecule is disrupted by at least one technique selected from the group consisting of a point mutation, a truncation, an inversion, a deletion, an addition, a substitution and homologous recombination;

b) a nucleic acid molecule comprising the nucleotide sequence of SEQ ID NO: 1, 3, 5, 7, 31, 33, 35, 37, 102, 104, 106, 108, 110, 112, 135, 137 or 139, wherein the nucleic acid molecule comprises one or more nucleic acid modifications as compared to the sequence set forth in SEQ ID NO: 1, 3, 5, 7, 31, 33, 35, 37, 102, 104, 106, 108, 110, 112, 135, 137 or 139, wherein the modification is selected from the group consisting of a point mutation, a truncation, an inversion, a deletion, an addition and a substitution; and c) a nucleic acid molecule comprising the nucleotide sequence of SEQ ID NO: 1, 3, 5, 7, 31, 33, 35, 37, 102, 104, 106, 108, 110, 112, 135, 137 or 139, wherein the regulatory region of the nucleic acid molecule is modified relative to the wild-type regulatory region of the molecule by at least one technique selected from the group consisting of a point mutation, a truncation, an inversion, a deletion, an addition, a substitution and homologous recombination.

The contents of all references cited throughout this application are herewith incorporated by reference in general and with respect to their specific disclosure content referred to above.

FIGURES

FIG. 2 shows the alignment of SEQ ID NOS: 2, 4, 6, 8, 32, 34, 36 and 38 based on the ClustalW algorithm.

EXAMPLES

Figure 1:
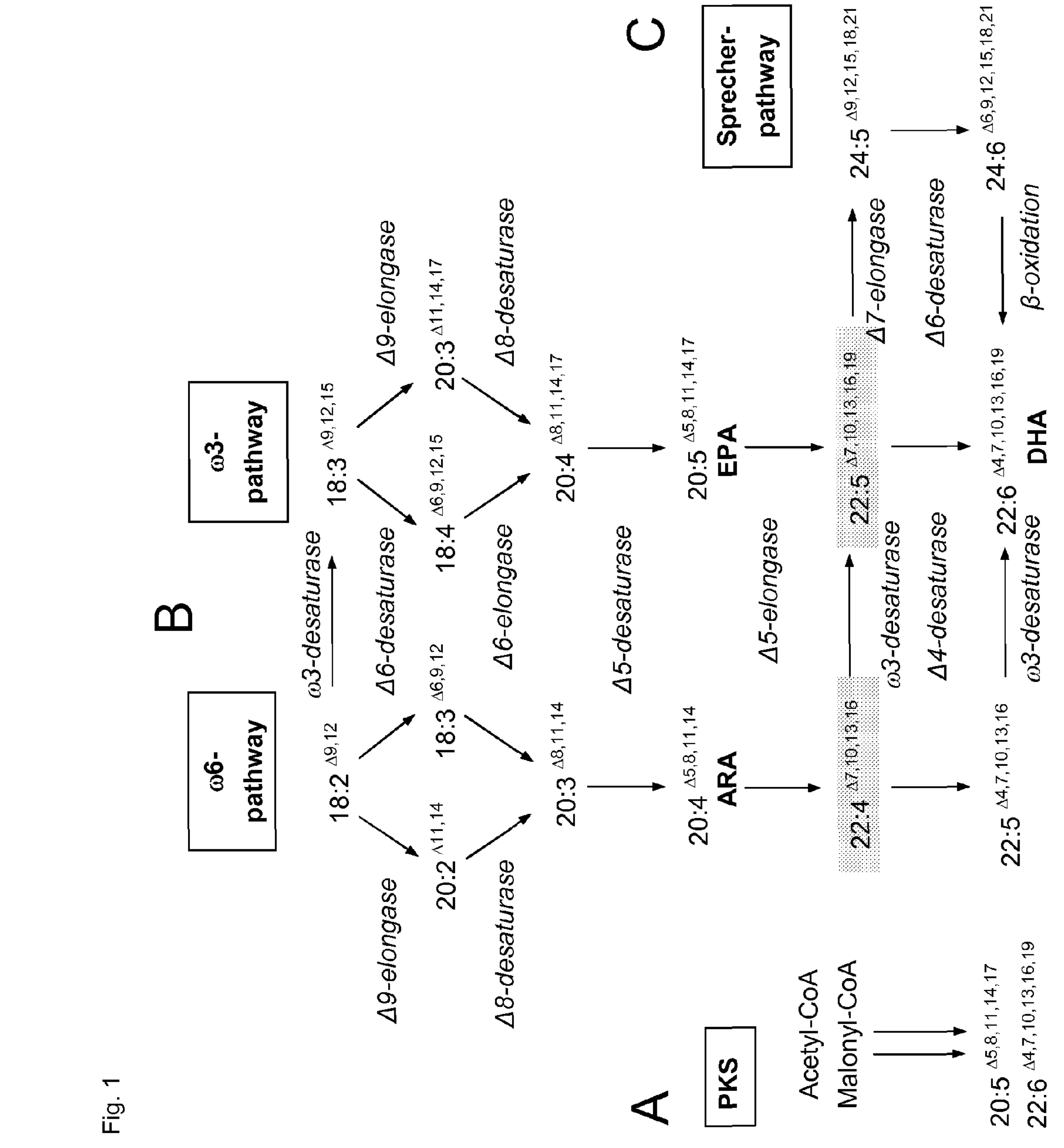
FIG. 1 shows various synthetic pathways for the biosynthesis of ω6 and ω3 fatty acids.

The invention will now be described in greater detail with reference to the following Examples which, however, shall not be construed whatsoever to limit the scope of this invention.

Example 1

Cloning of Desaturases from *Drechsler Tritici-Repentis, Cylindorcarpon Heteronema, Diplodia Natalensis, Stagonospora Nodorum, Microdochium Nivalae* and *Periplaneta Americana*

Materials and Methods.

Growth and harvesting of *Drechsler tritici-repentis, Cylindorcarpon heteronema, Diplodia natalensis, Stagonospora nodorum* and *Microdochium nivalae*

The fungi were obtained from DSMZ (German collection of microorgamisms and cells, Braunschweig) and grown on plates under following conditions:

| | | |
|---|---|---|
| *Drechsler tritici-repentis* | 2% malt, 0.8% agar | 18-22° C. |
| *Cylindorcarpon heteronema* | 2% Lima-Bean, 0.8% agar | 24° C. |
| *Diplodia natalensis* | 2% malt, 0.8% agar | 22° C. |
| *Stagonospora nodorum* | CzapekDox-V8-Agar with 15 g sucrose | 18° C. |

RNA isolation was done according to manufactures protocol using the RNAeasy Kit from Qiagen.

Growth and Harvesting of *P. Americana.*

*Periplaneta americana* were cultivated at 25-30° C. at 70-80% humidity on garden soil. As feed dog food added with fresh vegetables was used. RNA isolation was done as described in EP0464553.

Nucleic Acid Manipulation and PCR-Based Cloning.

RNA isolation was done as described above. Transcripts were analyzed by reverse transcriptase PCR(RT-PCR). First strand cDNA was synthesised from total RNA using the SMART RACE cDNA Amplification kit (BD-Clontech, Basingstoke, UK) according to the manufacture's instructions. Single-stranded cDNAs were amplified with following primers.

Used primer for cloning of *Drechsler tritici-repentis, Cylindorcarpon heteronema, Diplodia natalensis, Stagonospora nodorum* and *Microdochium nivalae* desaturases:

```
Zan 348
                                    SEQ ID NO: 88
(F) ACI GGI BTI TGG RTI BTI GSI CAY

Zan 349
                                    SEQ ID NO: 89
(F) SAI GAR YTI KBI GGI TGG SMI

Zan 350
                                    SEQ ID NO: 90
(R) IGT DAT IRV IAC IAR CCA RTG

Zan 351
                                    SEQ ID NO: 91
(R) RTG IDW IYS IAY DAT ICC RTG
```

Used primer for cloning of *Periplaneta americana* desaturases:

```
Sen012 (F):
                                    SEQ ID NO: 92
GAC CAY CGH VWG CAY CAY

Sen013 (F):
                                    SEQ ID NO: 93
GAR ACX RAY GSN GAY CC

Sen014 (F):
                                    SEQ ID NO: 94
GAR ACX RAY GSN GAY CCY XXX AAY KG

Sen015 (R):
                                    SEQ ID NO: 95
GYY YKG TAR TCC CAK GGG WA

Sen016 (R):
                                    SEQ ID NO: 96
TCC CAX GGR WAX RYR TGR TGR WAR TTG TG

Sen021d (F):
                                    SEQ ID NO: 97
GAY CCI CAY AAY GCI AAR MGI GGI

Sen022d (F):
                                    SEQ ID NO: 98
IGI GGI TTY TTY TTY WSI CAY

Sen023d (F):
                                    SEQ ID NO: 99
TTY TTY WSI CAY GTI GGI TGG

Sen024d (R):
                                   SEQ ID NO: 100
RTG IGC IGC ISW RTT IAC IAR CCA

Sen025d (R):
                                   SEQ ID NO: 101
YTT RTC RTA IGG ICW ISW ICC CCA
```

Degenerated primers are in IUPAC standard nomenclature.

PCR amplification was done in the following way: The reactions were heated to 95 C for 2 min followed by 30 cycles at 94 C for 30 s, 30 s at temperatures ranging from 55 to 72 according to the primer design and 72 C for 2 min, then a single step at 72 C for 10 min. PCR amplification products were cloned into TOPO vector (Invitrogen) and verified by sequencing.

From the above described set of primer only the primer pairs Zan348-350 and Sen014-015 delivered fragments with sequence homologies to desaturases.

By using the Smart-RACE Kit (BD-Clontech, Basingstoke, UK) according to manufactures protocol 5' and 3' regions of the DNA pieces were further exploited.

Full-length sequences were obtained with the primer pairs described in Table 1.

TABLE 1

Amplification of full-length desaturase genes

| Gene name | SEQ ID | Primer pair | Fragment length | ORF length |
|---|---|---|---|---|
| D12Des(Dt) | 1 | 5'-ctgagagaacatgacg acgac SEQ ID 39<br>5'-gtcgcttactcgttgt cactctc SEQ ID 40 | 1445 | 1344 |
| D15Des(Cyh) | 3 | 5'-gatactaagccaccaa catgg SEQ ID 41<br>5'-cgttctacgagccctc tatttc SEQ ID 42 | 1259 | 1227 |
| D12Des(Dn) | 5 | 5'-caaccacccatcatgg ccac SEQ ID 43<br>5'-atcgcttcatgcgtca ttgtc SEQ ID 44 | 1501 | 1482 |
| D12Des(Sn) | 7 | 5'-caccatcatggccacc acaac SEQ ID 45<br>5'-agctctactcgttgtc ggactc SEQ ID 46 | 1496 | 1485 |
| D12Des(Mn) | 31 | 5'-atgggccatgagtgtg gacac SEQ ID 47<br>5'-ctatttggccatcttg gtaggggg SEQ ID 48 | 975 | 975 |
| D15Des(Mn) | 33 | 5'-atgattgcgaccaccc agac SEQ ID 49<br>5'-ctaaaggtccttgcgg ggtgcg SEQ ID 50 | 1209 | 1209 |
| dXDes(Pa)_1 | 35 | 5'-atggctccgaacatta caagttc SEQ ID 51<br>5'-ctacttgagcttcttg ttgatg SEQ ID 52 | 1074 | 1074 |
| dXDes(Pa)_2 | 37 | 5'-atggcccctaatataa ctagtac SEQ ID 53<br>5'-ttaatctttcttgttg attatttg SEQ ID 54 | 1071 | 1071 |

From the full-length fragments the ORF sequences and the amino acid sequences deduced (Table 2).

TABLE 2

Amino acid sequences from desaturase genes

| Gene name | Amino acid sequence length | SEQ ID |
|---|---|---|
| D12Des(Dt) | 447 | 2 |
| D15Des(Cyh) | 408 | 4 |
| D12Des(Dn) | 493 | 6 |
| D12Des(Sn) | 494 | 8 |
| D12Des(Mn) | 324 | 32 |
| D15Des(Mn) | 402 | 34 |

TABLE 2-continued

Amino acid sequences from desaturase genes

| Gene name | Amino acid sequence length | SEQ ID |
|---|---|---|
| dXDes(Pa)_1 | 357 | 36 |
| dXDes(Pa)_2 | 356 | 38 |

PCR fragments for full-length sequences were cloned into pCR-bluntll-TOPO vector (Invitrogen) according to manufactures protocol and verified by sequencing.

Cloning of Yeast Expression Vectors

For expression and characterization in yeast ORF sequences of new desaturase genes were cloned into the vector pYES2-TOPO (Invitrogen) by amplifying the ORF sequence with primers adding a Kozak sequence at the 5'-end (Table 3). The same PCR protocol as described above was used. The vectors described in Table 4 were generated and used for functional characterization of the new desaturase genes.

TABLE 3

Primer pairs for amplification of ORF sequences from new desaturases

| Gene name | Primer pair | SEQ ID |
|---|---|---|
| D12Des(Dt) | 5'-accatggacgagcagcctgccgtc<br>5'-ttactcgttgtcactctcag | 55<br>56 |
| D15Des(Cyh) | 5'-accatggcggtccgacaacgcacc<br>5'-ctatttcgcccacctcatcgc | 57<br>58 |
| D12Des(Dn) | 5'-accatggccaccaccgccatggctc<br>5'-tcatgcgtcattgtcgctgtcg | 59<br>60 |
| D12Des(Sn) | 5'-accatggccaccacaactgcccgcgc<br>5'-ctactcgttgtcggactcagggcc | 61<br>62 |
| D12Des(Mn) | 5'-accatgggccatgagtgtggacacc<br>5'-ctatttggccatcttggtaggggg | 63<br>64 |
| D15Des(Mn) | 5'-accatgattgcgaccacccagac<br>5'-ctaaaggtccttgcggggtgcg | 65<br>66 |
| dXDes(Pa)_1 | 5'-accatggctccgaacattacaag<br>5'-ctacttgagcttcttgttgatg | 67<br>68 |
| dXDes(Pa)_2 | 5'-accatggcccctaatataactag<br>5'-ttaatctttcttgttgattatttg | 69<br>70 |

TABLE 4

Yeast expression vectors

| Gene name | ORF SEQ ID NO: | Expression vector | Short name of expression vector |
|---|---|---|---|
| D12Des(Dt) | 126 | pYES2-bluntII-TOPO-d12Des(Dt) | pYES-Dt |
| D15Des(Cyh) | 127 | pYES2-bluntII-TOPO-d12Des(Cyh) | pYES-Cyh |
| D12Des(Dn) | 128 | pYES2-bluntII-TOPO-d12Des(Dn) | pYES-Dn |
| D12Des(Sn) | 129 | pYES2-bluntII-TOPO-d12Des(Sn) | pYES-Sn |
| D12Des(Mn) | 31 | pYES2-bluntII-TOPO-d12Des(Mn) | pYES-12Mn |

TABLE 4-continued

| Yeast expression vectors | | | |
|---|---|---|---|
| Gene name | ORF SEQ ID NO: | Expression vector | Short name of expression vector |
| D15Des(Mn) | 130 | pYES2-bluntII-TOPO-d12Des(Mn) | pYES-15Mn |
| dXDes(Pa)_1 | 131 | pYES2-bluntII-TOPO-d12Des(Pa) | pYES-Pa1 |
| dXDes(Pa)_2 | 132 | pYES2-bluntII-TOPO-d12Des(Pa) | pYES-Pa2 |

Functional Characterisation in *Saccharomyces cerevisiae.*

*S. cerevisiae* strain INVSC (Invitrogen) was transformed with the constructs described in Table 4 or the empty vector (pYES2-bluntII-TOPO) as a control. Transformed cells were grown in a minimal medium containing raffinose and induced with 2% galactose. After 48 h of growth total yeast fatty acids were extracted and the resulting FAMEs analysed by GC.

Figure 3:
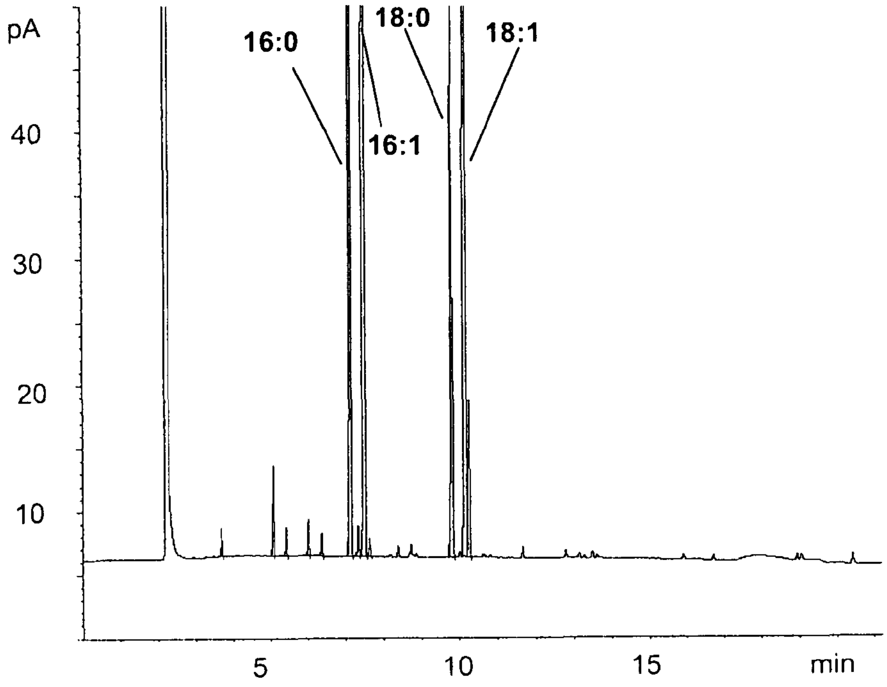
FIG. 3 shows gas chromatography traces demonstrating the conversion of oleic acid (18:1Δ9) into linoleic acid (18:2Δ9,12) proving the Δ12-desaturase activity of d12Des(Dt) (B), d12Des(Dn) (C) and d12Des(Sn) (D). In (A) the vector control is shown without any d12-desaturase activity.
Figure 3:
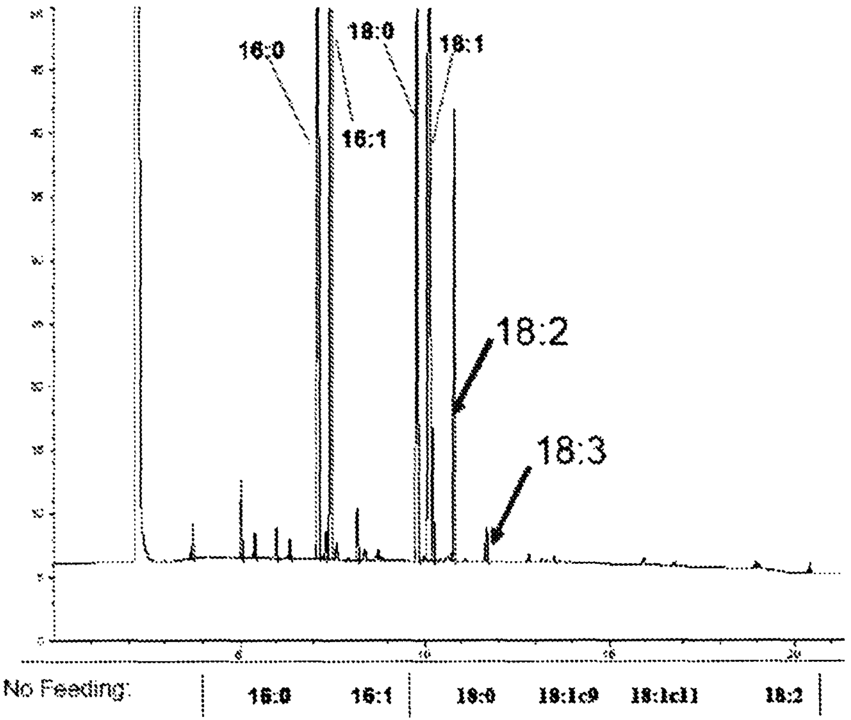
Figure 3:
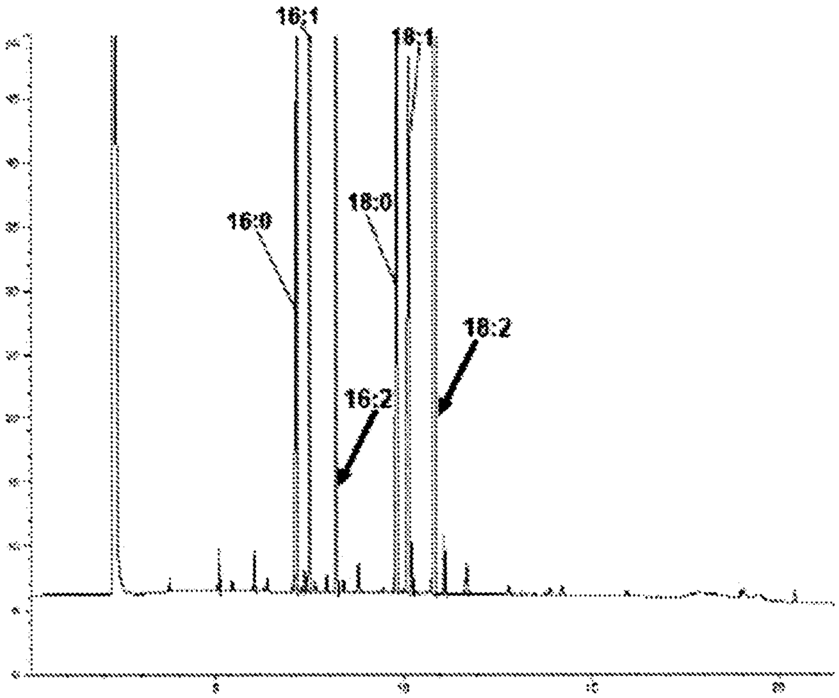
Figure 3:
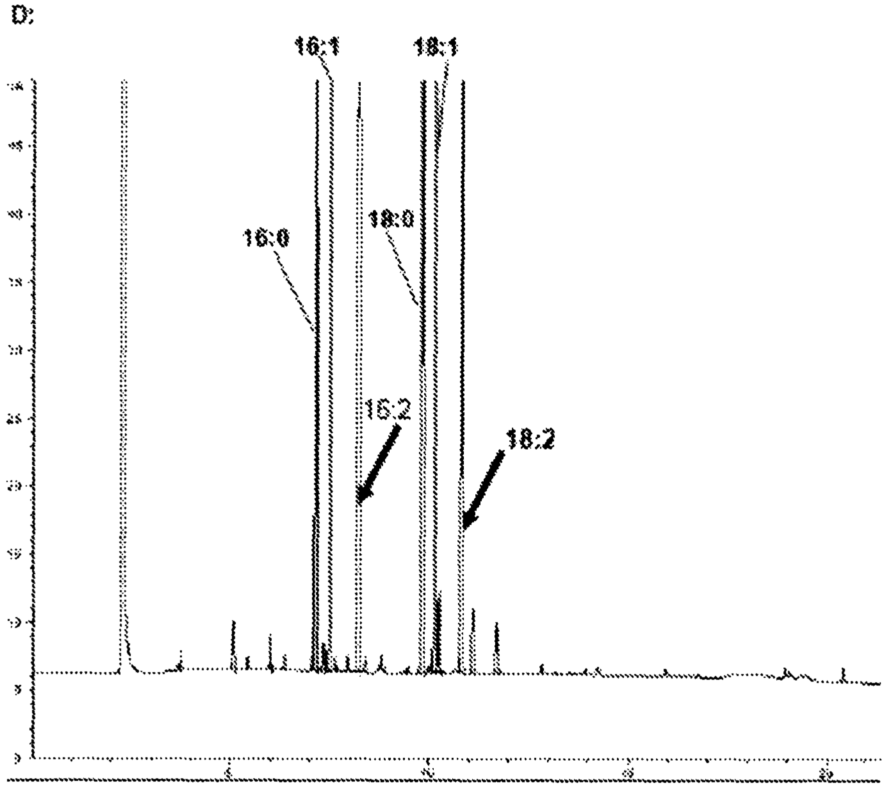
Figure 4:
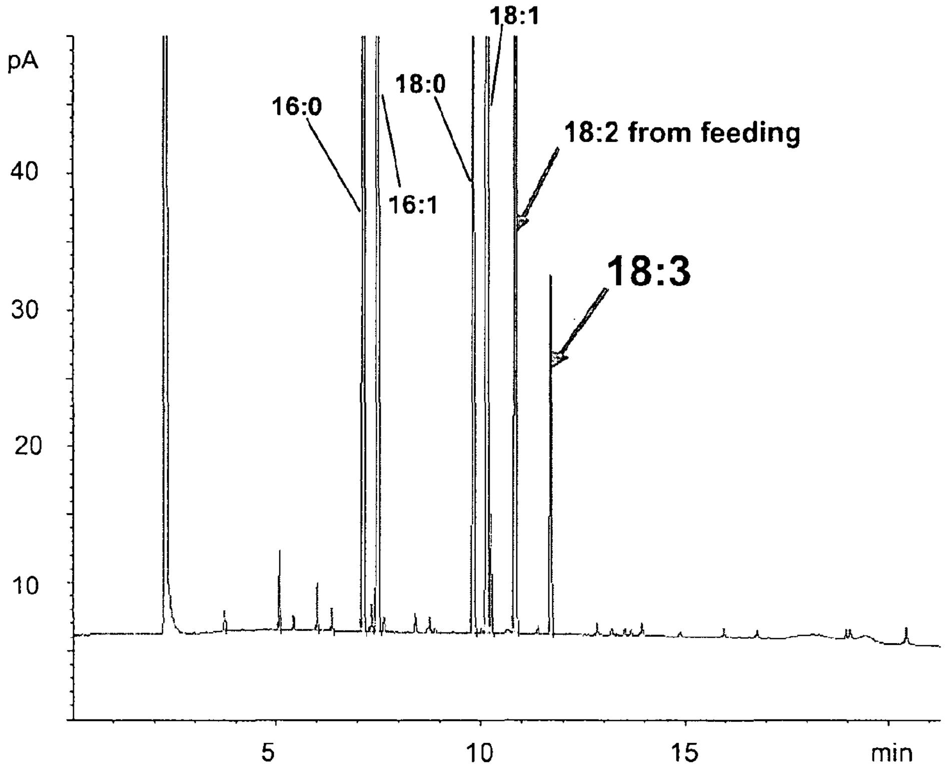
FIG. 4 shows gas chromatography traces demonstrating the conversion of linoleic acid (18:2Δ9,12) to α-linolenic acid (18:3Δ9,12,15) proving the Δ15-desaturase activity of d15Des(Cyh) (A). In (B) the absence of a Δ12-desaturase activity for d15Des(Cyh) is shown.
Figure 4:
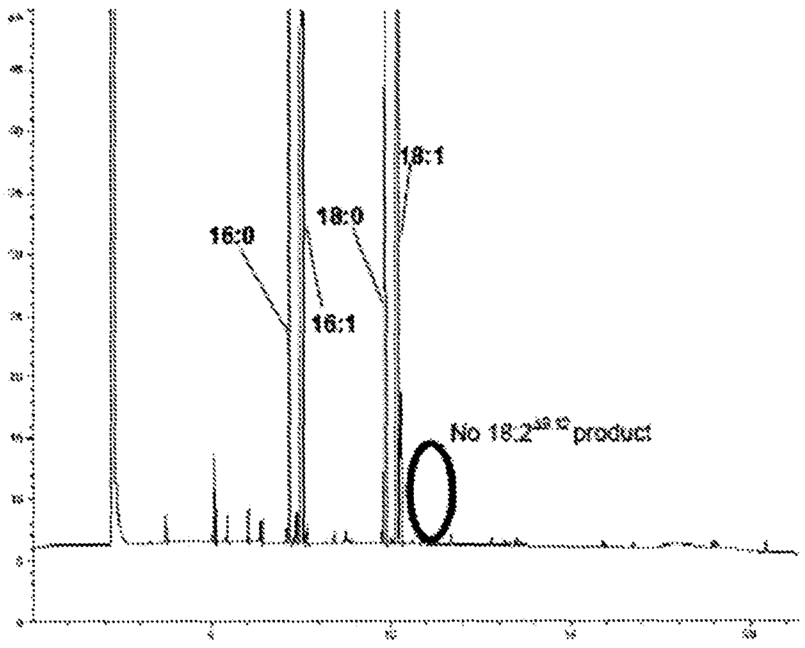

GC analysis of yeast transformed with pYES-Dt, pYES-Dn and pYES-Sn (FIG. 3) revealed that an additional fatty acid was produced, which was identified as linoleic acid indicating that the gene we had cloned encoded a delta12 desaturase. Yeast cells expressing the delta12 desaturases are capable of recognizing C18:$1^{\Delta 9}$ substrate. When the fatty acid 18:$2^{\Delta 9,12}$ was added to the yeast medium, further differences between each desaturase could be identified. Yet further, another fatty acid from yeast lipid composition 16:$1^{\Delta 7}$ is also converted to 16:$2^{\Delta 7,10}$ in yeast transformed with pYES-Dn and pYES-Sn, whereas cells with pYES-Dt do not show this activity.

The different activities as indicated in Table 5 demonstrate the functional activity of the new desaturases. Based on the major activity they are named as d12-desaturase. Further the other activities are proof that the newly found desaturases are distinct from each other and show new activities for this class of enzymes which has not been demonstrated before. Especially the high activity of the d12Des(Dn) was unexpected and to our knowledge not reported for any known d12-desaturase.

For d15Des(Cyh) only activity with 18:$2^{\Delta 9,12}$ could be shown, converting 18:$2^{\Delta 9,12}$ into 18:$3^{\Delta 9,12,15}$. Therefore the d15Des(Cyh) has delta15-desaturase activity and was named therefore Δ15-desaturase.

The percentage conversion is calculated for example of 18:$1^{\Delta 9}$ to 18:$2^{\Delta 9,12}$ by following equation:

$$\%\ \text{conversion} = \frac{[18{:}\ 2^{\Delta 9,12}]}{[18{:}\ 2^{\Delta 9,12}] + [18{:}\ 1^{\Delta 9}]} \times 100$$

TABLE 5

| Functional characterization of newly found desaturases | | | |
|---|---|---|---|
| Gene name | Conversion rate of 18:1 to 18:2 in % | Conversion rate of 16:1 to 16:2 in % | Conversion rate of 18:2 to 18:3 in % |
| D12Des(Dt) | 27.5 | — | 6.3 |
| D15Des(Cyh) | — | — | 14.9 |
| D12Des(Dn) | 76.3 | 49.3 | — |
| D12Des(Sn) | 52.5 | 31.2 | — |

Example 2

Production of Constructs for Expression in Plants

For the expression of new desaturase genes in plant, binary plasmids for *Agrobacterium* transformation are designed.

Further, constructs for the multiple expression of the whole pathway towards eicosapentaenoic acid were constructed. These constructs utilize a number of enzymatic activities, namely d12-desaturase (conversion of oleic to linoleic acid), d15-desaturase (conversion of linoleic to linolenic acid), d6-desaturase (conversion of linoleic and linolenic acid to γ-linolenic and stearidonic acid, respectively), d6-elongase (conversion of γ-linolenic and stearidonic acid to dihomogammalinolenic and eicosatetraenoic acid), d5-desaturase (conversion of dihomogammalinolenic and eicosatetraenoic acid to ARA and EPA), ω3-desaturase (conversion of ARA to EPA). Such a construct was assembled by using standard molecular biology methods known to a person skilled in the art. The sequence of the complete binary vector (LJB1139) is listed in SEQ ID NO: 71. The vector elements are described in Table 6.

TABLE 6

| Functional elements of binary vector LJB1139 depicted from SEQ ID NO: 68. | | | |
|---|---|---|---|
| Element | Description | Position from start | SEQ ID NO: |
| D6Elo(Tp) | D6-elongase *Thalassiosira pseudonana* | 1780-2598 | 11 |
| D6Des(Ot) | D6-desaturase *Ostreococcus tauri* | 3756-5126 | 19 |
| D12Des(Ps) | D12-desaturase *Phytophtora sojae* | 6484-7680 | 21 |
| O3Des(Pi) | ω3-desaturase *Phytophtora infestans* | 8873-9958 | 17 |
| D5Des(Tc) | D5-desaturase *Thraustochytrium* ssp. | 11622-12941 | 13 |
| D15Des(At) | D15-desaturase *Arabidopsis thaliana* | 17834-18994 | 23 |
| BnFae1 | Promoter BnFAE1 | 347-1776 | 76 |
| t-bnfae1 | Terminator bnfae1 | 2612-3011 | 77 |
| VfUSP | Promoter VfUSP | 3061-3744 | 78 |
| t-camv | Terminator CaMV-35S | 5179-5394 | 79 |
| BnACP | Promoter BnACP | 5466-6465 | 80 |
| t-bnacp | Terminator BnACP | 7694-8075 | 81 |
| BnNapin | Promoter BnNApin | 8206-8869 | 82 |
| tE9 | Terminator tE9 | 9959-10516 | 83 |
| LuCon | Promoter LuCon | 10545-11583 | 84 |
| tOCS | Terminator tOCS | 12993-13184 | 85 |
| BnNapin | Promoter BnNApin | 13263-13926 | 82 |
| tE9 | Terminator tE9 | 15348-15905 | 83 |
| VfSBP | Promoter VfSBP | 16827-17824 | 86 |
| tCatpA | Terminator tCatpA | 19022-19256 | 87 |

Further other binary vectors were constructed according to following experimental steps:

For building the constructs Napin-3, Napin-4 and Napin-5, a triple cassette containing three napin promoters, three different multiple cloning site linkers and three octopine synthase (OCS) terminators was constructed in the plasmid pUC19 (Genbank M77789). A three-gene construct was built by inserting PiΔ6, a Δ6 desaturase gene from *Pythium irregulare* (Hong et al., 2002 High-level production of γ-linolenic acid in *Brassica juncea* using a Δ6 desaturase from *Pythium irregulare*. Plant Physiol. 129, 354-362) (SEQ ID NO: 9), TcΔ5, a Δ5 desaturase gene from *Thraustochytrium* sp. ATCC 26185 (Qiu et al., 2001 Identification of a Δ4 fatty acid desaturase from *Thraustochytrium* sp. involved in the biosynthesis of docosahexanoic acid by heterologous expression in *Saccharomyces cerevisiae* and *Brassica juncea*. J. Biol.

Figure 5:
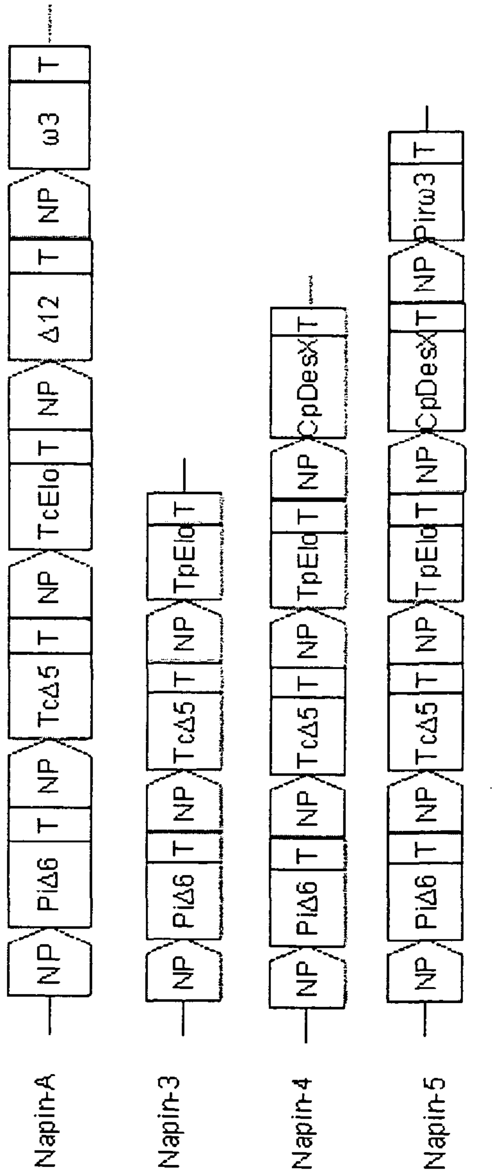
FIG. 5 shows the construction of binary vectors Napin-A, Napin-3, Napin-4, Napin-5 for plant transformation.

Chem. 276, 31561-31566) (SEQ ID NO: 13) and TpElo, an elongase gene from *Thalassiosira pseudonana* (Meyer et al., 2004 Novel fatty acid elongases and their use for the reconstitution of docosahexaenoic acid biosynthesis. J. Lipid Res. 45, 1899-1909) (SEQ ID NO: 11) into this cassette. For the four gene construct Napin-4, an XhoI/SalI fragment containing the desaturase gene CpDesX from *Claviceps purpurea* (Meesapyodsuk et al., 2007 Primary structure, regioselectivity, and evolution of the membrane-bound fatty acid desaturases of *Claviceps purpurea*. J. Biol. Chem. 282, 20191-20199) (SEQ ID NO: 25) linked to a napin promoter and OCS terminator was removed from a single-gene construct and subcloned into the triple gene construct. For the five gene construct Napin-5, the same approach was used to add an ω3 desaturase gene from *Pythium irregulare* (Pi-ω3) (SEQ ID NO: 17). Finally these 3-, 4-, and 5-gene constructs were removed from pUC19 by digestion with AscI, and cloned into the binary vector pSUN2 (FIG. 5). The Napin-A construct, which contained the same a Δ5 and Δ6 desaturases described above, plus a Δ6 elongase from *Thraustochytrium* sp. (SEQ ID NO: 15), an ω3 desaturase gene from *Phytophtera infestans* (SEQ ID NO: 17), and a Δ12 desaturase from *Calendula officianalis* (SEQ ID NO: 72), was constructed as described in Wu et al. (2005) Stepwise engineering to produce high yields of very long-chain polyunsaturated fatty acids in plants. Nat. Biotechnol. 23, 1013-1017). Napin-A represents a five-gene construct with each gene under the control of napin promoter. All binary vectors were transferred into *Agrobacterium tumefaciens* strain GV3101 (pMP90) by electroporation.

The resulting *Agrobacterium* strains were subsequently used for the production of transgenic plants (Deblaere et al. 1984, Nucl. Acids. Res. 13: 4777-4788).

Example 3

Production of Transgenic Plants a) Generation of Transgenic Rape Seed Plants (Amended Protocol According to Moloney et al. 1992, Plant Cell Reports, 8:238-242)

For the transformation of rapeseed plants a 1:50 dilution of an overnight culture of positive transformed acrobacteria colonies grown in Murashige-Skoog Medium (Murashige and Skoog 1962 Physiol. Plant. 15, 473) supplemented by 3% saccharose (3MS-Medium) was used. Petiols or Hypocotyledones of sterial rapeseed plants were incubated in a petri dish with a 1:50 acrobacterial dilusion for 5-10 minutes. This was followed by a tree day co-incubation in darkness at 25° C. on 3MS-Medium with 0.8% bacto-Agar. After three days the culture was put on to 16 hours light/8 hours darkness weekly on MS-medium containing 500 mg/l Claforan (Cefotaxime-Natrium), 50 mg/l Kanamycine, 20 mikroM Benzylaminopurin (BAP) and 1.6 g/l Glucose. Growing sprouts were transferred to MS-Medium containing 2% saccharose, 250 mg/l Claforan and 0.8% Bacto-Agar. Even after three weeks no root formation was observed, a growth hormone 2-Indolbutyl acid was added to the medium for enhancing root formation.

Regenerated sprouts have been obtained on 2MS-Medium with Kanamycine and Claforan and were transferred to the green house for sprouting. After flowering, the mature seeds were harvested and analysed for expression of the genes via lipid analysis as described in Qui et al. 2001, J. Biol. Chem. 276, 31561-31566.

b) Generation of Transgenic *Brassica carinata* Plants (Amended Protocol According to Moloney et al. 1992, Plant Cell Reports, 8:238-242)

Seeds of *B. carinata* lines 090-1163 (high erucic acid line) and 10H3 (zero-erucic acid line) were used for transformation. The protocol described by Moloney et al. (1992) was used for *B. carinata* transformation. Cotyledon petioles from 5 to 6 days old seedlings were excised and inoculated with *A. tumefaciens* strain GV3101 containing the desired gene construct and co-cultured for two days at 22° C. before being transferred to the regeneration medium containing 25 mg/L kanamycin.

c) Production of Transgenic Flax Plants

The production of transgenic flax plants can be carried out according to the method of Bell et al., 1999, In Vitro Cell. Dev. Biol. Plant 35(6):456-465 using particle bombardment. Acrobacterial transformation could be carried out according to Mlynarova et al. (1994), Plant Cell Report 13: 282-285.

All obtained putative transgenic plants for all experiments were validated by PCR analysis.

Example 4

Lipid Extraction

Lipids can be extracted as described in the standard literature including Ullman, Encyclopedia of Industrial Chemistry, Bd. A2, S. 89-90 and S. 443-613, VCH: Weinheim (1985); Fallon, A., et al., (1987) "Applications of HPLC in Biochemistry" in: Laboratory Techniques in Biochemistry and Molecular Biology, Bd. 17; Rehm et al. (1993) Biotechnology, Bd. 3, Kapitel III: "Product recovery and purification", S. 469-714, VCH: Weinheim; Better, P. A., et al. (1988) Bioseparations: downstream processing for Biotechnology, John Wiley and Sons; Kennedy, J. F., und Cabral, J. M. S. (1992) Recovery processes for biological Materials, John Wiley and Sons; Shaeiwitz, J. A., und Henry, J. D. (1988) Biochemical Separations, in: Ullmann's Encyclopedia of Industrial Chemistry, Bd. B3; Kapitel 11, S. 1-27, VCH: Weinheim; und Dechow, F. J. (1989) Separation and purification techniques in biotechnology, Noyes Publications.

Alternatively, extraction will be carried out as described in Cahoon et al. (1999) Proc. Natl. Acad. Sci. USA 96 (22): 12935-12940, und Browse et al. (1986) Analytic Biochemistry 152:141-145. Quantitative and qualitative analysis of lipids or fatty acids are described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 S. (Oily Press Lipid Library; 1); "Progress in Lipid Research, Oxford: Pergamon Press, 1 (1952)-16 (1977) u.d.T.: Progress in the Chemistry of Fats and Other Lipids CODEN.

Based on the analysed lipids, the expression of the introduced genes (desaturases and elongases) can be determined since the lipid pattern of successfully transformed plant seeds will differ from the pattern of control plant seeds. Fatty acid analyses of seeds were performed by GC as described by Qiu et al. J. Biol. Chem. 276, 31561-31566.

Example 5

Production of Novel Plant Oils

Figure 6:
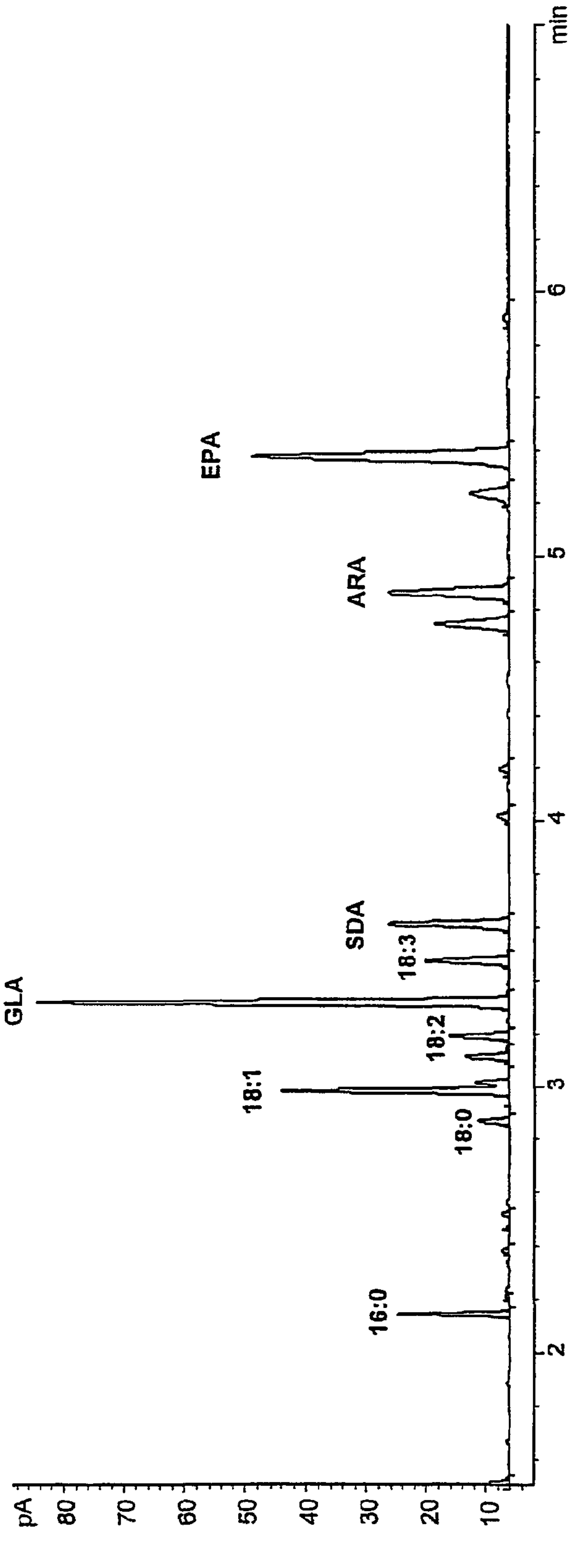
FIG. 6 shows gas chromatography traces of seed oil from *Brassica napus* lines transformed with construct LJB1139 producing high levels of EPA.

For the construct LJB1139 (SEQ ID NO: 71) transgenic *Brassica napus* plants were obtained. Fatty acid analysis of seeds revealed that the expected new fatty acids were produced (FIG. 6). Oleic and linoleic acid were reduced compared to non-transgenic *Brassica napus* oil to 11.7% and 2.3%, respectively. GLA (24.4%) and SDA (6.8%) are newly produced fatty acids. Further high levels of EPA could be achieved (up to 21.7% EPA). The oil constitutes very beneficial fatty acids for human consumption and feed. Other gene combinations producing beneficial fatty acid compositions are with removing SEQ ID NO: 23 in LJB1139 and adding SEQ ID NO: 25, SEQ ID NO: 27 or SEQ ID NO: 29, respectively. Further removing SEQ ID NO: 11 and adding SEQ ID NO: 133 results in another novel fatty acid spectrum For the high-erucic acid *B. carinata* line transgenic plants carrying the Napin-A construct were obtained. The plants produced the expected new fatty acids (Table 7). In these plants, GLA and SDA averaged 18.2% and 2.9% of total fatty acids in seed, respectively. The amount of ARA ranged from 0.4-4.3% (average: 2.8%), while EPA reached an average level of 9.3%, with the highest value observed being 13.7%. The average amount of DPA was 1.4%. Both □6 and □5 desaturases functioned very well, with conversion levels of 81.5% and 87.1%, respectively, while the □6 elongase showed a conversion level of 42.5%.

TABLE 7

Gas chromatographic analysis of seed oil from transgenic high-erucic acid *B. carinata* lines.

| | *B. carinata* high erucic line | |
|---|---|---|
| Fatty acid | Control | Transgenic |
| 16:0 | 5.3 ± 0.7 | 6.3 ± 1.2 |
| 18:0 | 1.2 ± 0.2 | 1.5 ± 0.4 |
| 18:1n-9 (OA) | 7.3 ± 0.7 | 5.5 ± 3.9 |
| 18:1n-11 | 1.5 ± 0.2 | 1.7 ± 0.2 |
| 18:2n-9 | 0.0 | 0.2 ± 0.3 |
| 18:2n-6 (LA) | 16.5 ± 0.9 | 5.8 ± 4.2 |
| 18:3n-6 (GLA) | 0.0 | 18.2 ± 4.2 |
| | | (8.9-23.3) |
| 18:3n-3 (ALA) | 16.0 ± 1.3 | 2.4 ± 2.1 |
| 18:4n-3 (SDA) | 0.0 | 2.9 ± 0.6 |
| | | (2.8-4.5) |
| 20:1n-9 | 6.2 ± 1.0 | 4.5 ± 0.6 |
| 20:1n-7 | 1.4 ± 0.1 | 1.7 ± 0.3 |
| 20:3n-6 (DGLA) | 0.0 | 0.9 ± 0.2 |
| 20:4n-6 (AA) | 0.0 | 2.8 ± 1.5 |
| | | (0.4-4.3) |
| 20:4n-3 (ETA) | 0.0 | 1.0 ± 0.4 |
| 20:5n-3 (EPA) | 0.0 | 9.3 ± 4.4 |
| | | (1.4-13.7) |
| 22:5n-3 (DPA) | 0.0 | 1.4 ± 0.9 |
| Erucic | 36.1 ± 2.4 | 25.7 ± 3.6 |
| Other | 8.5 ± 1.5 | 8.4 ± 1.8 |

For the low-erucic acid *Brassica carinata* line transgenic plants carrying the Napin-A construct were obtained, and the seeds contained the expected novel fatty acids at various levels (Table 8). The amounts of GLA and SDA averaged 29.6% (range: 27.7-31.7%) and 6.2% (range: 3.9-8.1%) of total fatty acids, respectively. While ARA had an average level of 6.5% (range: 6.1-6.9%), EPA reached 25.0% in an individual seed with an average of 20.2%. DPA content averaged 2.5%. The aggregate amount of novel fatty acids reached 69.2% of total fatty acids. Both the □6 and □5 desaturases functioned very well, with conversion levels of 91.2% and 87.7%, respectively. The □6 elongase showed a conversion level of 47.9% in the low-erucic acid *B. carinata* line, which was higher than was observed in either the high-erucic acid *B. carinata* line. Transgenic low-erucic acid *B. carinata* produced one of the highest levels of 22-carbon PUFAs obtained to date, and this was achieved without the use of an elongase specific for □5-desaturated products.

TABLE 8

Gas chromatographic analysis of seed oil from transgenic low-erucic acid *B. carinata* lines.

| | *B. carinata* low erucic-acid | |
|---|---|---|
| Fatty acid | Control | Transgenic |
| 16:0 | 7.1 ± 0.6 | 5.8 ± 0.5 |
| 18:0 | 1.7 ± 0.3 | 2.1 ± 0.6 |
| 18:1n-9 (OA) | 18.9 ± 8.0 | 4.1 ± 3.3 |
| 18:1n-11 | 3.5 ± 0.3 | 3.8 ± 0.4 |
| 18:2n-9 | 0.0 | 0.4 ± 0.8 |
| 18:2n-6 (LA) | 44.1 ± 3.6 | 4.4 ± 1.2 |
| 18:3n-6 (GLA) | 0.0 | 29.6 ± 1.6 |
| | | (27.7-31.7) |
| 18:3n-3 (ALA) | 21.0 ± 6.4 | 2.3 ± 0.7 |
| 18:4n-3 (SDA) | 0.0 | 6.2 ± 1.7 |
| | 0.0 | (3.9-8.1) |
| 20:1n-9 | 0.0 | 0.0 |
| 20:1n-7 | 0.0 | 0.0 |
| 20:3n-6 (DGLA) | 0.0 | 2.0 ± 0.7 |
| 20:4n-6 (AA) | 0.0 | 6.5 ± 0.3 |
| | 0.0 | (6.1-6.9) |
| 20:4n-3 (ETA) | 0.0 | 2.1 ± 0.7 |
| 20:5n-3 (EPA) | 0.0 | 20.2 ± 4.5 |
| | 0.0 | (15.3-25.0) |
| 22:5n-3 (DPA) | 0.0 | 2.5 ± 0.7 |
| Erucic | 0.0 | 0.0 |
| Other | 3.8 ± 0.7 | 8.1 ± 0.5 |

The effects of two desaturases on EPA production in *B. carinata*

A minimal set of three genes, comprising a$^{\Delta}$5 desaturase, a$^{\Delta}$6 desaturase and a$^{\Delta}$6 elongase, is required for the synthesis of ARA and EPA from endogenous LA ($18:2^{\Delta 9,12}$) and ALA ($18:3^{\Delta 9,12,51}$). In order to quantify the contributions of the two novel desaturase genes, CpDesX and Pi-ω3, to EPA production in transgenic plants, we needed to know the base levels of ARA and EPA in plants carrying the minimal set of three trangenes. For this purpose, gene construct Napin-3 (FIG. 5) containing a$^{\Delta}$6 desaturase from *Pythium irregulare* (SEQ ID NO:9), a$^{\Delta}$5 desaturase from *Thraustochytrium* sp. (SEQ ID NO: 13), and a$^{\Delta}$6 elongase from *Thalassiosira pseudonana* (SEQ ID NO: 11) was introduced into the high-erucic *B. carinata* line. In transgenic seeds of plants carrying Napin-3, GLA and SDA averaged 17.6% and 4.3% of total fatty acids, respectively (Table 9). The amount of ARA reached 12.2% (average: 8.4%), and EPA had an average level of 2.3% (range: 0.8%-3.5%). The $^{\Delta}$6 and $^{\Delta}$5 desaturases functioned very well, with substrate conversion levels of 73.7% and 85.6%, respectively, while the conversion level of the $^{\Delta}$6 elongase was 36.3%. The total amount of novel ω-6 fatty acids (GLA, DGLA and AA) represented 27.5% of seed fatty acids, while ω3 fatty acids (SDA, ETA and EPA) represented 6.9%, indicating that the ω6 pathway was operating more effectively than the ω3 pathway.

TABLE 9

Gas chromatographic analysis of seed oil from transgenic high-erucic acid *B. carinata* lines transformed with construct Napin-3.

| Fatty acid | Wild type | Napin-3 |
|---|---|---|
| 16:0 | 5.3 ± 0.7 | 7.2 ± 1.5 |
| 18:0 | 1.2 ± 0.2 | 1.4 ± 0.4 |
| 18:1n-9 (OA) | 7.3 ± 0.7 | 8.2 ± 3.8 |
| 18:1n-11 | 1.5 ± 0.2 | 2.2 ± 0.7 |

TABLE 9-continued

Gas chromatographic analysis of seed oil from transgenic high-erucic acid *B. carinata* lines transformed with construct Napin-3.

| Fatty acid | Wild type | Napin-3 |
|---|---|---|
| 18:2n-9 | 0.0 | 2.0 ± 1.6 |
| 18:2n-6 (LA) | 16.5 ± 0.9 | 3.6 ± 6.9 |
| 18:3n-6 (GLA) | 0.0 | 17.6 ± 3.8 (13.7-24.2) |
| 18:3n-3 (ALA) | 16.0 ± 1.3 | 2.0 ± 0.6 |
| 18:4n-3 (SDA) | 0.0 | 4.3 ± 1.3 (2.4-6.3) |
| 20:1n-9 | 6.2 ± 1.0 | 4.8 ± 1.3 |
| 20:1n-7 | 1.4 ± 0.1 | 1.8 ± 0.5 |
| 20:3n-6 (DGLA) | 0.0 | 1.5 ± 0.9 |
| 20:4n-6 (AA) | 0.0 | 8.4 ± 2.5 (4.3-12.2) |
| 20:4n-3 (ETA) | 0.0 | 0.3 ± 0.4 |
| 20:5n-3 (EPA) | 0.0 | 2.3 ± 0.8 (0.8-3.5) |
| Erucic | 36.1 ± 2.4 | 25.3 ± 7.3 |
| Other | 8.5 ± 1.5 | 7.2 ± 1.0 |

In experiments in yeast, the 18-carbon ω3 desaturase gene CpDesX was able to convert LA to ALA, and GLA to SDA (Meesapyodsuk et al., 2007). We felt that an increase in the initial ω3 substrate ALA and/or the conversion GLA to SDA might lead to higher EPA production. To determine if CpDesX could increase the level of ω3 fatty acids in plants, this gene was added to the three-gene construct Napin-3, producing the four-gene construct Napin-4. Transgenic plants were obtained. The expression of CpDesX (SEQ ID NO: 25) substantially increased the levels of ω3 fatty acids; SDA reached 9.4% in an individual seed and the average level was 6.3%, while average EPA levels increased to 4.2% from the 2.3% found in transgenic seeds carrying Napin-3 (Table 10). The total amounts of novel ω6 and ω3 fatty acids averaged 19.0% and 10.9%, respectively, indicating an increase of flux through the ω3 pathway due to the activity of the CpDesX desaturase. This increase of ω3 fatty acids suggests that CpDesX can make an important contribution to EPA production in transgenic plants.

TABLE 10

Gas chromatographic analysis of seed oil from transgenic high-erucic acid *B. carinata* lines transformed with construct Napin-4.

| Fatty acid | Wild type | Napin-4 |
|---|---|---|
| 16:0 | 5.3 ± 0.7 | 6.6 ± 1.5 |
| 18:0 | 1.2 ± 0.2 | 1.3 ± 0.4 |
| 18:1n-9 (OA) | 7.3 ± 0.7 | 7.8 ± 2.5 |
| 18:1n-11 | 1.5 ± 0.2 | 1.8 ± 0.5 |
| 18:2n-9 | 0.0 | 0.9 ± 0.6 |
| 18:2n-6 (LA) | 16.5 ± 0.9 | 4.0 ± 3.0 |
| 18:3n-6 (GLA) | 0.0 | 11.8 ± 1.6 (9.0-15.6) |
| 18:3n-3 (ALA) | 16.0 ± 1.3 | 3.2 ± 1.3 |
| 18:4n-3 (SDA) | 0.0 | 6.3 ± 2.0 (4.1-9.4) |
| 20:1n-9 | 6.2 ± 1.0 | 4.6 ± 1.1 |
| 20:1n-7 | 1.4 ± 0.1 | 1.8 ± 0.7 |
| 20:3n-6 (DGLA) | 0.0 | 0.7 ± 0.3 |
| 20:4n-6 (AA) | 0.0 | 6.5 ± 1.9 (1.8-9.5) |
| 20:4n-3 (ETA) | 0.0 | 0.4 ± 0.2 |
| 20:5n-3 (EPA) | 0.0 | 4.2 ± 1.4 (1.0-5.6) |
| Erucic | 36.1 ± 2.4 | 31.2 ± 5.3 |
| Other | 8.5 ± 1.5 | 6.9 ± 2.4 |

To test the activity of the 20-carbon ω3 desaturase Pi-ω3 in converting ARA to EPA in plants, Pi-ω3 was added to the four gene construct Napin-4. Transgenic plants were obtained with producing containing the expected novel fatty acids at various levels (Table 11). Expression of the Pi-ω3 desaturase (SEQ ID NO: 17) results in the effective conversion of ARA to EPA. With the addition of this gene, EPA content increased substantially, from an average level of 4.2% in transgenic seeds carrying Napin-4 to an average level of 9.7% in transgenic seeds with Napin-5, with the highest value observed being 15.5%. The level of novel ω6 and ω3 fatty acids averaged 13.0% and 16.5%, respectively. The high levels of EPA achieved in transgenic seeds carrying the Napin-5 construct can be attributed to the activities of the two novel desaturase genes (CpDesX and Pi-ω3).

TABLE 11

Gas chromatographic analysis of seed oil from transgenic high-erucic acid *B. carinata* lines transformed with construct Napin-5.

| Fatty acid | Wild type | Napin-5 |
|---|---|---|
| 16:0 | 5.3 ± 0.7 | 6.4 ± 1.1 |
| 18:0 | 1.2 ± 0.2 | 1.2 ± 0.2 |
| 18:1n-9 (OA) | 7.3 ± 0.7 | 6.3 ± 2.3 |
| 18:1n-11 | 1.5 ± 0.2 | 1.6 ± 0.2 |
| 18:2n-9 | 0.0 | 1.5 ± 0.9 |
| 18:2n-6 (LA) | 16.5 ± 0.9 | 3.7 ± 3.3 |
| 18:3n-6 (GLA) | 0.0 | 11.1 ± 2.4 (4.8-15.3) |
| 18:3n-3 (ALA) | 16.0 ± 1.3 | 3.4 ± 2.9 |
| 18:4n-3 (SDA) | 0.0 | 6.2 ± 1.8 (2.9-10.9) |
| 20:1n-9 | 6.2 ± 1.0 | 4.2 ± 1.2 |
| 20:1n-7 | 1.4 ± 0.1 | 2.1 ± 0.4 |
| 20:3n-6 (DGLA) | 0.0 | 0.6 ± 0.3 |
| 20:4n-6 (AA) | 0.0 | 1.3 ± 0.4 (0.6-1.8) |
| 20:4n-3 (ETA) | 0.0 | 0.6 ± 0.2 |
| 20:5n-3 (EPA) | 0.0 | 9.7 ± 3.4 (1.5-15.5) |
| Erucic | 36.1 ± 2.4 | 31.1 ± 3.8 |
| Other | 8.5 ± 1.5 | 9.0 ± 1.6 |

Example 6

Optimization of the Production of Novel Oil Products

As demonstrated in Example 5 by combination of different genes and regulatory elements it is possible to produce significant levels of novel fatty acids in the seed oil of different *Brassica* species. For further increase of special fatty acids like ARA, EPA and/or DHA or for the increase of overall production of novel fatty acids, additional genes might be required. Such additional genes could have functions in shuffling of different fatty acids from their respective pools of production (phospholipids, Acyl-CoA) or by esterifying the novel fatty acids to different molecules (diacylglycerol, lysophosphatic acid, lysophosphatidylcholine, lysophosphatidylethanolamine, lysophosphatidylglycerol, lysophosphatidylinositol, lysophosphatidylserine, 1-acyl-phosphatidylcholine etc.). Acyltransferases utilize such activities as described above. In the past there were a number of approaches to isolate such activities to increase the production of novel fatty acids (for example WO2004/076617, WO2004/087902). Beside introducing new gene activities by transforming above described genes in combination with genes as described in Example 5 another method is the modulation of endogenous genes with acyltransferase activities by overexpression or down-regulation (antisense RNA, inverted RNA or miRNA technologies).

For *Brassica* species a number of acyltransferases could be identified, which have beneficial acyltransferase activity in terms of increased levels of ARA, EPA and/or DHA or the overall production of novel fatty acids.

By using *Arabidopsis* homologues as described in Chen et al. (2007) FEBS Lett. 581:5511-5516 the cloning of a number of lysophosphatidyl-active acyltransferases could be isolated from *Brassica napus*. For isolation of the sequences standard PCR methods were used as described in Example 2 using following primer pairs (Table 12). The PCR reactions resulted in 6 fragments coding for full-length ORF sequences coding for amino acid sequences (Table 13).

The ORF sequences shown in Table 13 can be used as described in Example 5 for the production of overexpressing, antisense, inverted RNA or miRNA constructs to up or down-regulate the expression of the respective genes and thereby promoting changes in the levels of novel fatty acids.

TABLE 12

Primer pairs for amplification of *Brassica napus* acyltransferases.

| Name | Primer sequence | SEQ ID NO: |
|---|---|---|
| BnLPLAT1_A_40 | | |
| Fwd: | 5'-atgatatcgatggacatgga | 114 |
| Rev: | 5'-ttattcttctttacgtggctttg | 115 |
| BnLPLAT1_C_40 | | |
| Fwd: | 5'-atgatatcgatggacatgaattc | 116 |
| Rev: | 5'-ttattcctctttacgtggctttg | 117 |
| BnLPLAT2_C_50 | | |
| Fwd: | 5'-atggaatcgctcgacatgag | 118 |
| Rev: | 5'-ttattcttctttccgggtctttg | 119 |
| BnLPEAT1_A_50 | | |
| Fwd: | 5'-atggaatcggagctaaagaa | 120 |
| Rev: | 5'-ttattcttctttctgatggaaaac | 121 |
| BnLPEAT1_C_50 | | |
| Fwd: | 5'-atggagtcggagctaaagga | 122 |
| Rev: | 5'-tcattcttctttctgatggaaaac | 123 |
| BnLPEAT2_70 | | |
| Fwd: | 5'-atggcgaatcctgatttgtc | 124 |
| Rev: | 5'-ttatgttggggacaagatagg | 125 |

TABLE 13

ORF sequences of *Brassica napus* acyltransferases.

| Name | Activity | SEQ ID NO: |
|---|---|---|
| BnLPLAT1_A_40 | Lysophospholipid acyltransferase | 102 |
| BnLPLAT1_C_40 | Lysophospholipid acyltransferase | 104 |
| BnLPLAT2_C_50 | Lysophospholipid acyltransferase | 106 |
| BnLPEAT1_A_50 | Lysophosphatidyl ethanolamine acyltransferase | 108 |
| BnLPEAT1_C_50 | Lysophosphatidyl ethanolamine acyltransferase | 110 |
| BnLPEAT2_70 | Lysophosphatidyl ethanolamine acyltransferase | 112 |

Additional sequence variants of *Brassica napus* acyltransferases as described in Table 13 were identified. The additional sequences could be identified by a PCR approach as described in Example 6 using genomic DNA of the *Brassica napus* variety cv. Kumily as starting material. The sequence variants were functionally tested by overexpressing the respective ORF in a yeast KO mutant defective for the LPLAT activity (similar experimental yeast work as described in Example 1). The following sequence variants were identified:

BnLPLAT1_AA (ORF SEQ ID No. 137) is a variant of BnLPLAT1__40 (SEQ ID No.102);

BnLPLAT1_CC(ORF SEQ ID No. 139) is a variant of BnLPLAT1_C__40 (SEQ ID No.104); and BnLPLAT2_AA (ORF SEQ ID No. 135) is a variant of BnLPLAT2_C__50 (SEQ ID No. 106).

The invention claimed is:

1. An expression cassette comprising a nucleic acid molecule operatively linked to at least one expression control sequence, wherein said nucleic acid molecule is heterologous in relation to said at least one expression control sequence and is selected from the group consisting of:

a) a nucleic acid molecule comprising the nucleotide sequence of SEQ ID NO: 3, 5, 33, 35 or 37;

b) a nucleic acid molecule encoding a polypeptide comprising the amino acid sequence of SEQ ID NO: 4, 6, 34, 36 or 38;

c) a nucleic acid molecule comprising a nucleotide sequence having at least 95% sequence identity to the nucleotide sequence of SEQ ID NO: 3, 5, 33, 35 or 37, wherein said nucleic acid molecule encodes a polypeptide having desaturase activity; and d) a nucleic acid molecule encoding a polypeptide comprising an amino acid sequence having at least 90% sequence identity to the amino acid sequence of SEQ ID NO: 4, 6, 34, 36 or 38, wherein said polypeptide has desaturase activity.

2. A vector comprising the expression cassette of claim 1.

3. The vector of claim 2, which is an expression vector.

4. The vector of claim 3, wherein the at least one expression control sequence is a seed-specific promoter.

5. The vector of claim 4, wherein the seed-specific promoter is selected from the group consisting of Conlinin 1, Conlinin 2, napin, USP, LeB4, Arc, Fae, ACP, LuPXR, SBP and LuFad3.

6. A non-human host cell comprising the expression cassette of claim 1 or transformed with an expression vector comprising said expression cassette.

7. The non-human host cell of claim 6, wherein said host cell is a plant cell.

8. The non-human host cell of claim 7, wherein said plant cell is a cell obtained from an oilseed crop.

9. The non-human host cell of claim 8, wherein the oilseed crop is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, crambe, oil palm, coconuts, groundnuts, sesame seed, castor bean, lesquerella, tallow tree, sheanuts, tungnuts, kapok fruit, poppy seed, jojoba seeds and perilla.

10. The non-human host cell of claim 6, wherein said host cell is a microbial cell.

11. The non-human host cell of claim 10, wherein the microbial cell is selected from the group consisting of *Candida, Cryptococcus, Lipomyces, Rhodosporidium, Yarrowia, Thraustochytrium, Pythium, Schizochytrium* and *Crythecodinium.*

12. A plant or plant seed comprising:

a) the expression cassette of claim 1;

b) a vector comprising the expression cassette of a), or c) a host cell comprising the expression cassette of a) or transformed with the vector of b).

13. A method of producing a polypeptide comprising culturing the non-human host cell of claim 6 in an appropriate culture medium to, thereby, produce the polypeptide encoded by said nucleic acid molecule.

14. A polypeptide produced by the method of claim 13, wherein said polypeptide is a fusion protein comprising the polypeptide encoded by said nucleic acid molecule and a heterologous polypeptide.

15. A method for producing an unsaturated fatty acid, comprising culturing the non-human host cell of claim 6 or a plant or plant seed comprising said host cell such that the unsaturated fatty acid is produced, wherein said host cell is capable of producing oleic acid.

16. The method of claim 15, wherein said method further comprises a step of recovering the unsaturated fatty acid.

17. The method of claim 15, wherein the unsaturated fatty acid is selected from the group consisting of ARA 20:4 (5,8,11,14), EPA 20:5 (5,8,11,14,17), and DHA 22:6 (4,7,10,13,16,19).

18. A method for the manufacture of oil comprising producing an unsaturated fatty acid according to the method of claim 15 and formulating or isolating an oil comprising said unsaturated fatty acid.

19. A method of producing a non-human host cell, plant or plant seed capable of generating an unsaturated fatty acid comprising introducing into a non-human host cell, plant or plant seed the expression cassette of claim 1 or a vector comprising said expression cassette.

20. A method of modulating the production of an unsaturated fatty acid, comprising culturing the non-human host cell of claim 6 or a plant or plant seed comprising said host cell such that modulation of the production of the unsaturated fatty acid occurs.

21. The method of claim 20, wherein said method further comprises a step of recovering the unsaturated fatty acid from said culture.

22. The method of claim 20, wherein the unsaturated fatty acid is selected from the group consisting of ARA 20:4 (5,8,11,14), EPA 20:5 (5,8,11,14,17), and DHA 22:6 (4,7,10,13,16,19).

23. The expression cassette of claim 1, wherein the nucleic acid molecule comprises a nucleotide sequence having the nucleotide sequence of SEQ ID NO: 3, 5, 33, 35 or 37.

24. The expression cassette of claim 1, wherein the nucleic acid molecule comprises a nucleotide sequence that encodes a polypeptide comprising the amino acid sequence of SEQ ID NO: 4, 6, 34, 36 or 38.

25. The expression cassette of claim 1, wherein the nucleic acid molecule comprises a nucleotide sequence having at least 95% sequence identity to the nucleotide sequence of SEQ ID NO: 3, 5, 33, 35 or 37 wherein said nucleic acid molecule encodes a polypeptide having desaturase activity.

26. The expression cassette of claim 1, wherein the nucleic acid molecule comprises a nucleotide sequence that encodes a polypeptide comprising an amino acid sequence having at least 90% sequence identity to the amino acid sequence of SEQ ID NO: 4, 6, 34, 36 or 38, wherein said nucleic acid molecule encodes a polypeptide having desaturase activity.

27. The expression cassette of claim 1, wherein the nucleic acid molecule encodes a polypeptide having desaturase activity and comprising an amino acid sequence having at least 95% sequence identity to the amino acid sequence of SEQ ID NO: 4, 6, 34, 36 or 38.

* * * * *

SEQUENCE LISTING

```
<160> NUMBER OF SEQ ID NOS: 140

<210> SEQ ID NO 1
<211> LENGTH: 1445
<212> TYPE: DNA
<213> ORGANISM: Drechslera tritici-repentis

<400> SEQUENCE: 1

ctgagagaac atgacgacga ctcggccgcc aattccgtct cggcctcgcc ctttgactcg      60

ccggccgggt cagcctcaaa cacctcgctg tcctcgatgg acgagcagcc tgccgtccgc     120

aagaacggca agaggtccag tggcaagctc cttgacacgt acggcaatga gttcgagatc     180

ccggactaca ccatcaagga catccgcgat gccatcccca agcattgctt cgagcgctct     240

gctgtccgtg gtctgggcta cgttgcccgt gaccttgcct cgctcgccgc caccttctac     300

gtcttccaca actacgtgac gcccgagacg atcccttcaa tgccgctacg agctgctctc     360
```

-continued

```
tggaccctat acactgtcct ccagggcttc ttcggcactg gtctttggat cctggcccac    420

gagtgtggtc accaggcttt ctcagagtcc aagctgctca acgacaccgt cggctgggtc    480

tgccactcca tcctcctcgt cccatacttc tcatggaaga tctcccacgg caagcaccac    540

aaggccactg gccacatgga gcgtgacatg gtcttccttc ccaagacccg cgagacctac    600

gctacccgtg tcggcaagat ggtccacgag atctctgagc tcaccgagga ggctcctcta    660

gctaccctca tccacacctt cggccagcag attggtggat ggcctctgta cctcattgcc    720

aacgtcaccg gccacaacca ccacgatcgc cagatcgagg gcaagggtaa gggaaagaag    780

aacggcttct tcggcggtgt caaccacttc ttcccttcca gccccttgta cgagaagcgt    840

gatgagcacc tcatcctcct cagtgatctc ggtcttgcta tcgtcattgg tttcctcacc    900

tgggtcggca agaactgggg cttcaacaat gtcttcgtct ggtacatcat cccttacctg    960

tgggtcaacc actggctcgt tatgatcacc ttcctccagc acaccgaccc tgccctgccc   1020

cactacgacg ccgacacttg gacctacact cgcggtgccg ctgctaccat cgaccgtgag   1080

tttggcttca tcggacgcac tcttctccac ggcattgtcg agacccacgt tctccaccac   1140

tacatctcca ccatcccctt ctaccacgcc gacgaggcta ctgaggccat caagaaggtc   1200

atgggcaagc actaccgttc cgacaccaag ggtggcccaa tgggcttcat gaacgctttg   1260

tggaagacag cccgttggtg ccagtgggtc gagccgagcg ccgaggctga gggtgagggc   1320

aagggtgttc tcttcttccg caaccgcaac ggactaggtg taccacccac gaagatcgag   1380

cctgccggaa ccaagaaggc agccaagatg gaggtcggcc ctgagagtga caacgagtaa   1440

gcgac                                                               1445


<210> SEQ ID NO 2
<211> LENGTH: 475
<212> TYPE: PRT
<213> ORGANISM: Drechslera tritici-repentis

<400> SEQUENCE: 2

Met Thr Thr Thr Arg Pro Pro Ile Pro Ser Arg Leu Ala Phe Asp Ser
1               5                   10                  15

Pro Ala Gly Ser Ala Ser Asn Thr Ser Leu Ser Ser Met Asp Glu Gln
            20                  25                  30

Pro Ala Val Arg Lys Asn Gly Lys Arg Ser Ser Gly Lys Leu Leu Asp
        35                  40                  45

Thr Tyr Gly Asn Glu Phe Glu Ile Pro Asp Tyr Thr Ile Lys Asp Ile
    50                  55                  60

Arg Asp Ala Ile Pro Lys His Cys Phe Glu Arg Ser Ala Val Arg Gly
65                  70                  75                  80

Leu Gly Tyr Val Ala Arg Asp Leu Ala Ser Leu Ala Ala Thr Phe Tyr
                85                  90                  95

Val Phe His Asn Tyr Val Thr Pro Glu Thr Ile Pro Ser Met Pro Leu
            100                 105                 110

Arg Ala Ala Leu Trp Thr Leu Tyr Thr Val Leu Gln Gly Phe Phe Gly
        115                 120                 125

Thr Gly Leu Trp Ile Leu Ala His Glu Cys Gly His Gln Ala Phe Ser
    130                 135                 140

Glu Ser Lys Leu Leu Asn Asp Thr Val Gly Trp Val Cys His Ser Ile
145                 150                 155                 160

Leu Leu Val Pro Tyr Phe Ser Trp Lys Ile Ser His Gly Lys His His
                165                 170                 175
```

Lys Ala Thr Gly His Met Glu Arg Asp Met Val Phe Leu Pro Lys Thr
180 185 190

Arg Glu Thr Tyr Ala Thr Arg Val Gly Lys Met Val His Glu Ile Ser
195 200 205

Glu Leu Thr Glu Glu Ala Pro Leu Ala Thr Leu Ile His Thr Phe Gly
210 215 220

Gln Gln Ile Gly Gly Trp Pro Leu Tyr Leu Ile Ala Asn Val Thr Gly
225 230 235 240

His Asn His His Asp Arg Gln Ile Glu Gly Lys Gly Lys Gly Lys Lys
245 250 255

Asn Gly Phe Phe Gly Gly Val Asn His Phe Phe Pro Ser Ser Pro Leu
260 265 270

Tyr Glu Lys Arg Asp Glu His Leu Ile Leu Leu Ser Asp Leu Gly Leu
275 280 285

Ala Ile Val Ile Gly Phe Leu Thr Trp Val Gly Lys Asn Trp Gly Phe
290 295 300

Asn Asn Val Phe Val Trp Tyr Ile Ile Pro Tyr Leu Trp Val Asn His
305 310 315 320

Trp Leu Val Met Ile Thr Phe Leu Gln His Thr Asp Pro Ala Leu Pro
325 330 335

His Tyr Asp Ala Asp Thr Trp Thr Tyr Thr Arg Gly Ala Ala Ala Thr
340 345 350

Ile Asp Arg Glu Phe Gly Phe Ile Gly Arg Thr Leu Leu His Gly Ile
355 360 365

Val Glu Thr His Val Leu His His Tyr Ile Ser Thr Ile Pro Phe Tyr
370 375 380

His Ala Asp Glu Ala Thr Glu Ala Ile Lys Lys Val Met Gly Lys His
385 390 395 400

Tyr Arg Ser Asp Thr Lys Gly Gly Pro Met Gly Phe Met Asn Ala Leu
405 410 415

Trp Lys Thr Ala Arg Trp Cys Gln Trp Val Glu Pro Ser Ala Glu Ala
420 425 430

Glu Gly Glu Gly Lys Gly Val Leu Phe Phe Arg Asn Arg Asn Gly Leu
435 440 445

Gly Val Pro Pro Thr Lys Ile Glu Pro Ala Gly Thr Lys Lys Ala Ala
450 455 460

Lys Met Glu Val Gly Pro Glu Ser Asp Asn Glu
465 470 475

<210> SEQ ID NO 3
<211> LENGTH: 1259
<212> TYPE: DNA
<213> ORGANISM: Cylindrocarpon heteronema

<400> SEQUENCE: 3
gatactaagc caccaacatg gcggtccgac aacgcacctc gtcgaccacg actacgctcg 60
tggtcgagaa gccggctacc actgtcatcg tggagcccgt cactcagatc ctccctgagc 120
ccattttccc cgacatcaag tccatcaagg atgccatccc cgcccactgc ttccagccct 180
ccctcttcac gtcctactac tatgtcgtcc gcgacttcac catggtcggc accctcgtct 240
gggccgccct gaccttcatc ccctccatcc ccgatccgat cctccgcggc gccgcctgga 300
tgctgtacgg cttcgtccag ggcctcttct gtaccggcat ctggattctc ggccacgagt 360
gcggccacgg cgccttctcc ctgcacaaca aggtcaacaa catcaccggc tgggccctcc 420

-continued

```
acagcttcct cctggtcccc ttcttctcgt ggaagttctc ccaccaccgc caccatctct    480

accacggcca catggagaag gacatggcct ttgtccccgc caccgagccc aagacgtcgc    540

gccagactat gctcgccggt atcggtctcg acgagctgtt tgaggacact cccctcttcc    600

agaccctgcg cctcgtcggc caccagctct ttggctggca gatctacctg ctgttcaacg    660

ccacctcggg caagggcagc atgcagcgtg aggttggcgg catcagcaag tggcttcgcg    720

tgagccattt cgaccccacc agcgccgtct tccgccccaa cgaggccatc ttcatcttcc    780

tctccgacgt cggcctggcc ctcatggcca ccgtgctgta ctttgtctcc cagaagatcg    840

gtgtctcgac caccttcctc ctctacggcg ttccctacct ctgggttcac cactggcttg    900

tcgccatcac ctacctccac caccaccacg ccgacgtccc tcactacacc cccgagggct    960

ggacatacgt caagggcgcg ctggccactg tcgaccggga gtttggcttc atcggcaagc   1020

accttttcca cggaattatc gagaagcacg tcatccacca ccttttccct cgcattccct   1080

tctacaaggc tgacgaggcc accgaggctg ccctgccggt gctgggcaag cattacgttc   1140

gagactctcg cagcttcctt ggacagcttt ggtctgtctt tggatcgctc aagtatgttg   1200

agcacgaccc cacccgccct ggcgcgatga ggtgggcgaa atagagggct cgtagaacg    1259
```

<210> SEQ ID NO 4
<211> LENGTH: 408
<212> TYPE: PRT
<213> ORGANISM: Cylindrocarpon heteronema

<400> SEQUENCE: 4

```
Met Ala Val Arg Gln Arg Thr Ser Ser Thr Thr Thr Thr Leu Val Val
1               5                   10                  15

Glu Lys Pro Ala Thr Thr Val Ile Val Glu Pro Val Thr Gln Ile Leu
            20                  25                  30

Pro Glu Pro Ile Phe Pro Asp Ile Lys Ser Ile Lys Asp Ala Ile Pro
        35                  40                  45

Ala His Cys Phe Gln Pro Ser Leu Phe Thr Ser Tyr Tyr Tyr Val Val
    50                  55                  60

Arg Asp Phe Thr Met Val Gly Thr Leu Val Trp Ala Ala Leu Thr Phe
65                  70                  75                  80

Ile Pro Ser Ile Pro Asp Pro Ile Leu Arg Gly Ala Ala Trp Met Leu
                85                  90                  95

Tyr Gly Phe Val Gln Gly Leu Phe Cys Thr Gly Ile Trp Ile Leu Gly
            100                 105                 110

His Glu Cys Gly His Gly Ala Phe Ser Leu His Asn Lys Val Asn Asn
        115                 120                 125

Ile Thr Gly Trp Ala Leu His Ser Phe Leu Leu Val Pro Phe Phe Ser
    130                 135                 140

Trp Lys Phe Ser His His Arg His His Leu Tyr His Gly His Met Glu
145                 150                 155                 160

Lys Asp Met Ala Phe Val Pro Ala Thr Glu Pro Lys Thr Ser Arg Gln
                165                 170                 175

Thr Met Leu Ala Gly Ile Gly Leu Asp Glu Leu Phe Glu Asp Thr Pro
            180                 185                 190

Leu Phe Gln Thr Leu Arg Leu Val Gly His Gln Leu Phe Gly Trp Gln
        195                 200                 205

Ile Tyr Leu Leu Phe Asn Ala Thr Ser Gly Lys Gly Ser Met Gln Arg
    210                 215                 220

Glu Val Gly Gly Ile Ser Lys Trp Leu Arg Val Ser His Phe Asp Pro
```

-continued

```
225                 230                 235                 240

Thr Ser Ala Val Phe Arg Pro Asn Glu Ala Ile Phe Ile Phe Leu Ser
                245                 250                 255

Asp Val Gly Leu Ala Leu Met Ala Thr Val Leu Tyr Phe Val Ser Gln
            260                 265                 270

Lys Ile Gly Val Ser Thr Thr Phe Leu Leu Tyr Gly Val Pro Tyr Leu
        275                 280                 285

Trp Val His His Trp Leu Val Ala Ile Thr Tyr Leu His His His His
    290                 295                 300

Ala Asp Val Pro His Tyr Thr Pro Glu Gly Trp Thr Tyr Val Lys Gly
305                 310                 315                 320

Ala Leu Ala Thr Val Asp Arg Glu Phe Gly Phe Ile Gly Lys His Leu
                325                 330                 335

Phe His Gly Ile Ile Glu Lys His Val Ile His His Leu Phe Pro Arg
            340                 345                 350

Ile Pro Phe Tyr Lys Ala Asp Glu Ala Thr Glu Ala Ala Leu Pro Val
        355                 360                 365

Leu Gly Lys His Tyr Val Arg Asp Ser Arg Ser Phe Leu Gly Gln Leu
    370                 375                 380

Trp Ser Val Phe Gly Ser Leu Lys Tyr Val Glu His Asp Pro Thr Arg
385                 390                 395                 400

Pro Gly Ala Met Arg Trp Ala Lys
                405


<210> SEQ ID NO 5
<211> LENGTH: 1501
<212> TYPE: DNA
<213> ORGANISM: Diplodia natalensis

<400> SEQUENCE: 5

caaccaccca tcatggccac caccgccatg gctcagaacc ctgtcctgag gaggaacgtt      60

acggccacct cgaccgcctc ttcgtccgct ccctcggttg cagtctcgcc caacgactcg     120

cccgcccagt cgccctcgtc gacttcgctg tcgtcgatgg cttcggttga gcccgaggtc     180

aagaactccc gcggcaagct catcgacacg tacggaaacg aattcgagat ccccgactac     240

accatcaagc agatctacga cgccatcccc aagcactgct tcgagcgctc cgccatccgc     300

tccctgagct acgtcgcccg cgatgtcgcc gtcctcgcct ccgtcttcta cgtcttctac     360

aactatgtca ccccggagta catcccctcg accccggtgc gtgctgttct ctgggccctg     420

tacacggtcg tccagggtct gttcggtacc ggcgtctggg tcctagccca cgagtgcggc     480

caccaggcct tctctccctc caagacgctg aacgacaccg tcggctggat ctgccactcg     540

gctctcctcg tcccgtactt ctcgtggaag atttcccacg gcaagcacca caaggccacc     600

ggccacctca ccagggatat ggttttcgtg cccaagacgc gtgaggagta cgcttcgcgc     660

atcggcaagt tcgtccacga gctccacgag ctgaccgagg agacgcccat cgccaccgcc     720

acccacatga tcggccagca gctcgccggc tggttgctgt acctgttcat caacgtcacc     780

ggccacaacc agcacgagaa gcagaaggag ggcaagggcg tcggcaagaa gaacggctgg     840

ttcggcggcg tcaaccactt catgcctagc agccctctgt acgagaagaa ggacgagaag     900

ctcatcctcc tgagcgacct tggtctcgcc atcacgggct acgtcctgta ccaggtcggc     960

tccaagttcg gtttcgccaa cctcttcgtc tggtacatcg tgccgtacct ctgggtcaac    1020

cactggctgg tcgccatcac ctacctccag cacaccgacc cttcgctgcc ccactacgac    1080
```

-continued

```
gccgccacct ggaccttcac gcgtggcgcc gccgccacca tcgaccgcga gtttggcttc   1140

atcggccgcc acatcctgca tggcatcatc gagacgcacg tcctgcacca ctacgtgtcg   1200

accatcccct tctacaacgc cgacgaggcc agcgaggcca tcaagcccgt catgggccgc   1260

cactaccgcg ccgacgtcga ggatggcccc atcggcttcc tcaaggccat gtggaagagc   1320

gcccgctggt gccagtgggt tgagcccagc gccgaggccc agggcgaggg caagggcgtc   1380

ctcttcttcc gcaacaggaa cggcctcggc gtcccgcccg tcgtcattcc ggcgcccggc   1440

accgagaaga aggcaggcat gattgtcggc agcgacagcg acaatgacgc atgaagcgat   1500

g                                                                   1501


<210> SEQ ID NO 6
<211> LENGTH: 493
<212> TYPE: PRT
<213> ORGANISM: Diplodia natalensis

<400> SEQUENCE: 6

Met Ala Thr Thr Ala Met Ala Gln Asn Pro Val Leu Arg Arg Asn Val
1               5                   10                  15

Thr Ala Thr Ser Thr Ala Ser Ser Ser Ala Pro Ser Val Ala Val Ser
            20                  25                  30

Pro Asn Asp Ser Pro Ala Gln Ser Pro Ser Ser Thr Ser Leu Ser Ser
        35                  40                  45

Met Ala Ser Val Glu Pro Glu Val Lys Asn Ser Arg Gly Lys Leu Ile
    50                  55                  60

Asp Thr Tyr Gly Asn Glu Phe Glu Ile Pro Asp Tyr Thr Ile Lys Gln
65                  70                  75                  80

Ile Tyr Asp Ala Ile Pro Lys His Cys Phe Glu Arg Ser Ala Ile Arg
                85                  90                  95

Ser Leu Ser Tyr Val Ala Arg Asp Val Ala Val Leu Ala Ser Val Phe
            100                 105                 110

Tyr Val Phe Tyr Asn Tyr Val Thr Pro Glu Tyr Ile Pro Ser Thr Pro
        115                 120                 125

Val Arg Ala Val Leu Trp Ala Leu Tyr Thr Val Val Gln Gly Leu Phe
    130                 135                 140

Gly Thr Gly Val Trp Val Leu Ala His Glu Cys Gly His Gln Ala Phe
145                 150                 155                 160

Ser Pro Ser Lys Thr Leu Asn Asp Thr Val Gly Trp Ile Cys His Ser
                165                 170                 175

Ala Leu Leu Val Pro Tyr Phe Ser Trp Lys Ile Ser His Gly Lys His
            180                 185                 190

His Lys Ala Thr Gly His Leu Thr Arg Asp Met Val Phe Val Pro Lys
        195                 200                 205

Thr Arg Glu Glu Tyr Ala Ser Arg Ile Gly Lys Phe Val His Glu Leu
    210                 215                 220

His Glu Leu Thr Glu Glu Thr Pro Ile Ala Thr Ala Thr His Met Ile
225                 230                 235                 240

Gly Gln Gln Leu Ala Gly Trp Leu Leu Tyr Leu Phe Ile Asn Val Thr
                245                 250                 255

Gly His Asn Gln His Glu Lys Gln Lys Glu Gly Lys Gly Val Gly Lys
            260                 265                 270

Lys Asn Gly Trp Phe Gly Gly Val Asn His Phe Met Pro Ser Ser Pro
        275                 280                 285

Leu Tyr Glu Lys Lys Asp Glu Lys Leu Ile Leu Leu Ser Asp Leu Gly
```

```
    290                 295                 300

Leu Ala Ile Thr Gly Tyr Val Leu Tyr Gln Val Gly Ser Lys Phe Gly
305                 310                 315                 320

Phe Ala Asn Leu Phe Val Trp Tyr Ile Val Pro Tyr Leu Trp Val Asn
                325                 330                 335

His Trp Leu Val Ala Ile Thr Tyr Leu Gln His Thr Asp Pro Ser Leu
            340                 345                 350

Pro His Tyr Asp Ala Ala Thr Trp Thr Phe Thr Arg Gly Ala Ala Ala
        355                 360                 365

Thr Ile Asp Arg Glu Phe Gly Phe Ile Gly Arg His Ile Leu His Gly
    370                 375                 380

Ile Ile Glu Thr His Val Leu His His Tyr Val Ser Thr Ile Pro Phe
385                 390                 395                 400

Tyr Asn Ala Asp Glu Ala Ser Glu Ala Ile Lys Pro Val Met Gly Arg
                405                 410                 415

His Tyr Arg Ala Asp Val Glu Asp Gly Pro Ile Gly Phe Leu Lys Ala
            420                 425                 430

Met Trp Lys Ser Ala Arg Trp Cys Gln Trp Val Glu Pro Ser Ala Glu
        435                 440                 445

Ala Gln Gly Glu Gly Lys Gly Val Leu Phe Phe Arg Asn Arg Asn Gly
    450                 455                 460

Leu Gly Val Pro Pro Val Val Ile Pro Ala Pro Gly Thr Glu Lys Lys
465                 470                 475                 480

Ala Gly Met Ile Val Gly Ser Asp Ser Asp Asn Asp Ala
                485                 490
```

```
<210> SEQ ID NO 7
<211> LENGTH: 1497
<212> TYPE: DNA
<213> ORGANISM: Stagonospora nodorum

<400> SEQUENCE: 7

ccactatcat ggccaccaca actgcccgcg ctcaggctcc agccatgaag aggaacgtca     60

caacagactc ctcgccctcc acccacgcca acaactcgcc gttcgactcg cctgcgggat    120

cggcttccaa cacctcgctg tcgtcccttg acgagagtcc cgctcagtcc aagagcaacc    180

gcggtgtgct tctcgacaca tacggcaacg agtttgagat tccagactac accatcaagc    240

agatccgtga tgccatcccc aagcactgct tcgagcgctc aggtcttcgt ggtctcggct    300

acgttgcccg tgacatcgct tcgcttgcgg ccgtcttcta cgtcttccac aactatgtca    360

cacccgagac aattccctcg actcctgtcc gcgctggtct gtgggccgtc tacactgtca    420

tccagggtct tttcggtacc ggcctgtggg ttctcgccca tgagtgcggc caccagtcct    480

tctctccctc caaggtgttg aacgacaccg ttggctggtt ctgtcactcc gccctcctcg    540

tcccatactt ctcttggaag atctcgcacg gcaagcacca caaggccact ggtcacatgg    600

agcgcgacat ggtcttcgtc cccaagacgc gagaggtcta cgcttcgcgt atcggaaaga    660

tgatccacga gctcgatgag ctgaccgagg agactcccat cgccactctc ctccacagca    720

tcggtcagca gctcgctgga tggcctttgt acatcatcct caacgttacc ggacacaact    780

accacgagcg ccaggccgag ggcaagggca agggcaagca caatggccca ggcggtggtg    840

tcaaccactt cttcccatcc agccctctgt atgaacgcaa ggatgagcac ctcatcctgc    900

tcagtgatct tggtatcgcc atcaccctcg gtgctcttac ctgggttggc aagaacttcg    960

gattcgccaa cctcttcgtc tggtacatcc tcccctacct ctgggtcaac cactggcttg   1020
```

```
ttgccatcac cttcctccag cacaccgacc ccaccctgcc ccactacgat gccaacacct   1080

ggacttacac tcgtggcgcc gctgccacca tcgaccgcga gtttggcttc atcggacggg   1140

aaattctcca cggcattgtc gagacccacg ttctccacca ctacatctcc acaatcccct   1200

tctaccacgc cgacgaggct tcagaggcta tcaagcctgt catgggcagg cattaccgct   1260

cggatgttga gggcggtcct attggcttct tgaaggccat gtggaagagc gctcgctggt   1320

gccagtgggt cgagcccagc gcggacgccg agggcgaggg caagggtgta ctcttcttcc   1380

gcaaccacaa cggtctcggt gtacctcctc agaagctttc tgccccggtg gccaagtcga   1440

ctgctggcca gcgtgcgaaa atggaggttg gccctgagtc cgacaacgag tagagct      1497
```

<210> SEQ ID NO 8
<211> LENGTH: 494
<212> TYPE: PRT
<213> ORGANISM: Stagonospora nodorum

<400> SEQUENCE: 8

```
Met Ala Thr Thr Thr Ala Arg Ala Gln Ala Pro Ala Met Lys Arg Asn
1               5                   10                  15

Val Thr Thr Asp Ser Ser Pro Ser Thr His Ala Asn Asn Ser Pro Phe
            20                  25                  30

Asp Ser Pro Ala Gly Ser Ala Ser Asn Thr Ser Leu Ser Ser Leu Asp
        35                  40                  45

Glu Ser Pro Ala Gln Ser Lys Ser Asn Arg Gly Val Leu Leu Asp Thr
    50                  55                  60

Tyr Gly Asn Glu Phe Glu Ile Pro Asp Tyr Thr Ile Lys Gln Ile Arg
65                  70                  75                  80

Asp Ala Ile Pro Lys His Cys Phe Glu Arg Ser Gly Leu Arg Gly Leu
                85                  90                  95

Gly Tyr Val Ala Arg Asp Ile Ala Ser Leu Ala Ala Val Phe Tyr Val
            100                 105                 110

Phe His Asn Tyr Val Thr Pro Glu Thr Ile Pro Ser Thr Pro Val Arg
        115                 120                 125

Ala Gly Leu Trp Ala Val Tyr Thr Val Ile Gln Gly Leu Phe Gly Thr
    130                 135                 140

Gly Leu Trp Val Leu Ala His Glu Cys Gly His Gln Ser Phe Ser Pro
145                 150                 155                 160

Ser Lys Val Leu Asn Asp Thr Val Gly Trp Phe Cys His Ser Ala Leu
                165                 170                 175

Leu Val Pro Tyr Phe Ser Trp Lys Ile Ser His Gly Lys His His Lys
            180                 185                 190

Ala Thr Gly His Met Glu Arg Asp Met Val Phe Val Pro Lys Thr Arg
        195                 200                 205

Glu Val Tyr Ala Ser Arg Ile Gly Lys Met Ile His Glu Leu Asp Glu
    210                 215                 220

Leu Thr Glu Glu Thr Pro Ile Ala Thr Leu Leu His Ser Ile Gly Gln
225                 230                 235                 240

Gln Leu Ala Gly Trp Pro Leu Tyr Ile Ile Leu Asn Val Thr Gly His
                245                 250                 255

Asn Tyr His Glu Arg Gln Ala Glu Gly Lys Gly Lys Gly Lys His Asn
            260                 265                 270

Gly Pro Gly Gly Gly Val Asn His Phe Phe Pro Ser Ser Pro Leu Tyr
        275                 280                 285
```

-continued

```
Glu Arg Lys Asp Glu His Leu Ile Leu Leu Ser Asp Leu Gly Ile Ala
    290                 295                 300

Ile Thr Leu Gly Ala Leu Thr Trp Val Gly Lys Asn Phe Gly Phe Ala
305                 310                 315                 320

Asn Leu Phe Val Trp Tyr Ile Leu Pro Tyr Leu Trp Val Asn His Trp
                325                 330                 335

Leu Val Ala Ile Thr Phe Leu Gln His Thr Asp Pro Thr Leu Pro His
            340                 345                 350

Tyr Asp Ala Asn Thr Trp Thr Tyr Thr Arg Gly Ala Ala Ala Thr Ile
        355                 360                 365

Asp Arg Glu Phe Gly Phe Ile Gly Arg Glu Ile Leu His Gly Ile Val
    370                 375                 380

Glu Thr His Val Leu His His Tyr Ile Ser Thr Ile Pro Phe Tyr His
385                 390                 395                 400

Ala Asp Glu Ala Ser Glu Ala Ile Lys Pro Val Met Gly Arg His Tyr
                405                 410                 415

Arg Ser Asp Val Glu Gly Gly Pro Ile Gly Phe Leu Lys Ala Met Trp
            420                 425                 430

Lys Ser Ala Arg Trp Cys Gln Trp Val Glu Pro Ser Ala Asp Ala Glu
        435                 440                 445

Gly Glu Gly Lys Gly Val Leu Phe Phe Arg Asn His Asn Gly Leu Gly
    450                 455                 460

Val Pro Pro Gln Lys Leu Ser Ala Pro Val Ala Lys Ser Thr Ala Gly
465                 470                 475                 480

Gln Arg Ala Lys Met Glu Val Gly Pro Glu Ser Asp Asn Glu
                485                 490
```

<210> SEQ ID NO 9
<211> LENGTH: 1380
<212> TYPE: DNA
<213> ORGANISM: Pythium irregulare

<400> SEQUENCE: 9

```
atggtggacc tcaagcctgg agtgaagcgc ctggtgagct ggaaggagat ccgcgagcac     60

gcgacgcccg cgaccgcgtg gatcgtgatt caccacaagg tctacgacat ctccaagtgg    120

gactcgcacc cgggtggctc cgtgatgctc acgcaggccg gcgaggacgc cacggacgcc    180

ttcgcggtct tccacccgtc ctcggcgctc aagctgctcg agcagttcta cgtcggcgac    240

gtggacgaaa cctccaaggc cgagatcgag ggggagccgg cgagcgacga ggagcgcgcg    300

cgccgcgagc gcatcaacga gttcatcgcg tcctaccgtc gtctgcgcgt caaggtcaag    360

ggcatggggc tctacgacgc cagcgcgctc tactacgcgt ggaagctcgt gagcacgttc    420

ggcatcgcgg tgctctcgat ggcgatctgc ttcttcttca acagtttcgc catgtacatg    480

gtcgccggcg tgattatggg gctcttctac cagcagtccg gatggctggc gcacgacttc    540

ttgcacaacc aggtgtgcga gaaccgcacg ctcggcaacc ttatcggctg cctcgtgggc    600

aacgcctggc agggcttcag catgcagtgg tggaagaaca agcacaacct gcaccacgcg    660

gtgccgaacc tgcacagcgc caaggacgag ggcttcatcg gcgacccgga catcgacacc    720

atgccgctgc tggcgtggtc taaggagatg gcgcgcaagg cgttcgagtc ggcgcacggc    780

ccgttcttca tccgcaacca ggcgttccta tacttcccgc tgctgctgct cgcgcgcctg    840

agctggctcg cgcagtcgtt cttctacgtg ttcaccgagt tctcgttcgg catcttcgac    900

aaggtcgagt tcgacggacc ggagaaggcg ggtctgatcg tgcactacat ctggcagctc    960
```

-continued gcgatcccgt acttctgcaa catgagcctg tttgagggcg tggcatactt cctcatgggc 1020
caggcgtcct gcggcttgct cctggcgctg gtgttcagta ttggccacaa cggcatgtcg 1080
gtgtacgagc gcgaaaccaa gccggacttc tggcagctgc aggtgaccac gacgcgcaac 1140
atccgcgcgt cggtattcat ggactggttc accggtggct tgaactacca gatcgaccat 1200
cacctgttcc cgctcgtgcc gcgccacaac ttgccaaagg tcaacgtgct catcaagtcg 1260
ctatgcaagg agttcgacat cccgttccac gagaccggct tctgggaggg catctacgag 1320
gtcgtggacc acctggcgga catcagcaag gaattcatca ccgagttccc agcgatgtaa 1380

<210> SEQ ID NO 10
<211> LENGTH: 459
<212> TYPE: PRT
<213> ORGANISM: Pythium irregulare

<400> SEQUENCE: 10

Met Val Asp Leu Lys Pro Gly Val Lys Arg Leu Val Ser Trp Lys Glu
1 5 10 15

Ile Arg Glu His Ala Thr Pro Ala Thr Ala Trp Ile Val Ile His His
20 25 30

Lys Val Tyr Asp Ile Ser Lys Trp Asp Ser His Pro Gly Gly Ser Val
35 40 45

Met Leu Thr Gln Ala Gly Glu Asp Ala Thr Asp Ala Phe Ala Val Phe
50 55 60

His Pro Ser Ser Ala Leu Lys Leu Leu Glu Gln Phe Tyr Val Gly Asp
65 70 75 80

Val Asp Glu Thr Ser Lys Ala Glu Ile Glu Gly Glu Pro Ala Ser Asp
85 90 95

Glu Glu Arg Ala Arg Arg Glu Arg Ile Asn Glu Phe Ile Ala Ser Tyr
100 105 110

Arg Arg Leu Arg Val Lys Val Lys Gly Met Gly Leu Tyr Asp Ala Ser
115 120 125

Ala Leu Tyr Tyr Ala Trp Lys Leu Val Ser Thr Phe Gly Ile Ala Val
130 135 140

Leu Ser Met Ala Ile Cys Phe Phe Phe Asn Ser Phe Ala Met Tyr Met
145 150 155 160

Val Ala Gly Val Ile Met Gly Leu Phe Tyr Gln Gln Ser Gly Trp Leu
165 170 175

Ala His Asp Phe Leu His Asn Gln Val Cys Glu Asn Arg Thr Leu Gly
180 185 190

Asn Leu Ile Gly Cys Leu Val Gly Asn Ala Trp Gln Gly Phe Ser Met
195 200 205

Gln Trp Trp Lys Asn Lys His Asn Leu His His Ala Val Pro Asn Leu
210 215 220

His Ser Ala Lys Asp Glu Gly Phe Ile Gly Asp Pro Asp Ile Asp Thr
225 230 235 240

Met Pro Leu Leu Ala Trp Ser Lys Glu Met Ala Arg Lys Ala Phe Glu
245 250 255

Ser Ala His Gly Pro Phe Phe Ile Arg Asn Gln Ala Phe Leu Tyr Phe
260 265 270

Pro Leu Leu Leu Leu Ala Arg Leu Ser Trp Leu Ala Gln Ser Phe Phe
275 280 285

Tyr Val Phe Thr Glu Phe Ser Phe Gly Ile Phe Asp Lys Val Glu Phe
290 295 300

-continued

Asp Gly Pro Glu Lys Ala Gly Leu Ile Val His Tyr Ile Trp Gln Leu
305 310 315 320

Ala Ile Pro Tyr Phe Cys Asn Met Ser Leu Phe Glu Gly Val Ala Tyr
325 330 335

Phe Leu Met Gly Gln Ala Ser Cys Gly Leu Leu Leu Ala Leu Val Phe
340 345 350

Ser Ile Gly His Asn Gly Met Ser Val Tyr Glu Arg Glu Thr Lys Pro
355 360 365

Asp Phe Trp Gln Leu Gln Val Thr Thr Thr Arg Asn Ile Arg Ala Ser
370 375 380

Val Phe Met Asp Trp Phe Thr Gly Gly Leu Asn Tyr Gln Ile Asp His
385 390 395 400

His Leu Phe Pro Leu Val Pro Arg His Asn Leu Pro Lys Val Asn Val
405 410 415

Leu Ile Lys Ser Leu Cys Lys Glu Phe Asp Ile Pro Phe His Glu Thr
420 425 430

Gly Phe Trp Glu Gly Ile Tyr Glu Val Val Asp His Leu Ala Asp Ile
435 440 445

Ser Lys Glu Phe Ile Thr Glu Phe Pro Ala Met
450 455

<210> SEQ ID NO 11
<211> LENGTH: 819
<212> TYPE: DNA
<213> ORGANISM: Thalassiosira pseudonana

<400> SEQUENCE: 11
atggacgcct acaacgctgc tatggacaag attggtgctg ctattattga ctggtctgat 60
cccgatggaa agttccgtgc cgatagagag gactggtggc tctgcgactt ccgtagcgcc 120
atcaccatcg ccctcatcta catcgccttc gtcatcctcg gttccgccgt catgcaatcc 180
ctccccgcaa tggatcccta ccccatcaaa ttcctctaca acgtctccca aatcttcctt 240
tgtgcctaca tgactgtcga ggcgggattt ttggcctacc gcaatggata taccgtcatg 300
ccttgcaatc atttcaatgt gaatgatcct cccgtggcga atcttctttg gttgttttat 360
atttccaagg tgtgggactt ttgggatacc attttcattg tgttggggaa gaagtggcgt 420
caattatctt tcttgcatgt ataccatcac accaccatct ttctattcta ttggctgaat 480
gccaatgtct tgtacgatgg tgacatcttc cttaccatct tgctcaatgg attcatccac 540
acggtgatgt acacgtatta cttcatctgt atgcatacca aagattccaa gacgggcaag 600
agtcttccta tatggtggaa gtcgagtttg acggcgtttc agttgttgca attcactatc 660
atgatgagtc aggctaccta ccttgtcttc cacgggtgtg ataaggtgtc gcttcgtatc 720
acgattgtgt actttgtgta cattttgagt ttgttcttcc tttttgctca gttctttgtg 780
caatcataca tggcacccaa aaagaagaag agtgcttag 819

<210> SEQ ID NO 12
<211> LENGTH: 272
<212> TYPE: PRT
<213> ORGANISM: Thalassiosira pseudonana

<400> SEQUENCE: 12

Met Asp Ala Tyr Asn Ala Ala Met Asp Lys Ile Gly Ala Ala Ile Ile
1 5 10 15

Asp Trp Ser Asp Pro Asp Gly Lys Phe Arg Ala Asp Arg Glu Asp Trp
20 25 30

-continued

```
Trp Leu Cys Asp Phe Arg Ser Ala Ile Thr Ile Ala Leu Ile Tyr Ile
        35                  40                  45

Ala Phe Val Ile Leu Gly Ser Ala Val Met Gln Ser Leu Pro Ala Met
    50                  55                  60

Asp Pro Tyr Pro Ile Lys Phe Leu Tyr Asn Val Ser Gln Ile Phe Leu
65                  70                  75                  80

Cys Ala Tyr Met Thr Val Glu Ala Gly Phe Leu Ala Tyr Arg Asn Gly
                85                  90                  95

Tyr Thr Val Met Pro Cys Asn His Phe Asn Val Asn Asp Pro Pro Val
            100                 105                 110

Ala Asn Leu Leu Trp Leu Phe Tyr Ile Ser Lys Val Trp Asp Phe Trp
        115                 120                 125

Asp Thr Ile Phe Ile Val Leu Gly Lys Lys Trp Arg Gln Leu Ser Phe
    130                 135                 140

Leu His Val Tyr His His Thr Thr Ile Phe Leu Phe Tyr Trp Leu Asn
145                 150                 155                 160

Ala Asn Val Leu Tyr Asp Gly Asp Ile Phe Leu Thr Ile Leu Leu Asn
                165                 170                 175

Gly Phe Ile His Thr Val Met Tyr Thr Tyr Tyr Phe Ile Cys Met His
            180                 185                 190

Thr Lys Asp Ser Lys Thr Gly Lys Ser Leu Pro Ile Trp Trp Lys Ser
        195                 200                 205

Ser Leu Thr Ala Phe Gln Leu Leu Gln Phe Thr Ile Met Met Ser Gln
    210                 215                 220

Ala Thr Tyr Leu Val Phe His Gly Cys Asp Lys Val Ser Leu Arg Ile
225                 230                 235                 240

Thr Ile Val Tyr Phe Val Tyr Ile Leu Ser Leu Phe Phe Leu Phe Ala
                245                 250                 255

Gln Phe Phe Val Gln Ser Tyr Met Ala Pro Lys Lys Lys Lys Ser Ala
            260                 265                 270
```

```
<210> SEQ ID NO 13
<211> LENGTH: 1320
<212> TYPE: DNA
<213> ORGANISM: Thraustochytrium ssp.

<400> SEQUENCE: 13

atgggcaagg gcagcgaggg ccgcagcgcg gcgcgcgaga tgacggccga ggcgaacggc      60

gacaagcgga aaacgattct gatcgagggc gtcctgtacg acgcgacgaa ctttaagcac     120

ccgggcggtt cgatcatcaa cttcttgacc gagggcgagg ccggcgtgga cgcgacgcag     180

gcgtaccgcg agtttcatca gcggtccggc aaggccgaca agtacctcaa gtcgctgccg     240

aagctggatg cgtccaaggt ggagtcgcgg ttctcggcca aagagcaggc gcggcgcgac     300

gccatgacgc gcgactacgc ggcctttcgc gaggagctcg tcgccgaggg gtactttgac     360

ccgtcgatcc cgcacatgat ttaccgcgtc gtggagatcg tggcgctctt cgcgctctcg     420

ttctggctca tgtccaaggc ctcgcccacc tcgctcgtgc tgggcgtggt gatgaacggc     480

attgcgcagg gccgctgcgg ctgggtcatg cacgagatgg gccacgggtc gttcacgggc     540

gtcatctggc tcgacgaccg gatgtgcgag ttcttctacg gcgtcggctg cggcatgagc     600

gggcactact ggaagaacca gcacagcaag caccacgccg cgcccaaccg cctcgagcac     660

gatgtcgatc tcaacacgct gcccctggtc gcctttaacg agcgcgtcgt gcgcaaggtc     720

aagccgggat cgctgctggc gctctggctg cgcgtgcagg cgtacctctt tgcgcccgtc     780
```

-continued

```
tcgtgcctgc tcatcggcct tggctggacg ctctacctgc acccgcgcta catgctgcgc     840

accaagcggc acatggagtt cgtctggatc ttcgcgcgct acattggctg gttctcgctc     900

atgggcgctc tcggctactc gccgggcacc tcggtcggga tgtacctgtg ctcgttcggc     960

ctcggctgca tttacatttt cctgcagttc gccgtcagcc acacgcacct gccggtgacc    1020

aacccggagg accagctgca ctggctcgag tacgcggccg accacacggt gaacattagc    1080

accaagtcct ggctcgtcac gtggtggatg tcgaacctga actttcagat cgagcaccac    1140

ctcttcccca cggcgccgca gttccgcttc aaggaaatca gtcctcgcgt cgaggccctc    1200

ttcaagcgcc acaacctccc gtactacgac ctgccctaca cgagcgcggt ctcgaccacc    1260

tttgccaatc tttattccgt cggccactcg gtcggcgccg acaccaagaa gcaggactga    1320
```

```
<210> SEQ ID NO 14
<211> LENGTH: 439
<212> TYPE: PRT
<213> ORGANISM: Thraustochytrium ssp.

<400> SEQUENCE: 14

Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
            20                  25                  30

Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
```

-continued

```
        275                 280                 285

Trp Ile Phe Ala Arg Tyr Ile Gly Trp Phe Ser Leu Met Gly Ala Leu
    290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350

Ala Asp His Thr Val Asn Ile Ser Thr Lys Ser Trp Leu Val Thr Trp
        355                 360                 365

Trp Met Ser Asn Leu Asn Phe Gln Ile Glu His His Leu Phe Pro Thr
    370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
            420                 425                 430

Ala Asp Thr Lys Lys Gln Asp
        435
```

<210> SEQ ID NO 15
<211> LENGTH: 831
<212> TYPE: DNA
<213> ORGANISM: Thraustochytrium ssp.

<400> SEQUENCE: 15

```
atggacgtcg tcgagcagca atggcgccgc ttcgtggacg ccgtggacaa cggaatcgtg      60

gagttcatgg agcatgagaa gcccaacaag ctgaacgagg gcaagctctt cacctcgacc     120

gaggagatga tggcgcttat cgtcggctac ctggcgttcg tggtcctcgg gtccgccttc     180

atgaaggcct ttgtcgataa gcctttcgag ctcaagttcc tcaagctcgt gcacaacatc     240

ttcctcaccg gtctgtccat gtacatggcc accgagtgcg cgcgccaggc atacctcggc     300

ggctacaagc tctttggcaa cccgatggag aagggcaccg agtcgcacgc cccgggcatg     360

gccaacatca tctacatctt ctacgtgagc aagttcctcg aattcctcga caccgtcttc     420

atgatcctcg gcaagaagtg gaagcagctc agctttctcc acgtctacca ccacgcgagc     480

atcagcttca tctggggcat catcgcccgc ttcgcgcccg gtggcgacgc ctacttctct     540

accatcctca acagcagcgt gcatgtcgtg ctctacggct actacgcctc gaccaccctc     600

ggctacacct tcatgcgccc gctgcgcccg tacattacca ccattcagct cacgcagttc     660

atggccatgg tcgtccagtc cgtctatgac tactacaacc cctgcgacta cccgcagccc     720

ctcgtcaagc tgctcttctg gtacatgctc accatgctcg gcctcttcgg caacttcttc     780

gtgcagcagt acctcaagcc caaggcgccc aagaagcaga agaccatcta a              831
```

<210> SEQ ID NO 16
<211> LENGTH: 276
<212> TYPE: PRT
<213> ORGANISM: Thraustochytrium ssp.

<400> SEQUENCE: 16

```
Met Asp Val Val Glu Gln Gln Trp Arg Arg Phe Val Asp Ala Val Asp
1               5                   10                  15
```

-continued

```
Asn Gly Ile Val Glu Phe Met Glu His Glu Lys Pro Asn Lys Leu Asn
            20                  25                  30

Glu Gly Lys Leu Phe Thr Ser Thr Glu Glu Met Met Ala Leu Ile Val
        35                  40                  45

Gly Tyr Leu Ala Phe Val Val Leu Gly Ser Ala Phe Met Lys Ala Phe
    50                  55                  60

Val Asp Lys Pro Phe Glu Leu Lys Phe Leu Lys Leu Val His Asn Ile
65                  70                  75                  80

Phe Leu Thr Gly Leu Ser Met Tyr Met Ala Thr Glu Cys Ala Arg Gln
                85                  90                  95

Ala Tyr Leu Gly Gly Tyr Lys Leu Phe Gly Asn Pro Met Glu Lys Gly
            100                 105                 110

Thr Glu Ser His Ala Pro Gly Met Ala Asn Ile Ile Tyr Ile Phe Tyr
        115                 120                 125

Val Ser Lys Phe Leu Glu Phe Leu Asp Thr Val Phe Met Ile Leu Gly
    130                 135                 140

Lys Lys Trp Lys Gln Leu Ser Phe Leu His Val Tyr His His Ala Ser
145                 150                 155                 160

Ile Ser Phe Ile Trp Gly Ile Ile Ala Arg Phe Ala Pro Gly Gly Asp
                165                 170                 175

Ala Tyr Phe Ser Thr Ile Leu Asn Ser Ser Val His Val Val Leu Tyr
            180                 185                 190

Gly Tyr Tyr Ala Ser Thr Thr Leu Gly Tyr Thr Phe Met Arg Pro Leu
        195                 200                 205

Arg Pro Tyr Ile Thr Thr Ile Gln Leu Thr Gln Phe Met Ala Met Val
    210                 215                 220

Val Gln Ser Val Tyr Asp Tyr Tyr Asn Pro Cys Asp Tyr Pro Gln Pro
225                 230                 235                 240

Leu Val Lys Leu Leu Phe Trp Tyr Met Leu Thr Met Leu Gly Leu Phe
                245                 250                 255

Gly Asn Phe Phe Val Gln Gln Tyr Leu Lys Pro Lys Ala Pro Lys Lys
            260                 265                 270

Gln Lys Thr Ile
        275
```

<210> SEQ ID NO 17
<211> LENGTH: 1086
<212> TYPE: DNA
<213> ORGANISM: Phytophtora infestans

<400> SEQUENCE: 17

```
atggcgacga aggaggcgta tgtgttcccc actctgacgg agatcaagcg gtcgctacct      60

aaagactgtt tcgaggcttc ggtgcctctg tcgctctact acaccgtgcg ttgtctggtg     120

atcgcggtgg ctctaacctt cggtctcaac tacgctcgcg ctctgcccga ggtcgagagc     180

ttctgggctc tggacgccgc actctgcacg ggctacatct tgctgcaggg catcgtgttc     240

tggggcttct tcacggtggg ccacgatgcc ggccacggcg ccttctcgcg ctaccacctg     300

cttaacttcg tggtgggcac tttcatgcac tcgctcatcc tcacgccctt cgagtcgtgg     360

aagctcacgc accgtcacca ccacaagaac acgggcaaca ttgaccgtga cgaggtcttc     420

tacccgcaac gcaaggccga cgaccacccg ctgtctcgca acctgattct ggcgctcggg     480

gcagcgtggc tcgcctattt ggtcgagggc ttccctcctc gtaaggtcaa ccacttcaac     540

ccgttcgagc ctctgttcgt gcgtcaggtg tcagctgtgg taatctctct tctcgcccac     600
```

ttcttcgtgg ccggactctc catctatctg agcctccagc tgggccttaa gacgatggca 660
atctactact atggacctgt tttgtgttc ggcagcatgc tggtcattac caccttccta 720
caccacaatg atgaggagac cccatggtac gccgactcgg agtggacgta cgtcaagggc 780
aacctctcgt ccgtggaccg atcgtacggc gcgctcattg acaacctgag ccacaacatc 840
ggcacgcacc agatccacca ccttttccct atcattccgc actacaaact caagaaagcc 900
actgcggcct tccaccaggc tttccctgag ctcgtgcgca agagcgacga gccaattatc 960
aaggctttct tccgggttgg acgtctctac gcaaactacg gcgttgtgga ccaggaggcg 1020
aagctcttca cgctaaagga agccaaggcg gcgaccgagg cggcggccaa gaccaagtcc 1080
acgtaa 1086

<210> SEQ ID NO 18
<211> LENGTH: 361
<212> TYPE: PRT
<213> ORGANISM: Phytophtora infestans

<400> SEQUENCE: 18

Met Ala Thr Lys Glu Ala Tyr Val Phe Pro Thr Leu Thr Glu Ile Lys
1 5 10 15

Arg Ser Leu Pro Lys Asp Cys Phe Glu Ala Ser Val Pro Leu Ser Leu
20 25 30

Tyr Tyr Thr Val Arg Cys Leu Val Ile Ala Val Ala Leu Thr Phe Gly
35 40 45

Leu Asn Tyr Ala Arg Ala Leu Pro Glu Val Glu Ser Phe Trp Ala Leu
50 55 60

Asp Ala Ala Leu Cys Thr Gly Tyr Ile Leu Leu Gln Gly Ile Val Phe
65 70 75 80

Trp Gly Phe Phe Thr Val Gly His Asp Ala Gly His Gly Ala Phe Ser
85 90 95

Arg Tyr His Leu Leu Asn Phe Val Val Gly Thr Phe Met His Ser Leu
100 105 110

Ile Leu Thr Pro Phe Glu Ser Trp Lys Leu Thr His Arg His His His
115 120 125

Lys Asn Thr Gly Asn Ile Asp Arg Asp Glu Val Phe Tyr Pro Gln Arg
130 135 140

Lys Ala Asp Asp His Pro Leu Ser Arg Asn Leu Ile Leu Ala Leu Gly
145 150 155 160

Ala Ala Trp Leu Ala Tyr Leu Val Glu Gly Phe Pro Pro Arg Lys Val
165 170 175

Asn His Phe Asn Pro Phe Glu Pro Leu Phe Val Arg Gln Val Ser Ala
180 185 190

Val Val Ile Ser Leu Leu Ala His Phe Phe Val Ala Gly Leu Ser Ile
195 200 205

Tyr Leu Ser Leu Gln Leu Gly Leu Lys Thr Met Ala Ile Tyr Tyr Tyr
210 215 220

Gly Pro Val Phe Val Phe Gly Ser Met Leu Val Ile Thr Thr Phe Leu
225 230 235 240

His His Asn Asp Glu Glu Thr Pro Trp Tyr Ala Asp Ser Glu Trp Thr
245 250 255

Tyr Val Lys Gly Asn Leu Ser Ser Val Asp Arg Ser Tyr Gly Ala Leu
260 265 270

Ile Asp Asn Leu Ser His Asn Ile Gly Thr His Gln Ile His His Leu
275 280 285

```
Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
        355                 360
```

<210> SEQ ID NO 19
<211> LENGTH: 1371
<212> TYPE: DNA
<213> ORGANISM: Ostreococcus tauri

<400> SEQUENCE: 19

```
atgtgtgttg agaccgagaa caacgatgga atccctactg tggagatcgc tttcgatgga     60

gagagagaaa gagctgaggc taacgtgaag ttgtctgctg agaagatgga acctgctgct    120

ttggctaaga ccttcgctag aagatacgtg gttatcgagg gagttgagta cgatgtgacc    180

gatttcaaac atcctggagg aaccgtgatt ttctacgctc tctctaacac tggagctgat    240

gctactgagg ctttcaagga gttccaccac agatctagaa aggctaggaa ggctttggct    300

gctttgcctt ctagacctgc taagaccgct aaagtggatg atgctgagat gctccaggat    360

ttcgctaagt ggagaaagga gttggagagg gacggattct tcaagccttc tcctgctcat    420

gttgcttaca gattcgctga gttggctgct atgtacgctt tgggaaccta cttgatgtac    480

gctagatacg ttgtgtcctc tgtgttggtt tacgcttgct tcttcggagc tagatgtgga    540

tgggttcaac atgagggagg acattcttct ttgaccggaa acatctggtg ggataagaga    600

atccaagctt tcactgctgg attcggattg gctggatctg gagatatgtg gaactccatg    660

cacaacaagc accatgctac tcctcaaaaa gtgaggcacg atatggattt ggataccact    720

cctgctgttg ctttcttcaa caccgctgtg gaggataata gacctagggg attctctaag    780

tactggctca gattgcaagc ttggaccttc attcctgtga cttctggatt ggtgttgctc    840

ttctggatgt tcttcctcca tccttctaag gctttgaagg gaggaaagta cgaggagctt    900

gtgtggatgt tggctgctca tgtgattaga acctggacca ttaaggctgt tactggattc    960

accgctatgc aatcctacgg actcttcttg gctacttctt gggtttccgg atgctacttg   1020

ttcgctcact tctctacttc tcacacccat ttggatgttg ttcctgctga tgagcatttg   1080

tcttgggtta ggtacgctgt ggatcacacc attgatatcg atccttctca gggatgggtt   1140

aactggttga tgggatactt gaactgccaa gtgattcatc acctcttccc ttctatgcct   1200

caattcagac aacctgaggt gtccagaaga ttcgttgctt tcgctaagaa gtggaacctc   1260

aactacaagg tgatgactta tgctggagct tggaaggcta ctttgggaaa cctcgataat   1320

gtgggaaagc actactacgt gcacggacaa cattctggaa agaccgcttg a            1371
```

<210> SEQ ID NO 20
<211> LENGTH: 456
<212> TYPE: PRT
<213> ORGANISM: Ostreococcus tauri

<400> SEQUENCE: 20

```
Met Cys Val Glu Thr Glu Asn Asn Asp Gly Ile Pro Thr Val Glu Ile
```

-continued

```
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
    210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Leu Phe Trp Met Phe Phe Leu His Pro
        275                 280                 285

Ser Lys Ala Leu Lys Gly Gly Lys Tyr Glu Glu Leu Val Trp Met Leu
    290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
            340                 345                 350

Val Val Pro Ala Asp Glu His Leu Ser Trp Val Arg Tyr Ala Val Asp
        355                 360                 365

His Thr Ile Asp Ile Asp Pro Ser Gln Gly Trp Val Asn Trp Leu Met
    370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Ala Gly Ala Trp Lys
            420                 425                 430
```

```
Ala Thr Leu Gly Asn Leu Asp Asn Val Gly Lys His Tyr Tyr Val His
        435                 440                 445

Gly Gln His Ser Gly Lys Thr Ala
    450                 455


<210> SEQ ID NO 21
<211> LENGTH: 1197
<212> TYPE: DNA
<213> ORGANISM: Phytophtora sojae

<400> SEQUENCE: 21

atggctattt tgaaccctga ggctgattct gctgctaacc tcgctactga ttctgaggct      60

aagcaaagac aattggctga ggctggatac actcatgttg agggtgctcc tgctcctttg     120

cctttggagt tgcctcattt ctctctcaga gatctcagag ctgctattcc taagcactgc     180

ttcgagagat ctttcgtgac ctccacctac tacatgatca agaacgtgtt gacttgcgct     240

gctttgttct acgctgctac cttcattgat agagctggag ctgctgctta tgttttgtgg     300

cctgtgtact ggttcttcca gggatcttac ttgactggag tgtgggttat cgctcatgag     360

tgtggacatc aggcttattg ctcttctgag gtggtgaaca acttgattgg actcgtgttg     420

cattctgctt tgttggtgcc ttaccactct tggagaatct ctcacagaaa gcaccattcc     480

aacactggat cttgcgagaa cgatgaggtt ttcgttcctg tgaccagatc tgtgttggct     540

tcttcttgga acgagacctt ggaggattct cctctctacc aactctaccg tatcgtgtac     600

atgttggttg ttggatggat gcctggatac ctcttcttca acgctactgg acctactaag     660

tactggggaa agtctaggtc tcacttcaac ccttactccg ctatctatgc tgatagggag     720

agatggatga tcgtgctctc cgatattttc ttggtggcta tgttggctgt tttggctgct     780

ttggtgcaca ctttctcctt caacaccatg gtgaagttct acgtggtgcc ttacttcatt     840

gtgaacgctt acttggtgtt gattacctac ctccaacaca ccgataccta catccctcat     900

ttcagagagg gagagtggaa ttggttgaga ggagctttgt gcactgtgga tagatcattt     960

ggtccattcc tcgattctgt ggtgcataga atcgtggata cccatgtttg ccaccacatc    1020

ttctccaaga tgcctttcta tcattgcgag gaggctacca acgctattaa gcctctcctc    1080

ggaaagttct acttgaagga taccactcct gttcctgttg ctctctggag atcttacacc    1140

cattgcaagt tcgttgagga tgatggaaag gtggtgttct acaagaacaa gctctag       1197


<210> SEQ ID NO 22
<211> LENGTH: 398
<212> TYPE: PRT
<213> ORGANISM: Phytophtora sojae

<400> SEQUENCE: 22

Met Ala Ile Leu Asn Pro Glu Ala Asp Ser Ala Ala Asn Leu Ala Thr
1               5                   10                  15

Asp Ser Glu Ala Lys Gln Arg Gln Leu Ala Glu Ala Gly Tyr Thr His
            20                  25                  30

Val Glu Gly Ala Pro Ala Pro Leu Pro Leu Glu Leu Pro His Phe Ser
        35                  40                  45

Leu Arg Asp Leu Arg Ala Ala Ile Pro Lys His Cys Phe Glu Arg Ser
    50                  55                  60

Phe Val Thr Ser Thr Tyr Tyr Met Ile Lys Asn Val Leu Thr Cys Ala
65                  70                  75                  80

Ala Leu Phe Tyr Ala Ala Thr Phe Ile Asp Arg Ala Gly Ala Ala Ala
```

```
                85                  90                  95

Tyr Val Leu Trp Pro Val Tyr Trp Phe Phe Gln Gly Ser Tyr Leu Thr
            100                 105                 110

Gly Val Trp Val Ile Ala His Glu Cys Gly His Gln Ala Tyr Cys Ser
        115                 120                 125

Ser Glu Val Val Asn Asn Leu Ile Gly Leu Val Leu His Ser Ala Leu
    130                 135                 140

Leu Val Pro Tyr His Ser Trp Arg Ile Ser His Arg Lys His His Ser
145                 150                 155                 160

Asn Thr Gly Ser Cys Glu Asn Asp Glu Val Phe Val Pro Val Thr Arg
                165                 170                 175

Ser Val Leu Ala Ser Ser Trp Asn Glu Thr Leu Glu Asp Ser Pro Leu
            180                 185                 190

Tyr Gln Leu Tyr Arg Ile Val Tyr Met Leu Val Val Gly Trp Met Pro
        195                 200                 205

Gly Tyr Leu Phe Phe Asn Ala Thr Gly Pro Thr Lys Tyr Trp Gly Lys
    210                 215                 220

Ser Arg Ser His Phe Asn Pro Tyr Ser Ala Ile Tyr Ala Asp Arg Glu
225                 230                 235                 240

Arg Trp Met Ile Val Leu Ser Asp Ile Phe Leu Val Ala Met Leu Ala
                245                 250                 255

Val Leu Ala Ala Leu Val His Thr Phe Ser Phe Asn Thr Met Val Lys
            260                 265                 270

Phe Tyr Val Val Pro Tyr Phe Ile Val Asn Ala Tyr Leu Val Leu Ile
        275                 280                 285

Thr Tyr Leu Gln His Thr Asp Thr Tyr Ile Pro His Phe Arg Glu Gly
    290                 295                 300

Glu Trp Asn Trp Leu Arg Gly Ala Leu Cys Thr Val Asp Arg Ser Phe
305                 310                 315                 320

Gly Pro Phe Leu Asp Ser Val Val His Arg Ile Val Asp Thr His Val
                325                 330                 335

Cys His His Ile Phe Ser Lys Met Pro Phe Tyr His Cys Glu Glu Ala
            340                 345                 350

Thr Asn Ala Ile Lys Pro Leu Leu Gly Lys Phe Tyr Leu Lys Asp Thr
        355                 360                 365

Thr Pro Val Pro Val Ala Leu Trp Arg Ser Tyr Thr His Cys Lys Phe
    370                 375                 380

Val Glu Asp Asp Gly Lys Val Val Phe Tyr Lys Asn Lys Leu
385                 390                 395
```

<210> SEQ ID NO 23
<211> LENGTH: 1161
<212> TYPE: DNA
<213> ORGANISM: Arabidopsis thaliana

<400> SEQUENCE: 23

```
atggttgttg ctatggacca acgcaccaat gtgaacggag atcccggcgc cggagaccgg      60

aagaaagaag aaaggtttga tccgagtgca caaccaccgt tcaagatcgg agatataagg     120

gcggcgattc ctaagcactg ttgggttaag agtcctttga gatcaatgag ttacgtcgtc     180

agagacatta tcgccgtcgc ggctttggcc atcgctgccg tgtatgttga tagctggttc     240

ctttggcctc tttattgggc cgcccaagga acacttttct gggccatctt tgttctcggc     300

cacgactgtg gacatgggag tttctcagac attcctctac tgaatagtgt ggttggtcac     360
```

```
attcttcatt ctttcatcct cgttccttac catggttgga gaataagcca ccggacacac    420

caccagaacc atggccatgt tgaaaacgac gagtcatggg ttccgttacc agaaagggtg    480

tacaagaaat tgccccacag tactcggatg ctcagataca ctgtccctct ccccatgctc    540

gcatatcctc tctatttgtg ctacagaagt cctggaaaag aaggatcaca ttttaaccca    600

tacagtagtt tatttgctcc aagcgagaga aagcttattg caacttcaac tacttgttgg    660

tccataatgt tcgtcagtct tatcgctcta tctttcgtct tcggtccact cgcggttctt    720

aaagtctacg gtgtaccgta cattatcttt gtgatgtggt tggatgctgt cacgtatttg    780

catcatcatg gtcacgatga gaagttgcct tggtatagag gcaaggaatg gagttatcta    840

cgtggaggat taacaacaat tgatagagat tacggaatct ttaacaacat tcatcacgac    900

attggaactc acgtgatcca tcatctcttc ccacaaatcc ctcactatca cttggtcgac    960

gccacgaaag cagctaaaca tgtgttggga agatactaca gagaaccgaa gacgtcagga   1020

gcaataccga ttcacttggt ggagagtttg gtcgcaagta ttaaaaaaga tcattacgtc   1080

agtgacactg gtgatattgt cttctacgag acagatccag atctctacgt ttatgcttct   1140

gacaaatcta aaatcaatta g                                              1161
```

```
<210> SEQ ID NO 24
<211> LENGTH: 386
<212> TYPE: PRT
<213> ORGANISM: Arabidopsis thaliana

<400> SEQUENCE: 24

Met Val Val Ala Met Asp Gln Arg Thr Asn Val Asn Gly Asp Pro Gly
1               5                   10                  15

Ala Gly Asp Arg Lys Lys Glu Glu Arg Phe Asp Pro Ser Ala Gln Pro
            20                  25                  30

Pro Phe Lys Ile Gly Asp Ile Arg Ala Ala Ile Pro Lys His Cys Trp
        35                  40                  45

Val Lys Ser Pro Leu Arg Ser Met Ser Tyr Val Val Arg Asp Ile Ile
    50                  55                  60

Ala Val Ala Ala Leu Ala Ile Ala Ala Val Tyr Val Asp Ser Trp Phe
65                  70                  75                  80

Leu Trp Pro Leu Tyr Trp Ala Ala Gln Gly Thr Leu Phe Trp Ala Ile
                85                  90                  95

Phe Val Leu Gly His Asp Cys Gly His Gly Ser Phe Ser Asp Ile Pro
            100                 105                 110

Leu Leu Asn Ser Val Val Gly His Ile Leu His Ser Phe Ile Leu Val
        115                 120                 125

Pro Tyr His Gly Trp Arg Ile Ser His Arg Thr His His Gln Asn His
    130                 135                 140

Gly His Val Glu Asn Asp Glu Ser Trp Val Pro Leu Pro Glu Arg Val
145                 150                 155                 160

Tyr Lys Lys Leu Pro His Ser Thr Arg Met Leu Arg Tyr Thr Val Pro
                165                 170                 175

Leu Pro Met Leu Ala Tyr Pro Leu Tyr Leu Cys Tyr Arg Ser Pro Gly
            180                 185                 190

Lys Glu Gly Ser His Phe Asn Pro Tyr Ser Ser Leu Phe Ala Pro Ser
        195                 200                 205

Glu Arg Lys Leu Ile Ala Thr Ser Thr Thr Cys Trp Ser Ile Met Phe
    210                 215                 220

Val Ser Leu Ile Ala Leu Ser Phe Val Phe Gly Pro Leu Ala Val Leu
```

-continued

```
225                 230                 235                 240

Lys Val Tyr Gly Val Pro Tyr Ile Ile Phe Val Met Trp Leu Asp Ala
                245                 250                 255

Val Thr Tyr Leu His His His Gly His Asp Glu Lys Leu Pro Trp Tyr
            260                 265                 270

Arg Gly Lys Glu Trp Ser Tyr Leu Arg Gly Gly Leu Thr Thr Ile Asp
        275                 280                 285

Arg Asp Tyr Gly Ile Phe Asn Asn Ile His His Asp Ile Gly Thr His
    290                 295                 300

Val Ile His His Leu Phe Pro Gln Ile Pro His Tyr His Leu Val Asp
305                 310                 315                 320

Ala Thr Lys Ala Ala Lys His Val Leu Gly Arg Tyr Tyr Arg Glu Pro
                325                 330                 335

Lys Thr Ser Gly Ala Ile Pro Ile His Leu Val Glu Ser Leu Val Ala
            340                 345                 350

Ser Ile Lys Lys Asp His Tyr Val Ser Asp Thr Gly Asp Ile Val Phe
        355                 360                 365

Tyr Glu Thr Asp Pro Asp Leu Tyr Val Tyr Ala Ser Asp Lys Ser Lys
    370                 375                 380

Ile Asn
385
```

<210> SEQ ID NO 25
<211> LENGTH: 1434
<212> TYPE: DNA
<213> ORGANISM: Claviceps purpurea

<400> SEQUENCE: 25

```
atggctgcta ctacctctgc tatgagcaag gatgctgttc ttagaagaac tgctgctgct     60

actactgcta tcgatcacga aagctctacc tctgcttctc cagctgattc tcctagactc    120

tctgcttctt ctacctctct ctcttctctc agctctctcg acgctaagga taaggatgat    180

gagtacgctg gacttcttga tacttacgga aacgctttca cccctcctga tttcactatc    240

aaggatatca gagatgctat ccctaagcac tgcttcgagc gttctgctat caagggatac    300

gcttatatcc tcagagatgt ggcttgcctt tctaccactt tctacctctt ccacaacttc    360

gttacccctg agaacgttcc ttacacccct cttagagttt tcctctgggg agtttacact    420

gctcttcagg gacttttcgg aactggactc tggattatcg ctcacgagtg tggacacggt    480

gctttctctc cttctaccct cactaacgat cttactggat gggttctcca ctctgctctt    540

ctcgtgcctt acttctcttg gaagttctct cactctgctc accacaaggg aaccggaaat    600

atggaaaggg atatggcttt cctccctaga actagggctc aatacgctac cagattcgga    660

agagctatgg atcagcttgg agatctttgc gaggaaaccc ctatctacac tgctggattc    720

cttgttttcc agcagcttct tggatggcct tcttacttga tcgctaacgt tactggacac    780

gatcttcacg agagacagag agagggaaga ggaaagggaa agaagaacgg attcggagga    840

actgttaacc acttcgaccc tcgttctcct atcttcgatg acaagcacgc taagtttatc    900

gttctcagcg atatcggact tggacttgct atcgctgctc ttgtttacct cggaaacaga    960

ttcggatggg ctaacgttgc tgtttggtac ttcgttcctt acctctgggt taaccactgg   1020

atcgttgcta tcactttcct tcagcacact gatcctactc ttcctcacta cactgctgag   1080

gaatggaact tcgttcgtgg agctgctgct acaatcgata gagagatggg atttatcggt   1140

agacacctct tccacggaat cgttgagact cacgtgcttc accactacgt ttcttcaatc   1200
```

-continued

```
cctttctaca acgctgatga ggcttctgag gctatcaagc ctgttatggg aaagcactac   1260

cgttctgaga ctaaggatgg acctatgggt tttatcaggg ctttgtggaa aactgctaga   1320

tggtgtcaat gggttgagcc ttctgctgat gctcaaggtg ctggtgaagg tgttctcttc   1380

ttcaggaaca gaaacggact tggaactaag cctatctcta tgaggaccca gtga         1434


<210> SEQ ID NO 26
<211> LENGTH: 477
<212> TYPE: PRT
<213> ORGANISM: Claviceps purpurea

<400> SEQUENCE: 26

Met Ala Ala Thr Thr Ser Ala Met Ser Lys Asp Ala Val Leu Arg Arg
1               5                   10                  15

Thr Ala Ala Ala Thr Thr Ala Ile Asp His Glu Ser Ser Thr Ser Ala
            20                  25                  30

Ser Pro Ala Asp Ser Pro Arg Leu Ser Ala Ser Ser Thr Ser Leu Ser
        35                  40                  45

Ser Leu Ser Ser Leu Asp Ala Lys Asp Lys Asp Asp Glu Tyr Ala Gly
    50                  55                  60

Leu Leu Asp Thr Tyr Gly Asn Ala Phe Thr Pro Pro Asp Phe Thr Ile
65                  70                  75                  80

Lys Asp Ile Arg Asp Ala Ile Pro Lys His Cys Phe Glu Arg Ser Ala
                85                  90                  95

Ile Lys Gly Tyr Ala Tyr Ile Leu Arg Asp Val Ala Cys Leu Ser Thr
            100                 105                 110

Thr Phe Tyr Leu Phe His Asn Phe Val Thr Pro Glu Asn Val Pro Tyr
        115                 120                 125

Thr Pro Leu Arg Val Phe Leu Trp Gly Val Tyr Thr Ala Leu Gln Gly
    130                 135                 140

Leu Phe Gly Thr Gly Leu Trp Ile Ile Ala His Glu Cys Gly His Gly
145                 150                 155                 160

Ala Phe Ser Pro Ser Thr Leu Thr Asn Asp Leu Thr Gly Trp Val Leu
                165                 170                 175

His Ser Ala Leu Leu Val Pro Tyr Phe Ser Trp Lys Phe Ser His Ser
            180                 185                 190

Ala His His Lys Gly Thr Gly Asn Met Glu Arg Asp Met Ala Phe Leu
        195                 200                 205

Pro Arg Thr Arg Ala Gln Tyr Ala Thr Arg Phe Gly Arg Ala Met Asp
    210                 215                 220

Gln Leu Gly Asp Leu Cys Glu Glu Thr Pro Ile Tyr Thr Ala Gly Phe
225                 230                 235                 240

Leu Val Phe Gln Gln Leu Leu Gly Trp Pro Ser Tyr Leu Ile Ala Asn
                245                 250                 255

Val Thr Gly His Asp Leu His Glu Arg Gln Arg Glu Gly Arg Gly Lys
            260                 265                 270

Gly Lys Lys Asn Gly Phe Gly Gly Thr Val Asn His Phe Asp Pro Arg
        275                 280                 285

Ser Pro Ile Phe Asp Asp Lys His Ala Lys Phe Ile Val Leu Ser Asp
    290                 295                 300

Ile Gly Leu Gly Leu Ala Ile Ala Ala Leu Val Tyr Leu Gly Asn Arg
305                 310                 315                 320

Phe Gly Trp Ala Asn Val Ala Val Trp Tyr Phe Val Pro Tyr Leu Trp
                325                 330                 335
```

```
Val Asn His Trp Ile Val Ala Ile Thr Phe Leu Gln His Thr Asp Pro
            340                 345                 350

Thr Leu Pro His Tyr Thr Ala Glu Glu Trp Asn Phe Val Arg Gly Ala
        355                 360                 365

Ala Ala Thr Ile Asp Arg Glu Met Gly Phe Ile Gly Arg His Leu Phe
    370                 375                 380

His Gly Ile Val Glu Thr His Val Leu His His Tyr Val Ser Ser Ile
385                 390                 395                 400

Pro Phe Tyr Asn Ala Asp Glu Ala Ser Glu Ala Ile Lys Pro Val Met
                405                 410                 415

Gly Lys His Tyr Arg Ser Glu Thr Lys Asp Gly Pro Met Gly Phe Ile
            420                 425                 430

Arg Ala Leu Trp Lys Thr Ala Arg Trp Cys Gln Trp Val Glu Pro Ser
        435                 440                 445

Ala Asp Ala Gln Gly Ala Gly Glu Gly Val Leu Phe Phe Arg Asn Arg
    450                 455                 460

Asn Gly Leu Gly Thr Lys Pro Ile Ser Met Arg Thr Gln
465                 470                 475


<210> SEQ ID NO 27
<211> LENGTH: 1224
<212> TYPE: DNA
<213> ORGANISM: Acanthamoeba castellanii

<400> SEQUENCE: 27

atgactatta ctactaccca gaccttgaac cagaaggctg ctaagaaggg aggaaaggag      60

agggctccaa ttattccaaa ggagaacgct ccattcactt tgggacagat caagggagct     120

atcccacctc atctcttcaa gcactccatg ttgaagtctt tctcctactt gggagtggat     180

ttgttggagt ctaccatctg gttgttcctc atcttgtact tggatggact cactaaggag     240

aacaccttgt tgaactggac ttgctgggtt gcatactggt tgtaccaagg attgacttgg     300

actggaattt gggtgttggc tcatgagtgt ggacatggag gattcgttgc tcaagagtgg     360

ttgaacgata ccgtgggttt cattttccat accgtgctct acgttccata cttctcctgg     420

aagttctctc atgctaagca ccatcactac accaaccaca tgactaagga tgagccattc     480

gtgccacata caatcactcc agagcaaagg gctaaagtgg atcaaggaga gttgccacat     540

ccaaacaagc catccctctt cgctttctac gagagatggg tgatcccatt cgtgatgttg     600

ttcttgggat ggccactcta cttgtctatc aacgcttctg gaccaccaaa gaaggagttg     660

gtttcccact acgatccaaa ggcttccatc ttcaacaaga aagattggtg gaagatcttg     720

ctctctgatt tgggattggt tgcttggact ttggctttgt ggaagttggg agagactttc     780

ggattcggat tggtggctgc tctttacatt ccaccagtgc tcgttaccaa ctcttacttg     840

gtggctatca ccttcttgca acacaccgat gatatcctcc cacattacga tgctactgag     900

tggacttggt tgagaggagc tttgtgcact gtggatagat ctttgggatg gttcggagat     960

tacaagaccc atcacatcgt tgatactcat gtgacccacc acatcttctc ttacctccca    1020

ttctataacg ctgaggaggc tactaaggct attaagccag tgttgaagga gtatcactgc    1080

gaggataaga gaggattctt ccacttctgg tacttgttct tcaagaccgc tgctgagaac    1140

tctgttgtgg ataacgagac caacaagtcc ccaggaatct tctacttctt cagggaggag    1200

attaagcacg gaaaggctca ttga                                           1224
```

<210> SEQ ID NO 28
<211> LENGTH: 407
<212> TYPE: PRT
<213> ORGANISM: Acanthamoeba castellanii

<400> SEQUENCE: 28

```
Met Thr Ile Thr Thr Thr Gln Thr Leu Asn Gln Lys Ala Ala Lys Lys
1               5                   10                  15

Gly Gly Lys Glu Arg Ala Pro Ile Ile Pro Lys Glu Asn Ala Pro Phe
            20                  25                  30

Thr Leu Gly Gln Ile Lys Gly Ala Ile Pro Pro His Leu Phe Lys His
        35                  40                  45

Ser Met Leu Lys Ser Phe Ser Tyr Leu Gly Val Asp Leu Leu Glu Ser
    50                  55                  60

Thr Ile Trp Leu Phe Leu Ile Leu Tyr Leu Asp Gly Leu Thr Lys Glu
65                  70                  75                  80

Asn Thr Leu Leu Asn Trp Thr Cys Trp Val Ala Tyr Trp Leu Tyr Gln
                85                  90                  95

Gly Leu Thr Trp Thr Gly Ile Trp Val Leu Ala His Glu Cys Gly His
            100                 105                 110

Gly Gly Phe Val Ala Gln Glu Trp Leu Asn Asp Thr Val Gly Phe Ile
        115                 120                 125

Phe His Thr Val Leu Tyr Val Pro Tyr Phe Ser Trp Lys Phe Ser His
    130                 135                 140

Ala Lys His His His Tyr Thr Asn His Met Thr Lys Asp Glu Pro Phe
145                 150                 155                 160

Val Pro His Thr Ile Thr Pro Glu Gln Arg Ala Lys Val Asp Gln Gly
                165                 170                 175

Glu Leu Pro His Pro Asn Lys Pro Ser Leu Phe Ala Phe Tyr Glu Arg
            180                 185                 190

Trp Val Ile Pro Phe Val Met Leu Phe Leu Gly Trp Pro Leu Tyr Leu
        195                 200                 205

Ser Ile Asn Ala Ser Gly Pro Pro Lys Lys Glu Leu Val Ser His Tyr
    210                 215                 220

Asp Pro Lys Ala Ser Ile Phe Asn Lys Lys Asp Trp Trp Lys Ile Leu
225                 230                 235                 240

Leu Ser Asp Leu Gly Leu Val Ala Trp Thr Leu Ala Leu Trp Lys Leu
                245                 250                 255

Gly Glu Thr Phe Gly Phe Gly Leu Val Ala Ala Leu Tyr Ile Pro Pro
            260                 265                 270

Val Leu Val Thr Asn Ser Tyr Leu Val Ala Ile Thr Phe Leu Gln His
        275                 280                 285

Thr Asp Asp Ile Leu Pro His Tyr Asp Ala Thr Glu Trp Thr Trp Leu
    290                 295                 300

Arg Gly Ala Leu Cys Thr Val Asp Arg Ser Leu Gly Trp Phe Gly Asp
305                 310                 315                 320

Tyr Lys Thr His His Ile Val Asp Thr His Val Thr His His Ile Phe
                325                 330                 335

Ser Tyr Leu Pro Phe Tyr Asn Ala Glu Glu Ala Thr Lys Ala Ile Lys
            340                 345                 350

Pro Val Leu Lys Glu Tyr His Cys Glu Asp Lys Arg Gly Phe Phe His
        355                 360                 365

Phe Trp Tyr Leu Phe Phe Lys Thr Ala Ala Glu Asn Ser Val Val Asp
    370                 375                 380
```

Asn Glu Thr Asn Lys Ser Pro Gly Ile Phe Tyr Phe Phe Arg Glu Glu
385 390 395 400

Ile Lys His Gly Lys Ala His
405

<210> SEQ ID NO 29
<211> LENGTH: 1116
<212> TYPE: DNA
<213> ORGANISM: Lottia gigantea

<400> SEQUENCE: 29
atgaacgaag ctaacaacca cgtgttcgat acaactactg gtgaagagca gcacctctct 60
aagagaaacg gatctagcaa cggaactagc aagaacggtg tcgctaacaa gatcccttct 120
atcagcgaga tcaaggctgc tatccctaac cactgcttca agtcaacaat caagcagtct 180
atgtactacg tgttcaagga catcatcctc atcattgcac tctactgttt cggacattgg 240
gttctccagt gcaactctat catccttaag accgctctta gccctgttta ctggttcctt 300
cagggaactc ttctcttcgc tgttttcgtt cttggacacg attgcaacca cggatctttc 360
tcttcatacg ctctcctcaa cgattgtctt ggaaccgttc tccactcttt cgttatgacc 420
ccttactacc cttggaagat ctctcatagg caccaccata acaacaccgg aaacatggat 480
aaggacgaga tcttctaccc tatcaggaag aaggacaaca acaagaacag cttcgctctt 540
ttcttcggac ttggattcgg atggcttgct tacctttgga gaggattcgg acctagacag 600
atgaaccact ggattcctag acacgctatc ttcgctaaac acgtggttgg ttgcatcctt 660
tctatcggag ttgttggaat ctgggttggt atcctcggtt actacgttca gctcatggga 720
atggtttctc tcgtgtacca ctacatgatc cctgttttca tctgcggatg ctacatcgtt 780
atggtgactt tcctccacca ctctgatatc aacctccctt ggtactctga tgataactgg 840
gacagcgtta agggaaagct ctcttctgtg gatagagact acggaatctt ccacgatgtt 900
atccacacta tcggaactca ccaggttcac cacctcttcc ctatcatccc tcactacaac 960
cttagagagg ctactaccca cttcagaaag gctttccctc agctcgttca catcaacgac 1020
aagagcatct tccctgcttt caccgagatg ttcttcaagt actcctctca gtgcatcgtt 1080
gagaacgatg ctaagatcca ctactacaag tgatga 1116

<210> SEQ ID NO 30
<211> LENGTH: 370
<212> TYPE: PRT
<213> ORGANISM: Lottia gigantea

<400> SEQUENCE: 30

Met Asn Glu Ala Asn Asn His Val Phe Asp Thr Thr Thr Gly Glu Glu
1 5 10 15

Gln His Leu Ser Lys Arg Asn Gly Ser Ser Asn Gly Thr Ser Lys Asn
20 25 30

Gly Val Ala Asn Lys Ile Pro Ser Ile Ser Glu Ile Lys Ala Ala Ile
35 40 45

Pro Asn His Cys Phe Lys Ser Thr Ile Lys Gln Ser Met Tyr Tyr Val
50 55 60

Phe Lys Asp Ile Ile Leu Ile Ile Ala Leu Tyr Cys Phe Gly His Trp
65 70 75 80

Val Leu Gln Cys Asn Ser Ile Ile Leu Lys Thr Ala Leu Ser Pro Val
85 90 95

Tyr Trp Phe Leu Gln Gly Thr Leu Leu Phe Ala Val Phe Val Leu Gly

```
            100                 105                 110

His Asp Cys Asn His Gly Ser Phe Ser Ser Tyr Ala Leu Leu Asn Asp
        115                 120                 125

Cys Leu Gly Thr Val Leu His Ser Phe Val Met Thr Pro Tyr Tyr Pro
    130                 135                 140

Trp Lys Ile Ser His Arg His His His Asn Asn Thr Gly Asn Met Asp
145                 150                 155                 160

Lys Asp Glu Ile Phe Tyr Pro Ile Arg Lys Lys Asp Asn Asn Lys Asn
                165                 170                 175

Ser Phe Ala Leu Phe Phe Gly Leu Gly Phe Gly Trp Leu Ala Tyr Leu
            180                 185                 190

Trp Arg Gly Phe Gly Pro Arg Gln Met Asn His Trp Ile Pro Arg His
        195                 200                 205

Ala Ile Phe Ala Lys His Val Val Gly Cys Ile Leu Ser Ile Gly Val
    210                 215                 220

Val Gly Ile Trp Val Gly Ile Leu Gly Tyr Tyr Val Gln Leu Met Gly
225                 230                 235                 240

Met Val Ser Leu Val Tyr His Tyr Met Ile Pro Val Phe Ile Cys Gly
                245                 250                 255

Cys Tyr Ile Val Met Val Thr Phe Leu His His Ser Asp Ile Asn Leu
            260                 265                 270

Pro Trp Tyr Ser Asp Asp Asn Trp Asp Ser Val Lys Gly Lys Leu Ser
        275                 280                 285

Ser Val Asp Arg Asp Tyr Gly Ile Phe His Asp Val Ile His Thr Ile
    290                 295                 300

Gly Thr His Gln Val His His Leu Phe Pro Ile Ile Pro His Tyr Asn
305                 310                 315                 320

Leu Arg Glu Ala Thr Thr His Phe Arg Lys Ala Phe Pro Gln Leu Val
                325                 330                 335

His Ile Asn Asp Lys Ser Ile Phe Pro Ala Phe Thr Glu Met Phe Phe
            340                 345                 350

Lys Tyr Ser Ser Gln Cys Ile Val Glu Asn Asp Ala Lys Ile His Tyr
        355                 360                 365

Tyr Lys
    370


<210> SEQ ID NO 31
<211> LENGTH: 975
<212> TYPE: DNA
<213> ORGANISM: Microdochium nivalae

<400> SEQUENCE: 31

atgggccatg agtgtggaca ccaggctttc tctccttcca aggtgctcaa tgacaccgtt      60

ggttggatct gccactctgc tctgctcgtg ccttacttct cctggaagat ctcccacggc     120

aagcaccaca aggctaccgg taacctcgcc cgtgacatgg ttttcgtccc ccgcactcgt     180

gaggagcacg ctcaccgtgt cggtggcacc atcgagcagc tcggtgagct gatggaggag     240

acccccatcg ccactgctct caacctgctt ctccagcagc tcttcggatg gcccatgtac     300

ctcataacca acgtcactgg ccacaacaac cacaccaagc agatcgaggg tcgcggcaag     360

ggcaaggcca acggctggtt cggcggtgtc aaccacttca accccagcag ccctctgtac     420

gaggctcggg acgccaagta cattgctctg agtgatctcg gtctcgccat caccggctct     480

gctctgtact atgtcggatc cacctatggc tggctcaacc tgctcgtctg gtacggtatc     540
```

-continued

```
ccctacctct gggtgaacca ctggctcgtt gccatcactt tcctccagca caccgaccct    600

accctccccc actatacccc tgagtcctgg aactttgccc gtggtgccgc tgccactatt    660

gaccgtgact tcggtttcgt cggtcgtcac ctcctccacg gtatcatcga gactcacgtc    720

ctgcaccact atgtcagcaa catccccttc tacaacgccg acgaggcgtc cgaggccatc    780

cagaaggtca tgggctcgca ctaccgcacc gaagcccaga ccggctggac tggattcttc    840

aaggccctct ggaccagcgc ccgtgtctgc cagtgggtcg agccctccga gggaaccaca    900

ggcgagaacc agggagtgat gttcttccgc aacaccaacg gtctcggtgt tccccctacc    960

aagatggcca aatag                                                     975


<210> SEQ ID NO 32
<211> LENGTH: 324
<212> TYPE: PRT
<213> ORGANISM: Microdochium nivalae

<400> SEQUENCE: 32

Met Gly His Glu Cys Gly His Gln Ala Phe Ser Pro Ser Lys Val Leu
1               5                   10                  15

Asn Asp Thr Val Gly Trp Ile Cys His Ser Ala Leu Leu Val Pro Tyr
            20                  25                  30

Phe Ser Trp Lys Ile Ser His Gly Lys His His Lys Ala Thr Gly Asn
        35                  40                  45

Leu Ala Arg Asp Met Val Phe Val Pro Arg Thr Arg Glu Glu His Ala
    50                  55                  60

His Arg Val Gly Gly Thr Ile Glu Gln Leu Gly Glu Leu Met Glu Glu
65                  70                  75                  80

Thr Pro Ile Ala Thr Ala Leu Asn Leu Leu Leu Gln Gln Leu Phe Gly
                85                  90                  95

Trp Pro Met Tyr Leu Ile Thr Asn Val Thr Gly His Asn Asn His Thr
            100                 105                 110

Lys Gln Ile Glu Gly Arg Gly Lys Gly Lys Ala Asn Gly Trp Phe Gly
        115                 120                 125

Gly Val Asn His Phe Asn Pro Ser Ser Pro Leu Tyr Glu Ala Arg Asp
    130                 135                 140

Ala Lys Tyr Ile Ala Leu Ser Asp Leu Gly Leu Ala Ile Thr Gly Ser
145                 150                 155                 160

Ala Leu Tyr Tyr Val Gly Ser Thr Tyr Gly Trp Leu Asn Leu Leu Val
                165                 170                 175

Trp Tyr Gly Ile Pro Tyr Leu Trp Val Asn His Trp Leu Val Ala Ile
            180                 185                 190

Thr Phe Leu Gln His Thr Asp Pro Thr Leu Pro His Tyr Thr Pro Glu
        195                 200                 205

Ser Trp Asn Phe Ala Arg Gly Ala Ala Ala Thr Ile Asp Arg Asp Phe
    210                 215                 220

Gly Phe Val Gly Arg His Leu Leu His Gly Ile Ile Glu Thr His Val
225                 230                 235                 240

Leu His His Tyr Val Ser Asn Ile Pro Phe Tyr Asn Ala Asp Glu Ala
                245                 250                 255

Ser Glu Ala Ile Gln Lys Val Met Gly Ser His Tyr Arg Thr Glu Ala
            260                 265                 270

Gln Thr Gly Trp Thr Gly Phe Phe Lys Ala Leu Trp Thr Ser Ala Arg
        275                 280                 285

Val Cys Gln Trp Val Glu Pro Ser Glu Gly Thr Thr Gly Glu Asn Gln
```

```
    290                 295                 300

Gly Val Met Phe Phe Arg Asn Thr Asn Gly Leu Gly Val Pro Pro Thr
305                 310                 315                 320

Lys Met Ala Lys
```

<210> SEQ ID NO 33
<211> LENGTH: 1593
<212> TYPE: DNA
<213> ORGANISM: Microdochium nivalae

<400> SEQUENCE: 33

```
ttcctcttct tctggaagcc ctcgctacat cctgccattc agtgtttggc agaagaaaac      60

accagcagtc cttcaccatg attgcgacca cccagaccaa gacggccgtc acggaccgcg     120

ggacggtaag cctctcttga ctcttggtgc cctgcaacca cctgctgact ttttgtgtgt     180

ttctcgcctt gccagacccg gatgagaggc tcgtcaacag cccaggagtt cccagacatc     240

cagaccatcc gcgatgctat ccccaagcac tgctttgagc cctcaacagt ccgttccttg     300

agctatgtcg cccgcgatgt aaccatggcc tcggccctca tctgggcggc cgtccgcttc     360

atcccccaga tcgaggactc ggtcctgcgc ttctcggcct ggatggtcta cggccttgtc     420

cagggcatgg tctgcaccgg cgtctggatc ctcgcccacg agtgcggcca cggcgccttc     480

agcaagcacc agaccctcaa cgactttgtc ggctgggtcc tgcactcgag tctcggcgtc     540

ccctacttct catggaagtt ctcacaccac cgccaccacc gcttcactgg caacatggag     600

aaggacatgg tctttgtccc cgccgtcaag accgaggagc cccctaagcg ccgcctcgcc     660

tccttctacc tcgaccctga gatcctcgag gacgccccca ttgtcagcct catccagctc     720

attgcccacc agctcgccgg ctggcagatg tacatgctct tcaacgtctc atcgggcaag     780

gacagcaagc agcgcaacca gtctggctgg ctgcgcgtca gccactttga gcccaccagc     840

gccgtcttcc gccctagcga ggcctggtac atcttcctcg ccgacgtcgg ccttgctctc     900

accggcgccg ccatctacta cggctccacc cttgtcggct ggcccaccat gttctttgtc     960

tactttgtcc cctacatgtg gtggaaccac tggctcgttg ccatcaccta cctccaccac    1020

acccacccgg aagtccacca ctacgaggcg gacagctgga cctacgtcaa gggcgccctc    1080

gccaccgtcg accgcgactt tggctggatt gacaagcacc tcttccagta cgtttttgac    1140

attcgctctg cccatttttg accaacaacg aatgacctac taactctctc cactgcagcg    1200

gcatcattgg cttccacgtc atccaccaca tctttgccaa gatccccttc tactacgccg    1260

aggaggccac cgcggccatc cagcccgtca ttggcaacca ctaccaccgt gctcccggct    1320

ccttcctcgg cgacctctgg ctcactttca ccaagtgccg cttcgtcgag aaggaccccg    1380

agcaccctgg cgccatgcgc tggtcgcac cccgcaagga cctttagatt ttcctggagc    1440

agagactaga gacttatgat ccatcggtgc agaaagctgc cgaggataga tgcgagaaca    1500

aaaggcgacc aactccccca ggcccagtag atttgtaaca ggcactagac cctgcagatt    1560

ctggacggtt agataaaaaa aaaaaaaaaa aaa                                  1593
```

<210> SEQ ID NO 34
<211> LENGTH: 402
<212> TYPE: PRT
<213> ORGANISM: Microdochium nivalae

<400> SEQUENCE: 34

```
Met Ile Ala Thr Thr Gln Thr Lys Thr Ala Val Thr Asp Arg Gly Thr
1               5                   10                  15
```

```
Thr Arg Met Arg Gly Ser Ser Thr Ala Gln Glu Phe Pro Asp Ile Gln
            20                  25                  30

Thr Ile Arg Asp Ala Ile Pro Lys His Cys Phe Glu Pro Ser Thr Val
        35                  40                  45

Arg Ser Leu Ser Tyr Val Ala Arg Asp Val Thr Met Ala Ser Ala Leu
    50                  55                  60

Ile Trp Ala Ala Val Arg Phe Ile Pro Gln Ile Glu Asp Ser Val Leu
65                  70                  75                  80

Arg Phe Ser Ala Trp Met Val Tyr Gly Leu Val Gln Gly Met Val Cys
                85                  90                  95

Thr Gly Val Trp Ile Leu Ala His Glu Cys Gly His Gly Ala Phe Ser
            100                 105                 110

Lys His Gln Thr Leu Asn Asp Phe Val Gly Trp Val Leu His Ser Ser
        115                 120                 125

Leu Gly Val Pro Tyr Phe Ser Trp Lys Phe Ser His His Arg His His
    130                 135                 140

Arg Phe Thr Gly Asn Met Glu Lys Asp Met Val Phe Val Pro Ala Val
145                 150                 155                 160

Lys Thr Glu Glu Pro Pro Lys Arg Arg Leu Ala Ser Phe Tyr Leu Asp
                165                 170                 175

Pro Glu Ile Leu Glu Asp Ala Pro Ile Val Ser Leu Ile Gln Leu Ile
            180                 185                 190

Ala His Gln Leu Ala Gly Trp Gln Met Tyr Met Leu Phe Asn Val Ser
        195                 200                 205

Ser Gly Lys Asp Ser Lys Gln Arg Asn Gln Ser Gly Trp Leu Arg Val
    210                 215                 220

Ser His Phe Glu Pro Thr Ser Ala Val Phe Arg Pro Ser Glu Ala Trp
225                 230                 235                 240

Tyr Ile Phe Leu Ala Asp Val Gly Leu Ala Leu Thr Gly Ala Ala Ile
                245                 250                 255

Tyr Tyr Gly Ser Thr Leu Val Gly Trp Pro Thr Met Phe Phe Val Tyr
            260                 265                 270

Phe Val Pro Tyr Met Trp Trp Asn His Trp Leu Val Ala Ile Thr Tyr
        275                 280                 285

Leu His His Thr His Pro Glu Val His His Tyr Glu Ala Asp Ser Trp
    290                 295                 300

Thr Tyr Val Lys Gly Ala Leu Ala Thr Val Asp Arg Asp Phe Gly Trp
305                 310                 315                 320

Ile Asp Lys His Leu Phe His Gly Ile Ile Gly Phe His Val Ile His
                325                 330                 335

His Ile Phe Ala Lys Ile Pro Phe Tyr Tyr Ala Glu Glu Ala Thr Ala
            340                 345                 350

Ala Ile Gln Pro Val Ile Gly Asn His Tyr His Arg Ala Pro Gly Ser
        355                 360                 365

Phe Leu Gly Asp Leu Trp Leu Thr Phe Thr Lys Cys Arg Phe Val Glu
    370                 375                 380

Lys Asp Pro Glu His Pro Gly Ala Met Arg Trp Val Ala Pro Arg Lys
385                 390                 395                 400

Asp Leu
```

<210> SEQ ID NO 35
<211> LENGTH: 1557
<212> TYPE: DNA

<213> ORGANISM: Periplaneta americana

<400> SEQUENCE: 35

```
gagtactcag ttcactacca gaccagtttg ggttcgtcat aaccagcgag tttgttttag     60
ttcagagact gtgctgagtt aactgtatta agttagtggt ttcttgtatt attttattcg    120
agtgtggtga atttcagcga ttacatcatg gctccgaaca ttacaagttc tcctaccggt    180
gtcctatttg aggatgatac tatagaaact gtaacattac caacgatcga gactaaaact    240
gatgattcca aaccagctga gaaatacaaa agaaaaattg tatggagaaa cgtcatcctc    300
tttgtatatt tgcatatggc agcactctac ggggcttacc ttatgctgac atcctgtaaa    360
ttgatcacag ctatatgggc tattcttctg tatcaggcag gtggtctagg tataactgca    420
ggtgcacata gattatggtc acaccgtgct tacaaggcaa agtggccttt gagacttatc    480
ctcgtgatat tcaacactct tgcattccag aaccacgttt acgaatgggc tcgcgaccac    540
agagtacacc acaagttcag tgaaactgat gctgaccctc ataatgccaa gcgcggcttc    600
tttttctctc atgttggttg gctacttgtc cgtaagcatc cagatgttaa agtaaagggc    660
aaaggaatcg atatgtctga tctcgatgct gatccactca tcgcattcca gaagaagtga    720
gtatctatct tgtctattgc aataacatga gtcacttaga cctttccatt tacatactat    780
gtagccatgt atatagttcc ttgtctgata ctaagatatg ttcatcatta aactctggct    840
gctttactca aggaaaagaa ttccattacg catttcttga aagtgaaagt tatgacaaag    900
tgtagctatt gtttcagtat attcgccact ctgtcaatta gagttaacgc tagtttcttg    960
acattatgaa attgtgatat tttgttttca gacactacct gatcctcatg ccaattatat   1020
gctttattct accaacaatc atacctgtgt atttttgggg tgagacctgg tcaaatgctt   1080
ggtttgtggt tgcgatgttt cgctacacct tcactctcaa cgcgtcctgg cttgtgaaca   1140
gtgcagcaca catgtgggga agccgacctt atgacaagta catcaatcca tcagaaaatc   1200
tcggcgtttc tatgctagct ctgggcgagg gttggcacaa ctaccatcac gtgtttcctt   1260
gggactacaa gactgccgaa cttggaaact acagcaccaa cttgacgact gcattcatcg   1320
acttcttttc tcgcattggc tgggcatatg acctcaagac tgtaccgatg tccatggtga   1380
agcagagagt acaacgcaca ggtgacggaa gccatgatgt atggggttgg ggtgacaagg   1440
acatgagcca ggaggacatg gatgaggccc tggtcatcaa caagaagctc aagtaggact   1500
aatcctttgt caggattagt ctcagttccc gcgtactctg cgttgatacc actgctt      1557
```

<210> SEQ ID NO 36
<211> LENGTH: 357
<212> TYPE: PRT
<213> ORGANISM: Periplaneta americana

<400> SEQUENCE: 36

```
Met Ala Pro Asn Ile Thr Ser Ser Pro Thr Gly Val Leu Phe Glu Asp
1               5                   10                  15

Asp Thr Ile Glu Thr Val Thr Leu Pro Thr Ile Glu Thr Lys Thr Asp
            20                  25                  30

Asp Ser Lys Pro Ala Glu Lys Tyr Lys Arg Lys Ile Val Trp Arg Asn
        35                  40                  45

Val Ile Leu Phe Val Tyr Leu His Met Ala Ala Leu Tyr Gly Ala Tyr
    50                  55                  60

Leu Met Leu Thr Ser Cys Lys Leu Ile Thr Ala Ile Trp Ala Ile Leu
65                  70                  75                  80
```

-continued

```
Leu Tyr Gln Ala Gly Gly Leu Gly Ile Thr Ala Gly Ala His Arg Leu
                85                  90                  95

Trp Ser His Arg Ala Tyr Lys Ala Lys Trp Pro Leu Arg Leu Ile Leu
            100                 105                 110

Val Ile Phe Asn Thr Leu Ala Phe Gln Asn His Val Tyr Glu Trp Ala
        115                 120                 125

Arg Asp His Arg Val His His Lys Phe Ser Glu Thr Asp Ala Asp Pro
    130                 135                 140

His Asn Ala Lys Arg Gly Phe Phe Phe Ser His Val Gly Trp Leu Leu
145                 150                 155                 160

Val Arg Lys His Pro Asp Val Lys Val Lys Gly Lys Gly Ile Asp Met
                165                 170                 175

Ser Asp Leu Asp Ala Asp Pro Leu Ile Ala Phe Gln Lys Lys His Tyr
            180                 185                 190

Leu Ile Leu Met Pro Ile Ile Cys Phe Ile Leu Pro Thr Ile Ile Pro
        195                 200                 205

Val Tyr Phe Trp Gly Glu Thr Trp Ser Asn Ala Trp Phe Val Val Ala
    210                 215                 220

Met Phe Arg Tyr Thr Phe Thr Leu Asn Ala Ser Trp Leu Val Asn Ser
225                 230                 235                 240

Ala Ala His Met Trp Gly Ser Arg Pro Tyr Asp Lys Tyr Ile Asn Pro
                245                 250                 255

Ser Glu Asn Leu Gly Val Ser Met Leu Ala Leu Gly Glu Gly Trp His
            260                 265                 270

Asn Tyr His His Val Phe Pro Trp Asp Tyr Lys Thr Ala Glu Leu Gly
        275                 280                 285

Asn Tyr Ser Thr Asn Leu Thr Thr Ala Phe Ile Asp Phe Phe Ser Arg
    290                 295                 300

Ile Gly Trp Ala Tyr Asp Leu Lys Thr Val Pro Met Ser Met Val Lys
305                 310                 315                 320

Gln Arg Val Gln Arg Thr Gly Asp Gly Ser His Asp Val Trp Gly Trp
                325                 330                 335

Gly Asp Lys Asp Met Ser Gln Glu Asp Met Asp Glu Ala Leu Val Ile
            340                 345                 350

Asn Lys Lys Leu Lys
        355
```

<210> SEQ ID NO 37
<211> LENGTH: 1156
<212> TYPE: DNA
<213> ORGANISM: Periplaneta americana

<400> SEQUENCE: 37

```
acagtcagtc gatcttcagc ttctagtgaa cgaagacttg attacgccag tgtttaatcc      60

acaaattccg gcatggcccc taatataact agtactccca cgggagttct atacgaagaa     120

gacttcgctg cagccgaaaa agcaacttca actgagacta aagagggcat taaacctaaa     180

cgggagtaca agaagcaaat tgtgtggccc aacgtgatta tgcatttcct cctccatgtt     240

ggcgcagtct acggagctta cctcatgctt acttctgcca aaatactcac aggaatatgg     300

gctttctttc tgtatgaagt gggtatccta ggcattacgg ccggcgcaca tcgactctgg     360

tcacatcgct cttataaagc cacatggcag atgaggctga tcctcatgat ttgtcagact     420

gtgtcttttc agacatctgt tcatgaatgg gctcgaaatc atagggtgca ccataaacat     480

agcgacactg atggcgatcc tcacaatgtc aatcgcggct tgtttttctc tcacgccggt     540
```

```
tggatgatgt gccgtataca tcccgaagtt aaggagaagg gcaagcagat tgacctgtca    600

gatcttgatg ccgatccaat tctgatgttt caaaaaaagt actacctaat tctcatgccc    660

ttcatgtgct tcttcttacc tacctggatt cctgtatatt tttggggtga aacatggcac    720

aatgcgtatt ttgttgctgc tatcttccgc catgtgttca ctctgaacat gactttgatg    780

gtcaacagca tcactcacaa tacatgggga aacagaccat atgacaaaaa tattaaccct    840

gctgaaaatg ctatagtgtc tttgatgacc cttggtgaag gctggcataa ctaccatcat    900

gtatttccat gggattacaa aacggccgaa cttggagtct tacgtatcaa tatgacgacg    960

ctcttcattg atctgtgtgc aaaaaattgga tgggcctatg acttgaagac tgtaccaatg   1020

gatatggtca aaagaagggt ggaacgcact ggagatggga cgcacgagat ttggggctgg   1080

ggagacaagg atatgacgga gaaggagaga gaaatagcac aaataatcaa caagaaagat   1140

taaaaacgat atttca                                                    1156
```

<210> SEQ ID NO 38
<211> LENGTH: 356
<212> TYPE: PRT
<213> ORGANISM: Periplaneta americana

<400> SEQUENCE: 38

```
Met Ala Pro Asn Ile Thr Ser Thr Pro Thr Gly Val Leu Tyr Glu Glu
1               5                   10                  15

Asp Phe Ala Ala Ala Glu Lys Ala Thr Ser Thr Glu Thr Lys Glu Gly
            20                  25                  30

Ile Lys Pro Lys Arg Glu Tyr Lys Lys Gln Ile Val Trp Pro Asn Val
        35                  40                  45

Ile Met His Phe Leu Leu His Val Gly Ala Val Tyr Gly Ala Tyr Leu
    50                  55                  60

Met Leu Thr Ser Ala Lys Ile Leu Thr Gly Ile Trp Ala Phe Phe Leu
65                  70                  75                  80

Tyr Glu Val Gly Ile Leu Gly Ile Thr Ala Gly Ala His Arg Leu Trp
                85                  90                  95

Ser His Arg Ser Tyr Lys Ala Thr Trp Gln Met Arg Leu Ile Leu Met
            100                 105                 110

Ile Cys Gln Thr Val Ser Phe Gln Thr Ser Val His Glu Trp Ala Arg
        115                 120                 125

Asn His Arg Val His His Lys His Ser Asp Thr Asp Gly Asp Pro His
    130                 135                 140

Asn Val Asn Arg Gly Leu Phe Phe Ser His Ala Gly Trp Met Met Cys
145                 150                 155                 160

Arg Lys His Pro Glu Val Lys Glu Lys Gly Lys Gln Ile Asp Leu Ser
                165                 170                 175

Asp Leu Asp Ala Asp Pro Ile Leu Met Phe Gln Lys Lys Tyr Tyr Leu
            180                 185                 190

Ile Leu Met Pro Phe Met Cys Phe Phe Leu Pro Thr Trp Ile Pro Val
        195                 200                 205

Tyr Phe Trp Gly Glu Thr Trp His Asn Ala Tyr Phe Val Ala Ala Ile
    210                 215                 220

Phe Arg His Val Phe Thr Leu Asn Met Thr Leu Met Val Asn Ser Ile
225                 230                 235                 240

Thr His Asn Thr Trp Gly Asn Arg Pro Tyr Asp Lys Asn Ile Asn Pro
                245                 250                 255
```

```
Ala Glu Asn Ala Ile Val Ser Leu Met Thr Leu Gly Glu Gly Trp His
            260                 265                 270

Asn Tyr His His Val Phe Pro Trp Asp Tyr Lys Thr Ala Glu Leu Gly
        275                 280                 285

Val Leu Arg Ile Asn Met Thr Thr Leu Phe Ile Asp Leu Cys Ala Lys
    290                 295                 300

Ile Gly Trp Ala Tyr Asp Leu Lys Thr Val Pro Met Asp Met Val Lys
305                 310                 315                 320

Arg Arg Val Glu Arg Thr Gly Asp Gly Thr His Glu Ile Trp Gly Trp
                325                 330                 335

Gly Asp Lys Asp Met Thr Glu Lys Glu Arg Glu Ile Ala Gln Ile Ile
            340                 345                 350

Asn Lys Lys Asp
        355
```

<210> SEQ ID NO 39
<211> LENGTH: 21
<212> TYPE: DNA
<213> ORGANISM: Artificial sequence
<220> FEATURE:
<223> OTHER INFORMATION: primer

<400> SEQUENCE: 39
ctgagagaac atgacgacga c 21

<210> SEQ ID NO 40
<211> LENGTH: 23
<212> TYPE: DNA
<213> ORGANISM: Artificial sequence
<220> FEATURE:
<223> OTHER INFORMATION: primer

<400> SEQUENCE: 40
gtcgcttact cgttgtcact ctc 23

<210> SEQ ID NO 41
<211> LENGTH: 21
<212> TYPE: DNA
<213> ORGANISM: Artificial sequence
<220> FEATURE:
<223> OTHER INFORMATION: primer

<400> SEQUENCE: 41
gatactaagc caccaacatg g 21

<210> SEQ ID NO 42
<211> LENGTH: 22
<212> TYPE: DNA
<213> ORGANISM: Artificial sequence
<220> FEATURE:
<223> OTHER INFORMATION: primer

<400> SEQUENCE: 42
cgttctacga gccctctatt tc 22

<210> SEQ ID NO 43
<211> LENGTH: 19
<212> TYPE: DNA
<213> ORGANISM: Artificial sequence
<220> FEATURE:
<223> OTHER INFORMATION: primer

<400> SEQUENCE: 43

-continued caaccaccca tcatggcca 19

<210> SEQ ID NO 44
<211> LENGTH: 21
<212> TYPE: DNA
<213> ORGANISM: Artificial sequence
<220> FEATURE:
<223> OTHER INFORMATION: primer

<400> SEQUENCE: 44
atcgcttcat gcgtcattgt c 21

<210> SEQ ID NO 45
<211> LENGTH: 21
<212> TYPE: DNA
<213> ORGANISM: Artificial sequence
<220> FEATURE:
<223> OTHER INFORMATION: primer

<400> SEQUENCE: 45
caccatcatg gccaccacaa c 21

<210> SEQ ID NO 46
<211> LENGTH: 21
<212> TYPE: DNA
<213> ORGANISM: Artificial sequence
<220> FEATURE:
<223> OTHER INFORMATION: primer

<400> SEQUENCE: 46
agctctactc gttgtcggac t 21

<210> SEQ ID NO 47
<211> LENGTH: 21
<212> TYPE: DNA
<213> ORGANISM: Artificial sequence
<220> FEATURE:
<223> OTHER INFORMATION: primer

<400> SEQUENCE: 47
atgggccatg agtgtggaca c 21

<210> SEQ ID NO 48
<211> LENGTH: 24
<212> TYPE: DNA
<213> ORGANISM: Artificial sequence
<220> FEATURE:
<223> OTHER INFORMATION: primer

<400> SEQUENCE: 48
ctatttggcc atcttggtag gggg 24

<210> SEQ ID NO 49
<211> LENGTH: 20
<212> TYPE: DNA
<213> ORGANISM: Artificial sequence
<220> FEATURE:
<223> OTHER INFORMATION: primer

<400> SEQUENCE: 49
atgattgcga ccacccagac 20

<210> SEQ ID NO 50
<211> LENGTH: 22
<212> TYPE: DNA
<213> ORGANISM: Artificial sequence
<220> FEATURE:
<223> OTHER INFORMATION: primer

<400> SEQUENCE: 50
ctaaaggtcc ttgcggggtg cg 22

<210> SEQ ID NO 51
<211> LENGTH: 23
<212> TYPE: DNA
<213> ORGANISM: Artificial sequence
<220> FEATURE:
<223> OTHER INFORMATION: primer

<400> SEQUENCE: 51
atggctccga acattacaag ttc 23

<210> SEQ ID NO 52
<211> LENGTH: 22
<212> TYPE: DNA
<213> ORGANISM: Artificial sequence
<220> FEATURE:
<223> OTHER INFORMATION: primer

<400> SEQUENCE: 52
ctacttgagc ttcttgttga tg 22

<210> SEQ ID NO 53
<211> LENGTH: 23
<212> TYPE: DNA
<213> ORGANISM: Artificial sequence
<220> FEATURE:
<223> OTHER INFORMATION: primer

<400> SEQUENCE: 53
atggccccta atataactag tac 23

<210> SEQ ID NO 54
<211> LENGTH: 24
<212> TYPE: DNA
<213> ORGANISM: Artificial sequence
<220> FEATURE:
<223> OTHER INFORMATION: primer

<400> SEQUENCE: 54
ttaatctttc ttgttgatta tttg 24

<210> SEQ ID NO 55
<211> LENGTH: 24
<212> TYPE: DNA
<213> ORGANISM: Artificial sequence
<220> FEATURE:
<223> OTHER INFORMATION: primer

<400> SEQUENCE: 55
accatggacg agcagcctgc cgtc 24

<210> SEQ ID NO 56
<211> LENGTH: 20
<212> TYPE: DNA
<213> ORGANISM: Artificial sequence
<220> FEATURE:
<223> OTHER INFORMATION: primer

<400> SEQUENCE: 56
ttactcgttg tcactctcag 20

-continued

<210> SEQ ID NO 57
<211> LENGTH: 24
<212> TYPE: DNA
<213> ORGANISM: Artificial sequence
<220> FEATURE:
<223> OTHER INFORMATION: primer

<400> SEQUENCE: 57
accatggcgg tccgacaacg cacc 24

<210> SEQ ID NO 58
<211> LENGTH: 21
<212> TYPE: DNA
<213> ORGANISM: Artificial sequence
<220> FEATURE:
<223> OTHER INFORMATION: primer

<400> SEQUENCE: 58
ctatttcgcc cacctcatcg c 21

<210> SEQ ID NO 59
<211> LENGTH: 25
<212> TYPE: DNA
<213> ORGANISM: Artificial sequence
<220> FEATURE:
<223> OTHER INFORMATION: primer

<400> SEQUENCE: 59
accatggcca ccaccgccat ggctc 25

<210> SEQ ID NO 60
<211> LENGTH: 22
<212> TYPE: DNA
<213> ORGANISM: Artificial sequence
<220> FEATURE:
<223> OTHER INFORMATION: primer

<400> SEQUENCE: 60
tcatgcgtca ttgtcgctgt cg 22

<210> SEQ ID NO 61
<211> LENGTH: 26
<212> TYPE: DNA
<213> ORGANISM: Artificial sequence
<220> FEATURE:
<223> OTHER INFORMATION: primer

<400> SEQUENCE: 61
accatggcca ccacaactgc ccgcgc 26

<210> SEQ ID NO 62
<211> LENGTH: 24
<212> TYPE: DNA
<213> ORGANISM: Artificial sequence
<220> FEATURE:
<223> OTHER INFORMATION: primer

<400> SEQUENCE: 62
ctactcgttg tcggactcag ggcc 24

<210> SEQ ID NO 63
<211> LENGTH: 25
<212> TYPE: DNA
<213> ORGANISM: Artificial sequence
<220> FEATURE:
<223> OTHER INFORMATION: primer

<400> SEQUENCE: 63
accatgggcc atgagtgtgg acacc 25

<210> SEQ ID NO 64
<211> LENGTH: 24
<212> TYPE: DNA
<213> ORGANISM: Artificial sequence
<220> FEATURE:
<223> OTHER INFORMATION: primer

<400> SEQUENCE: 64
ctatttggcc atcttggtag gggg 24

<210> SEQ ID NO 65
<211> LENGTH: 23
<212> TYPE: DNA
<213> ORGANISM: Artificial sequence
<220> FEATURE:
<223> OTHER INFORMATION: primer

<400> SEQUENCE: 65
accatgattg cgaccaccca gac 23

<210> SEQ ID NO 66
<211> LENGTH: 22
<212> TYPE: DNA
<213> ORGANISM: Artificial sequence
<220> FEATURE:
<223> OTHER INFORMATION: primer

<400> SEQUENCE: 66
ctaaaggtcc ttgcggggtg cg 22

<210> SEQ ID NO 67
<211> LENGTH: 23
<212> TYPE: DNA
<213> ORGANISM: Artificial sequence
<220> FEATURE:
<223> OTHER INFORMATION: primer

<400> SEQUENCE: 67
accatggctc cgaacattac aag 23

<210> SEQ ID NO 68
<211> LENGTH: 22
<212> TYPE: DNA
<213> ORGANISM: Artificial sequence
<220> FEATURE:
<223> OTHER INFORMATION: primer

<400> SEQUENCE: 68
ctacttgagc ttcttgttga tg 22

<210> SEQ ID NO 69
<211> LENGTH: 23
<212> TYPE: DNA
<213> ORGANISM: Artificial sequence
<220> FEATURE:
<223> OTHER INFORMATION: primer

<400> SEQUENCE: 69
accatggccc ctaatataac tag 23

<210> SEQ ID NO 70

<211> LENGTH: 24
<212> TYPE: DNA
<213> ORGANISM: Artificial sequence
<220> FEATURE:
<223> OTHER INFORMATION: primer

<400> SEQUENCE: 70
ttaatctttc ttgttgatta tttg 24

<210> SEQ ID NO 71
<211> LENGTH: 28875
<212> TYPE: DNA
<213> ORGANISM: Artificial sequence
<220> FEATURE:
<223> OTHER INFORMATION: sequence of the complete binary vector LJB1139

<400> SEQUENCE: 71
acatacaaat ggacgaacgg ataaaccttt tcacgccctt ttaaatatcc gattattcta 60
ataaacgctc ttttctctta ggtttacccg ccaatatatc ctgtcaaaca ctgatagttt 120
aaactgaagg cgggaaacga caatcagatc tagtaggaaa cagctatgac catgattacg 180
ccaagcttat ttaaatcgta ccgtactagt aacggccgcc agtgtgctgg aattcgccct 240
taaaaaagat atcgattacg ccaagctatc aactttgtat agaaaagttg ccatgattac 300
gccaagcttg gccactaagg ccaatttaaa tctactaggc cggccaaagc tttacaacgc 360
tacacaaaac ttataaccgt aatcaccatt cattaactta actactatca catgcattca 420
tgaattgaaa cgagaaggat gtaaatagtt gggaagttat ctccacgttg aagagatcgt 480
tagcgagagc tgaaagaccg agggaggaga cgccgtcaac acggacagag tcgtcgaccc 540
tcacatgaag taggaggaat ctccgtgagg agccagagag acgtctttgg tcttcggttt 600
cgatccttga tctgacggag aagacgagag aagtgcgact ggactccgtg aggaccaaca 660
gagtcgtcct cggtttcgat cgtcggtatt ggtggagaag gcggaggaat ctccgtgacg 720
agccagagag atgtcgtcgg tcttcggttt cgatccttga tctgacggag aagacgagag 780
aagtgcgacg agactccgtg aggaccaaca gagttgtcct cggtttcgat cgtcggtttc 840
ggcggagaag gcggaggaat ctccgtgagg agccagagag acgtcgttgg tcttcggttt 900
cgatccttga tctgttggag aagacgagac aagtgggacg agactcaacg acggagtcag 960
agacgtcgtc ggtcttcggt ttcggccgag aaggcggagt cggtcttcgg tttcggccga 1020
gaaggcggag gagacgtctt cgatttgggt ctctcctctt gacgaagaaa acaaagaaca 1080
cgagaaataa tgagaaagag aacaaaagaa aaaaaaataa aaataaaaat aaaatttggt 1140
cctcttatgt ggtgacacgt ggtttgaaac ccaccaaata atcgatcaca aaaaacctaa 1200
gttaaggatc ggtaataacc tttctaatta attttgattt atattaaatc actcttttta 1260
tttataaacc ccactaaatt atgcgatatt gattgtctaa gtacaaaaat tctctcgaat 1320
tcaatacaca tgtttcatat atttagccct gttcatttaa tattactagc gcatttttaa 1380
tttaaaattt tgtaaacttt tttggtcaaa gaacattttt ttaattagag acagaaatct 1440
agactcttta tttggaataa tagtaataaa gatatattag gcaatgagtt tatgatgtta 1500
tgtttatata gtttatttca ttttaaattg aaaagcatta tttttatcga aatgaatcta 1560
gtatacaatc aatatttatg ttttttcatc agatactttc ctattttttg gcacctttca 1620
tcggactact gatttatttc aatgtgtatg catgcatgag catgagtata cacatgtctt 1680
ttaaaatgca tgtaaagcgt aacggaccac aaaagaggat ccatacaaat acatctcatc 1740
gcttcctcta ctattctccg acacacacac tgagcaacca tggatgctta taacgctgct 1800

```
atggataaga ttggagctgc tatcatcgat tggagtgatc cagatggaaa gttcagagct   1860
gatagggagg attggtggtt gtgcgatttc agatccgcta tcaccattgc tctcatctac   1920
atcgctttcg tgatcttggg atctgctgtg atgcaatctc tcccagctat ggacccatac   1980
cctatcaagt tcctctacaa cgtgtctcaa atcttcctct gcgcttacat gactgttgag   2040
gctggattcc tcgcttatag gaacggatac accgttatgc catgcaacca cttcaacgtg   2100
aacgatccac cagttgctaa cttgctctgg ctcttctaca tctccaaagt gtgggatttc   2160
tgggatacca tcttcattgt gctcggaaag aagtggagac aactctcttt cttgcacgtg   2220
taccatcata ccaccatctt cctcttctac tggttgaacg ctaacgtgct ctacgatgga   2280
gatatcttct tgaccatcct cctcaacgga ttcattcaca ccgtgatgta cacctactac   2340
ttcatctgca tgcacaccaa ggattctaag accggaaagt ctttgccaat ctggtggaag   2400
tcatctttga ccgctttcca actcttgcaa ttcaccatca tgatgtccca agctacctac   2460
ttggttttcc acggatgcga taaggtttcc ctcagaatca ccatcgtgta cttcgtgtac   2520
attctctccc ttttcttcct cttcgctcag ttcttcgtgc aatcctacat ggctccaaag   2580
aagaagaagt ccgcttgatt aattaactaa gtttgatgta tctgagtgcc aacgtttact   2640
ttgtctttcc tttcttttat tggttatgat tagatgttta ctatgttctc tctttttcgt   2700
tataaataaa gaagttcaat tcttctatag tttcaaacgc gattttaagc gtttctattt   2760
aggtttacat gatttctttt acaaaatcat ctttaaaata cagtatattt ttagttttca   2820
taaaatattt aaagaaatga aagtttataa acattcactc ctattctcta attaaggatt   2880
tgtaaaacaa aaattttgta agcatatcga tttatgcgtt ttgtcttaat tagctcacta   2940
aataataaat aatagcttat gttgtgggac tgtttaatta cctaacttag aactaaaatc   3000
aactctttgt gggcgcctac taccggtaat tcccgggata cctgcaggtt aggccggcca   3060
ctgcagcaaa tttacacatt gccactaaac gtctaaaccc ttgtaatttg tttttgtttt   3120
actatgtgtg ttatgtattt gatttgcgat aaatttttat atttggtact aaatttataa   3180
caccttttat gctaacgttt gccaacactt agcaatttgc aagttgatta attgattcta   3240
aattattttt gtcttctaaa tacatatact aatcaactgg aaatgtaaat atttgctaat   3300
atttctacta taggagaatt aaagtgagtg aatatggtac cacaaggttt ggagatttaa   3360
ttgttgcaat gctgcatgga tggcatatac accaaacatt caataattct tgaggataat   3420
aatggtacca cacaagattt gaggtgcatg aacgtcacgt ggacaaaagg tttagtaatt   3480
tttcaagaca acaatgttac cacacacaag ttttgaggtg catgcatgga tgccctgtgg   3540
aaagtttaaa aatattttgg aaatgatttg catggaagcc atgtgtaaaa ccatgacatc   3600
cacttggagg atgcaataat gaagaaaact acaaatttac atgcaactag ttatgcatgt   3660
agtctatata atgaggattt tgcaatactt tcattcatac acactcacta agttttacac   3720
gattataatt tcttcatagc cagtggcgcg ccaccatgtg tgttgagacc gagaacaacg   3780
atggaatccc tactgtggag atcgctttcg atggagagag agaaagagct gaggctaacg   3840
tgaagttgtc tgctgagaag atggaacctg ctgctttggc taagaccttc gctagaagat   3900
acgtggttat cgagggagtt gagtacgatg tgaccgattt caaacatcct ggaggaaccg   3960
tgattttcta cgctctctct aacactggag ctgatgctac tgaggctttc aaggagttcc   4020
accacagatc tagaaaggct aggaaggctt tggctgcttt gccttctaga cctgctaaga   4080
ccgctaaagt ggatgatgct gagatgctcc aggatttcgc taagtggaga aaggagttgg   4140
```

```
agagggacgg attcttcaag ccttctcctg ctcatgttgc ttacagattc gctgagttgg   4200
ctgctatgta cgctttggga acctacttga tgtacgctag atacgttgtg tcctctgtgt   4260
tggtttacgc ttgcttcttc ggagctagat gtggatgggt tcaacatgag ggaggacatt   4320
cttctttgac cggaaacatc tggtgggata agagaatcca agctttcact gctggattcg   4380
gattggctgg atctggagat atgtggaact ccatgcacaa caagcaccat gctactcctc   4440
aaaaagtgag gcacgatatg gatttggata ccactcctgc tgttgctttc ttcaacaccg   4500
ctgtggagga taatagacct aggggattct ctaagtactg gctcagattg caagcttgga   4560
ccttcattcc tgtgacttct ggattggtgt tgctcttctg gatgttcttc ctccatcctt   4620
ctaaggcttt gaagggagga aagtacgagg agcttgtgtg gatgttggct gctcatgtga   4680
ttagaacctg gaccattaag gctgttactg gattcaccgc tatgcaatcc tacggactct   4740
tcttggctac ttcttgggtt tccggatgct acttgttcgc tcacttctct acttctcaca   4800
cccatttgga tgttgttcct gctgatgagc atttgtcttg ggttaggtac gctgtggatc   4860
acaccattga tatcgatcct tctcagggat gggttaactg gttgatggga tacttgaact   4920
gccaagtgat tcatcacctc ttcccttcta tgcctcaatt cagacaacct gaggtgtcca   4980
gaagattcgt tgctttcgct aagaagtgga acctcaacta caaggtgatg acttatgctg   5040
gagcttggaa ggctactttg ggaaacctcg ataatgtggg aaagcactac tacgtgcacg   5100
gacaacattc tggaaagacc gcttgataat taattaaggc cgcagatctc caccgcggtg   5160
gcgctctagc ccgatatctc gacaagctcg agtttctcca taataatgtg tgagtagttc   5220
ccagataagg gaattagggt tcctataggg tttcgctcat gtgttgagca tataagaaac   5280
ccttagtatg tatttgtatt tgtaaaatac ttctatcaat aaaatttcta attcctaaaa   5340
ccaaaatcca gtactaaaat ccagatcccc cgaattaatt cggcgttaat tcagggcgcc   5400
taccggtacg gtccgtagcg gccgctagtc tgtgcgcact tgtatcctgc aggttaggcc   5460
ggccagtcga cctgcagcca gaaggataaa gaaattttgg acgcctgaag aagaggcagt   5520
tctgagggaa ggagtaaaag agtatgtctc cttaactcta ctatcaagtt tcaagaagct   5580
gagcttggct ctaccttgat atgtttattg ctgttgtgca ggtatggtaa atcatggaaa   5640
gagataaaga atgcaaaccc tgaagtattc gcagagagga ctgaggtgag agagcatgtc   5700
acttttgtgt tactcatctg aattatctta tatgcgaatt gtgagtggta ctaaaaaagg   5760
ttgtaacttt tggtaggttg atttgaagga taaatggagg aacttggttc ggtagccgta   5820
acaagttttt gggaatctct tgggttttaa attgctatgg agtttttttt tgcctgcgtg   5880
acaacatatc atcagctgtt gagaaggaag atggttaata gaaagggtct ttctttcaca   5940
ttttgtgttg tggacaaata ttaaagtcaa atgtggcaca tggattttaa ttcggccggt   6000
atggtttggt taagactggt ttaacatgta taattagtct ttgttttatt tggctcagcg   6060
gtttgttggt gttggttagg aacttaggct tgtctctttc tgataagatc tgattggtaa   6120
gatatgggta ctgtttggtt tatatgtttt gactattcag tcactatggc cccccataaat   6180
tttaattcgg ctggtatgtc tcggttaaga ccggtttgac atggttcatt tcagttcaat   6240
tatgtgaatc tggcacgtga tatgtttacc ttcacacgaa cattagtaat gatgggctaa   6300
tttaagactt aacagcctag aaaggcccat cttattacgt aacgacatcg tttagagtgc   6360
accaagctta taaatgacga cgagctacct cggggcatca cgctctttgt acactccgcc   6420
atctctctct ccttcgagca cagatctctc tcgtgaatat cgacaaggcg cgccggatcc   6480
gccatggcta ttttgaaccc tgaggctgat tctgctgcta acctcgctac tgattctgag   6540
```

```
gctaagcaaa gacaattggc tgaggctgga tacactcatg ttgagggtgc tcctgctcct   6600
ttgcctttgg agttgcctca tttctctctc agagatctca gagctgctat tcctaagcac   6660
tgcttcgaga gatctttcgt gacctccacc tactacatga tcaagaacgt gttgacttgc   6720
gctgctttgt tctacgctgc taccttcatt gatagagctg gagctgctgc ttatgttttg   6780
tggcctgtgt actggttctt ccagggatct tacttgactg gagtgtgggt tatcgctcat   6840
gagtgtggac atcaggctta ttgctcttct gaggtggtga acaacttgat tggactcgtg   6900
ttgcattctg ctttgttggt gccttaccac tcttggagaa tctctcacag aaagcaccat   6960
tccaacactg gatcttgcga gaacgatgag gttttcgttc ctgtgaccag atctgtgttg   7020
gcttcttctt ggaacgagac cttggaggat tctcctctct accaactcta ccgtatcgtg   7080
tacatgttgg ttgttggatg gatgcctgga tacctcttct tcaacgctac tggacctact   7140
aagtactggg gaaagtctag gtctcacttc aaccccttact ccgctatcta tgctgatagg   7200
gagagatgga tgatcgtgct ctccgatatt ttcttggtgg ctatgttggc tgttttggct   7260
gctttggtgc acactttctc cttcaacacc atggtgaagt tctacgtggt gccttacttc   7320
attgtgaacg cttacttggt gttgattacc tacctccaac acaccgatac ctacatccct   7380
catttcagag agggagagtg gaattggttg agaggagctt tgtgcactgt ggatagatca   7440
tttggtccat tcctcgattc tgtggtgcat agaatcgtgg atacccatgt ttgccaccac   7500
atcttctcca agatgccttt ctatcattgc gaggaggcta ccaacgctat taagcctctc   7560
ctcggaaagt tctacttgaa ggataccact cctgttcctg ttgctctctg gagatcttac   7620
acccattgca agttcgttga ggatgatgga aaggtggtgt tctacaagaa caagctctag   7680
ttaattaact aagcttttag tattaagaga agaaccaaag gctttgttgt tttcataatc   7740
tttctgtcat tttcttttat tatgatgtca agtcaagcga ctctttgcta gtaatctgta   7800
tgctcatgga tctctctctc tatttgtcga ctgaaaactt ttgggttaca catgaaagct   7860
ttttcttttt ctaaaatcca aaatgaaaga gttgtattaa cagatacata agtgaaagag   7920
tagtccctaa gatgacacta gcttcattta taaacaatcc tatcacattg tatatacagg   7980
ttatgattta ttcccaatca gcgtcaaaga atccagcatc tttcatctct gaatagtaga   8040
cattctccaa gtttagatct tcctcctcga tcaaaggcgc ctacggtcaa acactgtacg   8100
gaccgtggcc taataggccg gtacccaagt ttgtacaaaa aagcaggctc catgattacg   8160
ccaagcttgg ccactaaggc caatttaaat ctactaggcc ggccataagg atgacctacc   8220
cattcttgag acaaatgtta cattttagta tcagagtaaa atgtgtacct ataactcaaa   8280
ttcgattgac atgtatccat tcaacataaa attaaaccag cctgcacctg catccacatt   8340
tcaagtattt tcaaaccgtt cggctcctat ccaccgggtg taacaagacg gattccgaat   8400
ttggaagatt ttgactcaaa ttcccaattt atattgaccg tgactaaatc aactttaact   8460
tctataattc tgattaagct cccaatttat attcccaacg gcactacctc caaaatttat   8520
agactctcat cccctttttaa accaacttag taaacgtttt ttttttaatt ttatgaagtt   8580
aagtttttac cttgttttta aaaagaatcg ttcataagat gccatgccag aacattagct   8640
acacgttaca catagcatgc agccgcggag aattgttttt cttcgccact tgtcactccc   8700
ttcaaacacc taagagcttc tctctcacag cacacacata caatcacatg cgtgcatgca   8760
ttattacacg tgatcgccat gcaaatctcc tttatagcct ataaattaac tcatcggctt   8820
cactctttac tcaaaccaaa actcatcaat acaaacaaga ttaaaaacaa ccatggctac   8880
```

-continued

```
aaaggaggct tacgttttcc caactctcac cgagatcaag agatctctcc caaaggattg   8940
cttcgaggct tctgtgcctt tgtctctcta ctacactgtg agatgcttgg ttattgctgt   9000
ggctttgacc ttcggattga actacgctag agctttgcca gaggttgagt ctttctgggc   9060
tttggatgct gctttgtgca ctggatatat cctcctccag ggaattgtgt tctggggatt   9120
cttcactgtt ggacacgatg ctggacacgg agctttctct agataccacc tcttgaactt   9180
cgttgtggga accttcatgc actctctcat cttgacccca ttcgagtctt ggaagttgac   9240
ccacagacac caccacaaga acaccggaaa catcgataga gatgaggtgt tctacccaca   9300
gagaaaggct gatgatcacc cattgtccag gaacttgatc ttggctttgg gagctgcttg   9360
gcttgcttat ttggtggagg gattcccacc aagaaaggtg aaccacttca acccattcga   9420
gccacttttt gtgagacaag tgtccgctgt ggttatctct ttgctcgctc acttcttcgt   9480
tgctggactc tctatctact tgtctctcca gttgggactt aagaccatgg ctatctacta   9540
ctacggacca gttttcgtgt tcggatctat gttggtgatt accaccttct tgcaccacaa   9600
cgatgaggag actccatggt atgctgattc tgagtggact tacgtgaagg gaaacttgtc   9660
ctctgtggat agatcttacg gtgctctcat cgataacctc tcccacaaca tcggaactca   9720
ccagatccac cacctcttcc caattatccc acactacaag ctcaagaagg ctactgctgc   9780
tttccaccaa gctttcccag agcttgtgag aaagtccgat gagccaatca tcaaggcttt   9840
cttcagagtg ggaaggttgt atgctaacta cggagtggtt gatcaagagg ctaagctctt   9900
cactttgaag gaggctaagg ctgctactga agctgctgct aagaccaagt ctacctgagt   9960
tcgagtatta tggcattggg aaaactgttt ttcttgtacc atttgttgtg cttgtaattt  10020
actgtgtttt ttattcggtt ttcgctatcg aactgtgaaa tggaaatgga tggagaagag  10080
ttaatgaatg atatggtcct tttgttcatt ctcaaattaa tattatttgt tttttctctt  10140
atttgttgtg tgttgaattt gaaattataa gagatatgca aacattttgt tttgagtaaa  10200
aatgtgtcaa atcgtggcct ctaatgaccg aagttaatat gaggagtaaa acacttgtag  10260
ttgtaccatt atgcttattc actaggcaac aaatatattt tcagacctag aaaagctgca  10320
aatgttactg aatacaagta tgtcctcttg tgttttagac atttatgaac tttcctttat  10380
gtaattttcc agaatccttg tcagattcta atcattgctt tataattata gttatactca  10440
tggatttgta gttgagtatg aaaatatttt ttaatgcatt ttatgacttg ccaattgatt  10500
gacaacatgc atcaatgggg gatacctgca ggttaggccg gccattagca gatatttggt  10560
gtctaaatgt ttattttgtg atatgttcat gtttgaaatg gtggtttcga aaccagggac  10620
aacgttggga tctgataggg tgtcaaagag tattatggat tgggacaatt tcggtcatga  10680
gttgcaaatt caagtatatc gttcgattat gaaaattttc gaagaatatc ccatttgaga  10740
gagtctttac ctcattaatg tttttagatt atgaaatttt atcatagttc atcgtagtct  10800
ttttggtgta aaggctgtaa aaagaaattg ttcacttttg ttttcgttta tgtgaaggct  10860
gtaaaagatt gtaaaagact attttggtgt tttggataaa atgatagttt ttatagattc  10920
ttttgctttt agaagaaata catttgaaat tttttccatg ttgagtataa aataccgaaa  10980
tcgattgaag atcatagaaa tattttaact gaaaacaaat ttataactga ttcaattctc  11040
tccattttta tacctattta accgtaatcg attctaatag atgatcgatt ttttatataa  11100
tcctaattaa ccaacggcat gtattggata attaaccgat caactctcac ccctaataga  11160
atcagtattt tccttcgacg ttaattgatc ctacactatg taggtcatat ccatcgtttt  11220
aatttttggc caccattcaa ttctgtcttg cctttaggga tgtgaatatg aacggccaag  11280
```

-continued

```
gtaagagaat aaaaataatc caaattaaag caagagaggc caagtaagat aatccaaatg  11340
tacacttgtc attgccaaaa ttagtaaaat actcggcata ttgtattccc acacattatt  11400
aaaataccgt atatgtattg gctgcatttg catgaataat actacgtgta agcccaaaag  11460
aacccacgtg tagcccatgc aaagttaaca ctcacgaccc cattcctcag tctccactat  11520
ataaacccac catccccaat ctcaccaaac ccaccacaca actcacaact cactctcaca  11580
ccttctagag gatctgatat ctgcggccgc ggcgcgccac catgggaaaa ggatctgagg  11640
gaagatctgc tgctagagag atgactgctg aggctaacgg agataagaga aagaccatcc  11700
tcattgaggg agtgttgtac gatgctacca acttcaaaca cccaggaggt tccattatta  11760
acttcctcac cgagggagaa gctggagttg atgctaccca agcttacaga gagttccatc  11820
agagatccgg aaaggctgat aagtacctca agtccctccc aaagttggat gcttctaagg  11880
tggagtctag gttctctgct aaggagcagg ctagaaggga cgctatgacc agggattacg  11940
ctgctttcag agaggagttg gttgctgagg gatacttcga tccatctatc ccacacatga  12000
tctacagagt ggtggagatt gtggctttgt tcgctttgtc tttctggttg atgtctaagg  12060
cttctccaac ctctttggtt ttgggagtgg tgatgaacgg aatcgctcaa ggaagatgcg  12120
gatgggttat gcatgagatg ggacacggat ctttcactgg agttatctgg ctcgatgata  12180
ggatgtgcga gttcttctac ggagttggat gtggaatgtc tggacactac tggaagaacc  12240
agcattctaa gcaccatgct gctccaaaca gattggagca cgatgtggat ttgaacacct  12300
tgccactcgt tgctttcaac gagagagttg tgaggaaggt taagccagga tctttgttgg  12360
ctttgtggct cagagttcag gcttatttgt tcgctccagt gtcttgcttg ttgatcggat  12420
tgggatggac cttgtacttg cacccaagat atatgctcag gaccaagaga catatggagt  12480
ttgtgtggat cttcgctaga tatatcggat ggttctcctt gatgggagct ttgggatatt  12540
ctcctggaac ttctgtggga atgtacctct gctctttcgg acttggatgc atctacatct  12600
tcctccaatt cgctgtgtct catacccatt tgccagttac caacccagag gatcaattgc  12660
attggcttga gtacgctgct gatcataccg tgaacatctc taccaagtct tggttggtta  12720
cctggtggat gtctaacctc aacttccaaa tcgagcatca tttgttccca accgctccac  12780
aattcaggtt caaggagatc tctccaagag ttgaggctct cttcaagaga cataacctcc  12840
cttactacga tttgccatac acctctgctg tttctactac cttcgctaac ctctactctg  12900
ttggacattc tgttggagct gataccaaga agcaggattg attaattaag gccgcctcga  12960
gcatgcatct agagggcccg ctagcgttaa ccctgcttta atgagatatg cgagacgcct  13020
atgatcgcat gatatttgct ttcaattctg ttgtgcacgt tgtaaaaaac ctgagcatgt  13080
gtagctcaga tccttaccgc cggtttcggt tcattctaat gaatatatca cccgttacta  13140
tcgtattttt atgaataata ttctccgttc aatttactga ttgtggcgcc tactaccggt  13200
aattcccggg attagcggcc gctagtctgt gcgcacttgt atcctgcagg ttaggccggc  13260
cataaggatg acctacccat tcttgagaca aatgttacat tttagtatca gagtaaaatg  13320
tgtacctata actcaaattc gattgacatg tatccattca acataaaatt aaaccagcct  13380
gcacctgcat ccacatttca agtattttca aaccgttcgg ctcctatcca ccgggtgtaa  13440
caagacggat tccgaatttg gaagattttg actcaaattc ccaatttata ttgaccgtga  13500
ctaaatcaac tttaacttct ataattctga ttaagctccc aatttatatt cccaacggca  13560
ctacctccaa aatttataga ctctcatccc cttttaaacc aacttagtaa acgttttttt  13620
```

-continued

```
tttaatttta tgaagttaag tttttacctt gtttttaaaa agaatcgttc ataagatgcc  13680
atgccagaac attagctaca cgttacacat agcatgcagc cgcggagaat tgtttttctt  13740
cgccacttgt cactcccttc aaacacctaa gagcttctct ctcacagcac acacatacaa  13800
tcacatgcgt gcatgcatta ttacacgtga tcgccatgca aatctccttt atagcctata  13860
aattaactca tcggcttcac tctttactca aaccaaaact catcaataca aacaagatta  13920
aaaacaccgc gccggggccc aaaatggtgg acctcaagcc tggagtgaag cgcctggtga  13980
gctggaagga gatccgcgag cacgcgacgc ccgcgaccgc gtggatcgtg attcaccaca  14040
aggtctacga catctccaag tgggactcgc acccgggtgg ctccgtgatg ctcacgcagg  14100
ccggcgagga cgccacggac gccttcgcgg tcttccaccc gtcctcggcg ctcaagctgc  14160
tcgagcagtt ctacgtcggc gacgtggacg aaacctccaa ggccgagatc gagggggagc  14220
cggcgagcga cgaggagcgc gcgcgccgcg agcgcatcaa cgagttcatc gcgtcctacc  14280
gccgtctgcg cgtcaaggtc aagggcatgg ggctctacga cgccagcgcg ctctactacg  14340
cgtggaagct cgtgagcacg ttcggcatcg cggtgctctc gatggcgatc tgcttcttct  14400
tcaacagttt cgccatgtac atggtcgccg gcgtgattat ggggctcttc taccagcagt  14460
ccggatggct ggcgcacgac ttcttgcaca accaggtgtg cgagaaccgc acgctcggca  14520
accttatcgg ctgcctcgtg ggcaacgcct ggcagggctt cagcatgcag tggtggaaga  14580
acaagcacaa cctgcaccac gcggtgccga acctgcacag cgccaaggac gagggcttca  14640
tcggcgaccc ggacatcgac accatgccgc tgctggcgtg gtctaaggag atggcgcgca  14700
aggcgttcga gtcggcgcac ggcccgttct tcatccgcaa ccaggcgttc ctatacttcc  14760
cgctgctgct gctcgcgcgc ctgagctggc tcgcgcagtc gttcttctac gtgttcaccg  14820
agttctcgtt cggcatcttc gacaaggtcg agttcgacgg accggagaag gcgggtctga  14880
tcgtgcacta catctggcag ctcgcgatcc cgtacttctg caacatgagc ctgtttgagg  14940
gcgtggcata cttcctcatg ggccaggcgt cctgcggctt gctcctggcg ctggtgttca  15000
gtattggcca caacggcatg tcggtgtacg agcgcgaaac caagccggac ttctggcagc  15060
tgcaggtgac cacgacgcgc aacatccgcg cgtcggtatt catggactgg ttcaccggtg  15120
gcttgaacta ccagatcgac catcacctgt tcccgctcgt gccgcgccac aacttgccaa  15180
aggtcaacgt gctcatcaag tcgctatgca aggagttcga catcccgttc cacgagaccg  15240
gcttctggga gggcatctac gaggtcgtgg accacctggc ggacatcagc aaggaattta  15300
tcaccgagtt cccagcgatg taagttaact taattaataa ttgattggtt cgagtattat  15360
ggcattggga aaactgtttt tcttgtacca tttgttgtgc ttgtaattta ctgtgttttt  15420
tattcggttt tcgctatcga actgtgaaat ggaaatggat ggagaagagt taatgaatga  15480
tatggtcctt ttgttcattc tcaaattaat attatttgtt ttttctctta tttgttgtgt  15540
gttgaatttg aaattataag agatatgcaa acattttgtt ttgagtaaaa atgtgtcaaa  15600
tcgtggcctc taatgaccga agttaatatg aggagtaaaa cacttgtagt tgtaccatta  15660
tgcttattca ctaggcaaca aatatatttt cagacctaga aaagctgcaa atgttactga  15720
atacaagtat gtcctcttgt gttttagaca tttatgaact ttcctttatg taattttcca  15780
gaatccttgt cagattctaa tcattgcttt ataattatag ttatactcat ggatttgtag  15840
ttgagtatga aaatattttt taatgcattt tatgacttgc caattgattg acaacatgca  15900
tcaatggcaa acactgtacg gaccgtggcc taataggccg gtaccaccca gctttcttgt  15960
acaaagtggc catgattacg ccaagcttgg ccactaaggc caatttaaat ctactaggcc  16020
```

```
ggccatcgac ggcccggact gtatccaact tctgatcttt gaatctctct gttccaacat  16080
gttctgaagg agttctaaga cttttcagaa agcttgtaac atgctttgta gactttcttt  16140
gaattactct tgcaaactct gattgaacct acgtgaaaac tgctccagaa gttctaacca  16200
aattccgtct tgggaaggcc caaaatttat tgagtacttc agtttcatgg acgtgtcttc  16260
aaagatttat aacttgaaat cccatcattt ttaagagaag ttctgttccg caatgtctta  16320
gatctcattg aaatctacaa ctcttgtgtc agaagttctt ccagaatcaa cttgcatcat  16380
ggtgaaaatc tggccagaag ttctgaactt gtcatatttc ttaacagtta gaaaaatttc  16440
taagtgttta gaattttgac ttttccaaag caaacttgac ttttgacttt cttaataaaa  16500
caaacttcat attctaacat gtcttgatga aatgtgattc ttgaaatttg atgttgatgc  16560
aaaagtcaaa gtttgacttt tcagtgtgca attgaccatt ttgctcttgt gccaattcca  16620
aacctaaatt gatgtatcag tgctgcaaac ttgatgtcat ggaagatctt atgagaaaat  16680
tcttgaagac tgagaggaaa aattttgtag tacaacacaa agaatcctgt ttttcatagt  16740
cggactagac acattaacat aaaacaccac ttcattcgaa gagtgattga agaaggaaat  16800
gtgcagttac ctttctgcag ttcataagag caacttacag acacttttac taaaatacta  16860
caaagaggaa gattttaaca acttagagaa gtaatgggag ttaaagagca acacattaag  16920
ggggagtgtt aaaattaatg tgttgtaacc accactacct ttagtaagta ttataagaaa  16980
attgtaatca tcacattata attattgtcc ttatttaaaa ttatgataaa gttgtatcat  17040
taagattgag aaaaccaaat agtcctcgtc ttgatttttg aattattgtt ttctatgtta  17100
cttttcttca agcctatata aaaactttgt aatgctaaat tgtatgctgg aaaaaaatgt  17160
gtaatgaatt gaatagaaat tatggtattt caaagtccaa aatccatcaa tagaaattta  17220
gtacaaaacg taactcaaaa atattctctt attttaaatt ttacaacaat ataaaaatat  17280
tctcttattt taaattttac aataatataa tttatcacct gtcaccttta gaataccacc  17340
aacaatatta atacttagat attttattct taataatttt gagatctctc aatatatctg  17400
atatttattt tatatttgtg tcatattttc ttatgtttta gagttaaccc ttatatcttg  17460
gtcaaactag taattcaata tatgagtttg tgaaggacac attgacatct tgaaacattg  17520
gttttaacct tgttggaatg ttaaaggtaa taaaacattc agaattatga ccatctatta  17580
atatacttcc tttgtctttt aaaaaagtgt gcatgaaaat gctctatggt aagctagagt  17640
gtcttgctgg cctgtgtata tcaattccat ttccagatgg tagaaactgc cactacgaat  17700
aattagtcat aagacacgta tgttaacaca cgtccccttg catgtttttt gccatatatt  17760
ccgtctcttt ctttttcttc acgtataaaa caatgaacta attaatagag cgatcaagct  17820
gaaccgcgcc accatggttg ttgctatgga ccaacgcacc aatgtgaacg gagatcccgg  17880
cgccggagac cggaagaaag aagaaaggtt tgatccgagt gcacaaccac cgttcaagat  17940
cggagatata agggcggcga ttcctaagca ctgttgggtt aagagtcctt tgagatcaat  18000
gagttacgtc gtcagagaca ttatcgccgt cgcggctttg gccatcgctg ccgtgtatgt  18060
tgatagctgg ttcctttggc ctctttattg ggccgcccaa ggaacacttt tctgggccat  18120
ctttgttctc ggccacgact gtggacatgg gagtttctca gacattcctc tactgaatag  18180
tgtggttggt cacattcttc attctttcat cctcgttcct taccatggtt ggagaataag  18240
ccaccggaca caccaccaga accatggcca tgttgaaaac gacgagtcat gggttccgtt  18300
accagaaagg gtgtacaaga aattgcccca cagtactcgg atgctcagat acactgtccc  18360
```

-continued

```
tctccccatg ctcgcatatc ctctctattt gtgctacaga agtcctggaa aagaaggatc  18420
acattttaac ccatacagta gtttatttgc tccaagcgag agaaagctta ttgcaacttc  18480
aactacttgt tggtccataa tgttcgtcag tcttatcgct ctatctttcg tcttcggtcc  18540
actcgcggtt cttaaagtct acggtgtacc gtacattatc tttgtgatgt ggttggatgc  18600
tgtcacgtat ttgcatcatc atggtcacga tgagaagttg ccttggtata gaggcaagga  18660
atggagttat ctacgtggag gattaacaac aattgataga gattacggaa tctttaacaa  18720
cattcatcac gacattggaa ctcacgtgat ccatcatctc ttcccacaaa tccctcacta  18780
tcacttggtc gacgccacga aagcagctaa acatgtgttg ggaagatact acagagaacc  18840
aaagacgtca ggagcaatac cgatccactt ggtggagagt ttggtcgcaa gtattaagaa  18900
agatcattac gtcagcgaca ctggtgatat tgtcttctac gagacagatc cagatctcta  18960
cgtttacgct tctgacaaat ctaaaatcaa ttagttaatt aaggccgcct cgaccgtacc  19020
ccctgcagat agactatact atgttttagc ctgcctgctg gctagctact atgttatgtt  19080
atgttgtaaa ataaacacct gctaaggtat atctatctat attttagcat ggctttctca  19140
ataaattgtc tttccttatc gtttactatc ttatacctaa taatgaaata ataatatcac  19200
atatgaggaa cggggcaggt ttaggcatat atatacgagt gtagggcgga gtggggggcg  19260
cctactaccg gtaattcccg ggattagcgg ccgctagtct gtgcgcactt gtatcctgca  19320
ggtcaatcgt ttaaacactg tacggaccgt ggcctaatag gccggtaccc aactttatta  19380
tacatagttg ataattcact ggccggatat ctttttaag ggcgaattct gcagatatcc  19440
atcacactgg cggccgctcg aggtaccatc gttcaaacat ttggcaataa agtttcttaa  19500
gattgaatcc tgttgccggt cttgcgatga ttatcatata atttctgttg aattacgtta  19560
agcatgtaat aattaacatg taatgcatga cgttatttat gagatgggtt tttatgatta  19620
gagtcccgca attatacatt taatacgcga tagaaaacaa aatatagcgc gcaaactagg  19680
ataaattatc gcgcgcggtg tcatctatgt tactagatcg ggcattaccc tgttatccct  19740
agaggggaaa attcgaatcc aaaaattacg gatatgaata taggcatatc cgtatccgaa  19800
ttatccgttt gacagctagc aacgattgta caattgcttc tttaaaaaag gaagaaagaa  19860
agaaagaaaa gaatcaacat cagcgttaac aaacggcccc gttacggccc aaacggtcat  19920
atagagtaac ggcgttaagc gttgaaagac tcctatcgaa atacgtaacc gcaaacgtgt  19980
catagtcaga tcccctcttc cttcaccgcc tcaaacacaa aaataatctt ctacagccta  20040
tatatacaac cccccttct atctctcctt tctcacaatt catcatcttt ctttctctac  20100
ccccaatttt aagaaatcct ctcttctcct cttcattttc aaggtaaatc tctctctctc  20160
tctctctctc tgttattcct tgttttaatt aggtatgtat tattgctagt ttgttaatct  20220
gcttatctta tgtatgcctt atgtgaatat ctttatcttg ttcatctcat ccgtttagaa  20280
gctataaatt tgttgatttg actgtgtatc tacacgtggt tatgtttata tctaatcaga  20340
tatgaatttc ttcatattgt tgcgtttgtg tgtaccaatc cgaaatcgtt gattttttc  20400
atttaatcgt gtagctaatt gtacgtatac atatggatct acgtatcaat tgttcatctg  20460
tttgtgtttg tatgtataca gatctgaaaa catcacttct ctcatctgat tgtgttgtta  20520
catacataga tatagatctg ttatatcatt tttttatta attgtgtata tatatatgtg  20580
catagatctg gattacatga ttgtgattat ttacatgatt ttgttattta cgtatgtata  20640
tatgtagatc tggacttttt ggagttgttg acttgattgt atttgtgtgt gtatatgtgt  20700
gttctgatct tgatatgtta tgtatgtgca gctgaaccat ggcggcggca acaacaacaa  20760
```

```
caacaacatc ttcttcgatc tccttctcca ccaaaccatc tccttcctcc tccaaatcac  20820
cattaccaat ctccagattc tccctcccat tctccctaaa ccccaacaaa tcatcctcct  20880
cctcccgccg ccgcggtatc aaatccagct ctccctcctc catctccgcc gtgctcaaca  20940
caaccaccaa tgtcacaacc actccctctc caaccaaacc taccaaaccc gaaacattca  21000
tctcccgatt cgctccagat caaccccgca aaggcgctga tatcctcgtc gaagctttag  21060
aacgtcaagg cgtagaaacc gtattcgctt accctggagg tacatcaatg gagattcacc  21120
aagccttaac ccgctcttcc tcaatccgta acgtccttcc tcgtcacgaa caaggaggtg  21180
tattcgcagc agaaggatac gctcgatcct caggtaaacc aggtatctgt atagccactt  21240
caggtcccgg agctacaaat ctcgttagcg gattagccga tgcgttgtta gatagtgttc  21300
ctcttgtagc aatcacagga caagtccctc gtcgtatgat tggtacagat gcgtttcaag  21360
agactccgat tgttgaggta acgcgttcga ttacgaagca taactatctt gtgatggatg  21420
ttgaagatat ccctaggatt attgaggaag ctttcttttt agctacttct ggtagacctg  21480
gacctgtttt ggttgatgtt cctaaagata ttcaacaaca gcttgcgatt cctaattggg  21540
aacaggctat gagattacct ggttatatgt ctaggatgcc taaacctccg gaagattctc  21600
atttggagca gattgttagg ttgatttctg agtctaagaa gcctgtgttg tatgttggtg  21660
gtggttgttt gaattctagc gatgaattgg gtaggtttgt tgagcttacg gggatccctg  21720
ttgcgagtac gttgatgggg ctgggatctt atccttgtga tgatgagttg tcgttacata  21780
tgcttggaat gcatgggact gtgtatgcaa attacgctgt ggagcatagt gatttgttgt  21840
tggcgtttgg ggtaaggttt gatgatcgtg tcacgggtaa gcttgaggct tttgctagta  21900
gggctaagat tgttcatatt gatattgact cggctgagat tgggaagaat aagactcctc  21960
atgtgtctgt gtgtggtgat gttaagctgg ctttgcaagg gatgaataag gttcttgaga  22020
accgagcgga ggagcttaag cttgattttg gagtttggag gaatgagttg aacgtacaga  22080
aacagaagtt tccgttgagc tttaagacgt ttggggaagc tattcctcca cagtatgcga  22140
ttaaggtcct tgatgagttg actgatggaa aagccataat aagtactggt gtcgggcaac  22200
atcaaatgtg ggcggcgcag ttctacaatt acaagaaacc aaggcagtgg ctatcatcag  22260
gaggccttgg agctatggga tttggacttc ctgctgcgat tggagcgtct gttgctaacc  22320
ctgatgcgat agttgtggat attgacggag atggaagctt tataatgaat gtgcaagagc  22380
tagccactat tcgtgtagag aatcttccag tgaaggtact tttattaaac aaccagcatc  22440
ttggcatggt tatgcaatgg gaagatcggt tctacaaagc taaccgagct cacacatttc  22500
tcggggatcc ggctcaggag gacgagatat tcccgaacat gttgctgttt gcagcagctt  22560
gcgggattcc agcggcgagg gtgacaaaga aagcagatct ccgagaagct attcagacaa  22620
tgctggatac accaggacct tacctgttgg atgtgatttg tccgcaccaa gaacatgtgt  22680
tgccgatgat cccgaatggt ggcactttca acgatgtcat aacggaagga gatggccgga  22740
ttaaatactg atagggataa cagggtaatt tcccgaccca agctctagat cttgctgcgt  22800
tcggatattt tcgtggagtt cccgccacag acccggatga tccccgatcg ttcaaacatt  22860
tggcaataaa gtttcttaag attgaatcct gttgccggtc ttgcgatgat tatcatataa  22920
tttctgttga attacgttaa gcatgtaata attaacatgt aatgcatgac gttatttatg  22980
agatgggttt ttatgattag agtcccgcaa ttatacattt aatacgcgat agaaaacaaa  23040
atatagcgcg caaactagga taaattatcg cgcgcggtgt catctatgtt actagatcgg  23100
```

gcctcctgtc aagctctgct tggtaataat tgtcattaga ttgtttttat gcatagatgc 23160
actcgaaatc agccaatttt agacaagtat caaacggatg ttaattcagt acattaaaga 23220
cgtccgcaat gtgttattaa gttgtctaag cgtcaatttg tttacaccac aatatatcct 23280
gccaccagcc agccaacagc tccccgaccg gcagctcggc acaaaatcac cacgcgttac 23340
caccacgccg gccggccgca tggtgttgac cgtgttcgcc ggcattgccg agttcgagcg 23400
ttccctaatc atcgaccgca cccggagcgg gcgcgaggcc gccaaggccc gaggcgtgaa 23460
gtttggcccc cgccctaccc tcaccccggc acagatcgcg cacgcccgcg agctgatcga 23520
ccaggaaggc cgcaccgtga aagaggcggc tgcactgctt ggcgtgcatc gctcgaccct 23580
gtaccgcgca cttgagcgca gcgaggaagt gacgcccacc gaggccaggc ggcgcggtgc 23640
cttccgtgag gacgcattga ccgaggccga cgccctggcg gccgccgaga atgaacgcca 23700
agaggaacaa gcatgaaacc gcaccaggac ggccaggacg aaccgttttt cattaccgaa 23760
gagatcgagg cggagatgat cgcggccggg tacgtgttcg agccgcccgc gcacgtctca 23820
accgtgcggc tgcatgaaat cctggccggt ttgtctgatg ccaagctggc ggcctggccg 23880
gccagcttgg ccgctgaaga aaccgagcgc cgccgtctaa aaaggtgatg tgtatttgag 23940
taaaacagct tgcgtcatgc ggtcgctgcg tatatgatgc gatgagtaaa taaacaaata 24000
cgcaagggga acgcatgaag gttatcgctg tacttaacca gaaaggcggg tcaggcaaga 24060
cgaccatcgc aacccatcta gcccgcgccc tgcaactcgc cggggccgat gttctgttag 24120
tcgattccga tccccagggc agtgcccgcg attgggcggc cgtgcgggaa gatcaaccgc 24180
taaccgttgt cggcatcgac cgcccgacga ttgaccgcga cgtgaaggcc atcggccggc 24240
gcgacttcgt agtgatcgac ggagcgcccc aggcggcgga cttggctgtg tccgcgatca 24300
aggcagccga cttcgtgctg attccggtgc agccaagccc ttacgacata tgggccaccg 24360
ccgacctggt ggagctggtt aagcagcgca ttgaggtcac ggatggaagg ctacaagcgg 24420
cctttgtcgt gtcgcgggcg atcaaaggca cgcgcatcgg cggtgaggtt gccgaggcgc 24480
tggccgggta cgagctgccc attcttgagt cccgtatcac gcagcgcgtg agctacccag 24540
gcactgccgc cgccggcaca accgttcttg aatcagaacc cgagggcgac gctgcccgcg 24600
aggtccaggc gctggccgct gaaattaaat caaaactcat ttgagttaat gaggtaaaga 24660
gaaaatgagc aaaagcacaa acacgctaag tgccggccgt ccgagcgcac gcagcagcaa 24720
ggctgcaacg ttggccagcc tggcagacac gccagccatg aagcgggtca actttcagtt 24780
gccggcggag gatcacacca agctgaagat gtacgcggta cgccaaggca agaccattac 24840
cgagctgcta tctgaataca tcgcgcagct accagagtaa atgagcaaat gaataaatga 24900
gtagatgaat tttagcggct aaaggaggcg gcatggaaaa tcaagaacaa ccaggcaccg 24960
acgccgtgga atgccccatg tgtggaggaa cgggcggttg gccaggcgta agcggctggg 25020
ttgtctgccg gccctgcaat ggcactggaa cccccaagcc cgaggaatcg gcgtgagcgg 25080
tcgcaaacca tccggcccgg tacaaatcgg cgcggcgctg ggtgatgacc tggtggagaa 25140
gttgaaggcc gcgcaggccg cccagcggca acgcatcgag gcagaagcac gccccggtga 25200
atcgtggcaa gcggccgctg atcgaatccg caaagaatcc cggcaaccgc cggcagccgg 25260
tgcgccgtcg attaggaagc cgcccaaggg cgacgagcaa ccagattttt tcgttccgat 25320
gctctatgac gtgggcaccc gcgatagtcg cagcatcatg gacgtggccg ttttccgtct 25380
gtcgaagcgt gaccgacgag ctggcgaggt gatccgctac gagcttccag acgggcacgt 25440
agaggtttcc gcagggccgg ccggcatggc cagtgtgtgg gattacgacc tggtactgat 25500
ggcggtttcc catctaaccg aatccatgaa ccgataccgg gaagggaagg gagacaagcc 25560
cggccgcgtg ttccgtccac acgttgcgga cgtactcaag ttctgccggc gagccgatgg 25620
cggaaagcag aaagacgacc tggtagaaac ctgcattcgg ttaaacacca cgcacgttgc 25680
catgcagcgt acgaagaagg ccaagaacgg ccgcctggtg acggtatccg agggtgaagc 25740
cttgattagc cgctacaaga tcgtaaagag cgaaaccggg cggccggagt acatcgagat 25800
cgagctagct gattggatgt accgcgagat cacagaaggc aagaacccgg acgtgctgac 25860
ggttcacccc gattactttt tgatcgatcc cggcatcggc cgttttctct accgcctggc 25920
acgccgcgcc gcaggcaagg cagaagccag atggttgttc aagacgatct acgaacgcag 25980
tggcagcgcc ggagagttca agaagttctg tttcaccgtg cgcaagctga tcgggtcaaa 26040
tgacctgccg gagtacgatt tgaaggagga ggcggggcag gctggcccga tcctagtcat 26100
gcgctaccgc aacctgatcg agggcgaagc atccgccggt tcctaatgta cggagcagat 26160
gctagggcaa attgccctag caggggaaaa aggtcgaaaa ggtctctttc ctgtggatag 26220
cacgtacatt gggaacccaa agccgtacat tgggaaccgg aacccgtaca ttgggaaccc 26280
aaagccgtac attgggaacc ggtcacacat gtaagtgact gatataaaag agaaaaaagg 26340
cgatttttcc gcctaaaact ctttaaaact tattaaaact cttaaaaccc gcctggcctg 26400
tgcataactg tctggccagc gcacagccga agagctgcaa aaagcgccta cccttcggtc 26460
gctgcgctcc ctacgccccg ccgcttcgcg tcggcctatc gcggccgctg gccgctcaaa 26520
aatggctggc ctacggccag gcaatctacc agggcgcgga caagccgcgc cgtcgccact 26580
cgaccgccgg cgcccacatc aaggcaccct gcctcgcgcg tttcggtgat gacggtgaaa 26640
acctctgaca catgcagctc ccggagacgg tcacagcttg tctgtaagcg gatgccggga 26700
gcagacaagc ccgtcagggc gcgtcagcgg gtgttggcgg gtgtcggggc gcagccatga 26760
cccagtcacg tagcgatagc ggagtgtata ctggcttaac tatgcggcat cagagcagat 26820
tgtactgaga gtgcaccata tgcggtgtga aataccgcac agatgcgtaa ggagaaaata 26880
ccgcatcagg cgctcttccg cttcctcgct cactgactcg ctgcgctcgg tcgttcggct 26940
gcggcgagcg gtatcagctc actcaaaggc ggtaatacgg ttatccacag aatcagggga 27000
taacgcagga aagaacatgt gagcaaaagg ccagcaaaag gccaggaacc gtaaaaaggc 27060
cgcgttgctg gcgtttttcc ataggctccg cccccctgac gagcatcaca aaaatcgacg 27120
ctcaagtcag aggtggcgaa acccgacagg actataaaga taccaggcgt ttccccctgg 27180
aagctccctc gtgcgctctc ctgttccgac cctgccgctt accggatacc tgtccgcctt 27240
tctcccttcg ggaagcgtgg cgctttctca tagctcacgc tgtaggtatc tcagttcggt 27300
gtaggtcgtt cgctccaagc tgggctgtgt gcacgaaccc cccgttcagc ccgaccgctg 27360
cgccttatcc ggtaactatc gtcttgagtc caacccggta agacacgact tatcgccact 27420
ggcagcagcc actggtaaca ggattagcag agcgaggtat gtaggcggtg ctacagagtt 27480
cttgaagtgg tggcctaact acggctacac tagaaggaca gtatttggta tctgcgctct 27540
gctgaagcca gttaccttcg gaaaaagagt tggtagctct tgatccggca aacaaaccac 27600
cgctggtagc ggtggttttt ttgtttgcaa gcagcagatt acgcgcagaa aaaaaggatc 27660
tcaagaagat cctttgatct tttctacggg gtctgacgct cagtggaacg aaaactcacg 27720
ttaagggatt ttggtcatgc atgatatatc tcccaatttg tgtagggctt attatgcacg 27780
cttaaaaata ataaaagcag acttgacctg atagtttggc tgtgagcaat tatgtgctta 27840

```
gtgcatctaa cgcttgagtt aagccgcgcc gcgaagcggc gtcggcttga acgaatttct  27900
agctagacat tatttgccga ctaccttggt gatctcgcct ttcacgtagt ggacaaattc  27960
ttccaactga tctgcgcgcg aggccaagcg atcttcttct tgtccaagat aagcctgtct  28020
agcttcaagt atgacgggct gatactgggc cggcaggcgc tccattgccc agtcggcagc  28080
gacatccttc ggcgcgattt tgccggttac tgcgctgtac caaatgcggg acaacgtaag  28140
cactacattt cgctcatcgc cagcccagtc gggcggcgag ttccatagcg ttaaggtttc  28200
atttagcgcc tcaaatagat cctgttcagg aaccggatca aagagttcct ccgccgctgg  28260
acctaccaag gcaacgctat gttctcttgc ttttgtcagc aagatagcca gatcaatgtc  28320
gatcgtggct ggctcgaaga tacctgcaag aatgtcattg cgctgccatt ctccaaattg  28380
cagttcgcgc ttagctggat aacgccacgg aatgatgtcg tcgtgcacaa caatggtgac  28440
ttctacagcg cggagaatct cgctctctcc aggggaagcc gaagtttcca aaaggtcgtt  28500
gatcaaagct cgccgcgttg tttcatcaag ccttacggtc accgtaacca gcaaatcaat  28560
atcactgtgt ggcttcaggc cgccatccac tgcggagccg tacaaatgta cggccagcaa  28620
cgtcggttcg agatggcgct cgatgacgcc aactacctct gatagttgag tcgatacttc  28680
ggcgatcacc gcttccccca tgatgtttaa ctttgtttta gggcgactgc cctgctgcgt  28740
aacatcgttg ctgctccata acatcaaaca tcgacccacg gcgtaacgcg cttgctgctt  28800
ggatgcccga ggcatagact gtaccccaaa aaaacagtca taacaagcca tgaaaaccgc  28860
cactgcgttc catgg                                                    28875
```

<210> SEQ ID NO 72
<211> LENGTH: 1152
<212> TYPE: DNA
<213> ORGANISM: Calendula officinalis

<400> SEQUENCE: 72

```
atgggtgcag gcggtcgaat gcaagatccc accaacggtg gcaacaaaac cgagcccgaa     60
ccaatccaac gggtcccaca tgaaaaaccc ccattcacag ttggagacat caagaaagcg    120
atcccacctc attgtttcaa ccgatcggta attcgttcat tttcatacgt cttttacgac    180
ctcacaatcg cgtcaatctt gtactacatt gccaacaatt acatctctac cctccctagc    240
ccgctcgcct acgtggcatg gcccgtttac tgggccgtcc aagggtgcgt cttaaccggg    300
gtgtgggtca tagcccacga atgtggccat catgctttta gcgaccacca atggctcgat    360
gacaccgtgg gtctcgtctt gcactcgttc ctactcgtgc cctacttttc gtggaaatat    420
agccaccgta ggcaccactc gaacacgggt tcgatcgagc acgatgaggt tttcgtcccg    480
aagttgaaat cgggcgtccg gtcaaccgcc cggtacctaa acaacccacc gggccgaatc    540
ttgaccctac tcgtaaccct aaccctcggt tggcctctat acctcacgtt caacgtttcg    600
ggccgttact acgaccggtt cgcgtgccat ttcgacccga atagcccgat ctactcgaag    660
cgcgaacggg ctcaaatctt catatccgac gccgggatct tagccgtagt cttcgtactc    720
ttccgactcg caatgaccaa agggctcacg tgggtcctaa ccatgtacgg tggcccgtta    780
ctcgtggtca acggtttcct agtcttgatc acattcctac aacacactca cccttcgctc    840
ccgcactatg actcaaccga atgggattgg ttacgtgggg ccctcaccac aatcgaccgt    900
gattacggga tcctaaacaa agtgttccat aacataaccg acactcacgt ggcccaccat    960
ttgttctcta caatgcctca ttaccatgca atggaagcca cgaaggtgat caaaccgatt   1020
ttgggcgatt attatcagtt tgacgggacc tcgattttta aggcgatgta tcgggaaaca   1080
```

aaggagtgca tttatgttga taaggatgag gaggtgaaag atggtgttta ttggtatcgt 1140
aataagattt aa 1152

<210> SEQ ID NO 73
<211> LENGTH: 383
<212> TYPE: PRT
<213> ORGANISM: Calendula officinalis

<400> SEQUENCE: 73

Met Gly Ala Gly Gly Arg Met Gln Asp Pro Thr Asn Gly Gly Asn Lys
1 5 10 15

Thr Glu Pro Glu Pro Ile Gln Arg Val Pro His Glu Lys Pro Pro Phe
20 25 30

Thr Val Gly Asp Ile Lys Lys Ala Ile Pro Pro His Cys Phe Asn Arg
35 40 45

Ser Val Ile Arg Ser Phe Ser Tyr Val Phe Tyr Asp Leu Thr Ile Ala
50 55 60

Ser Ile Leu Tyr Tyr Ile Ala Asn Asn Tyr Ile Ser Thr Leu Pro Ser
65 70 75 80

Pro Leu Ala Tyr Val Ala Trp Pro Val Tyr Trp Ala Val Gln Gly Cys
85 90 95

Val Leu Thr Gly Val Trp Val Ile Ala His Glu Cys Gly His His Ala
100 105 110

Phe Ser Asp His Gln Trp Leu Asp Asp Thr Val Gly Leu Val Leu His
115 120 125

Ser Phe Leu Leu Val Pro Tyr Phe Ser Trp Lys Tyr Ser His Arg Arg
130 135 140

His His Ser Asn Thr Gly Ser Ile Glu His Asp Glu Val Phe Val Pro
145 150 155 160

Lys Leu Lys Ser Gly Val Arg Ser Thr Ala Arg Tyr Leu Asn Asn Pro
165 170 175

Pro Gly Arg Ile Leu Thr Leu Leu Val Thr Leu Thr Leu Gly Trp Pro
180 185 190

Leu Tyr Leu Thr Phe Asn Val Ser Gly Arg Tyr Tyr Asp Arg Phe Ala
195 200 205

Cys His Phe Asp Pro Asn Ser Pro Ile Tyr Ser Lys Arg Glu Arg Ala
210 215 220

Gln Ile Phe Ile Ser Asp Ala Gly Ile Leu Ala Val Val Phe Val Leu
225 230 235 240

Phe Arg Leu Ala Met Thr Lys Gly Leu Thr Trp Val Leu Thr Met Tyr
245 250 255

Gly Gly Pro Leu Leu Val Val Asn Gly Phe Leu Val Leu Ile Thr Phe
260 265 270

Leu Gln His Thr His Pro Ser Leu Pro His Tyr Asp Ser Thr Glu Trp
275 280 285

Asp Trp Leu Arg Gly Ala Leu Thr Thr Ile Asp Arg Asp Tyr Gly Ile
290 295 300

Leu Asn Lys Val Phe His Asn Ile Thr Asp Thr His Val Ala His His
305 310 315 320

Leu Phe Ser Thr Met Pro His Tyr His Ala Met Glu Ala Thr Lys Val
325 330 335

Ile Lys Pro Ile Leu Gly Asp Tyr Tyr Gln Phe Asp Gly Thr Ser Ile
340 345 350

Phe Lys Ala Met Tyr Arg Glu Thr Lys Glu Cys Ile Tyr Val Asp Lys
355 360 365

Asp Glu Glu Val Lys Asp Gly Val Tyr Trp Tyr Arg Asn Lys Ile
370 375 380

<210> SEQ ID NO 74
<211> LENGTH: 1176
<212> TYPE: DNA
<213> ORGANISM: Perilla fruticosa

<400> SEQUENCE: 74
atggctgttt cttctggagc taggctttct aagtctggag ctgatggaga agttttcgat 60
ggacagcaac agtacgaggg aattggaaag agagctgctg ataagtttga tcctgctgct 120
cctcctcctt tcaagatcgc tgatatcagg gctgctattc ctgctcattg ctgggttaag 180
aacccttgga ggagtctttc ttacgttgtg tgggatgttg ctgctgtttt cgctcttctt 240
gctgctgctg tgtacattaa ctcttgggct ttctggcctg tttactggat tgctcaggga 300
actatgttct gggctctttt cgttcttgga cacgattgtg gacacggatc tttctctgat 360
aacactactc ttaacaacgt tgtgggacac gttcttcact cttctatcct tgtgccttac 420
cacggatgga gaatctctca taggactcac catcagaacc atggacacgt tgagaaggat 480
gagtcttggg ttccacttcc tgagaacctt tacaagaagc ttgatttctc tactaagttc 540
cttaggtaca agatcccttt ccctatgttc gcttaccctc tttacctttg gtacagatct 600
cctggaaaga ctggatctca cttcaaccct tactctgatc ttttcaagcc taacgagagg 660
ggacttatcg tgacttctac tatgtgttgg gctgctatgg gagtgtttct tctttacgct 720
tctactatcg tgggtcctaa catgatgttc aagctttacg gagtgcctta ccttattttc 780
gtgatgtggc ttgatactgt gacttacctt caccaccacg gatacgataa gaagcttcct 840
tggtacaggt caaaggagtg gtcttacctt agaggaggac ttactactgt ggatcaggat 900
tacggattct tcaacaagat ccaccacgat attggaactc acgtgatcca tcaccttttc 960
cctcagattc ctcactacca ccttgttgag gctactagag aggctaagag ggtgttggga 1020
aactactacc gtgagcctag aaagtctgga cctgtgcctc ttcatcttat ccctgctctt 1080
ttgaagtctc ttggaaggga tcactacgtg tctgataacg gagatatcgt gtactaccag 1140
actgatgatg agcttttccc ttctaagaag atctga 1176

<210> SEQ ID NO 75
<211> LENGTH: 391
<212> TYPE: PRT
<213> ORGANISM: Perilla frutescens

<400> SEQUENCE: 75

Met Ala Val Ser Ser Gly Ala Arg Leu Ser Lys Ser Gly Ala Asp Gly
1 5 10 15

Glu Val Phe Asp Gly Gln Gln Gln Tyr Glu Gly Ile Gly Lys Arg Ala
20 25 30

Ala Asp Lys Phe Asp Pro Ala Ala Pro Pro Pro Phe Lys Ile Ala Asp
35 40 45

Ile Arg Ala Ala Ile Pro Ala His Cys Trp Val Lys Asn Pro Trp Arg
50 55 60

Ser Leu Ser Tyr Val Val Trp Asp Val Ala Ala Val Phe Ala Leu Leu
65 70 75 80

Ala Ala Ala Val Tyr Ile Asn Ser Trp Ala Phe Trp Pro Val Tyr Trp
85 90 95

```
Ile Ala Gln Gly Thr Met Phe Trp Ala Leu Phe Val Leu Gly His Asp
            100                 105                 110

Cys Gly His Gly Ser Phe Ser Asp Asn Thr Thr Leu Asn Asn Val Val
        115                 120                 125

Gly His Val Leu His Ser Ser Ile Leu Val Pro Tyr His Gly Trp Arg
    130                 135                 140

Ile Ser His Arg Thr His His Gln Asn His Gly His Val Glu Lys Asp
145                 150                 155                 160

Glu Ser Trp Val Pro Leu Pro Glu Asn Leu Tyr Lys Lys Leu Asp Phe
                165                 170                 175

Ser Thr Lys Phe Leu Arg Tyr Lys Ile Pro Phe Pro Met Phe Ala Tyr
            180                 185                 190

Pro Leu Tyr Leu Trp Tyr Arg Ser Pro Gly Lys Thr Gly Ser His Phe
        195                 200                 205

Asn Pro Tyr Ser Asp Leu Phe Lys Pro Asn Glu Arg Gly Leu Ile Val
    210                 215                 220

Thr Ser Thr Met Cys Trp Ala Ala Met Gly Val Phe Leu Leu Tyr Ala
225                 230                 235                 240

Ser Thr Ile Val Gly Pro Asn Met Met Phe Lys Leu Tyr Gly Val Pro
                245                 250                 255

Tyr Leu Ile Phe Val Met Trp Leu Asp Thr Val Thr Tyr Leu His His
            260                 265                 270

His Gly Tyr Asp Lys Lys Leu Pro Trp Tyr Arg Ser Lys Glu Trp Ser
        275                 280                 285

Tyr Leu Arg Gly Gly Leu Thr Thr Val Asp Gln Asp Tyr Gly Phe Phe
    290                 295                 300

Asn Lys Ile His His Asp Ile Gly Thr His Val Ile His His Leu Phe
305                 310                 315                 320

Pro Gln Ile Pro His Tyr His Leu Val Glu Ala Thr Arg Glu Ala Lys
                325                 330                 335

Arg Val Leu Gly Asn Tyr Tyr Arg Glu Pro Arg Lys Ser Gly Pro Val
            340                 345                 350

Pro Leu His Leu Ile Pro Ala Leu Leu Lys Ser Leu Gly Arg Asp His
        355                 360                 365

Tyr Val Ser Asp Asn Gly Asp Ile Val Tyr Tyr Gln Thr Asp Asp Glu
    370                 375                 380

Leu Phe Pro Ser Lys Lys Ile
385                 390
```

<210> SEQ ID NO 76
<211> LENGTH: 1430
<212> TYPE: DNA
<213> ORGANISM: Brassica napus

<400> SEQUENCE: 76

```
aagctttaca acgctacaca aaacttataa ccgtaatcac cattcattaa cttaactact      60

atcacatgca ttcatgaatt gaaacgagaa ggatgtaaat agttgggaag ttatctccac     120

gttgaagaga tcgttagcga gagctgaaag accgagggag gagacgccgt caacacggac     180

agagtcgtcg accctcacat gaagtaggag gaatctccgt gaggagccag agagacgtct     240

ttggtcttcg gtttcgatcc ttgatctgac ggagaagacg agagaagtgc gactggactc     300

cgtgaggacc aacagagtcg tcctcggttt cgatcgtcgg tattggtgga gaaggcggag     360

gaatctccgt gacgagccag agagatgtcg tcggtcttcg gtttcgatcc ttgatctgac     420
```

-continued

```
ggagaagacg agagaagtgc gacgagactc cgtgaggacc aacagagttg tcctcggttt    480

cgatcgtcgg tttcggcgga gaaggcggag gaatctccgt gaggagccag agagacgtcg    540

ttggtcttcg gtttcgatcc ttgatctgtt ggagaagacg agacaagtgg gacgagactc    600

aacgacggag tcagagacgt cgtcggtctt cggtttcggc cgagaaggcg gagtcggtct    660

tcggtttcgg ccgagaaggc ggaggagacg tcttcgattt gggtctctcc tcttgacgaa    720

gaaaacaaag aacacgagaa ataatgagaa agagaacaaa agaaaaaaaa ataaaaataa    780

aaataaaatt tggtcctctt atgtggtgac acgtggtttg aaacccacca aataatcgat    840

cacaaaaaac ctaagttaag gatcggtaat aacctttcta attaattttg atttatatta    900

aatcactctt tttatttata aaccccacta aattatgcga tattgattgt ctaagtacaa    960

aaattctctc gaattcaata cacatgtttc atatatttag ccctgttcat ttaatattac   1020

tagcgcattt ttaatttaaa attttgtaaa ctttttttggt caaagaacat ttttttaatt   1080

agagacagaa atctagactc tttatttgga ataatagtaa taaagatata ttaggcaatg   1140

agtttatgat gttatgttta tatagtttat ttcattttaa attgaaaagc attattttta   1200

tcgaaatgaa tctagtatac aatcaatatt tatgtttttt catcagatac tttcctattt   1260

tttggcacct ttcatcggac tactgattta tttcaatgtg tatgcatgca tgagcatgag   1320

tatacacatg tcttttaaaa tgcatgtaaa gcgtaacgga ccacaaaaga ggatccatac   1380

aaatacatct catcgcttcc tctactattc tccgacacac acactgagca              1430
```

<210> SEQ ID NO 77
<211> LENGTH: 400
<212> TYPE: DNA
<213> ORGANISM: Brassica napus

<400> SEQUENCE: 77

```
tttgatgtat ctgagtgcca acgtttactt tgtctttcct ttcttttatt ggttatgatt     60

agatgtttac tatgttctct ctttttcgtt ataaataaag aagttcaatt cttctatagt    120

ttcaaacgcg attttaagcg tttctattta ggtttacatg atttctttta caaaatcatc    180

tttaaaatac agtatatttt tagttttcat aaaatattta aagaaatgaa agtttataaa    240

cattcactcc tattctctaa ttaaggattt gtaaaacaaa aattttgtaa gcatatcgat    300

ttatgcgttt tgtcttaatt agctcactaa ataataaata atagcttatg ttgtgggact    360

gtttaattac ctaacttaga actaaaatca actctttgtg                          400
```

<210> SEQ ID NO 78
<211> LENGTH: 684
<212> TYPE: DNA
<213> ORGANISM: Vicia faba

<400> SEQUENCE: 78

```
ctgcagcaaa tttacacatt gccactaaac gtctaaaccc ttgtaatttg tttttgtttt     60

actatgtgtg ttatgtattt gatttgcgat aaatttttat atttggtact aaatttataa    120

caccttttat gctaacgttt gccaacactt agcaatttgc aagttgatta attgattcta    180

aattattttt gtcttctaaa tacatatact aatcaactgg aaatgtaaat atttgctaat    240

atttctacta taggagaatt aaagtgagtg aatatggtac cacaaggttt ggagatttaa    300

ttgttgcaat gctgcatgga tggcatatac accaaacatt caataattct tgaggataat    360

aatggtacca cacaagattt gaggtgcatg aacgtcacgt ggacaaaagg tttagtaatt    420
```

-continued

```
tttcaagaca acaatgttac cacacacaag ttttgaggtg catgcatgga tgccctgtgg    480

aaagtttaaa aatattttgg aaatgatttg catggaagcc atgtgtaaaa ccatgacatc    540

cacttggagg atgcaataat gaagaaaact acaaatttac atgcaactag ttatgcatgt    600

agtctatata atgaggattt tgcaatactt tcattcatac acactcacta agttttacac    660

gattataatt tcttcatagc cagt                                            684


<210> SEQ ID NO 79
<211> LENGTH: 216
<212> TYPE: DNA
<213> ORGANISM: Cauliflower mosaic virus

<400> SEQUENCE: 79

tcgacaagct cgagtttctc cataataatg tgtgagtagt tcccagataa gggaattagg     60

gttcctatag ggtttcgctc atgtgttgag catataagaa acccttagta tgtatttgta    120

tttgtaaaat acttctatca ataaaatttc taattcctaa aaccaaaatc cagtactaaa    180

atccagatcc cccgaattaa ttcggcgtta attcag                              216


<210> SEQ ID NO 80
<211> LENGTH: 1000
<212> TYPE: DNA
<213> ORGANISM: Brassica napus

<400> SEQUENCE: 80

gtcgacctgc agccagaagg ataaagaaat tttggacgcc tgaagaagag gcagttctga     60

gggaaggagt aaaagagtat gtctccttaa ctctactatc aagtttcaag aagctgagct    120

tggctctacc ttgatatgtt tattgctgtt gtgcaggtat ggtaaatcat ggaaagagat    180

aaagaatgca aaccctgaag tattcgcaga gaggactgag gtgagagagc atgtcacttt    240

tgtgttactc atctgaatta tcttatatgc gaattgtgag tggtactaaa aaaggttgta    300

acttttggta ggttgatttg aaggataaat ggaggaactt ggttcggtag ccgtaacaag    360

tttttgggaa tctcttgggt tttaaattgc tatggagttt ttttttgcct gcgtgacaac    420

atatcatcag ctgttgagaa ggaagatggt taatagaaag ggtctttctt tcacattttg    480

tgttgtggac aaatattaaa gtcaaatgtg gcacatggat tttaattcgg ccggtatggt    540

ttggttaaga ctggtttaac atgtataatt agtctttgtt ttatttggct cagcggtttg    600

ttggtgttgg ttaggaactt aggcttgtct ctttctgata agatctgatt ggtaagatat    660

gggtactgtt tggtttatat gttttgacta ttcagtcact atggccccca taaattttaa    720

ttcggctggt atgtctcggt taagaccggt ttgacatggt tcatttcagt tcaattatgt    780

gaatctggca cgtgatatgt ttaccttcac acgaacatta gtaatgatgg gctaatttaa    840

gacttaacag cctagaaagg cccatcttat tacgtaacga catcgtttag agtgcaccaa    900

gcttataaat gacgacgagc tacctcgggg catcacgctc tttgtacact ccgccatctc    960

tctctccttc gagcacagat ctctctcgtg aatatcgaca                        1000


<210> SEQ ID NO 81
<211> LENGTH: 382
<212> TYPE: DNA
<213> ORGANISM: Brassica napus

<400> SEQUENCE: 81

cttttagtat taagagaaga accaaaggct ttgttgtttt cataatcttt ctgtcatttt     60

cttttattat gatgtcaagt caagcgactc tttgctagta atctgtatgc tcatggatct    120
```

ctctctctat ttgtcgactg aaaacttttg ggttacacat gaaagctttt tctttttcta 180
aaatccaaaa tgaaagagtt gtattaacag atacataagt gaaagagtag tccctaagat 240
gacactagct tcatttataa acaatcctat cacattgtat atacaggtta tgatttattc 300
ccaatcagcg tcaaagaatc cagcatcttt catctctgaa tagtagacat tctccaagtt 360
tagatcttcc tcctcgatca aa 382

<210> SEQ ID NO 82
<211> LENGTH: 664
<212> TYPE: DNA
<213> ORGANISM: Brassica napus

<400> SEQUENCE: 82
taaggatgac ctacccattc ttgagacaaa tgttacattt tagtatcaga gtaaaatgtg 60
tacctataac tcaaattcga ttgacatgta tccattcaac ataaaattaa accagcctgc 120
acctgcatcc acatttcaag tattttcaaa ccgttcggct cctatccacc gggtgtaaca 180
agacggattc cgaatttgga agattttgac tcaaattccc aatttatatt gaccgtgact 240
aaatcaactt taacttctat aattctgatt aagctcccaa tttatattcc caacggcact 300
acctccaaaa tttatagact ctcatcccct tttaaaccaa cttagtaaac gttttttttt 360
taattttatg aagttaagtt tttaccttgt ttttaaaaag aatcgttcat aagatgccat 420
gccagaacat tagctacacg ttacacatag catgcagccg cggagaattg tttttcttcg 480
ccacttgtca ctcccttcaa acacctaaga gcttctctct cacagcacac acatacaatc 540
acatgcgtgc atgcattatt acacgtgatc gccatgcaaa tctcctttat agcctataaa 600
ttaactcatc ggcttcactc tttactcaaa ccaaaactca tcaatacaaa caagattaaa 660
aaca 664

<210> SEQ ID NO 83
<211> LENGTH: 558
<212> TYPE: DNA
<213> ORGANISM: Pisum sativum

<400> SEQUENCE: 83
gttcgagtat tatggcattg ggaaaactgt ttttcttgta ccatttgttg tgcttgtaat 60
ttactgtgtt ttttattcgg ttttcgctat cgaactgtga aatggaaatg gatggagaag 120
agttaatgaa tgatatggtc cttttgttca ttctcaaatt aatattattt gtttttttctc 180 ttatttgttg tgtgttgaat ttgaaattat aagagatatg caaacatttt gttttgagta 240
aaaatgtgtc aaatcgtggc ctctaatgac cgaagttaat atgaggagta aaacacttgt 300
agttgtacca ttatgcttat tcactaggca acaaatatat tttcagacct agaaaagctg 360
caaatgttac tgaatacaag tatgtcctct tgtgttttag acatttatga actttccttt 420
atgtaatttt ccagaatcct tgtcagattc taatcattgc tttataatta tagttatact 480
catggatttg tagttgagta tgaaaatatt ttttaatgca ttttatgact tgccaattga 540
ttgacaacat gcatcaat 558

<210> SEQ ID NO 84
<211> LENGTH: 1039
<212> TYPE: DNA
<213> ORGANISM: Linum usitatissimum

<400> SEQUENCE: 84

-continued

```
ttagcagata tttggtgtct aaatgtttat tttgtgatat gttcatgttt gaaatggtgg      60

tttcgaaacc agggacaacg ttgggatctg atagggtgtc aaagagtatt atggattggg     120

acaatttcgg tcatgagttg caaattcaag tatatcgttc gattatgaaa attttcgaag     180

aatatcccat ttgagagagt ctttacctca ttaatgtttt tagattatga aattttatca     240

tagttcatcg tagtcttttt ggtgtaaagg ctgtaaaaag aaattgttca cttttgtttt     300

cgtttatgtg aaggctgtaa aagattgtaa aagactattt tggtgttttg gataaaatga     360

tagtttttat agattctttt gcttttagaa gaaatacatt tgaaattttt tccatgttga     420

gtataaaata ccgaaatcga ttgaagatca tagaaatatt ttaactgaaa acaaatttat     480

aactgattca attctctcca tttttatacc tatttaaccg taatcgattc taatagatga     540

tcgatttttt atataatcct aattaaccaa cggcatgtat tggataatta accgatcaac     600

tctcacccct aatagaatca gtattttcct tcgacgttaa ttgatcctac actatgtagg     660

tcatatccat cgttttaatt tttggccacc attcaattct gtcttgcctt tagggatgtg     720

aatatgaacg gccaaggtaa gagaataaaa ataatccaaa ttaaagcaag agaggccaag     780

taagataatc caaatgtaca cttgtcattg ccaaaattag taaaatactc ggcatattgt     840

attcccacac attattaaaa taccgtatat gtattggctg catttgcatg aataatacta     900

cgtgtaagcc caaaagaacc cacgtgtagc ccatgcaaag ttaacactca cgaccccatt     960

cctcagtctc cactatataa acccaccatc cccaatctca ccaaacccac cacacaactc    1020

acaactcact ctcacacct                                                 1039
```

<210> SEQ ID NO 85
<211> LENGTH: 192
<212> TYPE: DNA
<213> ORGANISM: Agrobacterium tumefaciens

<400> SEQUENCE: 85

```
ctgctttaat gagatatgcg agacgcctat gatcgcatga tatttgcttt caattctgtt      60

gtgcacgttg taaaaaacct gagcatgtgt agctcagatc cttaccgccg gtttcggttc     120

attctaatga atatatcacc cgttactatc gtatttttat gaataatatt ctccgttcaa     180

tttactgatt gt                                                         192
```

<210> SEQ ID NO 86
<211> LENGTH: 1799
<212> TYPE: DNA
<213> ORGANISM: Vicia faba

<400> SEQUENCE: 86

```
tcgacggccc ggactgtatc caacttctga tctttgaatc tctctgttcc aacatgttct      60

gaaggagttc taagactttt cagaaagctt gtaacatgct ttgtagactt tctttgaatt     120

actcttgcaa actctgattg aacctacgtg aaaactgctc cagaagttct aaccaaattc     180

cgtcttggga aggcccaaaa tttattgagt acttcagttt catggacgtg tcttcaaaga     240

tttataactt gaaatcccat catttttaag agaagttctg ttccgcaatg tcttagatct     300

cattgaaatc tacaactctt gtgtcagaag ttcttccaga atcaacttgc atcatggtga     360

aaatctggcc agaagttctg aacttgtcat atttcttaac agttagaaaa atttctaagt     420

gtttagaatt ttgacttttc caaagcaaac ttgacttttg actttcttaa taaaacaaac     480

ttcatattct aacatgtctt gatgaaatgt gattcttgaa atttgatgtt gatgcaaaag     540

tcaaagtttg acttttcagt gtgcaattga ccattttgct cttgtgccaa ttccaaacct     600
```

-continued

```
aaattgatgt atcagtgctg caaacttgat gtcatggaag atcttatgag aaaattcttg    660

aagactgaga ggaaaaattt tgtagtacaa cacaaagaat cctgtttttc atagtcggac    720

tagacacatt aacataaaac accacttcat tcgaagagtg attgaagaag gaaatgtgca    780

gttacctttc tgcagttcat aagagcaact tacagacact tttactaaaa tactacaaag    840

aggaagattt taacaactta gagaagtaat gggagttaaa gagcaacaca ttaaggggga    900

gtgttaaaat taatgtgttg taaccaccac tacctttagt aagtattata agaaaattgt    960

aatcatcaca ttataattat tgtccttatt taaaattatg ataaagttgt atcattaaga   1020

ttgagaaaac caaatagtcc tcgtcttgat ttttgaatta ttgttttcta tgttactttt   1080

cttcaagcct atataaaaac tttgtaatgc taaattgtat gctggaaaaa aatgtgtaat   1140

gaattgaata gaaattatgg tatttcaaag tccaaaatcc atcaatagaa atttagtaca   1200

aaacgtaact caaaaatatt ctcttatttt aaattttaca acaatataaa aatattctct   1260

tattttaaat tttacaataa tataatttat cacctgtcac ctttagaata ccaccaacaa   1320

tattaatact tagatatttt attcttaata attttgagat ctctcaatat atctgatatt   1380

tattttatat ttgtgtcata ttttcttatg ttttagagtt aacccttata tcttggtcaa   1440

actagtaatt caatatatga gtttgtgaag gacacattga catcttgaaa cattggtttt   1500

aaccttgttg gaatgttaaa ggtaataaaa cattcagaat tatgaccatc tattaatata   1560

cttcctttgt cttttaaaaa agtgtgcatg aaaatgctct atggtaagct agagtgtctt   1620

gctggcctgt gtatatcaat tccatttcca gatggtagaa actgccacta cgaataatta   1680

gtcataagac acgtatgtta acacacgtcc ccttgcatgt tttttgccat atattccgtc   1740

tctttctttt tcttcacgta taaaacaatg aactaattaa tagagcgatc aagctgaac    1799
```

<210> SEQ ID NO 87
<211> LENGTH: 235
<212> TYPE: DNA
<213> ORGANISM: Vicia faba

<400> SEQUENCE: 87

```
cctgcagata gactatacta tgttttagcc tgcctgctgg ctagctacta tgttatgtta     60

tgttgtaaaa taaacacctg ctaaggtata tctatctata ttttagcatg gctttctcaa    120

taaattgtct ttccttatcg tttactatct tatacctaat aatgaaataa taatatcaca    180

tatgaggaac ggggcaggtt taggcatata tatacgagtg tagggcggag tgggg         235
```

<210> SEQ ID NO 88
<211> LENGTH: 18
<212> TYPE: DNA
<213> ORGANISM: Artificial sequence
<220> FEATURE:
<223> OTHER INFORMATION: primer

<400> SEQUENCE: 88

```
acggbttggr tbtgscay                                                   18
```

<210> SEQ ID NO 89
<211> LENGTH: 16
<212> TYPE: DNA
<213> ORGANISM: Artificial sequence
<220> FEATURE:
<223> OTHER INFORMATION: primer

<400> SEQUENCE: 89
sagarytkbg gtggsm 16

<210> SEQ ID NO 90
<211> LENGTH: 17
<212> TYPE: DNA
<213> ORGANISM: Artificial sequence
<220> FEATURE:
<223> OTHER INFORMATION: primer

<400> SEQUENCE: 90
gtdatrvaca rccartg 17

<210> SEQ ID NO 91
<211> LENGTH: 17
<212> TYPE: DNA
<213> ORGANISM: Artificial sequence
<220> FEATURE:
<223> OTHER INFORMATION: primer

<400> SEQUENCE: 91
rtgdwysayd atccrtg 17

<210> SEQ ID NO 92
<211> LENGTH: 18
<212> TYPE: DNA
<213> ORGANISM: Artificial sequence
<220> FEATURE:
<223> OTHER INFORMATION: primer

<400> SEQUENCE: 92
gaccaycghv wgcaycay 18

<210> SEQ ID NO 93
<211> LENGTH: 16
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (11)..(11)
<223> OTHER INFORMATION: n is a, c, g, or t

<400> SEQUENCE: 93
garacraygs ngaycc 16

<210> SEQ ID NO 94
<211> LENGTH: 22
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (11)..(11)
<223> OTHER INFORMATION: n is a, c, g, or t

<400> SEQUENCE: 94
garacraygs ngayccyaay kg 22

<210> SEQ ID NO 95
<211> LENGTH: 20
<212> TYPE: DNA
<213> ORGANISM: Artificial sequence
<220> FEATURE:
<223> OTHER INFORMATION: primer

<400> SEQUENCE: 95
gyyykgtart cccakgggwa 20

<210> SEQ ID NO 96
<211> LENGTH: 27
<212> TYPE: DNA
<213> ORGANISM: Artificial sequence
<220> FEATURE:
<223> OTHER INFORMATION: primer

<400> SEQUENCE: 96
tcccaggrwa ryrtgrtgrw arttgtg 27

<210> SEQ ID NO 97
<211> LENGTH: 20
<212> TYPE: DNA
<213> ORGANISM: Artificial sequence
<220> FEATURE:
<223> OTHER INFORMATION: primer

<400> SEQUENCE: 97
gaycccayaa ygcaarmggg 20

<210> SEQ ID NO 98
<211> LENGTH: 17
<212> TYPE: DNA
<213> ORGANISM: Artificial sequence
<220> FEATURE:
<223> OTHER INFORMATION: primer

<400> SEQUENCE: 98
gggttyttyt tywscay 17

<210> SEQ ID NO 99
<211> LENGTH: 18
<212> TYPE: DNA
<213> ORGANISM: Artificial sequence
<220> FEATURE:
<223> OTHER INFORMATION: primer

<400> SEQUENCE: 99
ttyttywsca ygtggtgg 18

<210> SEQ ID NO 100
<211> LENGTH: 19
<212> TYPE: DNA
<213> ORGANISM: Artificial sequence
<220> FEATURE:
<223> OTHER INFORMATION: primer

<400> SEQUENCE: 100
rtggcgcswr ttacarcca 19

<210> SEQ ID NO 101
<211> LENGTH: 20
<212> TYPE: DNA
<213> ORGANISM: Artificial sequence
<220> FEATURE:
<223> OTHER INFORMATION: primer

<400> SEQUENCE: 101
yttrtcrtag gcwswcccca 20

<210> SEQ ID NO 102
<211> LENGTH: 1401
<212> TYPE: DNA

<213> ORGANISM: Brassica napus

<400> SEQUENCE: 102

```
atgatatcga tggacatgga ttcgatggct gcttcgatcg gcgtatcggt cgccgtcctt     60
cgcttcctcc tctgcttcgt cgccaccatc cccgtctcct tcttctggcg aatcgttccg    120
agtcgactcg gcaagcacgt ctacgccgcc gcttcaggcg tgttcctctc ttacctctcc    180
ttcggcttct cctcgaatct ccacttcctc gtcccgatga cgatcggata cgcttccatg    240
gcgatgtatc ggcccaagtg tggaatcatc actttcttcc tcggctttgc ttatctcatc    300
ggctgtcatg tgttttacat gagtggtgat gcgtggaaag aaggagggat cgactccact    360
ggagcgttaa tggtgttaac gctgaaggtt atctcgtgtg cggttaatta caatgatggg    420
atgttgaagg aggaaggctt acgtgaagct cagaagaaga acagactgat cgagatgccg    480
tctttgatcg agtactttgg ttactgtctc tgttgcggta gccatttcgc tggtcctgtt    540
tacgaaatga aagattatct ccaatggaca gagggaacag gaatttggga tagttccgag    600
aaaagaaagc agccatcgcc ttatttagct acactgcgag ctatcttcca agctgggatt    660
tgcatggctt tgtatctcta tctagtccct cagttcccgt tgactcggtt tactgaaccg    720
gtgtaccaag aatggggatt ttggaagaag tttggttacc agtacatggc gggacagacg    780
gctcgctgga agtattactt catctggtcg atctcagagg cttctattat catctctggt    840
ttgggtttca gcggctggac tgatgacgat gcttcgccga aacccaaatg ggaccgtgcc    900
aagaacgtag acatcctcgg tgttgaactt gctaagagcg cggttcagat tccgcttgtg    960
tggaacatac aagtcagcac ctggctccgt cactacgtgt atgagagact agtgaagagt   1020
ggaaagaagg caggtttctt ccagttacta gctacacaaa ccgttagtgc ggtttggcat   1080
ggactgtatc ctggttacat gatgttcttt gttcagtcag ctttgatgat cgctggctca   1140
cgggttattt accgatggca acaagctatt agtccgaaat tgggagtgct gagaagtatg   1200
atggtgttca tcaacttcct ttacactgtt ttggttctca actactcagc cgtcggtttc   1260
atggttttaa gcttgcacga aacgctcact gcatacggga gcgtatacta cataggaaca   1320
atcatacctg ttggattgat tctcctcagc tacgttgttc ctgcgaaacc ctatcgagca   1380
aagccacgta aagaagaata a                                              1401
```

<210> SEQ ID NO 103
<211> LENGTH: 466
<212> TYPE: PRT
<213> ORGANISM: Brassica napus

<400> SEQUENCE: 103

```
Met Ile Ser Met Asp Met Asp Ser Met Ala Ala Ser Ile Gly Val Ser
1               5                   10                  15

Val Ala Val Leu Arg Phe Leu Leu Cys Phe Val Ala Thr Ile Pro Val
            20                  25                  30

Ser Phe Phe Trp Arg Ile Val Pro Ser Arg Leu Gly Lys His Val Tyr
        35                  40                  45

Ala Ala Ala Ser Gly Val Phe Leu Ser Tyr Leu Ser Phe Gly Phe Ser
    50                  55                  60

Ser Asn Leu His Phe Leu Val Pro Met Thr Ile Gly Tyr Ala Ser Met
65                  70                  75                  80

Ala Met Tyr Arg Pro Lys Cys Gly Ile Ile Thr Phe Phe Leu Gly Phe
                85                  90                  95

Ala Tyr Leu Ile Gly Cys His Val Phe Tyr Met Ser Gly Asp Ala Trp
```

-continued

```
            100                 105                 110

Lys Glu Gly Gly Ile Asp Ser Thr Gly Ala Leu Met Val Leu Thr Leu
        115                 120                 125

Lys Val Ile Ser Cys Ala Val Asn Tyr Asn Asp Gly Met Leu Lys Glu
    130                 135                 140

Glu Gly Leu Arg Glu Ala Gln Lys Lys Asn Arg Leu Ile Glu Met Pro
145                 150                 155                 160

Ser Leu Ile Glu Tyr Phe Gly Tyr Cys Leu Cys Cys Gly Ser His Phe
                165                 170                 175

Ala Gly Pro Val Tyr Glu Met Lys Asp Tyr Leu Gln Trp Thr Glu Gly
            180                 185                 190

Thr Gly Ile Trp Asp Ser Ser Glu Lys Arg Lys Gln Pro Ser Pro Tyr
        195                 200                 205

Leu Ala Thr Leu Arg Ala Ile Phe Gln Ala Gly Ile Cys Met Ala Leu
    210                 215                 220

Tyr Leu Tyr Leu Val Pro Gln Phe Pro Leu Thr Arg Phe Thr Glu Pro
225                 230                 235                 240

Val Tyr Gln Glu Trp Gly Phe Trp Lys Lys Phe Gly Tyr Gln Tyr Met
                245                 250                 255

Ala Gly Gln Thr Ala Arg Trp Lys Tyr Tyr Phe Ile Trp Ser Ile Ser
            260                 265                 270

Glu Ala Ser Ile Ile Ile Ser Gly Leu Gly Phe Ser Gly Trp Thr Asp
        275                 280                 285

Asp Asp Ala Ser Pro Lys Pro Lys Trp Asp Arg Ala Lys Asn Val Asp
    290                 295                 300

Ile Leu Gly Val Glu Leu Ala Lys Ser Ala Val Gln Ile Pro Leu Val
305                 310                 315                 320

Trp Asn Ile Gln Val Ser Thr Trp Leu Arg His Tyr Val Tyr Glu Arg
                325                 330                 335

Leu Val Lys Ser Gly Lys Lys Ala Gly Phe Phe Gln Leu Leu Ala Thr
            340                 345                 350

Gln Thr Val Ser Ala Val Trp His Gly Leu Tyr Pro Gly Tyr Met Met
        355                 360                 365

Phe Phe Val Gln Ser Ala Leu Met Ile Ala Gly Ser Arg Val Ile Tyr
    370                 375                 380

Arg Trp Gln Gln Ala Ile Ser Pro Lys Leu Gly Val Leu Arg Ser Met
385                 390                 395                 400

Met Val Phe Ile Asn Phe Leu Tyr Thr Val Leu Val Leu Asn Tyr Ser
                405                 410                 415

Ala Val Gly Phe Met Val Leu Ser Leu His Glu Thr Leu Thr Ala Tyr
            420                 425                 430

Gly Ser Val Tyr Tyr Ile Gly Thr Ile Ile Pro Val Gly Leu Ile Leu
        435                 440                 445

Leu Ser Tyr Val Val Pro Ala Lys Pro Tyr Arg Ala Lys Pro Arg Lys
    450                 455                 460

Glu Glu
465


<210> SEQ ID NO 104
<211> LENGTH: 1398
<212> TYPE: DNA
<213> ORGANISM: Brassica napus

<400> SEQUENCE: 104
```

-continued

```
atgatatcga tggacatgaa ttcgatggct gcttcgatcg gcgtatcggt cgccgtcctc     60
cgcttcctcc aatgcttcgt cgccacgatc cccgtctcct tcttctggcg aatcgttccg    120
agtcgactcg gcaagcacat ctacgccgcc gcttcaggcg tattcctctc ttacctctcc    180
ttcggcttct cctcaaatct ccacttcctc gttccgatga cgatcggata cgcttccatg    240
gcgatgtatc gacccaagtg tggaatcatc agtttcttcc tcggcttcgc ttatctcatc    300
ggctgtcatg tgttttacat gagtggtgat gcgtggaaag aaggtggcat cgactccact    360
ggagcgttaa tggtgttaac gctgaaggtt atctcatgtg cggttaatta caatgatggg    420
atgttgaagg aggaaggctt acgtgaagct cagaagaaga acagactgat cgagatgccg    480
tctttgatcg agtactttgg ttactgtctc tgttgcggta gccatttcgc tggtcctgtt    540
tacgaaatga aagattatct ccaatggaca gagggaacag gaatttggga tagttccgag    600
aaaagaaagc agccatcgcc ttatttagct acactgcgag ctatcttcca agctgggatt    660
tgcatggctc tgtatctcta tctagtccct cagttcccgt tgactcggtt cactgaaccg    720
gtgtaccaag aatgggggtt ttggaagaag tttggttacc agtacatggc gggacagacg    780
gctcgctgga agtattactt catctggtcg atctcagagg cttctattat catctctggt    840
ttgggtttca gtggctggac tgacgatgct tcgccaaaac ccaaatggga ccgtgccaag    900
aacgtggaca tcctcggtgt agaacttgct aagagcgcgg ttcagattcc gcttgtgtgg    960
aacatacaag tcagcacctg gctccgtcac tacgtgtatg agagacttgt gaagagtggg   1020
aagaaagcag gtttctttca gttactagct acacaaaccg tcagtgcggt ttggcatgga   1080
ctgtatcctg gttacatgat gttctttgtt caatcagctt tgatgattgc tggctcaaga   1140
gttatttacc gatggcaaca agctatcagt ccgaaactag caatcctgag aagtatcatg   1200
gtgttcatca actttcttta caccgtcttg gttctcaact actcagccgt tggtttcatg   1260
gttttaagct tgcacgaaac gctcactgcc tacgggagcg tatattacat tggaacaatc   1320
atacctgttg gattgattct cctcagctac gtggttcctg cgaagccctc tcggccaaag   1380
ccacgtaaag aggaataa                                                  1398

<210> SEQ ID NO 105
<211> LENGTH: 465
<212> TYPE: PRT
<213> ORGANISM: Brassica napus

<400> SEQUENCE: 105

Met Ile Ser Met Asp Met Asn Ser Met Ala Ala Ser Ile Gly Val Ser
1               5                   10                  15

Val Ala Val Leu Arg Phe Leu Gln Cys Phe Val Ala Thr Ile Pro Val
            20                  25                  30

Ser Phe Phe Trp Arg Ile Val Pro Ser Arg Leu Gly Lys His Ile Tyr
        35                  40                  45

Ala Ala Ala Ser Gly Val Phe Leu Ser Tyr Leu Ser Phe Gly Phe Ser
    50                  55                  60

Ser Asn Leu His Phe Leu Val Pro Met Thr Ile Gly Tyr Ala Ser Met
65                  70                  75                  80

Ala Met Tyr Arg Pro Lys Cys Gly Ile Ile Ser Phe Phe Leu Gly Phe
                85                  90                  95

Ala Tyr Leu Ile Gly Cys His Val Phe Tyr Met Ser Gly Asp Ala Trp
            100                 105                 110

Lys Glu Gly Gly Ile Asp Ser Thr Gly Ala Leu Met Val Leu Thr Leu
        115                 120                 125
```

-continued

```
Lys Val Ile Ser Cys Ala Val Asn Tyr Asn Asp Gly Met Leu Lys Glu
    130                 135                 140

Glu Gly Leu Arg Glu Ala Gln Lys Lys Asn Arg Leu Ile Glu Met Pro
145                 150                 155                 160

Ser Leu Ile Glu Tyr Phe Gly Tyr Cys Leu Cys Cys Gly Ser His Phe
                165                 170                 175

Ala Gly Pro Val Tyr Glu Met Lys Asp Tyr Leu Gln Trp Thr Glu Gly
            180                 185                 190

Thr Gly Ile Trp Asp Ser Ser Glu Lys Arg Lys Gln Pro Ser Pro Tyr
        195                 200                 205

Leu Ala Thr Leu Arg Ala Ile Phe Gln Ala Gly Ile Cys Met Ala Leu
    210                 215                 220

Tyr Leu Tyr Leu Val Pro Gln Phe Pro Leu Thr Arg Phe Thr Glu Pro
225                 230                 235                 240

Val Tyr Gln Glu Trp Gly Phe Trp Lys Lys Phe Gly Tyr Gln Tyr Met
                245                 250                 255

Ala Gly Gln Thr Ala Arg Trp Lys Tyr Tyr Phe Ile Trp Ser Ile Ser
            260                 265                 270

Glu Ala Ser Ile Ile Ile Ser Gly Leu Gly Phe Ser Gly Trp Thr Asp
        275                 280                 285

Asp Ala Ser Pro Lys Pro Lys Trp Asp Arg Ala Lys Asn Val Asp Ile
    290                 295                 300

Leu Gly Val Glu Leu Ala Lys Ser Ala Val Gln Ile Pro Leu Val Trp
305                 310                 315                 320

Asn Ile Gln Val Ser Thr Trp Leu Arg His Tyr Val Tyr Glu Arg Leu
                325                 330                 335

Val Lys Ser Gly Lys Lys Ala Gly Phe Phe Gln Leu Leu Ala Thr Gln
            340                 345                 350

Thr Val Ser Ala Val Trp His Gly Leu Tyr Pro Gly Tyr Met Met Phe
        355                 360                 365

Phe Val Gln Ser Ala Leu Met Ile Ala Gly Ser Arg Val Ile Tyr Arg
    370                 375                 380

Trp Gln Gln Ala Ile Ser Pro Lys Leu Ala Ile Leu Arg Ser Ile Met
385                 390                 395                 400

Val Phe Ile Asn Phe Leu Tyr Thr Val Leu Val Leu Asn Tyr Ser Ala
                405                 410                 415

Val Gly Phe Met Val Leu Ser Leu His Glu Thr Leu Thr Ala Tyr Gly
            420                 425                 430

Ser Val Tyr Tyr Ile Gly Thr Ile Ile Pro Val Gly Leu Ile Leu Leu
        435                 440                 445

Ser Tyr Val Val Pro Ala Lys Pro Ser Arg Pro Lys Pro Arg Lys Glu
    450                 455                 460

Glu
465
```

<210> SEQ ID NO 106
<211> LENGTH: 1404
<212> TYPE: DNA
<213> ORGANISM: Brassica napus

<400> SEQUENCE: 106

```
atggaatcgc tcgacatgag ttccatggcg gcctcgatcg gcgtatcggt cgccgttctc      60

cgtttcctac tctgcttcgt cgcaacgatc ccagtctcct tcgcgtggag attcgtcccg     120
```

```
agtcgactcg gtaaacacat ctactcagct gcttctggag ccctcctctc ttacctctcc    180

tttggcttct cgtcgaatct tcacttcctc gttcccatga ccattggcta cgcttcgatg    240

gcgatatata gaccaatgtg tggattcatc actttcttcc tcggtttcgc ttatctcatt    300

ggctgtcatg tgttttatat gagtggggat gcttggaaag aaggaggcat tgactctact    360

ggagctttga tggtgttgac gttgaaagtg atatcgtgtt ctataaacta caacgatggg    420

atgttgaagg aagagactct ccgtgaggct cagaggaaga accgtttggt tcggatgcct    480

tctctcattg agtactttgg ttactgcctt tgctgcggaa gccacttcgc tggccctgtc    540

ttcgaaatga aagactatct tgaatggacc gaagagaaag gaatttgggc tgttacttct    600

gggaaaggga agagaccatc gccttacgga gcaacacttc gagctatatt acaagctggg    660

atctgtatgg ctctgtatct ctacttagtc cctcagttcc cattaacccg gttcactgag    720

ccagtgtacc atgaatgggg tttctggaga agattcggtt accaatacat ggccggtttc    780

acggctcgtt ggaagtacta cttcatctgg tcgatctcag aggcttccat catcatctcc    840

ggtttgggtt tcagtggttg gaccgacgaa aacactcaaa caaaggccaa atggaccgt     900

gcaaagaacg tcgatatctt aggtgttgag ctagccaaga gtgctgttca gattcctctt    960

gtgtggaaca tacaagtcag cacttggctc cgtcactatg tgtatgagag aattgtgaag   1020

ccagggaaga aagctggctt cttccagctg ctagctactc aaaccgttag tgccgtgtgg   1080

catggactgt atcctggata cattatattc tttgttcaat cagcattgat gatcgatggt   1140

tcaaaagcta tttaccgttg gcaacaagca atgcctccga agatggcaat gctgagaagt   1200

gttatggttt tcatcaactt cctctacaca gttttggttc tcaattactc ctccgttggt   1260

ttcatggtat tgagcttgca cgaaacactc gtggcctaca agagtgtata tttcataggc   1320

actgtagtgc ctattgttgt gattctgctc agctatttgg ttcctgtgaa gcctgtgaga   1380

ccaaagaccc ggaaagaaga ataa                                           1404


<210> SEQ ID NO 107
<211> LENGTH: 467
<212> TYPE: PRT
<213> ORGANISM: Brassica napus

<400> SEQUENCE: 107

Met Glu Ser Leu Asp Met Ser Ser Met Ala Ala Ser Ile Gly Val Ser
1               5                   10                  15

Val Ala Val Leu Arg Phe Leu Leu Cys Phe Val Ala Thr Ile Pro Val
            20                  25                  30

Ser Phe Ala Trp Arg Phe Val Pro Ser Arg Leu Gly Lys His Ile Tyr
        35                  40                  45

Ser Ala Ala Ser Gly Ala Leu Leu Ser Tyr Leu Ser Phe Gly Phe Ser
    50                  55                  60

Ser Asn Leu His Phe Leu Val Pro Met Thr Ile Gly Tyr Ala Ser Met
65                  70                  75                  80

Ala Ile Tyr Arg Pro Met Cys Gly Phe Ile Thr Phe Phe Leu Gly Phe
                85                  90                  95

Ala Tyr Leu Ile Gly Cys His Val Phe Tyr Met Ser Gly Asp Ala Trp
            100                 105                 110

Lys Glu Gly Gly Ile Asp Ser Thr Gly Ala Leu Met Val Leu Thr Leu
        115                 120                 125

Lys Val Ile Ser Cys Ser Ile Asn Tyr Asn Asp Gly Met Leu Lys Glu
    130                 135                 140
```

-continued

```
Glu Thr Leu Arg Glu Ala Gln Arg Lys Asn Arg Leu Val Arg Met Pro
145                 150                 155                 160

Ser Leu Ile Glu Tyr Phe Gly Tyr Cys Leu Cys Cys Gly Ser His Phe
                165                 170                 175

Ala Gly Pro Val Phe Glu Met Lys Asp Tyr Leu Glu Trp Thr Glu Glu
            180                 185                 190

Lys Gly Ile Trp Ala Val Thr Ser Gly Lys Gly Lys Arg Pro Ser Pro
        195                 200                 205

Tyr Gly Ala Thr Leu Arg Ala Ile Leu Gln Ala Gly Ile Cys Met Ala
    210                 215                 220

Leu Tyr Leu Tyr Leu Val Pro Gln Phe Pro Leu Thr Arg Phe Thr Glu
225                 230                 235                 240

Pro Val Tyr His Glu Trp Gly Phe Trp Arg Arg Phe Gly Tyr Gln Tyr
                245                 250                 255

Met Ala Gly Phe Thr Ala Arg Trp Lys Tyr Tyr Phe Ile Trp Ser Ile
            260                 265                 270

Ser Glu Ala Ser Ile Ile Ile Ser Gly Leu Gly Phe Ser Gly Trp Thr
        275                 280                 285

Asp Glu Asn Thr Gln Thr Lys Ala Lys Trp Asp Arg Ala Lys Asn Val
    290                 295                 300

Asp Ile Leu Gly Val Glu Leu Ala Lys Ser Ala Val Gln Ile Pro Leu
305                 310                 315                 320

Val Trp Asn Ile Gln Val Ser Thr Trp Leu Arg His Tyr Val Tyr Glu
                325                 330                 335

Arg Ile Val Lys Pro Gly Lys Lys Ala Gly Phe Phe Gln Leu Leu Ala
            340                 345                 350

Thr Gln Thr Val Ser Ala Val Trp His Gly Leu Tyr Pro Gly Tyr Ile
        355                 360                 365

Ile Phe Phe Val Gln Ser Ala Leu Met Ile Asp Gly Ser Lys Ala Ile
    370                 375                 380

Tyr Arg Trp Gln Gln Ala Met Pro Pro Lys Met Ala Met Leu Arg Ser
385                 390                 395                 400

Val Met Val Phe Ile Asn Phe Leu Tyr Thr Val Leu Val Leu Asn Tyr
                405                 410                 415

Ser Ser Val Gly Phe Met Val Leu Ser Leu His Glu Thr Leu Val Ala
            420                 425                 430

Tyr Lys Ser Val Tyr Phe Ile Gly Thr Val Val Pro Ile Val Val Ile
        435                 440                 445

Leu Leu Ser Tyr Leu Val Pro Val Lys Pro Val Arg Pro Lys Thr Arg
    450                 455                 460

Lys Glu Glu
465
```

<210> SEQ ID NO 108
<211> LENGTH: 1179
<212> TYPE: DNA
<213> ORGANISM: Brassica napus

<400> SEQUENCE: 108

```
atggaatcgg agctaaagaa tatgaattcg aatccaccga cgagcaagga ggagcgccca      60

ttgctcaaat cggaatccga tgtctccgcc gccattgaag agctcgacaa aaagttcgcg     120

ccttacgcga ggacggactt gtacgggacg atggggttgg gtccttttcc ggcggcggag     180

aaagtcaagc tcgcggtggc gatggtgacg cttgtgcccg ttcggtttgt tctggcgatg     240
```

-continued

```
acgatcttgc ttctgtatta cttgatatgc agggtgttta ctctgttctc gtctccgcat    300

cgtgaagaag aggaagaaga ggaagttgtt caggaagatt atgctcacat gggagggtgg    360

agacggagtg tgatcgtgcg gtgtgggagg tttctctcga gggttttgct tttcgtgttt    420

gggttttatt ggattcctga gagacgtccg gatcgagatt cagcagctga ttccaatccc    480

aaaacaagtt cttctgagat tgcagagaaa ggggaaaccg ataaggagga acctgaaaga    540

cctggggtca ttgtgtctaa tcacgtttcg tacctggaca ttttgtatca tatgtctgct    600

tctttcccta gttttgttgc caagagatca gtgggcaaac ttcctcttgt tggcctcatc    660

agcaagtgcc ttggttgcgt ctatgtccag cgagaagcaa aatcacctga tttcaagggt    720

gtatctggca cagtaaatga gagagttaga gaagctcata ggaataaatc tgctccaact    780

attatgcttt ttccagaagg aacaaccacc aacggagact acttacttac attcaagaca    840

ggtgcatttt tggcaggaac tcctgttctt cctgttattt taaaataccc gtacgagcgt    900

ttcagtgcag catgggatac aatatccgga gcacgtcacg ttctcttcct tctctgtcaa    960

ttcgtaaacc acttggaggt gatacggtta cctgtatact acccttcaca agaagagaaa   1020

gataatccca aactatatgc tagcaacgtc cggaaactaa tggccagcga gggtaacatg   1080

atactgtcgg atttgggact tggagacaaa aggatatatc acgcgaccct caatggtaat   1140

cttagtcaac tccgtgtttt ccatcagaaa gaagaataa                          1179
```

<210> SEQ ID NO 109
<211> LENGTH: 392
<212> TYPE: PRT
<213> ORGANISM: Brassica napus

<400> SEQUENCE: 109

```
Met Glu Ser Glu Leu Lys Asn Met Asn Ser Asn Pro Pro Thr Ser Lys
1               5                   10                  15

Glu Glu Arg Pro Leu Leu Lys Ser Glu Ser Asp Val Ser Ala Ala Ile
            20                  25                  30

Glu Glu Leu Asp Lys Lys Phe Ala Pro Tyr Ala Arg Thr Asp Leu Tyr
        35                  40                  45

Gly Thr Met Gly Leu Gly Pro Phe Pro Ala Ala Glu Lys Val Lys Leu
    50                  55                  60

Ala Val Ala Met Val Thr Leu Val Pro Val Arg Phe Val Leu Ala Met
65                  70                  75                  80

Thr Ile Leu Leu Leu Tyr Tyr Leu Ile Cys Arg Val Phe Thr Leu Phe
                85                  90                  95

Ser Ser Pro His Arg Glu Glu Glu Glu Glu Glu Glu Val Val Gln Glu
            100                 105                 110

Asp Tyr Ala His Met Gly Gly Trp Arg Arg Ser Val Ile Val Arg Cys
        115                 120                 125

Gly Arg Phe Leu Ser Arg Val Leu Leu Phe Val Phe Gly Phe Tyr Trp
    130                 135                 140

Ile Pro Glu Arg Arg Pro Asp Arg Asp Ser Ala Ala Asp Ser Asn Pro
145                 150                 155                 160

Lys Thr Ser Ser Ser Glu Ile Ala Glu Lys Gly Glu Thr Asp Lys Glu
                165                 170                 175

Glu Pro Glu Arg Pro Gly Val Ile Val Ser Asn His Val Ser Tyr Leu
            180                 185                 190

Asp Ile Leu Tyr His Met Ser Ala Ser Phe Pro Ser Phe Val Ala Lys
        195                 200                 205
```

-continued

```
Arg Ser Val Gly Lys Leu Pro Leu Val Gly Leu Ile Ser Lys Cys Leu
    210                 215                 220

Gly Cys Val Tyr Val Gln Arg Glu Ala Lys Ser Pro Asp Phe Lys Gly
225                 230                 235                 240

Val Ser Gly Thr Val Asn Glu Arg Val Arg Glu Ala His Arg Asn Lys
                245                 250                 255

Ser Ala Pro Thr Ile Met Leu Phe Pro Glu Gly Thr Thr Thr Asn Gly
            260                 265                 270

Asp Tyr Leu Leu Thr Phe Lys Thr Gly Ala Phe Leu Ala Gly Thr Pro
        275                 280                 285

Val Leu Pro Val Ile Leu Lys Tyr Pro Tyr Glu Arg Phe Ser Ala Ala
    290                 295                 300

Trp Asp Thr Ile Ser Gly Ala Arg His Val Leu Phe Leu Leu Cys Gln
305                 310                 315                 320

Phe Val Asn His Leu Glu Val Ile Arg Leu Pro Val Tyr Tyr Pro Ser
                325                 330                 335

Gln Glu Glu Lys Asp Asn Pro Lys Leu Tyr Ala Ser Asn Val Arg Lys
            340                 345                 350

Leu Met Ala Ser Glu Gly Asn Met Ile Leu Ser Asp Leu Gly Leu Gly
        355                 360                 365

Asp Lys Arg Ile Tyr His Ala Thr Leu Asn Gly Asn Leu Ser Gln Leu
    370                 375                 380

Arg Val Phe His Gln Lys Glu Glu
385                 390
```

<210> SEQ ID NO 110
<211> LENGTH: 1194
<212> TYPE: DNA
<213> ORGANISM: Brassica napus

<400> SEQUENCE: 110

```
atggagtcgg agctaaagga tatgaatccg aatccaccgt cgtcgagcaa agaggaccgc      60

cccttgctca aatcggaatc cgacgtctcc gccgccatcg aagagctcga caaaaagttc     120

gcgccttacg cgaggacgga cttgtacggg acgatggggt tgggtccttt tccggcggcg     180

gagaaagtca agctcgcggt ggcgatggtg acgcttgtgc ccgttcggtt tgttctggcg     240

atgacgatct tgcttctgta ttacttggtg tgtagggtgt ttacgctgtt ctcgtctccg     300

tatcgtggag gagaggagga ggaggaggag gagggagggg ttgttcagga ggattatgct     360

catatgggag ggtggagaag ggttgtgatc gtgcggtgtg ggaggtttct ttcaagagtt     420

ttgctttttg tttttgggtt ttattggatt cctgagagct gtccagatcg agatgcagca     480

gctgattcca atcccaaaac aagttcttct gagattgcag agaatggtga aactgataag     540

gaggaacctg aaaggcctgg tgtcattgtg tctaatcacg tgtcgtacct ggacattttg     600

tatcatatgt ctgcttcttt cccaagtttt gtcgccaaga gatcagtggg caaacttcct     660

ctcgttggcc tcatcagcaa atgtcttggt tgcgtctatg ttcagcgaga agctaaatct     720

cctgatttca agggtgtatc tggcacagtg aatgaaagag ttagagaagc tcataggaac     780

aaatctgctc caactattat gctttttcca gaaggaacaa ctaccaatgg agactacttg     840

cttcaattca agacaggtgc atttcttgcc ggaactccgg ttcttcctgt tattttaaaa     900

tatccgtacg agcgtttcag tgtggcatgg gatacaatct ccggggcacg ccacattatc     960

ttccttctct gccaactcgt aaaccatttg gaggtgatac ggttacctgt atactaccct    1020

tcacaagaag agaaagataa tcccaaactg tacgctagca atgtccggag attaatggcc    1080
```

actgagggta acttgattct gtcggatttg ggacttggag acaagaggat atatcacgcg 1140
accctcaatg gtaatctcag acaactccgt gttttccatc agaaagaaga atga 1194

<210> SEQ ID NO 111
<211> LENGTH: 397
<212> TYPE: PRT
<213> ORGANISM: Brassica napus

<400> SEQUENCE: 111

Met Glu Ser Glu Leu Lys Asp Met Asn Pro Asn Pro Pro Ser Ser Ser
1 5 10 15

Lys Glu Asp Arg Pro Leu Leu Lys Ser Glu Ser Asp Val Ser Ala Ala
20 25 30

Ile Glu Glu Leu Asp Lys Lys Phe Ala Pro Tyr Ala Arg Thr Asp Leu
35 40 45

Tyr Gly Thr Met Gly Leu Gly Pro Phe Pro Ala Ala Glu Lys Val Lys
50 55 60

Leu Ala Val Ala Met Val Thr Leu Val Pro Val Arg Phe Val Leu Ala
65 70 75 80

Met Thr Ile Leu Leu Leu Tyr Tyr Leu Val Cys Arg Val Phe Thr Leu
85 90 95

Phe Ser Ser Pro Tyr Arg Gly Gly Glu Glu Glu Glu Glu Glu Glu Gly
100 105 110

Gly Val Val Gln Glu Asp Tyr Ala His Met Gly Gly Trp Arg Arg Val
115 120 125

Val Ile Val Arg Cys Gly Arg Phe Leu Ser Arg Val Leu Leu Phe Val
130 135 140

Phe Gly Phe Tyr Trp Ile Pro Glu Ser Cys Pro Asp Arg Asp Ala Ala
145 150 155 160

Ala Asp Ser Asn Pro Lys Thr Ser Ser Ser Glu Ile Ala Glu Asn Gly
165 170 175

Glu Thr Asp Lys Glu Glu Pro Glu Arg Pro Gly Val Ile Val Ser Asn
180 185 190

His Val Ser Tyr Leu Asp Ile Leu Tyr His Met Ser Ala Ser Phe Pro
195 200 205

Ser Phe Val Ala Lys Arg Ser Val Gly Lys Leu Pro Leu Val Gly Leu
210 215 220

Ile Ser Lys Cys Leu Gly Cys Val Tyr Val Gln Arg Glu Ala Lys Ser
225 230 235 240

Pro Asp Phe Lys Gly Val Ser Gly Thr Val Asn Glu Arg Val Arg Glu
245 250 255

Ala His Arg Asn Lys Ser Ala Pro Thr Ile Met Leu Phe Pro Glu Gly
260 265 270

Thr Thr Thr Asn Gly Asp Tyr Leu Leu Gln Phe Lys Thr Gly Ala Phe
275 280 285

Leu Ala Gly Thr Pro Val Leu Pro Val Ile Leu Lys Tyr Pro Tyr Glu
290 295 300

Arg Phe Ser Val Ala Trp Asp Thr Ile Ser Gly Ala Arg His Ile Ile
305 310 315 320

Phe Leu Leu Cys Gln Leu Val Asn His Leu Glu Val Ile Arg Leu Pro
325 330 335

Val Tyr Tyr Pro Ser Gln Glu Glu Lys Asp Asn Pro Lys Leu Tyr Ala
340 345 350

```
Ser Asn Val Arg Arg Leu Met Ala Thr Glu Gly Asn Leu Ile Leu Ser
        355                 360                 365

Asp Leu Gly Leu Gly Asp Lys Arg Ile Tyr His Ala Thr Leu Asn Gly
    370                 375                 380

Asn Leu Arg Gln Leu Arg Val Phe His Gln Lys Glu Glu
385                 390                 395


<210> SEQ ID NO 112
<211> LENGTH: 1584
<212> TYPE: DNA
<213> ORGANISM: Brassica napus

<400> SEQUENCE: 112

atggcgaatc ctgatttgtc ttctcctctg atcacatccg atcaaccaga ggtcttcatc      60

tctatcgatg acgacgacgg agatgacaac caccctcgtg gtttcgaatt cgaccatctt     120

aatccgatca accctttcgg gtttctcacc gacgccgagc ctccggttca gagtccaacg     180

acggtggatc cgttccggaa cgatactcct ggagtttgcg gactctacga agcggtcaag     240

atcgtgattt gcctcccgat tgcgttggtt cggcttgtcc tgtttggtgt tagcttagct     300

gttggttact tggcaacgaa gctagcactt gctgggtgga gagatagaca caaccctatg     360

cctcaatgga gatgcagagt catgtgggtt actcgcttct gtaccagatg catcctcttc     420

tcttttggtt atcagtggat aagacggaaa gggaaacctg ctcggaggga gattgctccc     480

atcattgtat caaaccatgt ctcgtatatt gaaccaatct tctacttcta tgagctatca     540

cccaccattg ttgcatcgga gtcacatgat tcacttcctt tggttggaac tattatcagg     600

gctatgcagg tgatatatgt taatagattc tcacaggcat caaggaagga cgctgtgggt     660

gaaataaaga gaaaagcctc ctccgataga ttcccccgtc tgctgctatt ccctgaagga     720

accaccacca atgggaaagt tctcatctcc ttccagctcg gcgctttcat ccctggttac     780

cctattcaac ctgtagtagt ccggtatccc catgtacatt ttgatcaatc ctgggggaat     840

atttctttgt tgatgctcat gtttagaatg ttcactcaat ttcacaactt catggaggtt     900

gaataccttc cagtaatcta tcccagtgac actcagaaac agaatgctgt gcgtctctca     960

cagaagacca gtcatgcgat tgcaacatct ttgaacgtgg tccaaacatc tcattcttat    1020

ggggacctca tgctattgaa cagagcaact gagttaaagc tggaaaaccc ctcaaattac    1080

atggttgaaa tggccaaggt tgcatcgcta ttccatataa gcagtttaga ggcagttcgg    1140

tatttggata cattttcttc catgaatccg gactctagtg gacgtgttac tctacatgac    1200

tttcttcgag ttcttagact gaagccttgc actctctcta aagggatatt cgggttcatc    1260

gatgtggaga aagctggatc aataactttc agacagttct tgtttgcctc ggctcatgta    1320

tcggcacagc cactttttca gcaaacatgc gagctagcat ttctcactg tgacgcagat     1380

ggagatggct ttatctccat tcaagaactt ggagacgcgc tgaaactcac aataccaaac    1440

tcgaacaagg acgagataca agggatgtac attttgctag acgaggacaa agatcaaaga    1500

atcagcaagg atgacttctt gtcctgctta agaagaaacc ctctgctcat agctgtcttt    1560

tcccctatct tgtccccaac ataa                                            1584


<210> SEQ ID NO 113
<211> LENGTH: 527
<212> TYPE: PRT
<213> ORGANISM: Brassica napus

<400> SEQUENCE: 113
```

```
Met Ala Asn Pro Asp Leu Ser Ser Pro Leu Ile Thr Ser Asp Gln Pro
1               5                   10                  15

Glu Val Phe Ile Ser Ile Asp Asp Asp Asp Gly Asp Asp Asn His Pro
            20                  25                  30

Arg Gly Phe Glu Phe Asp His Leu Asn Pro Ile Asn Pro Phe Gly Phe
        35                  40                  45

Leu Thr Asp Ala Glu Pro Pro Val Gln Ser Pro Thr Thr Val Asp Pro
    50                  55                  60

Phe Arg Asn Asp Thr Pro Gly Val Cys Gly Leu Tyr Glu Ala Val Lys
65                  70                  75                  80

Ile Val Ile Cys Leu Pro Ile Ala Leu Val Arg Leu Val Leu Phe Gly
                85                  90                  95

Val Ser Leu Ala Val Gly Tyr Leu Ala Thr Lys Leu Ala Leu Ala Gly
            100                 105                 110

Trp Arg Asp Arg His Asn Pro Met Pro Gln Trp Arg Cys Arg Val Met
        115                 120                 125

Trp Val Thr Arg Phe Cys Thr Arg Cys Ile Leu Phe Ser Phe Gly Tyr
    130                 135                 140

Gln Trp Ile Arg Arg Lys Gly Lys Pro Ala Arg Arg Glu Ile Ala Pro
145                 150                 155                 160

Ile Ile Val Ser Asn His Val Ser Tyr Ile Glu Pro Ile Phe Tyr Phe
                165                 170                 175

Tyr Glu Leu Ser Pro Thr Ile Val Ala Ser Glu Ser His Asp Ser Leu
            180                 185                 190

Pro Leu Val Gly Thr Ile Ile Arg Ala Met Gln Val Ile Tyr Val Asn
        195                 200                 205

Arg Phe Ser Gln Ala Ser Arg Lys Asp Ala Val Gly Glu Ile Lys Arg
    210                 215                 220

Lys Ala Ser Ser Asp Arg Phe Pro Arg Leu Leu Leu Phe Pro Glu Gly
225                 230                 235                 240

Thr Thr Thr Asn Gly Lys Val Leu Ile Ser Phe Gln Leu Gly Ala Phe
                245                 250                 255

Ile Pro Gly Tyr Pro Ile Gln Pro Val Val Val Arg Tyr Pro His Val
            260                 265                 270

His Phe Asp Gln Ser Trp Gly Asn Ile Ser Leu Leu Met Leu Met Phe
        275                 280                 285

Arg Met Phe Thr Gln Phe His Asn Phe Met Glu Val Glu Tyr Leu Pro
    290                 295                 300

Val Ile Tyr Pro Ser Asp Thr Gln Lys Gln Asn Ala Val Arg Leu Ser
305                 310                 315                 320

Gln Lys Thr Ser His Ala Ile Ala Thr Ser Leu Asn Val Val Gln Thr
                325                 330                 335

Ser His Ser Tyr Gly Asp Leu Met Leu Leu Asn Arg Ala Thr Glu Leu
            340                 345                 350

Lys Leu Glu Asn Pro Ser Asn Tyr Met Val Glu Met Ala Lys Val Ala
        355                 360                 365

Ser Leu Phe His Ile Ser Ser Leu Glu Ala Val Arg Tyr Leu Asp Thr
    370                 375                 380

Phe Ser Ser Met Asn Pro Asp Ser Ser Gly Arg Val Thr Leu His Asp
385                 390                 395                 400

Phe Leu Arg Val Leu Arg Leu Lys Pro Cys Thr Leu Ser Lys Gly Ile
                405                 410                 415

Phe Gly Phe Ile Asp Val Glu Lys Ala Gly Ser Ile Thr Phe Arg Gln
```

-continued

```
        420                 425                 430

Phe Leu Phe Ala Ser Ala His Val Ser Ala Gln Pro Leu Phe Gln Gln
        435                 440                 445

Thr Cys Glu Leu Ala Phe Ser His Cys Asp Ala Asp Gly Asp Gly Phe
    450                 455                 460

Ile Ser Ile Gln Glu Leu Gly Asp Ala Leu Lys Leu Thr Ile Pro Asn
465                 470                 475                 480

Ser Asn Lys Asp Glu Ile Gln Gly Met Tyr Ile Leu Leu Asp Glu Asp
                485                 490                 495

Lys Asp Gln Arg Ile Ser Lys Asp Asp Phe Leu Ser Cys Leu Arg Arg
            500                 505                 510

Asn Pro Leu Leu Ile Ala Val Phe Ser Pro Ile Leu Ser Pro Thr
        515                 520                 525
```

<210> SEQ ID NO 114
<211> LENGTH: 20
<212> TYPE: DNA
<213> ORGANISM: Artificial sequence
<220> FEATURE:
<223> OTHER INFORMATION: primer

<400> SEQUENCE: 114
atgatatcga tggacatgga 20

<210> SEQ ID NO 115
<211> LENGTH: 23
<212> TYPE: DNA
<213> ORGANISM: Artificial sequence
<220> FEATURE:
<223> OTHER INFORMATION: primer

<400> SEQUENCE: 115
ttattcttct ttacgtggct ttg 23

<210> SEQ ID NO 116
<211> LENGTH: 23
<212> TYPE: DNA
<213> ORGANISM: Artificial sequence
<220> FEATURE:
<223> OTHER INFORMATION: primer

<400> SEQUENCE: 116
atgatatcga tggacatgaa ttc 23

<210> SEQ ID NO 117
<211> LENGTH: 23
<212> TYPE: DNA
<213> ORGANISM: Artificial sequence
<220> FEATURE:
<223> OTHER INFORMATION: primer

<400> SEQUENCE: 117
ttattcctct ttacgtggct ttg 23

<210> SEQ ID NO 118
<211> LENGTH: 20
<212> TYPE: DNA
<213> ORGANISM: Artificial sequence
<220> FEATURE:
<223> OTHER INFORMATION: primer

<400> SEQUENCE: 118
atggaatcgc tcgacatgag 20

<210> SEQ ID NO 119
<211> LENGTH: 23
<212> TYPE: DNA
<213> ORGANISM: Artificial sequence
<220> FEATURE:
<223> OTHER INFORMATION: primer

<400> SEQUENCE: 119
ttattcttct ttccgggtct ttg 23

<210> SEQ ID NO 120
<211> LENGTH: 20
<212> TYPE: DNA
<213> ORGANISM: Artificial sequence
<220> FEATURE:
<223> OTHER INFORMATION: primer

<400> SEQUENCE: 120
atggaatcgg agctaaagaa 20

<210> SEQ ID NO 121
<211> LENGTH: 24
<212> TYPE: DNA
<213> ORGANISM: Artificial sequence
<220> FEATURE:
<223> OTHER INFORMATION: primer

<400> SEQUENCE: 121
ttattcttct ttctgatgga aaac 24

<210> SEQ ID NO 122
<211> LENGTH: 20
<212> TYPE: DNA
<213> ORGANISM: Artificial sequence
<220> FEATURE:
<223> OTHER INFORMATION: primer

<400> SEQUENCE: 122
atggagtcgg agctaaagga 20

<210> SEQ ID NO 123
<211> LENGTH: 24
<212> TYPE: DNA
<213> ORGANISM: Artificial sequence
<220> FEATURE:
<223> OTHER INFORMATION: primer

<400> SEQUENCE: 123
tcattcttct ttctgatgga aaac 24

<210> SEQ ID NO 124
<211> LENGTH: 20
<212> TYPE: DNA
<213> ORGANISM: Artificial sequence
<220> FEATURE:
<223> OTHER INFORMATION: primer

<400> SEQUENCE: 124
atggcgaatc ctgatttgtc 20

<210> SEQ ID NO 125
<211> LENGTH: 21
<212> TYPE: DNA
<213> ORGANISM: Artificial sequence
<220> FEATURE:

<223> OTHER INFORMATION: primer

<400> SEQUENCE: 125
ttatgttggg gacaagatag g 21

<210> SEQ ID NO 126
<211> LENGTH: 1425
<212> TYPE: DNA
<213> ORGANISM: Drechslera tritici-repentis

<400> SEQUENCE: 126
atgacgacga ctcggccgcc aattccgtct cggctcgcct ttgactcgcc ggccgggtca 60
gcctcaaaca cctcgctgtc ctcgatggac gagcagcctg ccgtccgcaa gaacggcaag 120
aggtccagtg gcaagctcct tgacacgtac ggcaatgagt tcgagatccc ggactacacc 180
atcaaggaca tccgcgatgc catccccaag cattgcttcg agcgctctgc tgtccgtggt 240
ctgggctacg ttgcccgtga ccttgcctcg ctcgccgcca ccttctacgt cttccacaac 300
tacgtgacgc ccgagacgat cccttcaatg ccgctacgag ctgctctctg gaccctatac 360
actgtcctcc agggcttctt cggcactggt ctttggatcc tggcccacga gtgtggtcac 420
caggctttct cagagtccaa gctgctcaac gacaccgtcg gctgggtctg ccactccatc 480
ctcctcgtcc catacttctc atggaagatc tcccacggca agcaccacaa ggccactggc 540
cacatggagc gtgacatggt cttccttccc aagacccgcg agacctacgc tacccgtgtc 600
ggcaagatgg tccacgagat ctctgagctc accgaggagg ctcctctagc taccctcatc 660
cacaccttcg gccagcagat tggtggatgg cctctgtacc tcattgccaa cgtcaccggc 720
cacaaccacc acgatcgcca gatcgagggc aagggtaagg gaaagaagaa cggcttcttc 780
ggcggtgtca accacttctt cccttccagc cccttgtacg agaagcgtga tgagcacctc 840
atcctcctca gtgatctcgg tcttgctatc gtcattggtt tcctcacctg ggtcggcaag 900
aactggggct tcaacaatgt cttcgtctgg tacatcatcc cttacctgtg ggtcaaccac 960
tggctcgtta tgatcacctt cctccagcac accgaccctg ccctgcccca ctacgacgcc 1020
gacacttgga cctacactcg cggtgccgct gctaccatcg accgtgagtt tggcttcatc 1080
ggacgcactc ttctccacgg cattgtcgag acccacgttc tccaccacta catctccacc 1140
atccccttct accacgccga cgaggctact gaggccatca agaaggtcat gggcaagcac 1200
taccgttccg acaccaaggg tggcccaatg ggcttcatga acgctttgtg gaagacagcc 1260
cgttggtgcc agtgggtcga gccgagcgcc gaggctgagg gtgagggcaa gggtgttctc 1320
ttcttccgca accgcaacgg actaggtgta ccacccacga agatcgagcc tgccggaacc 1380
aagaaggcag ccaagatgga ggtcggccct gagagtgaca acgag 1425

<210> SEQ ID NO 127
<211> LENGTH: 1224
<212> TYPE: DNA
<213> ORGANISM: Cylindrocarpon heteronema

<400> SEQUENCE: 127
atggcggtcc gacaacgcac ctcgtcgacc acgactacgc tcgtggtcga gaagccggct 60
accactgtca tcgtggagcc cgtcactcag atcctccctg agcccatttt ccccgacatc 120
aagtccatca aggatgccat ccccgcccac tgcttccagc cctccctctt cacgtcctac 180
tactatgtcg tccgcgactt caccatggtc ggcaccctcg tctgggccgc cctgaccttc 240
atcccctcca tccccgatcc gatcctccgc ggcgccgcct ggatgctgta cggcttcgtc 300
cagggcctct tctgtaccgg catctggatt ctcggccacg agtgcggcca cggcgccttc 360
tccctgcaca acaaggtcaa caacatcacc ggctgggccc tccacagctt cctcctggtc 420
cccttcttct cgtggaagtt ctcccaccac cgccaccatc tctaccacgg ccacatggag 480
aaggacatgg cctttgtccc cgccaccgag cccaagacgt cgcgccagac tatgctcgcc 540
ggtatcggtc tcgacgagct gtttgaggac actcccctct tccagaccct gcgcctcgtc 600
ggccaccagc tctttggctg gcagatctac ctgctgttca acgccacctc gggcaagggc 660
agcatgcagc gtgaggttgg cggcatcagc aagtggcttc gcgtgagcca tttcgacccc 720
accagcgccg tcttccgccc caacgaggcc atcttcatct tcctctccga cgtcggcctg 780
gccctcatgg ccaccgtgct gtactttgtc tcccagaaga tcggtgtctc gaccaccttc 840
ctcctctacg gcgttcccta cctctgggtt caccactggc ttgtcgccat cacctacctc 900
caccaccacc acgccgacgt ccctcactac acccccgagg gctggacata cgtcaagggc 960
gcgctggcca ctgtcgaccg ggagtttggc ttcatcggca agcacctttt ccacggaatt 1020
atcgagaagc acgtcatcca ccaccttttc cctcgcattc ccttctacaa ggctgacgag 1080
gccaccgagg ctgccctgcc ggtgctgggc aagcattacg ttcgagactc tcgcagcttc 1140
cttggacagc tttggtctgt ctttggatcg ctcaagtatg ttgagcacga ccccacccgc 1200
cctggcgcga tgaggtgggc gaaa 1224

<210> SEQ ID NO 128
<211> LENGTH: 1482
<212> TYPE: DNA
<213> ORGANISM: Diplodia natalensis

<400> SEQUENCE: 128
atggccacca ccgccatggc tcagaaccct gtcctgagga ggaacgttac ggccacctcg 60
accgcctctt cgtccgctcc ctcggttgca gtctcgccca acgactcgcc cgcccagtcg 120
ccctcgtcga cttcgctgtc gtcgatggct tcggttgagc ccgaggtcaa gaactcccgc 180
ggcaagctca tcgacacgta cggaaacgaa ttcgagatcc ccgactacac catcaagcag 240
atctacgacg ccatccccaa gcactgcttc gagcgctccg ccatccgctc cctgagctac 300
gtcgcccgcg atgtcgccgt cctcgcctcc gtcttctacg tcttctacaa ctatgtcacc 360
ccggagtaca tcccctcgac cccggtgcgt gctgttctct gggccctgta cacggtcgtc 420
cagggtctgt tcggtaccgg cgtctgggtc ctagcccacg agtgcggcca ccaggccttc 480
tctccctcca agacgctgaa cgacaccgtc ggctggatct gccactcggc tctcctcgtc 540
ccgtacttct cgtggaagat ttcccacggc aagcaccaca aggccaccgg ccacctcacc 600
agggatatgg ttttcgtgcc caagacgcgt gaggagtacg cttcgcgcat cggcaagttc 660
gtccacgagc tccacgagct gaccgaggag acgcccatcg ccaccgccac ccacatgatc 720
ggccagcagc tcgccggctg gttgctgtac ctgttcatca acgtcaccgg ccacaaccag 780
cacgagaagc agaaggaggg caagggcgtc ggcaagaaga acggctggtt cggcggcgtc 840
aaccacttca tgcctagcag ccctctgtac gagaagaagg acgagaagct catcctcctg 900
agcgaccttg gtctcgccat cacgggctac gtcctgtacc aggtcggctc caagttcggt 960
ttcgccaacc tcttcgtctg gtacatcgtg ccgtacctct gggtcaacca ctggctggtc 1020
gccatcacct acctccagca caccgaccct tcgctgcccc actacgacgc cgccacctgg 1080
accttcacgc gtggcgccgc cgccaccatc gaccgcgagt ttggcttcat cggccgccac 1140
atcctgcatg gcatcatcga gacgcacgtc ctgcaccact acgtgtcgac catccccttc 1200
tacaacgccg acgaggccag cgaggccatc aagcccgtca tgggccgcca ctaccgcgcc 1260
gacgtcgagg atggccccat cggcttcctc aaggccatgt ggaagagcgc ccgctggtgc 1320
cagtgggttg agcccagcgc cgaggcccag ggcgagggca agggcgtcct cttcttccgc 1380
aacaggaacg gcctcggcgt cccgcccgtc gtcattccgg cgcccggcac cgagaagaag 1440
gcaggcatga ttgtcggcag cgacagcgac aatgacgcat ga 1482

<210> SEQ ID NO 129
<211> LENGTH: 1485
<212> TYPE: DNA
<213> ORGANISM: Stagonospora nodorum

<400> SEQUENCE: 129
atggccacca caactgcccg cgctcaggct ccagccatga agaggaacgt cacaacagac 60
tcctcgccct ccacccacgc caacaactcg ccgttcgact cgcctgcggg atcggcttcc 120
aacacctcgc tgtcgtccct tgacgagagt cccgctcagt ccaagagcaa ccgcggtgtg 180
cttctcgaca catacggcaa cgagtttgag attccagact acaccatcaa gcagatccgt 240
gatgccatcc ccaagcactg cttcgagcgc tcaggtcttc gtggtctcgg ctacgttgcc 300
cgtgacatcg cttcgcttgc ggccgtcttc tacgtcttcc acaactatgt cacacccgag 360
acaattccct cgactcctgt ccgcgctggt ctgtgggccg tctacactgt catccagggt 420
cttttcggta ccggcctgtg ggttctcgcc catgagtgcg gccaccagtc cttctctccc 480
tccaaggtgt tgaacgacac cgttggctgg ttctgtcact ccgccctcct cgtcccatac 540
ttctcttgga agatctcgca cggcaagcac cacaaggcca ctggtcacat ggagcgcgac 600
atggtcttcg tccccaagac gcgagaggtc tacgcttcgc gtatcggaaa gatgatccac 660
gagctcgatg agctgaccga ggagactccc atcgccactc tcctccacag catcggtcag 720
cagctcgctg gatggccttt gtacatcatc ctcaacgtta ccggacacaa ctaccacgag 780
cgccaggccg agggcaaggg caagggcaag cacaatggcc caggcggtgg tgtcaaccac 840
ttcttcccat ccagccctct gtatgaacgc aaggatgagc acctcatcct gctcagtgat 900
cttggtatcg ccatcaccct cggtgctctt acctgggttg gcaagaactt cggattcgcc 960
aacctcttcg tctggtacat cctcccctac ctctgggtca accactggct tgttgccatc 1020
accttcctcc agcacaccga ccccaccctg ccccactacg atgccaacac ctggacttac 1080
actcgtggcg ccgctgccac catcgaccgc gagtttggct tcatcggacg ggaaattctc 1140
cacggcattg tcgagaccca cgttctccac cactacatct ccacaatccc cttctaccac 1200
gccgacgagg cttcagaggc tatcaagcct gtcatgggca ggcattaccg ctcggatgtt 1260
gagggcggtc ctattggctt cttgaaggcc atgtggaaga gcgctcgctg gtgccagtgg 1320
gtcgagccca gcgcggacgc cgagggcgag ggcaagggtg tactcttctt ccgcaaccac 1380
aacggtctcg gtgtacctcc tcagaagctt tctgccccgg tggccaagtc gactgctggc 1440
cagcgtgcga aaatggaggt tggccctgag tccgacaacg agtag 1485

<210> SEQ ID NO 130
<211> LENGTH: 1209
<212> TYPE: DNA
<213> ORGANISM: Microdochium nivalae

<400> SEQUENCE: 130
atgattgcga ccacccagac caagacggcc gtcacggacc gcgggacgac ccggatgaga 60

```
ggctcgtcaa cagcccagga gttcccagac atccagacca tccgcgatgc tatccccaag    120
cactgctttg agccctcaac agtccgttcc ttgagctatg tcgcccgcga tgtaaccatg    180
gcctcggccc tcatctgggc ggccgtccgc ttcatccccc agatcgagga ctcggtcctg    240
cgcttctcgg cctggatggt ctacggcctt gtccagggca tggtctgcac cggcgtctgg    300
atcctcgccc acgagtgcgg ccacggcgcc ttcagcaagc accagaccct caacgacttt    360
gtcggctggg tcctgcactc gagtctcggc gtcccctact tctcatggaa gttctcacac    420
caccgccacc accgcttcac tggcaacatg gagaaggaca tggtctttgt ccccgccgtc    480
aagaccgagg agcccctaa gcgccgcctc gcctccttct acctcgaccc tgagatcctc    540
gaggacgccc ccattgtcag cctcatccag ctcattgccc accagctcgc cggctggcag    600
atgtacatgc tcttcaacgt ctcatcgggc aaggacagca agcagcgcaa ccagtctggc    660
tggctgcgcg tcagccactt tgagcccacc agcgccgtct tccgccctag cgaggcctgg    720
tacatcttcc tcgccgacgt cggccttgct ctcaccggcg ccgccatcta ctacggctcc    780
acccttgtcg gctggcccac catgttcttt gtctactttg tcccctacat gtggtggaac    840
cactggctcg ttgccatcac ctacctccac cacacccacc cggaagtcca ccactacgag    900
gcggacagct ggacctacgt caagggcgcc ctcgccaccg tcgaccgcga ctttggctgg    960
attgacaagc acctcttcca cggcatcatt ggcttccacg tcatccacca catctttgcc   1020
aagatcccct tctactacgc cgaggaggcc accgcggcca tccagcccgt cattggcaac   1080
cactaccacc gtgctcccgg ctccttcctc ggcgacctct ggctcacttt caccaagtgc   1140
cgcttcgtcg agaaggaccc cgagcaccct ggcgccatgc gctgggtcgc accccgcaag   1200
gacctttag                                                           1209
```

<210> SEQ ID NO 131
<211> LENGTH: 1074
<212> TYPE: DNA
<213> ORGANISM: Periplaneta americana

<400> SEQUENCE: 131

```
atggctccga acattacaag ttctcctacc ggtgtcctat ttgaggatga tactatagaa     60
actgtaacat taccaacgat cgagactaaa actgatgatt ccaaaccagc tgagaaatac    120
aaaagaaaaa ttgtatggag aaacgtcatc ctctttgtat atttgcatat ggcagcactc    180
tacggggctt accttatgct gacatcctgt aaattgatca cagctatatg ggctattctt    240
ctgtatcagg caggtggtct aggtataact gcaggtgcac atagattatg gtcacaccgt    300
gcttacaagg caaagtggcc tttgagactt atcctcgtga tattcaacac tcttgcattc    360
cagaaccacg tttacgaatg ggctcgcgac cacagagtac accacaagtt cagtgaaact    420
gatgctgacc ctcataatgc caagcgcggc ttctttttct ctcatgttgg ttggctactt    480
gtccgtaagc atccagatgt taaagtaaag ggcaagggaa tcgatatgtc tgatctcgat    540
gctgatccac tcatcgcatt ccagaagaaa cactacctga tcctcatgcc aattatatgc    600
tttattctac caacaatcat acctgtgtat ttttggggtg agacctggtc aaatgcttgg    660
tttgtggttg cgatgtttcg ctacaccttc actctcaacg cgtcctggct tgtgaacagt    720
gcagcacaca tgtggggaag ccgaccttat gacaagtaca tcaatccatc agaaaatctc    780
ggcgtttcta tgctagctct gggcgagggt tggcacaact accatcacgt gtttccttgg    840
gactacaaga ctgccgaact tggaaactac agcaccaact tgacgactgc attcatcgac    900
```

ttcttttctc gcattggctg ggcatatgac ctcaagactg taccgatgtc catggtgaag 960
cagagagtac aacgcacagg tgacggaagc catgatgtat ggggttgggg tgacaaggac 1020
atgagccagg aggacatgga tgaggccctg gtcatcaaca agaagctcaa gtag 1074

<210> SEQ ID NO 132
<211> LENGTH: 1071
<212> TYPE: DNA
<213> ORGANISM: Periplaneta americana

<400> SEQUENCE: 132
atggccccta atataactag tactcccacg ggagttctat acgaagaaga cttcgctgca 60
gccgaaaaag caacttcaac tgagactaaa gagggcatta aacctaaacg ggagtacaag 120
aagcaaattg tgtggcccaa cgtgattatg catttcctcc tccatgttgg cgcagtctac 180
ggagcttacc tcatgcttac ttctgccaaa atactcacag gaatatgggc tttctttctg 240
tatgaagtgg gtatcctagg cattacggcc ggcgcacatc gactctggtc acatcgctct 300
tataaagcca catggcagat gaggctgatc ctcatgattt gtcagacagt gtcttttcag 360
acatctgttc atgaatgggc tcgaaatcat agggtgcacc ataaacatag cgacactgat 420
ggcgatcctc acaatgtcaa tcgtggcttg tttttctctc acgccggttg gatgatgtgc 480
cgtaaacatc ccgaagttaa ggagaagggc aagcagattg acctgtcaga tcttgatgcc 540
gatccaattc tgatgtttca aaaaaagtac tacctaattc tcatgccctt catgtgcttc 600
ttcttaccta cctggattcc tgtatatttt tggggtgaaa catggcacaa tgcgtatttt 660
gttgctgcta tcttccgcca tgtgttcact ctgaacatga ctttgatggt caacagcatc 720
actcacaata catggggaaa cagaccatat gacaaaaata ttaaccctgc tgaaaatgct 780
atagtgtctt tgatgaccct tggtgaaggc tggcataact accatcatgt atttccatgg 840
gattacaaaa cggccgaact tggagtctta cgtatcaata tgacgacgct cttcattgat 900
ctgtgtgcaa aaattggctg ggcctatgac ttgaagactg taccaatgga tatggtcaaa 960
agaagggtgg aacgcactgg agatgggacg cacgagattt ggggctgggg agacaaggat 1020
atgacggaga aggagagaga aatagcacaa ataatcaaca agaaagatta a 1071

<210> SEQ ID NO 133
<211> LENGTH: 822
<212> TYPE: DNA
<213> ORGANISM: Emiliana huxleyi

<400> SEQUENCE: 133
atgacccgca cgttcggcct gctcgcgtgt gccatcgcga gcgcgcgagc gctgcagtcg 60
cctatgtccg gccggtggcc acagcagcgg cgctccccag gcgtggacgc ggtcagcagc 120
agccagttgt ctattgactg gactgctcgc gagttatggg cgctagagga ctcggtgcct 180
cagtacaccg tcgccgtggg cgagggatcc ggcgcgcaaa tcatcctctg gcgaaggatg 240
cagctcgacg tccccgagct ctgcggccgc tccattagcg agctgcgcgg ccgctgggcg 300
gctgagcggg gcgcggcggc ggcggccgtg gcggctgtgg acagcccgcc gtgcctcgaa 360
cgatgggagc ggctccccga cggctcgtac cgcggcgagc tcacctcggc gcgtgctgcg 420
cgccgcacgc tccccgcctc tgccccggcc gctcctcatc gccgcttctc atcgccgccc 480
gtcgccggga tgcgcggcgg gcttgtggcg acggtggaga cggacccgga cgccgcgccc 540
gcctccaggg ccgaggcgga gggctggtgc gtccgctcca gggcgggaga cctcttcgag 600
ctcggcgcgc agagagtcga ggcggagccg gccgtcgccg ccgccgacgg cgcggagcag 660
cagctcgctc ccttctccgc cgccctcggc gccgcgccaa cgcccgaggc tgtcgcgcaa 720
ctggcgacgc cggcgctggc gctcgtcgcg ctcgccgccg ccgtgaacgt gggtatgagc 780
gcctttgggc accacgtgga tgtgtccgtc ttcatcgtct ga 822

<210> SEQ ID NO 134
<211> LENGTH: 264
<212> TYPE: PRT
<213> ORGANISM: Emiliana huxleyi

<400> SEQUENCE: 134

Met Leu Ala Asp Phe Ser Phe Ala Asp Ala Pro Leu Ser Ser Leu Trp
1 5 10 15

Ala Pro Ala Thr Gly Ser Ala Ala Tyr Val Ala Thr Val Leu Ala Leu
20 25 30

Ser Trp Tyr Met Arg Val Val Arg Gly Gly Ala Gly Val Glu Gly Pro
35 40 45

Leu Met Arg Leu Leu Gln Ala Ala His Asn Leu Val Leu Cys Leu Gly
50 55 60

Ser Leu Ala Met Leu Leu Gly Thr Leu Arg Glu Leu Ala Arg Arg Gly
65 70 75 80

Ala Ser Glu Ala Pro Ala Gly Pro Leu Gly Arg Ala Ser Phe Leu Phe
85 90 95

Cys Glu Arg Pro Asp Ala Val Ala Val Gly Pro Leu Tyr Ala Trp Ser
100 105 110

Tyr Leu Tyr Tyr Leu Ser Lys Tyr Tyr Glu Leu Leu Asp Thr Val Leu
115 120 125

Gln Leu Leu Lys Gly Arg Pro Pro Pro His Phe Phe Leu His Val Tyr
130 135 140

His His Ala Val Val Leu Phe Met Ala Trp Ser Trp Cys Ala Tyr Cys
145 150 155 160

Gln Ser Leu Gln Trp Gly Gly Leu Leu Phe Asn Thr Ala Val His Val
165 170 175

Leu Met Tyr Tyr Tyr Tyr Phe Arg Thr Val Leu Lys Leu Pro Thr Pro
180 185 190

Trp Lys Arg Leu Val Thr Gln Phe Gln Ile Val Gln Phe Gly Phe Ser
195 200 205

Leu Leu Cys Phe Leu Val Thr Ala Ala Leu Leu Ala Thr Gly Ser Ala
210 215 220

Cys Ala Gly Thr Gly Ala Leu Ala Phe Asn Leu Ala Phe Asn Val Thr
225 230 235 240

Leu Leu Leu Gln Phe Phe Gly Val Leu Gly Lys Asn Asp Ala Arg Ser
245 250 255

Gly Gly Ser Lys Lys Arg Arg Glu
260

<210> SEQ ID NO 135
<211> LENGTH: 1404
<212> TYPE: DNA
<213> ORGANISM: Brassica napus

<400> SEQUENCE: 135
atggaatcgc tcgacatgag ttccatggcg gcctcgatag gcgtctccgt cgccgttctc 60
cgtttcctcc tctgcttcgt cgcaacgata ccagtctcct tcgcgtggag attcgtcccg 120
agtcgactcg gtaaacacat ctactcagct gcttctggag ctctcctctc ttacctctcc 180

```
tttggcttct cctcgaatct ccacttcctc gttcccatga ccattggcta cgcttcgatg    240

gcgatctata gaccaatgtc tggattcatc actttcttcc tcggtttcgc ttatctcatt    300

ggctgtcatg tgttttatat gagtggtgat gcttggaaag aaggaggcat tgactctact    360

ggagctttga tggtgttgac gttgaaagtg atatcgtgtt cgattaatta taacgatggg    420

atgttgaagg aagaaggtct tcgtgaggct cagaagaaga accgtttggt tcggatgcct    480

tctctcattg agtactttgg ttactgcctt tgctgcggaa gccacttcgc tggccctgtc    540

ttcgaaatga aagattatct cgaatggacc gaagggaaag gaatttgggc tgttacttct    600

gggaaaggga agagaacatc gccttacgga gcaacacttc gagctatact acaagccggg    660

atctgtatgg ctctgtatct ctacttagtc cctcagttcc cattaacgcg gttcacagag    720

ccagtgtacc atgaatgggg tttctggaga agattcggtt accagtacat ggccggtttc    780

acggctcgtt ggaagtacta cttcatctgg tcgatctcag aggcttccat catcatctcc    840

ggtttgggtt tcagtggttg gaccgacgaa aacacacaaa caaaggccaa atgggaccgt    900

gcaaagaacg tcgatatcct aggtgttgag ctagctaaga gtgctgttca gattcctctt    960

gtgtggaaca tacaagtcag cacttggctc cgtcactatg tgtatgagag aattgtgaag   1020

ccagggaaga aagctggctt cttccagctg ctagctactc aaaccgttag tgccgtgtgg   1080

catggactgt atcctggata cattatcttc tttgttcaat cagcattgat gatcgatggt   1140

tctaaagcta tttaccgttg gcaacaatca atgcctccga agatggcaat gctgagaagt   1200

gttatggttt tcatcaactt cctctacaca gttttggttc tcaattactc atccgttggt   1260

ttcatggtgt tgagcttgca cgaaacactc gtggcctaca agagtgtata tttcatagga   1320

acagtggtgc ctattgctgt gattctactc agctacttgg ttcctgtgaa gcctgtgaga   1380

ccaaagaccc ggaaagaaga ataa                                          1404


<210> SEQ ID NO 136
<211> LENGTH: 467
<212> TYPE: PRT
<213> ORGANISM: Brassica napus

<400> SEQUENCE: 136

Met Glu Ser Leu Asp Met Ser Ser Met Ala Ala Ser Ile Gly Val Ser
1               5                   10                  15

Val Ala Val Leu Arg Phe Leu Leu Cys Phe Val Ala Thr Ile Pro Val
            20                  25                  30

Ser Phe Ala Trp Arg Phe Val Pro Ser Arg Leu Gly Lys His Ile Tyr
        35                  40                  45

Ser Ala Ala Ser Gly Ala Leu Leu Ser Tyr Leu Ser Phe Gly Phe Ser
    50                  55                  60

Ser Asn Leu His Phe Leu Val Pro Met Thr Ile Gly Tyr Ala Ser Met
65                  70                  75                  80

Ala Ile Tyr Arg Pro Met Ser Gly Phe Ile Thr Phe Phe Leu Gly Phe
                85                  90                  95

Ala Tyr Leu Ile Gly Cys His Val Phe Tyr Met Ser Gly Asp Ala Trp
            100                 105                 110

Lys Glu Gly Gly Ile Asp Ser Thr Gly Ala Leu Met Val Leu Thr Leu
        115                 120                 125

Lys Val Ile Ser Cys Ser Ile Asn Tyr Asn Asp Gly Met Leu Lys Glu
    130                 135                 140

Glu Gly Leu Arg Glu Ala Gln Lys Lys Asn Arg Leu Val Arg Met Pro
```

145 150 155 160

Ser Leu Ile Glu Tyr Phe Gly Tyr Cys Leu Cys Cys Gly Ser His Phe
165 170 175

Ala Gly Pro Val Phe Glu Met Lys Asp Tyr Leu Glu Trp Thr Glu Gly
180 185 190

Lys Gly Ile Trp Ala Val Thr Ser Gly Lys Gly Lys Arg Thr Ser Pro
195 200 205

Tyr Gly Ala Thr Leu Arg Ala Ile Leu Gln Ala Gly Ile Cys Met Ala
210 215 220

Leu Tyr Leu Tyr Leu Val Pro Gln Phe Pro Leu Thr Arg Phe Thr Glu
225 230 235 240

Pro Val Tyr His Glu Trp Gly Phe Trp Arg Arg Phe Gly Tyr Gln Tyr
245 250 255

Met Ala Gly Phe Thr Ala Arg Trp Lys Tyr Tyr Phe Ile Trp Ser Ile
260 265 270

Ser Glu Ala Ser Ile Ile Ile Ser Gly Leu Gly Phe Ser Gly Trp Thr
275 280 285

Asp Glu Asn Thr Gln Thr Lys Ala Lys Trp Asp Arg Ala Lys Asn Val
290 295 300

Asp Ile Leu Gly Val Glu Leu Ala Lys Ser Ala Val Gln Ile Pro Leu
305 310 315 320

Val Trp Asn Ile Gln Val Ser Thr Trp Leu Arg His Tyr Val Tyr Glu
325 330 335

Arg Ile Val Lys Pro Gly Lys Lys Ala Gly Phe Phe Gln Leu Leu Ala
340 345 350

Thr Gln Thr Val Ser Ala Val Trp His Gly Leu Tyr Pro Gly Tyr Ile
355 360 365

Ile Phe Phe Val Gln Ser Ala Leu Met Ile Asp Gly Ser Lys Ala Ile
370 375 380

Tyr Arg Trp Gln Gln Ser Met Pro Pro Lys Met Ala Met Leu Arg Ser
385 390 395 400

Val Met Val Phe Ile Asn Phe Leu Tyr Thr Val Leu Val Leu Asn Tyr
405 410 415

Ser Ser Val Gly Phe Met Val Leu Ser Leu His Glu Thr Leu Val Ala
420 425 430

Tyr Lys Ser Val Tyr Phe Ile Gly Thr Val Val Pro Ile Ala Val Ile
435 440 445

Leu Leu Ser Tyr Leu Val Pro Val Lys Pro Val Arg Pro Lys Thr Arg
450 455 460

Lys Glu Glu
465

<210> SEQ ID NO 137
<211> LENGTH: 1401
<212> TYPE: DNA
<213> ORGANISM: Brassica napus

<400> SEQUENCE: 137
atgatatcga tggacatgga ttcgatggct gcttcgatcg gcgtatcggt cgccgtcctt 60
cgcttcctcc tctgcttcgt cgccaccatc cccgtctcct tcttctggcg aatcgttccg 120
agtcgactcg gcaagcacgt ctacgccgcc gcttcaggcg tgttcctctc ttacctctcc 180
ttcggcttct cctcgaatct ccacttcctc gtcccgatga cgatcggata cgcttccatg 240
gcgatgtatc ggcccaagtg tggaatcatc actttcttcc tcggctttgc ttatctcatc 300

```
ggctgtcatg tgttttacat gagtggtgat gcgtggaaag aaggagggat cgactccact    360

ggagcgttaa tggtgttaac gctgaaggtt atctcgtgtg cggttaatta caatgatggg    420

atgttgaagg aggaaggctt acgtgaagct cagaagaaga acagactgat cgagatgccg    480

tctttgatcg agtactttgg ttactgtctc tgttgcggta gccatttcgc tggtcctgtt    540

tacgaaatga aagattatct tcaatggaca gagggaacag gaatttggga tagttccgag    600

aaacgaaagc agccatcgcc ttatttagct acactgcgag ctatcttcca agctgggatt    660

tgcatggctt tgtatctcta tctagtccct cagttcccgt tgactcggtt cactgaaccc    720

gtgtaccaag aatggggatt ttttaagaag tttggttacc agtacatggc gggacagacg    780

gctcgctgga agtattactt catctggtca atctcagagg cttctattat catctctggt    840

ttgggtttca gcggctggac tgatgatgag gcttcgccaa aacccaaatg ggaccgtgcc    900

aagaacgtag acatactcgg tgttgaactt gctaagagcg ctgttcagat tccgcttgtg    960

tggaacatac aagtcagcac ctggctccgt cactacgtgt atgagagact agtgaagagt   1020

gggaagaagg caggtttctt ccagttacta gctacacaaa ccgttagtgc ggtttggcat   1080

ggactgtatc ctggttacat gatgttcttt gttcagtcag ctttgatgat cgctggctca   1140

cgggttattt accgatggca acaagctatt agtccgaaat tgggagtgct gagaagtatg   1200

atggtgttca tcaacttcct ttacactgtt ttggttctca actactcagc cgtcggtttc   1260

atggttttaa gcttgcacga aacgctcact gcatacggga gcgtatacta cataggaaca   1320

atcatacctg ttggattgat tctcctcagc tacgttgttc ctgcgaaacc ctatcgagca   1380

aagccacgta aagaagaata a                                             1401
```

<210> SEQ ID NO 138
<211> LENGTH: 466
<212> TYPE: PRT
<213> ORGANISM: Brassica napus

<400> SEQUENCE: 138

```
Met Ile Ser Met Asp Met Asp Ser Met Ala Ala Ser Ile Gly Val Ser
1               5                   10                  15

Val Ala Val Leu Arg Phe Leu Leu Cys Phe Val Ala Thr Ile Pro Val
            20                  25                  30

Ser Phe Phe Trp Arg Ile Val Pro Ser Arg Leu Gly Lys His Val Tyr
        35                  40                  45

Ala Ala Ala Ser Gly Val Phe Leu Ser Tyr Leu Ser Phe Gly Phe Ser
    50                  55                  60

Ser Asn Leu His Phe Leu Val Pro Met Thr Ile Gly Tyr Ala Ser Met
65                  70                  75                  80

Ala Met Tyr Arg Pro Lys Cys Gly Ile Ile Thr Phe Phe Leu Gly Phe
                85                  90                  95

Ala Tyr Leu Ile Gly Cys His Val Phe Tyr Met Ser Gly Asp Ala Trp
            100                 105                 110

Lys Glu Gly Gly Ile Asp Ser Thr Gly Ala Leu Met Val Leu Thr Leu
        115                 120                 125

Lys Val Ile Ser Cys Ala Val Asn Tyr Asn Asp Gly Met Leu Lys Glu
    130                 135                 140

Glu Gly Leu Arg Glu Ala Gln Lys Lys Asn Arg Leu Ile Glu Met Pro
145                 150                 155                 160

Ser Leu Ile Glu Tyr Phe Gly Tyr Cys Leu Cys Cys Gly Ser His Phe
                165                 170                 175
```

Ala Gly Pro Val Tyr Glu Met Lys Asp Tyr Leu Gln Trp Thr Glu Gly
180 185 190

Thr Gly Ile Trp Asp Ser Ser Glu Lys Arg Lys Gln Pro Ser Pro Tyr
195 200 205

Leu Ala Thr Leu Arg Ala Ile Phe Gln Ala Gly Ile Cys Met Ala Leu
210 215 220

Tyr Leu Tyr Leu Val Pro Gln Phe Pro Leu Thr Arg Phe Thr Glu Pro
225 230 235 240

Val Tyr Gln Glu Trp Gly Phe Phe Lys Lys Phe Gly Tyr Gln Tyr Met
245 250 255

Ala Gly Gln Thr Ala Arg Trp Lys Tyr Tyr Phe Ile Trp Ser Ile Ser
260 265 270

Glu Ala Ser Ile Ile Ile Ser Gly Leu Gly Phe Ser Gly Trp Thr Asp
275 280 285

Asp Glu Ala Ser Pro Lys Pro Lys Trp Asp Arg Ala Lys Asn Val Asp
290 295 300

Ile Leu Gly Val Glu Leu Ala Lys Ser Ala Val Gln Ile Pro Leu Val
305 310 315 320

Trp Asn Ile Gln Val Ser Thr Trp Leu Arg His Tyr Val Tyr Glu Arg
325 330 335

Leu Val Lys Ser Gly Lys Lys Ala Gly Phe Phe Gln Leu Leu Ala Thr
340 345 350

Gln Thr Val Ser Ala Val Trp His Gly Leu Tyr Pro Gly Tyr Met Met
355 360 365

Phe Phe Val Gln Ser Ala Leu Met Ile Ala Gly Ser Arg Val Ile Tyr
370 375 380

Arg Trp Gln Gln Ala Ile Ser Pro Lys Leu Gly Val Leu Arg Ser Met
385 390 395 400

Met Val Phe Ile Asn Phe Leu Tyr Thr Val Leu Val Leu Asn Tyr Ser
405 410 415

Ala Val Gly Phe Met Val Leu Ser Leu His Glu Thr Leu Thr Ala Tyr
420 425 430

Gly Ser Val Tyr Tyr Ile Gly Thr Ile Ile Pro Val Gly Leu Ile Leu
435 440 445

Leu Ser Tyr Val Val Pro Ala Lys Pro Tyr Arg Ala Lys Pro Arg Lys
450 455 460

Glu Glu
465

<210> SEQ ID NO 139
<211> LENGTH: 1398
<212> TYPE: DNA
<213> ORGANISM: Brassica napus

<400> SEQUENCE: 139
atgatatcga tggacatgaa ttcgatggct gcttcgatcg gcgtatcggt cgccgtcctc 60
cgcttcctcc aatgcttcgt cgccacgatc cccgtctcct tcttctggcg aatcgttccg 120
agtcgactcg gcaagcacat ctacgccgcc gcttcaggcg tattcctctc ttacctctcc 180
ttcggcttct cctcaaatct ccacttcctc gttccgatga cgatcggata cgcttccatg 240
gcgatgtatc gacccaagtg tggaatcatc agtttcttcc tcggcttcgc ttatctcatc 300
ggctgtcatg tgttttacat gagtggtgat gcgtggaaag aaggtggcat cgactccact 360
ggagcgttaa tggtgttaac gctgaaggtt atctcatgtg cggttaatta caatgatggg 420

```
atgttgaagg aggaaggctt acgtgaagct cagaagaaga acagactgat cgagatgccg    480

tctttgatcg agtactttgg ttactgtctc tgttgcggta gccatttcgc tggtcctgtt    540

tacgaaatga aagattatct ccaatggaca gagggaacag gaatttggga tagttccgag    600

aaaagaaagc agccatcgcc ttatttagct acactgcgag ctatcttcca agctgggatt    660

tgcatggctc tgtatctcta tctagtccct cagttcccgt tgactcggtt cactgaacca    720

gtgtaccaag aatgggggtt ttggaagaag tttggttacc agtacatggc gggacagacg    780

gctcgctgga agtattactt catctggtcg atctcggagg cttctattat catctctggt    840

ttgggtttca gtggctggac tgatgatgct tcgccaaaac ccaaatggga ccgtgccaag    900

aacgtggaca tcctcggtgt agaacttgct aagagcgcgg ttcagattcc gcttgtgtgg    960

aacatacaag tcagcacctg gctccgtcac tacgtgtatg agagacttgt gaagagtggg   1020

aagaaagcag gtttctttca gttactaggt acacaaaccg tcagtgcggt ttggcatgga   1080

ctgtatcctg gttacatgat gttctttgtt caatcagctt tgatgattgc tggctcaaga   1140

gttatttacc gatggcaaca agctatcagt ccgaaactag caatcctgag aagtatcatg   1200

gtgttcatca actttcttta caccgtcttg gttctcaact actcagccgt tggtttcatg   1260

gttttaagct tgcacgaaac gctcactgcc tacgggagcg tatattacat tggaacaatc   1320

atacctgttg gattgattct cctcagctac gtggttcctg cgaagccctc tcggccaaag   1380

ccacgtaaag aggaataa                                                 1398
```

```
<210> SEQ ID NO 140
<211> LENGTH: 465
<212> TYPE: PRT
<213> ORGANISM: Brassica napus

<400> SEQUENCE: 140

Met Ile Ser Met Asp Met Asn Ser Met Ala Ala Ser Ile Gly Val Ser
1               5                   10                  15

Val Ala Val Leu Arg Phe Leu Gln Cys Phe Val Ala Thr Ile Pro Val
            20                  25                  30

Ser Phe Phe Trp Arg Ile Val Pro Ser Arg Leu Gly Lys His Ile Tyr
        35                  40                  45

Ala Ala Ala Ser Gly Val Phe Leu Ser Tyr Leu Ser Phe Gly Phe Ser
    50                  55                  60

Ser Asn Leu His Phe Leu Val Pro Met Thr Ile Gly Tyr Ala Ser Met
65                  70                  75                  80

Ala Met Tyr Arg Pro Lys Cys Gly Ile Ile Ser Phe Phe Leu Gly Phe
                85                  90                  95

Ala Tyr Leu Ile Gly Cys His Val Phe Tyr Met Ser Gly Asp Ala Trp
            100                 105                 110

Lys Glu Gly Gly Ile Asp Ser Thr Gly Ala Leu Met Val Leu Thr Leu
        115                 120                 125

Lys Val Ile Ser Cys Ala Val Asn Tyr Asn Asp Gly Met Leu Lys Glu
    130                 135                 140

Glu Gly Leu Arg Glu Ala Gln Lys Lys Asn Arg Leu Ile Glu Met Pro
145                 150                 155                 160

Ser Leu Ile Glu Tyr Phe Gly Tyr Cys Leu Cys Cys Gly Ser His Phe
                165                 170                 175

Ala Gly Pro Val Tyr Glu Met Lys Asp Tyr Leu Gln Trp Thr Glu Gly
            180                 185                 190
```

-continued

```
Thr Gly Ile Trp Asp Ser Ser Glu Lys Arg Lys Gln Pro Ser Pro Tyr
        195                 200                 205

Leu Ala Thr Leu Arg Ala Ile Phe Gln Ala Gly Ile Cys Met Ala Leu
    210                 215                 220

Tyr Leu Tyr Leu Val Pro Gln Phe Pro Leu Thr Arg Phe Thr Glu Pro
225                 230                 235                 240

Val Tyr Gln Glu Trp Gly Phe Trp Lys Lys Phe Gly Tyr Gln Tyr Met
                245                 250                 255

Ala Gly Gln Thr Ala Arg Trp Lys Tyr Tyr Phe Ile Trp Ser Ile Ser
            260                 265                 270

Glu Ala Ser Ile Ile Ile Ser Gly Leu Gly Phe Ser Gly Trp Thr Asp
        275                 280                 285

Asp Ala Ser Pro Lys Pro Lys Trp Asp Arg Ala Lys Asn Val Asp Ile
    290                 295                 300

Leu Gly Val Glu Leu Ala Lys Ser Ala Val Gln Ile Pro Leu Val Trp
305                 310                 315                 320

Asn Ile Gln Val Ser Thr Trp Leu Arg His Tyr Val Tyr Glu Arg Leu
                325                 330                 335

Val Lys Ser Gly Lys Lys Ala Gly Phe Phe Gln Leu Leu Gly Thr Gln
            340                 345                 350

Thr Val Ser Ala Val Trp His Gly Leu Tyr Pro Gly Tyr Met Met Phe
        355                 360                 365

Phe Val Gln Ser Ala Leu Met Ile Ala Gly Ser Arg Val Ile Tyr Arg
    370                 375                 380

Trp Gln Gln Ala Ile Ser Pro Lys Leu Ala Ile Leu Arg Ser Ile Met
385                 390                 395                 400

Val Phe Ile Asn Phe Leu Tyr Thr Val Leu Val Leu Asn Tyr Ser Ala
                405                 410                 415

Val Gly Phe Met Val Leu Ser Leu His Glu Thr Leu Thr Ala Tyr Gly
            420                 425                 430

Ser Val Tyr Tyr Ile Gly Thr Ile Ile Pro Val Gly Leu Ile Leu Leu
        435                 440                 445

Ser Tyr Val Val Pro Ala Lys Pro Ser Arg Pro Lys Pro Arg Lys Glu
    450                 455                 460

Glu
465
```